US008163736B2

(12) United States Patent
Gauzy et al.

(10) Patent No.: US 8,163,736 B2
(45) Date of Patent: Apr. 24, 2012

(54) CYTOTOXIC AGENTS COMPRISING NEW TOMAYMYCIN DERIVATIVES

(75) Inventors: Laurence Gauzy, Paris (FR); Herve Bouchard, Thiais (FR); Ravi V. J. Chari, Newton, MA (US); Alain Commercon, Vitry-sur-Seine (FR); Robert Zhao, Lexington, MA (US); Yonghong Deng, Arlington, MA (US); Wei Li, Winchester, MA (US)

(73) Assignee: sanofi-aventis, Paris (FR)

( * ) Notice: Subject to any disclaimer, the term of this patent is extended or adjusted under 35 U.S.C. 154(b) by 542 days.

(21) Appl. No.: 12/174,195

(22) Filed: Jul. 16, 2008

(65) Prior Publication Data

US 2009/0036431 A1 Feb. 5, 2009

Related U.S. Application Data

(63) Continuation of application No. PCT/IB2007/000142, filed on Jan. 22, 2007.

(30) Foreign Application Priority Data

Jan. 25, 2006 (EP) .................................. 06290154

(51) Int. Cl.
*C07D 519/00* (2006.01)
*C07D 487/00* (2006.01)
*A61K 31/5517* (2006.01)

(52) U.S. Cl. ........................................ 514/220; 540/496
(58) Field of Classification Search .................. 540/496; 514/220
See application file for complete search history.

(56) References Cited

U.S. PATENT DOCUMENTS

| 4,542,225 A | 9/1985 | Blattler et al. |
| 4,569,789 A | 2/1986 | Blattler et al. |
| 4,618,492 A | 10/1986 | Blattler et al. |
| 4,625,014 A | 11/1986 | Senter et al. |
| 4,764,368 A | 8/1988 | Blattler et al. |
| 5,208,020 A | 5/1993 | Chari et al. |

FOREIGN PATENT DOCUMENTS

| FR | 1516743 | 2/1968 |
| WO | WO 00/12507 | 3/2000 |
| WO | WO 00/12508 | 3/2000 |
| WO | WO 2004/087716 A1 | 10/2004 |
| WO | WO 2004/103272 | 12/2004 |
| WO | WO 2005/040170 A2 | 5/2005 |
| WO | WO 2005/085250 A1 | 9/2005 |
| WO | WO 2005/085259 A2 | 9/2005 |
| WO | WO 2005/085260 A1 | 9/2005 |
| WO | WO 2005/110423 A2 | 11/2005 |

OTHER PUBLICATIONS

Aboud-Pirak et al, Cytotoxic Activity of Daunorubicin or Vindesin Conjugated to a Monoclonal antibody on Cultured MCF-7 Breast Carcinoma Cells, Biochemical Pharmacology, vol. 38, No. 4, pp. 641-648, 1989.
Blattler et al, New Heterobifunctional Protein Cross-Linking Reagent that Forms an Acid-Labile Link, Biochemistry, 1985, 24, pp. 1517-1524.
Farmer et al, Synthesis and DNA Crosslinking Ability of a Dimeric Anthramycin Analog, Tetrahedron Letters, vol. 29, No. 40, pp. 5105-5108, 1988.
Greenfield et al, Evaluation in Vitro of Adriamycin Immunoconjugates Synthesized Using an Acid-sensitive Hydrazone Linker, Cancer Research, 50, pp. 6600-6607, Oct. 15, 1990.
Gregson et al, Linker Length Modulates DNA Cross-Linking Reactivity and Cytotoxic Potency of C8/C8' Ether-Linked C2-exo-Unsaturated Pyrrolo[2,1-c][1,4]benzodiazepine (PBD) Dimers, J. Med. Chem., 2004 (47) pp. 1161-1174.
Gregson et al, Synthesis of a novel C2/C2'-exo unsaturated pyrrolobenzodiazepine cross-linking agent with remarkable DNA binding affinity and cytotoxicity, Chem. Commun., 1999, pp. 797-798.
Kamal et al, DNA binding potential and cytotoxicity of newly designed pyrrolobenzodiazepine dimers linked through a piperazine side-armed-alkane spacer, Bioorganic & Medicinal Chemistry 14 (2006) pp. 385-394.
Kamal et al, Synthesis of fluorinated analogues of SJG-136 and their DNA-binding potential, Bioorganic & Medicinal Chemistry Letters 14 (2004) pp. 5699-5702.
Kamal et al, The effect of C2-fluoro group on the biological activity of DC-81 and its dimers, Bioorganic & Medicinal Chemistry Letters 14 (2004) pp. 2669-2672.
Kumar et al, Design, synthesis and in vitro cytotoxic studies of novel bis-pyrrolo[2,1][1,4]benzodiazepine-pyrrole and imidazole polyamide conjugates, European Journal of Medicinal Chemistry 40 (2005) pp. 641-654.
Laguzza et al, New Antitumor Monoclonal Antibody-Vinca Conjugates LY203725 and Related Compounds: Design, Preparation, and Representative in Vivo Activity, J. Med. Chem., 1989, 32, pp. 548-555.
Mori et al, Total Syntheses of Prothracarcin and Tomaymycin by Use of Palladium Catalyzed Carbonylation, Tetrahedron, vol. 42, No. 14, pp. 3793-3806, 1986.
Senter et al, Novel Photocleavable Protein Crosslinking Reagents and Their Use in the Preparation of Antibody-Toxin Conjugates, Photochemistry and Photobiology, vol. 42, No. 3, pp. 231-237, 1985.
Trouet et al, A Covalent Linkage Between Daunorubicin and Proteins that is Stable in Serum and Reversible by Lysosomal Hydrolases, as Required for a Lysosomotropic Drug-Carrier Conjugate: In Vitro and In Vivo Studies, Proc. Natl. Acad. Sci. USA, vol. 79, pp. 626-629, Jan. 1982.

*Primary Examiner* — Bruck Kifle
(74) *Attorney, Agent, or Firm* — Sandra Brockman-Lee

(57) ABSTRACT

The present invention is related to new tomaymycin derivatives, their process of preparation and their therapeutic uses.

24 Claims, 4 Drawing Sheets

CYTOTOXIC AGENTS COMPRISING NEW TOMAYMYCIN DERIVATIVES

FIELD OF THE INVENTION

The present invention relates to novel cytotoxic agents and their therapeutic use. More specifically, the invention relates to novel cytotoxic agents comprising tomaymycin derivatives and their therapeutic use. These novel cytotoxic agents have therapeutic use as a result of delivering the tomaymycin derivatives to a specific cell population in a targeted fashion by chemically linking the tomaymycin derivative to a cell binding agent.

BACKGROUND OF THE INVENTION

Many reports have appeared on the attempted specific targeting of tumor cells with monoclonal antibody-drug conjugates (Sela et al, in *Immuno-conjugates,* 189-216 (C. Vogel, ed. 1987); Ghose et al, in *Targeted Drugs* 1-22 (E. Goldberg, ed. 1983); Diener et al, in *Antibody mediated delivery systems,* 1-23 (J. Rodwell, ed. 1988); Pietersz et al, in *Antibody mediated delivery systems,* 25-53 (J. Rodwell, ed. 1988); Bumol et al, in *Antibody mediated delivery systems,* 55-79 (J. Rodwell, ed. 1988); G. A. Pietersz & K. Krauer, 2, *J. Drug Targeting,* 183-215 (1994); R. V. J. Chari, 31 *Adv. Drug Delivery Revs.,* 89-104 (1998); W. A. Blattler & R. V. J. Chari, in *Anticancer Agents, Frontiers in Cancer Chemotherapy,* 317-338, ACS Symposium Series 796; and I. Ojima et al eds, *American Chemical Society* 2001}. All references and patents cited herein are incorporated by reference.

Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46, *Cancer Res.* 2407-2412 (1986); Ohkawa et al 23, *Cancer Immunol. Immunother.* 81-86 (1986); Endo et al, 47 *Cancer Res.* 1076-1080 (1980)), dextran (Hurwitz et al, 2 *Appl. Biochem.* 25-35 (1980); Manabi et al, 34 *Biochem. Pharmacol.* 289-291 (1985); Dillman et al, 46 *Cancer Res.,* 4886-4891 (1986); Shoval et al, 85, *Proc. Natl. Acad. Sci.,* 8276-8280 (1988)), or polyglutamic acid (Tsukada et al, 73, *J. Natl. Canc. Inst.,* 721-729 (1984); Kato et al 27 *J. Med. Chem.,* 1602-1607 (1984); Tsukada et al, 52, *Br. J. Cancer,* 111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.,* 1048-1054 (1981)). Yang and Reisfeld used the same technique to conjugate daunorubicin to an anti-melanoma antibody (80 *J. Natl. Canc. Inst.* 1154-1159 (1988)). Dillman et al. also used an acid-labile linker in a similar fashion to prepare conjugates of daunorubicin with an anti-T cell antibody (48 *Cancer Res.* 6097-6102 (1988)).

An alternative approach, explored by Trouet et al, involved linking daunorubicin to an antibody via a peptide spacer arm (79 *Proc. Natl. Acad. Sci.* 626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies could be very inefficient. In the area of immunotoxins, conjugates formed via disulfide bridges between monoclonal antibodies and catalytically active protein toxins were shown to be more cytotoxic than conjugates containing other linkers. See, Lambert et al, 260 *J. Biol. Chem.* 12035-12041 (1985); Lambert et al, in *Immunotoxins* 175-209 (A. Frankel, ed. 1988); Ghetie et al, 48, *Cancer Res.* 2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al (260, *J. Biol. Chem.* 10905-10908 (1985)) described the conversion of methotrexate into a mercaptoethylamide derivative followed by conjugation with poly-D-lysine via a disulfide bond. Another report described the preparation of a conjugate of the trisulfide containing toxic drug calichemycin with an antibody (Hinman et al., 53 *Cancer Res.* 3336-3342 (1993)).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin, and vincristine. In order to achieve significant cytotoxicity, linkage of a large number of drug molecules, either directly to the antibody or through a polymeric carrier molecule, becomes necessary. However, such heavily modified antibodies often display impaired binding to the target antigen and fast in vivo clearance from the blood stream.

In spite of the above-described difficulties, useful cytotoxic agents comprising cell binding moieties and the group of cytotoxic drugs known as maytansinoids have been reported (U.S. Pat. Nos. 5,208,020, 5,416,064, and R. V. J. Chari, 31 *Advanced Drug Delivery Reviews* 89-104 (1998)). Similarly, useful cytotoxic agents comprising cell binding moieties and analogues and derivatives of the potent antitumor antibiotic CC-1065 have also been reported (U.S. Pat. Nos. 5,475,092, 5,585,499 and 6,756,397).

Tomaymycin derivatives are pyrrolo[1,4]benzodiazepines (PBDs), a known class of compounds exerting their biological properties by covalently binding to the N2 of guanine in the minor groove of DNA. PBDs include a number of minor groove binders such as anthramycin, neothramycin and DC-81. Tomaymycin antitumor activity is however limited because of its non-specific toxicity towards normal cells. Thus there is a need to increase the therapeutic activity, and diminish the non-specific toxic effects of tomaymycin compounds. The present inventors have shown that this need can be met by targeted delivery of tomaymcin compounds by linking them to cell binding agents. Additionally, there is a need to develop tomaymycin derivatives that are soluble and stable in aqueous solutions. Further, tomaymycin is not sufficiently potent to be used in conjugates of cell binding agents.

Recently, a few new PBD derivatives and their anti-tumour activity in preclinical models have been disclosed (WO 00/12508 and WO2005/085260). However, initial clinical trials in humans indicate that compounds of this class are severely toxic, based on the very low dose that can be administered to humans (I. Puzanov, Proc. AACR-NCI-EORTC International Conference, Philadelphia, USA 2005, Abstract #B117). Thus, it is desired to provide alternative derivatives that are more potent and/or may be bonded to cell binding agents.

Accordingly, a method of treating diseases with tomaymycin derivatives wherein their side effects are reduced without compromising their cytotoxicity is greatly needed.

SUMMARY OF THE INVENTION

As disclosed in a first embodiment, one object of the present invention is to provide tomaymycin derivatives that are highly toxic and that can still be effectively used in the treatment of many diseases.

Another object of the present invention is to provide novel tomaymycin derivatives, optionally linkable or linked to a cell binding agent.

In a second embodiment, the present invention provides a therapeutic composition comprising:
(A) an effective amount of one or more tomaymycin derivatives optionally linkable or linked to a cell binding agent, and
(B) a pharmaceutically acceptable carrier, diluent, or excipient In a third embodiment, the present invention provides a method of killing selected cell populations comprising contacting target cells or tissue containing target cells, with a cytotoxic amount of a cytotoxic agent comprising one or more tomaymycin derivatives, optionally linkable or linked to a cell binding agent.

DETAILED DESCRIPTION OF THE INVENTION

Figure 1A:
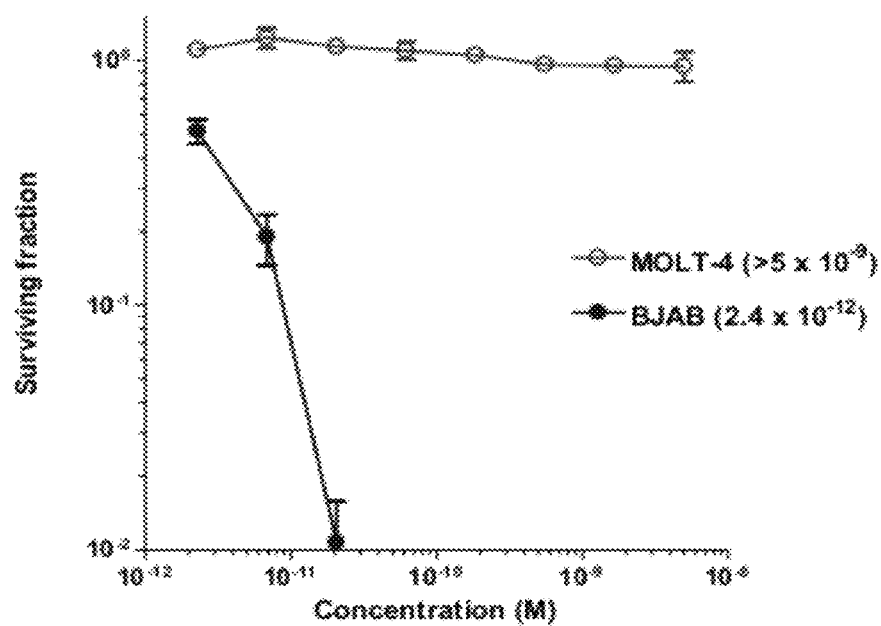
FIG. 1a represents in vitro potency of huB4-SPDB—compound of example 16 towards antigen positive BJAB cells and antigen negative MOLT-4 cells.

This invention is based on the synthesis of novel tomaymycin derivatives that retain high cytotoxicity and that can be effectively linked to cell binding agents. It has previously been shown that the linkage of highly cytotoxic drugs to antibodies using a cleavable link, such as a disulfide bond, ensures the release of fully active drugs inside the cell, and such conjugates are cytotoxic in an antigen specific manner (U.S. Pat. Nos. 6,340,701; 6,372,738; 6,436,931). However, the art reveals that it is extremely difficult to modify existing drugs without diminishing their cytotoxic potential. The disclosed invention overcomes this problem by modifying the disclosed tomaymycin derivatives with chemical moieties. As a result, the disclosed novel tomaymycin derivatives preserve, and in some cases could even enhance the cytotoxic potency of tomaymycin derivatives. The cell binding agent-tomaymycin derivative complexes permit the full measure of the cytotoxic action of the tomaymycin derivatives to be applied in a targeted fashion against unwanted cells only, therefore, avoiding side effects due to damage to non-targeted healthy cells. Thus, the invention provides useful agents for the elimination of diseased or abnormal cells that are to be killed or lysed such as tumor cells (particularly solid tumor cells).

The cytotoxic agent according to the present invention comprises one or more tomaymycin derivatives, optionally linkable or linked to a cell binding agent via a linking group. The linking group is part of a chemical moiety that is covalently bound to a tomaymycin derivative through conventional methods. In a preferred embodiment, the chemical moiety can be covalently bound to the tomaymycin derivative via a disulfide bond.

The tomaymycin derivatives useful in the present invention have the formula (I) shown below:

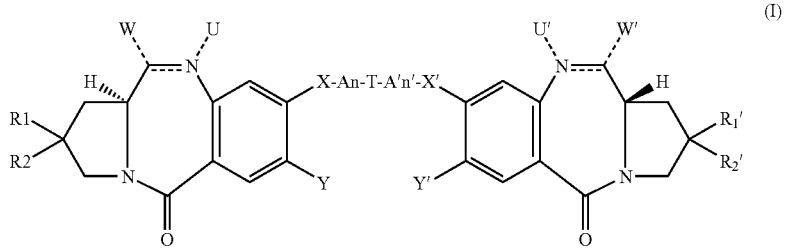

(I)

wherein
---- represents an optional single bond;
═══ represents either a single bond or a double bond
provided that when ═══ represents a single bond, U and U', the same or different, independently represent H, and W and W', the same or different, are independently selected from the group consisting of OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO$_3$⁻, a sulfonamide such as —NRSOOR, an amine such as —NRR', optionally cyclic amine such that N10 and C11 are a part of the cycle, a hydroxylamine derivative such as —NROR', an amide such as —NRCOR, an azido such as —N$_3$, a cyano, a halo, a trialkyl or triarylphosphonium, an aminoacid-derived group; Preferably W and W' are the same or different and are OH, OMe, OEt, NHCONH$_2$, SMe;

and when ▬▬represents a double bond, U and U' are absent and W and W' represent H;

R1, R2, R1', R2' are the same or different and independently chosen from Halide or Alkyl optionally substituted by one or more Hal, CN, NRR', CF$_3$, OR, Aryl, Het, S(O)$_q$R, or R1 and R2 and R1' and R2' form together a double bond containing group =B and =B' respectively.

Preferably, R1 and R2 and R1' and R2' form together a double bond containing group =B and =B' respectively.

B and B' are the same or different and independently chosen from Alkenyl being optionally substituted by one or more Hal, CN, NRR', CF$_3$, OR, Aryl, Het, S(O)$_q$R or B and B' represent an oxygen atom.

Preferably, B=B'.

More preferably, B=B'=CH$_2$ or =CH—CH$_3$,

X, X' are the same or different and independently chosen from one or more —O—, —NR—, —(C=O)—, —S(O)$_q$—.

Preferably, X=X'.

More preferably, X=X'=O.

A, A' are the same or different and independently chosen from Alkyl or Alkenyl optionally containing an oxygen, a nitrogen or a sulfur atom, each being optionally substituted by one or more Hal, CN, NRR', CF$_3$, OR, S(O)$_q$R, Aryl, Het, Alkyl, Alkenyl.

Preferably, A=A'.

More preferably, A=A'=linear unsubstituted alkyl.

Y, Y' are the same or different and independently chosen from H, OR;

Preferably, Y=Y'.

More preferably, Y=Y'=OAlkyl, more preferably OMethyl.

T is —NR—, —O—, —S(O)$_q$—, or a 4 to 10-membered aryl, cycloalkyl, heterocyclic or heteroaryl, each being optionally substituted by one or more Hal, CN, NRR', CF$_3$, R, OR, S(O)$_q$R, and/or linker(s), or a branched Alkyl, optionally substituted by one or more Hal, CN, NRR', CF$_3$, OR, S(O)$_q$R and/or linker(s), or a linear Alkyl substituted by one or more Hal, CN, NRR', CF$_3$, OR, S(O)$_q$R and/or linker(s).

Preferably, T is a 4 to 10-membered aryl or heteroaryl, more preferably phenyl or pyridyl, optionally substituted by one or more linker(s).

Said linker comprises a linking group. Suitable linking groups are well known in the art and include thiol, sulfide, disulfide groups, thioether groups, acid labile groups, photolabile groups, peptidase labile groups and esterase labile groups. Preferred are disulfide groups and thioether groups.

When the linking group is a thiol-, sulfide (or so-called thioether —S—) or disulfide (—S—S—)-containing group, the side chain carrying the thiol, the sulfide or disulfide group can be linear or branched, aromatic or heterocyclic. One of ordinary skill in the art can readily identify suitable side chains.

Preferably, said linker is of formula:

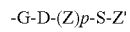

-G-D-(Z)p-S-Z' where

G is a single or double bond, —O—, —S— or —NR—;

D is a single bond or -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F—;

where E and F are the same or different and are independently chosen from linear or branched —(OCH$_2$CH$_2$)$_i$Alkyl(OCH$_2$CH$_2$)$_j$—, -Alkyl(OCH$_2$CH$_2$)$_i$-Alkyl-, —(OCH$_2$CH$_2$)$_i$—, —(OCH$_2$CH$_2$)$_i$Cycloalkyl(OCH$_2$CH$_2$)$_j$—, —(OCH$_2$CH$_2$)$_i$Heterocyclic(OCH$_2$CH$_2$)$_j$—, —(OCH$_2$CH$_2$)$_i$Aryl(OCH$_2$CH$_2$)$_j$—, —(OCH$_2$CH$_2$)$_i$Heteroaryl(OCH$_2$CH$_2$)$_j$—, -Alkyl-(OCH$_2$CH$_2$)$_i$Alkyl(OCH$_2$CH$_2$)$_j$—, -Alkyl-(OCH$_2$CH$_2$)$_i$—, -Alkyl-(OCH$_2$CH$_2$)$_i$Cycloalkyl(OCH$_2$CH$_2$)$_j$—, -Alkyl(OCH$_2$CH$_2$)$_i$Heterocyclic(OCH$_2$CH$_2$)$_j$—, -Alkyl-(OCH$_2$CH$_2$)$_i$Aryl(OCH$_2$CH$_2$)$_j$—, -Alkyl(OCH$_2$CH$_2$)$_i$Heteroaryl(OCH$_2$CH$_2$)$_j$—, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl- , -Heteroaryl-Alkyl-;

where i and j, identical or different are integers and independently chosen from 0, 1 to 2000;

Z is linear or branched -Alkyl-;

p is 0 or 1;

Z' represents H, a thiol protecting group such as COR, R$_{20}$ or SR$_{20}$, wherein R$_{20}$ represents H, methyl, Alkyl, optionally substituted Cycloalkyl, aryl, heteroaryl or heterocyclic, provided that when Z' is H, said compound is in equilibrium with the corresponding compound formed by intramolecular cyclisation resulting from addition of the thiol group —SH on the imine bond —NH= of one of the PBD moieties.

n, n', equal or different are 0 or 1.

q is 0, 1 or 2.

R, R' are equal or different and independently chosen from H, Alkyl, Aryl, each being optionally substituted by Hal, CN, NRR', CF$_3$, R, OR, S(O)$_q$R, Aryl, Het;

or their pharmaceutically acceptable salts, hydrates, or hydrated salts, or the polymorphic crystalline structures of these compounds or their optical isomers, racemates, diastereomers or enantiomers.

The present invention refers to following preferred embodiments or any combination of any of them:

G is a single bond or —O— or —NR—;

G is —O—;

D is a single bond or -E-, -E-NR—CO—, -ECO—, —CO-E-;

D is -E-, -E-NR—CO—;

D is -E-NR—CO—;

E is linear or branched -Alkyl-, —(OCH$_2$CH$_2$)$_i$— or -Alkyl-heterocyclic;

E is linear or branched -Alkyl-;

Z is —(CH$_2$)$_2$—C(CH$_3$)$_2$—;

p is 0 or 1;

Z' is H or SR$_{20}$, wherein R$_{20}$ represents Alkyl, aryl, heterocyclic or heteroaryl;

Z' is H or SR$_{20}$, wherein R$_{20}$ represents Alkyl.

Specific examples of the thiol-, sulfide- or disulfide-containing linkers include —$(CR_{13}R_{14})_t(CR_{15}R_{16})_u(OCH_2CH_2)_ySZ'$, —$(CR_{13}R_{14})_t(CR_{17}=CR_{18})(CR_{15}R_{16})_y(OCH_2CH_2)_ySZ'$, —$(CR_{13}R_{14})_t(NR_{19}CO)(CR_{15}R_{16})_u(OCH_2CH_2)_y$ SZ', —$(CR_{13}R_{14})_t(OCO)(R_{15}R_{16})_u(OCH_2CH_2)_ySZ'$, —$(CR_{13}R_{14})_t(CO)(CR_{15}R_{16})_u(OCH_2CH_2)_ySZ'$, —$(CR_{13}R_{14})_t(CONR_{19})(CR_{15}R_{16})_u(OCH_2CH_2)_ySZ'$, —$(CR_{13}R_{14})_t$-phenyl-CO$(CR_{15}R_{16})_uSZ'$, —$(CR_{13}R_{14})_t$-furyl-CO$(CR_{15}R_{16})_uSZ'$, —$(CR_{13}R_{14})_t$-oxazolyl-CO$(CR_{15}R_{16})_uSZ'$, —$(CR_{13}R_{14})_t$-thiazolyl-CO$(CR_{15}R_{16})_uSZ'$, —$(CR_{13}R_{14})_t$-thienyl-CO$(CR_{15}R_{16})_uSZ'$, —$(CR_{13}R_{14})_t$-imidazolyl-CO$(CR_{15}R_{16})_u$SZ', —$(CR_{13}R_{14})_t$-morpholino-CO$(CR_{15}R_{16})_uSZ'$, —$(CR_{13}R_{14})_t$piperazino-CO$(CR_{15}R_{16})_uSZ'$, —$(CR_{13}R_{14})_t$—N-methylpiperazin-CO$(CR_{15}R_{16})_uSZ'$, —$(CR_{13}R_{14})_t$-phenyl-QSZ', —$(CR_{13}R_{14})_t$-furyl-QSZ', —$(CR_{13}R_{14})_t$-oxazolyl-QSZ', —$(CR_{13}R_{14})_t$-thiazolyl-QSZ', —$(CR_{13}R_{14})_t$-thienyl-QSZ', —$(CR_{13}R_{14})_t$-imidazolyl-QSZ', —$(CR_{13}R_{14})_t$-morpholino-QSZ', —$(CR_{13}R_{14})_t$-piperazino-QSZ', —$(CR_{13}R_{14})_t$—N-methylpiperazino-QSZ', or —$O(CR_{13}R_{14})_t(CR_{15}R_{16})_u(OCH_2CH_2)_ySZ'$, —$O(CR_{13}R_{14})_t(NR_{19}CO)(CR_{15}R_{16})_u(OCH_2CH_2)_ySZ'$, —$O(CR_{13}R_{14})_t(CR_{17}=CR_{18})(CR_{15}R_{16})_t(OCH_2CH_2)_ySZ'$, —O-phenyl-QSZ', —O-furyl-QSZ', —O-oxazolyl-QSZ', —O-thiazolyl-QSZ', —O-thienyl-QSZ', —O-imidazolyl-QSZ', —O-morpholino-QSZ', —O-piperazino-QSZ', —O—N-methylpiperazino-QSZ', —$OCO(CR_{13}R_{14})_t(NR_{19}CO)_v(CR_{15}R_{16})_u(OCH_2CH_2)_y$ SZ', —OCO—$(CR_{13}R_{14})_t$ $(CR_{17}=CR_{18})(CR_{15}R_{16})_u(OCH_2CH_2)_ySZ'$, —$OCONR_{12}(CR_{13}R_{14})_t(CR_{15}R_{16})_u(OCH_2CH_2)_ySZ'$, —OCO-phenyl-QSZ', —OCO-furyl-QSZ', —OCO-oxazolyl-QSZ', —OCO-thiazolyl-QSZ', —OCO-thienyl-QSZ', —OCO-imidazolyl-QSZ', —OCO-morpholino-QSZ', —OCO-piperazino-QSZ', —OCO—N-methylpiperazino-QSZ', or —$CO(CR_{13}R_{14})_t(CR_{15}R_{16})_u$ $(OCH_2CH_2)_y$ SZ', —CO—$(CR_{13}R_{14})_t$ $(CR_{17}=CR_{18})(CR_{15}R_{16})_u(OCH_2CH_2)_ySZ'$, —$CONR_{12}(CR_{13}R_{14})_t(CR_{15}R_{16})_u$ $(OCH_2CH_2)_ySZ'$, —CO-phenyl-QSZ', —CO-furyl-QSZ', —CO-oxazolyl-QSZ', —CO-thiazolyl-QSZ', —CO-thienyl-QSZ', —CO-imidazolyl-QSZ', —CO-morpholino-QSZ', —CO-piperazino-QSZ', —CO-piperidino-QSZ', —CO—N-methylpiperazino-QSZ', —$NR_{19}(CR_{13}R_{14})_t(CR_{15}R_{16})_u(OCH_2CH_2)_ySZ'$, —$NR_{19}CO(CR_{13}R_{14})_t(CR_{15}R_{16})_u(OCH_2CH_2)_ySZ'$, —$NR_{19}(CR_{13}R_{14})_t$ $(CR_{17}=CR_{18})(CR_{15}R_{16})_t$ $(OCH_2CH_2)_ySZ'$, —$NR_{19}CO(CR_{13}R_{14})_t$ $(CR_{17}=CR_{18})(CR_{15}R_{16})_t(OCH_2CH_2)_ySZ'$, —$NR_{19}CONR_{12}(CR_{13}R_{14})_t(CR_{15}R_{16})_u(OCH_2CH_2)_ySZ'$, —$NR_{19}CONR_{12}$ $(CR_{13}R_{14})_t$ $(CR_{17}=CR_{18})(CR_{15}R_{16})_t$ $(OCH_2CH_2)_ySZ'$, —$NR_{19}CO$-phenyl-QSZ', —$NR_{19}CO$-furyl-QSZ', —$NR_{19}CO$-oxazolyl-QSZ', —$NR_{19}CO$-thiazolyl-QSZ', —$NR_{19}CO$-thienyl-QSZ', —$NR_{19}CO$-imidazolyl-QSZ', —$NR_{19}CO$-morpholino-QSZ', —$NR_{19}CO$-piperazino-QSZ', —$NR_{19}CO$-piperidino-QSZ', —$NR_{19}CO$—N-methylpiperazino-QSZ', —$NR_{19}$-phenyl-QSZ', —$NR_{19}$-furyl-QSZ', —$NR_{19}$-oxazolyl-QSZ', —$NR_{19}$-thiazolyl-QSZ', —$NR_{19}$-thienyl-QSZ', —$NR_{19}$-imidazolyl-QSZ', —$NR_{19}$-morpholino-QSZ', —$NR_{19}$-piperazino-QSZ', —$NR_{19}$-piperidino-QSZ', —$NR_{19}$—N-methylpiperazino-QSZ', —$NR_{19}CO$—$NR_{12}$-phenyl-QSZ', —$NR_{19}CO$—$NR_{12}$-oxazolyl-QSZ', —$NR_{19}CO$—$NR_{12}$-thiazolyl-QSZ', —$NR_{19}CO$—$NR_{12}$-thienyl-QSZ', —$NR_{19}CO$—$NR_{12}$-piperidino-QSZ', —$S(O)_q(CR_{13}R_{14})_t(CR_{15}R_{16})_u(OCH_2CH_2)_ySZ'$, —$S(O)_q(CR_{13}R_{14})_t(CR_{17}=CR_{18})(CR_{15}R_{16})_t(OCH_2CH_2)_ySZ'$, —$SCONR_{12}(CR_{13}R_{14})_t(CR_{15}R_{16})_u(OCH_2CH_2)_ySZ'$, —SCO-morpholino-QSZ', —SCO-piperazino-QSZ', —SCO-piperidino-QSZ', and —SCO—N-methylpiperazino-QSZ', wherein:

Z' is H, a thiol protecting group such as COR, $R_{20}$' or $SR_{20}$' wherein $R_{20}$' represents H, alkyl, aryl, heterocyclic or heteroaryl, wherein Q is a direct link or a linear alkyl or branched alkyl having from 1-10 carbon atoms or a polyethylene glycol spacer with 2 to 20 repeating ethylene oxy units;

$R_{19}$ and $R_{12}$ are the same or different and are linear alkyl, branched alkyl or cyclic alkyl having from 1 to 10 carbon atoms, or simple or substituted aryl or heterocyclic, and $R_{12}$ can in addition be H, $R_{13}$, $R_{14}$, $R_{15}$ and $R_{16}$ are the same or different and are H or a linear or branched alkyl having from 1 to 4 carbon atoms, $R_{17}$ and $R_{18}$ are H or alkyl, u is an integer from 1 to 10 and can also be 0, t is an integer from 1 to 10 and can also be 0, y is an integer from 1 to 20 and can also be 0.

When compound of formula (I) is in the form of a ion (eg. sulphonate), the counter ion may be present (eg. Na$^+$ or K$^+$).

According to a preferred aspect, compounds of the invention are those of formula (I) where T=aryl optionally substituted by one or more Hal, CN, NRR', $CF_3$, R, OR, $S(O)_qR$, and/or linker(s) and A, A', X, X', U, U', W, W', m, m', n, n', ----, ═══ are defined as above.

According to another preferred aspect, compounds of the invention are selected from the group consisting in:

8,8'-[1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-methoxy-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[4-(3-tert-butoxycarbonylaminopropyloxy)-2,6-pyridinediylbis-(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(3-aminopropyloxy)-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(N-methyl-3-tert-butoxycarbonylaminopropyl)-1,3-benzenediylbis-(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-{5-[3-(4-methyl-4-methyidisulfanyl-pentanoylamino)propyloxy]-1,3-benzenediylbis(methylenoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methylenoxy)]-bis[(S)-2-methylene-7-methoxy-1,2,3,11a-tetrahydro-5H-pyrrolo[2,1-c][1,4]benzodiazepin-5-one]

bis-{2-[(S)-2-methylene-7-methoxy-5-oxo-1,3,11a-tetrahydro-5H-pyrrolo[2,1-c][1,4]benzodiazepin-8-yloxy]-ethyl}-carbamic acid tert-butyl ester 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one]

8,8'-[5-(N-4-methyldithio-4,4-dimethylbutanoyl)-amino-1,3-benzenediylbis(methylenoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-mercapto-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-methyldithio-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

8,8'-[(4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(4-(4-methyl-4-methyldisulfanyl)-pentanamido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

as well as the corresponding mercapto derivatives,
or their pharmaceutically acceptable salts, hydrates, or hydrated salts, or the polymorphic crystalline structures of these compounds or their optical isomers, racemates, diastereomers or enantiomers.

Preferred compounds are those of formula:

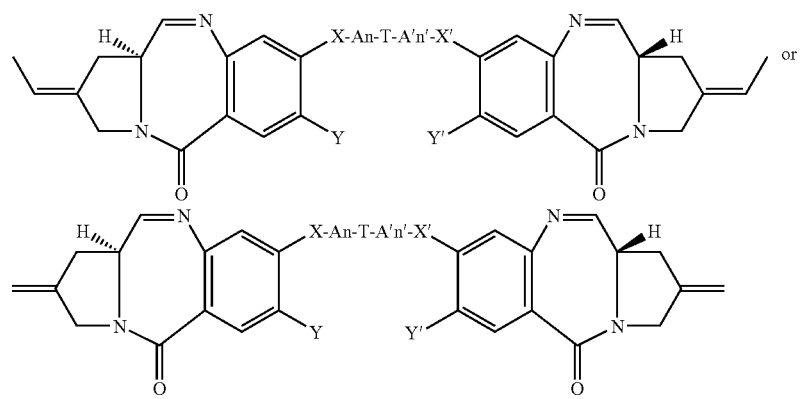

where X, X', A, A', Y, Y', T, n, n' are defined as above.

As used hereabove or hereafter:

Alk represents alkyl, alkene or alkyne.

"Alkyl" means an aliphatic hydrocarbon group which may be straight or branched having 1 to 20 carbon atoms in the chain or cyclic having 3 to 10 carbon atom. Preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl and cyclohexyl.

"Alkene" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkyne" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Halogen atom" refers to fluorine, chlorine, bromine or iodine atom; preferably fluorine and chlorine atom.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

"Het" means heterocycle or heteroaryl.

As used herein, the terms "heterocycle" or "heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics,* 76$^{th}$ Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrimidinyl, dihydrothiopyranyl, azepanyl, as well as the fused systems resulting from the condensation with a phenyl group.

As used herein, the term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2, 4-thiadiazolyl, isothiazolyl, triazolyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocycle" and the like refer also to the corresponding "alkylene", "cycloalkylene", "alkenylene", "alkynylene", "arylene", "heteroarylene", "heterocyclene" and the likes which are formed by the removal of two hydrogen atoms.

As used therein, the expression "linkable to a cell binding agent" refers to the tomaymycin derivatives comprising at least one linking group, or a precursor thereof, suitable to bond said derivatives to a cell binding agent; preferred linking groups are thiol or disulfide bonds, or precursors thereof.

As used therein, the expression "linked to a cell binding agent" refers to the conjugate molecule comprising at least one tomaymycin derivative bound to a cell binding agent via a suitable linking group, or a precursor thereof; preferred linking groups are thiol or disulfide bonds, or precursors thereof.

As used therein, "precursor" of a given group refers to any group which may lead to that group by any deprotection, chemical modification, or coupling reaction.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418, the disclosure of which is hereby incorporated by reference.

The compounds of the general formula (I) having geometrical and stereoisomers are also a part of the invention.

The N-10, C-11 double bond of tomaymycin derivatives of formula (I) is known to be readily convertible in a reversible manner to corresponding imine adducts in the presence of water, an alcohol, a thiol, a primary or secondary amine, urea and other nucleophiles. This process is reversible and can easily regenerate the corresponding tomaymycin derivatives in the presence of a dehydrating agent, in a non-protic organic solvent, in vacuum or at high temperatures (Z. Tozuka, 36, *J. Antibiotics,* 276 (1983).

Thus, this invention provides also for reversible derivatives of tomaymycin derivatives of general formula (II):

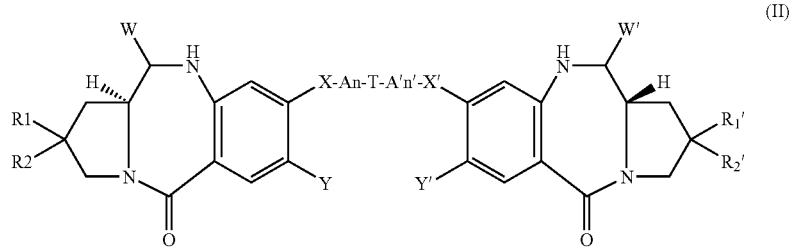

(II)

where A, X, Y, n, T, A', X', Y', n', R1, R2, R1', R2' are defined as in formula (I) and W, W' are the same or different and are selected from the group consisting of OH, an ether such as —OR, an ester (e.g. an acetate), such as —OCOR, —COOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —$SO_3^-$, a sulfonamide such as —NRSOOR, an amine such as —NRR', optionally cyclic amine such that N10 and C11 are a part of the cycle, a hydroxylamine derivative such as —NROR', an amide such as —NRCOR, —NRCONRR', an azido such as —$N_3$, a cyano, a halo, a trialkyl or triarylphosphonium, an aminoacid-derived group. Preferably, W and W' are the same or different and are OH, OMe, OEt, $NHCONH_2$, SMe.

Compounds of formula (II) may thus be considered as solvates, including water when the solvent is water; these solvates can be particularly useful.

According to a still further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations,* Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry,* $3^{rd}$ ed., John Wiley and Sons, 1999; J. F. W. McOmie in *Protective Groups in Organic Chemistry,* Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from −20° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, the process of preparation of the compounds of formula (I) comprises the step of deprotecting corresponding compounds of formula (III):

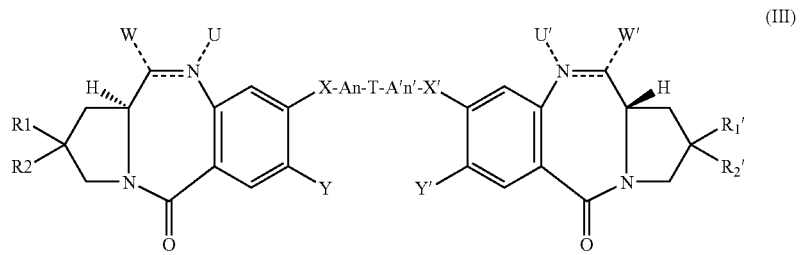

(III)

where Y, Y', X, A, A', X', n, n', W, W', U, U', ----, R1, R2, R1', R2', ═══ are defined as in formula (I) and T' corresponds to T where the functional group(s) has(ve) been protected.

Preferably, the SH function is protected and preferably the protecting group is acetyl, benzoyl, methanesulfonyl, methylthio, pyridylthio, nitropyridylthio, triisopropylsilyl (TIPS). Generally, the deprotection step is carried out using classical conditions such a base to remove the acetyl, benzoyl and methanesulfonyl protective groups, a reducing agent such as dithiothreitol or tris(2-carboxyethyl)phosphine (TCEP) to cleave a methylthio protective group or known by reacting the compounds with an ammonium fluoride to remove the TIPS.

The compounds of formula (II) may be obtained from coupling corresponding compounds of formulae (IV), (IV') and (V):

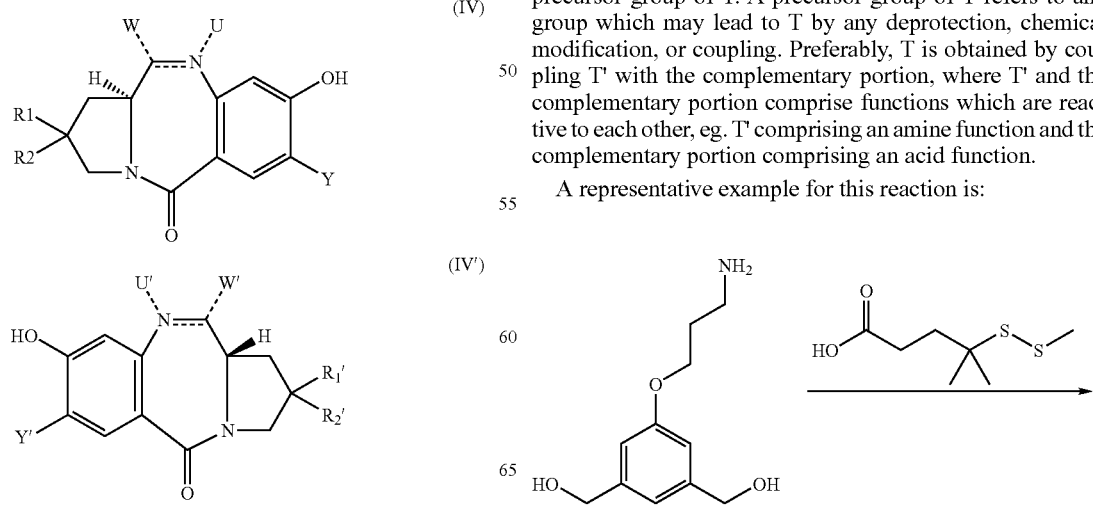

is where Y, Y', A, A', n, n', T', W, W', U, U', ----, ═══, R1, R2, R1', R2' are defined as in formula (III), and Lg is a leaving group such as a halogen, OMs, OTs or $OPPh_3^+$ (intermediate formed in a Mitsunobu reaction)

The compounds of formula (IV) and (IV') are generally known, as disclosed for instance in patent applications WO 00/12508, WW00/12507, WO 2005/040170, WO 2005/085260, or commercially available, and/or are available by total synthesis (M. Mori et al, 42 *Tetrahedron*, 3793-3806, 1986) or produced by *Streptomyces* species, in particular, following French patent Fr. 1,516,743 procedure or may be prepared by application or adaptation of the illustrative procedures given in the examples.

The compounds of formula (V) may be obtained from corresponding compounds of formula (VI):

HO-An-T'-A'n'-OH (VI)

where A, A', n, n', T' are defined as in formula (III).

This reaction is generally carried out in the presence of $PPh_3$ and $CHal_4$ or by reaction with a chlorosulfonate in the presence of a base such a triethylamine or potassium hydroxide, preferably triethylamine.

The compounds of formula (VI) may be obtained from corresponding compounds of formula (VII):

HO-An-T''-A'n'-OH (VII)

where A, A', n, n' are defined as in formula (III) and T'' is a precursor group of T. A precursor group of T refers to any group which may lead to T by any deprotection, chemical modification, or coupling. Preferably, T is obtained by coupling T' with the complementary portion, where T' and the complementary portion comprise functions which are reactive to each other, eg. T' comprising an amine function and the complementary portion comprising an acid function.

A representative example for this reaction is:

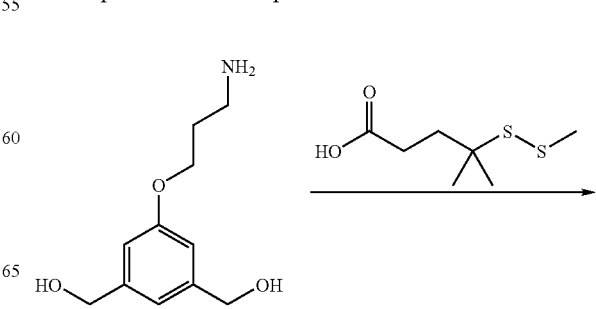

-continued
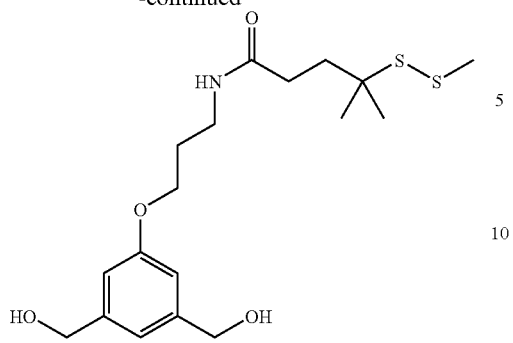
Generally, this reaction is carried out in the presence of N-hydroxysuccinimide and HOBT.
The compounds of formula (VII) may be commercially available or made by adaptation or application of known methods or according to the examples.
Exemplary non-limiting scheme for this embodiment of the process of the invention is given below:

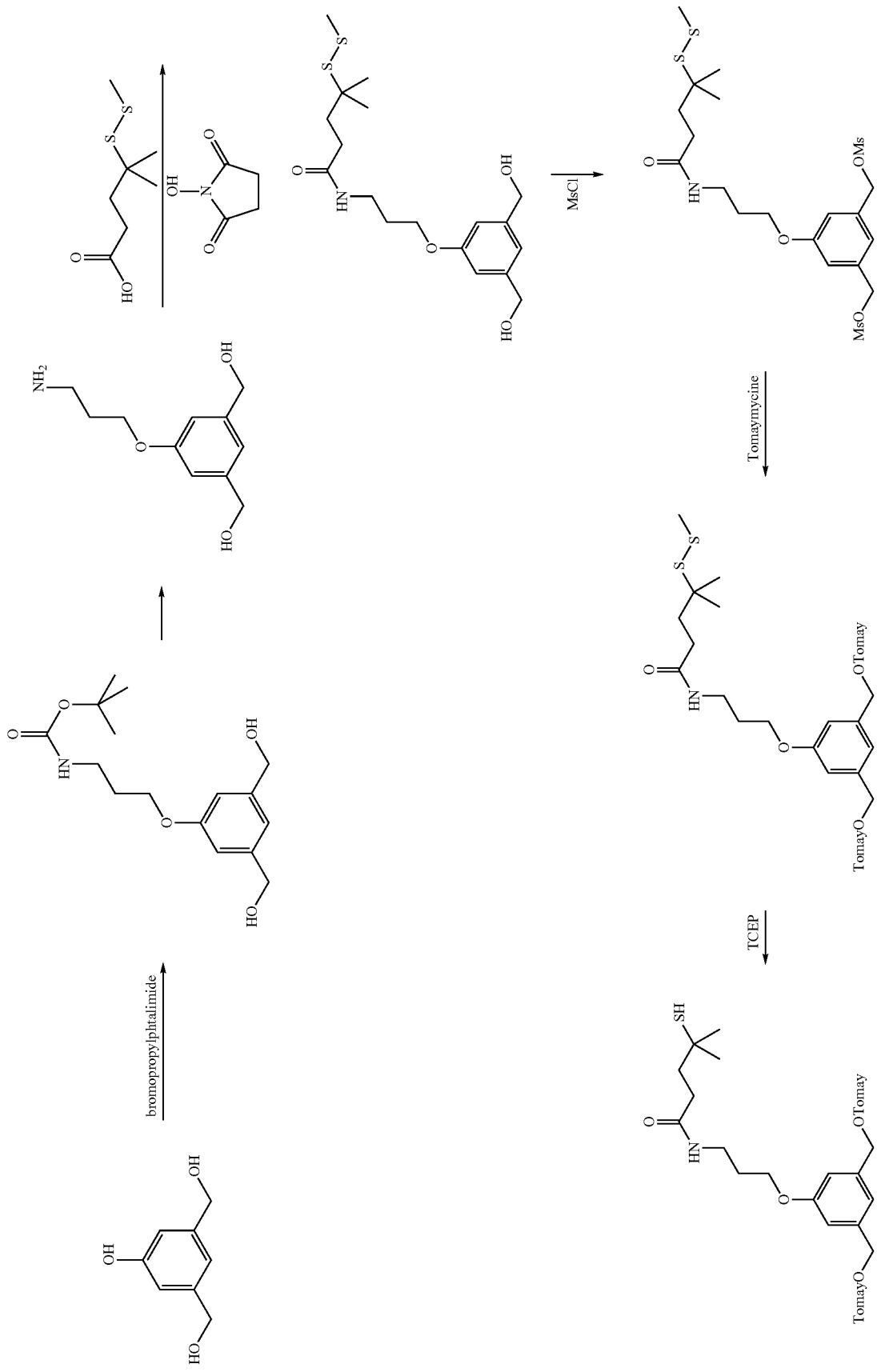

According to a second aspect, the compound of formula (I) may be obtained from the corresponding compound of formula (III'):

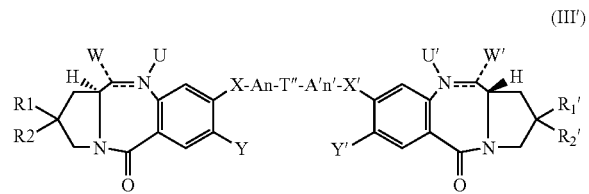

(III')

where Y, Y', X, A, A', X', n, n', W, W', U, U', ----, ▬▬, R1, R2, R1', R2' are defined as in formula (I) and T" is an optionally protected precursor group of T.

A precursor group of T refers to any group which may lead to T by chemical modification, or coupling. Preferably, T is obtained by coupling T' with the corresponding complementary portion, where T' and the complementary portion comprise functions which are reactive to each other, eg. T' comprising an amine function and the complementary portion comprising an acid function.

Generally, this reaction is carried out in the presence of: N-hydroxysuccinimide and HOBT.

The compound of formula (III') may be obtained from coupling the corresponding compound of formulae (IV), (IV') and (V'):

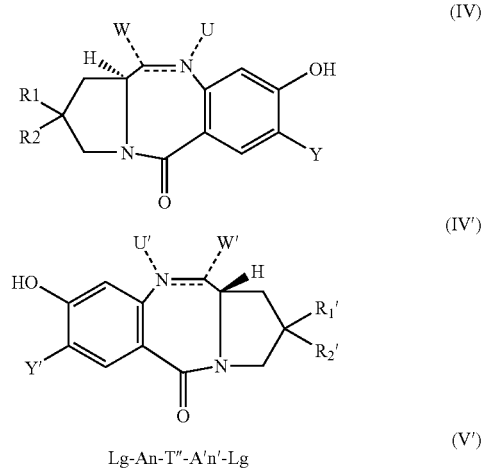

(IV)

(IV')

(V')

where Y, Y', A, A', n, n', W, W', U, U', ----, ▬▬, R1, R2, R1', R2' are defined as in formula (III'), T" is an optionally protected precursor group of T and Lg is a leaving group, such as halogen or OMs, OTs or PPh$_3^+$ (intermediate formed in a Mitsunobu reaction).

The compounds of formula (IV) and (IV') are generally known and are available by total synthesis (M. Mori et al, 42 *Tetrahedron*, 3793-3806, 1986) or produced by *Streptomyces* species, in particular, following French patent Fr. 1,516,743 procedure.

The compounds of formula (V') may be obtained from corresponding compounds of formula (VII):

HO-An-T"-A'n'-OH    (VII)

where A, A', n, n' are defined as in formula (I), T" is an optionally protected precursor group of T'.

This reaction is generally carried out in the presence of PPh$_3$ and CHal$_4$.

The compounds of formula (VII) may be commercially available or made by adaptation or application of known methods or according to the examples.

According to a third aspect, the process of preparation of the compound of formula (I) comprises the step of cyclizing the corresponding compound of formula (VIII):

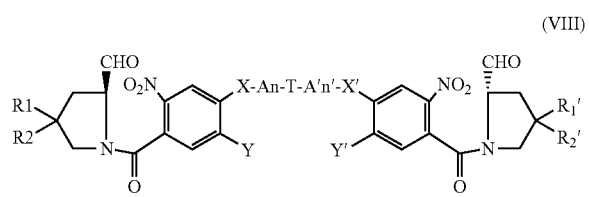

(VIII)

where Y, Y', X, A, A', X', n, n', R1, R2, R1', R2', T are defined as in formula (I). Generally, this reaction is carried out in the presence of a reagent such as sodium hydrosulfite (Na$_2$S$_2$O$_4$), in an appropriate solvent such as a mixture of THF and water, followed by addition of methanol and AcCl.

The compound of formula (VIII) may be obtained from the corresponding compound of formula (IX):

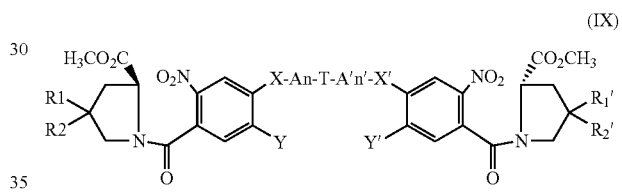

(IX)

where Y, Y', A, A', n, n', R1, R2, R1', R2', T are defined as in formula (I). Generally, this reaction is carried out in the presence of a reagent such as DIBAL-H in an appropriate solvent, such as toluene.

The compound of formula (IX) may be obtained from coupling the corresponding compounds of formula (X) and (XI):

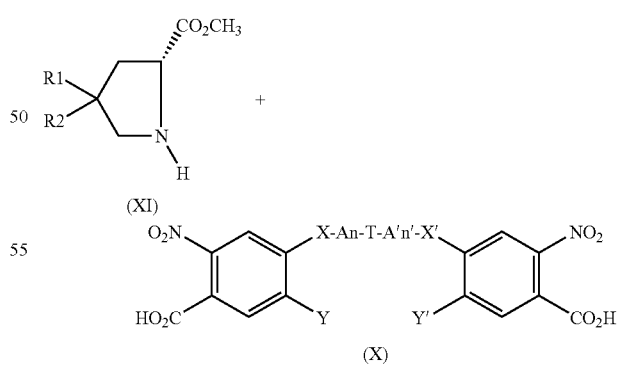

where Y, Y', A, A', n, n', R1, R2, R1', R2', T are defined as in formula (I).

Generally, this reaction is carried out by adding to (X) a reagent such as oxalyl chloride in an appropriate solvent, such as DMF, followed by adding (XI) in an appropriate solvent, such as THF.

A representative scheme is given below:

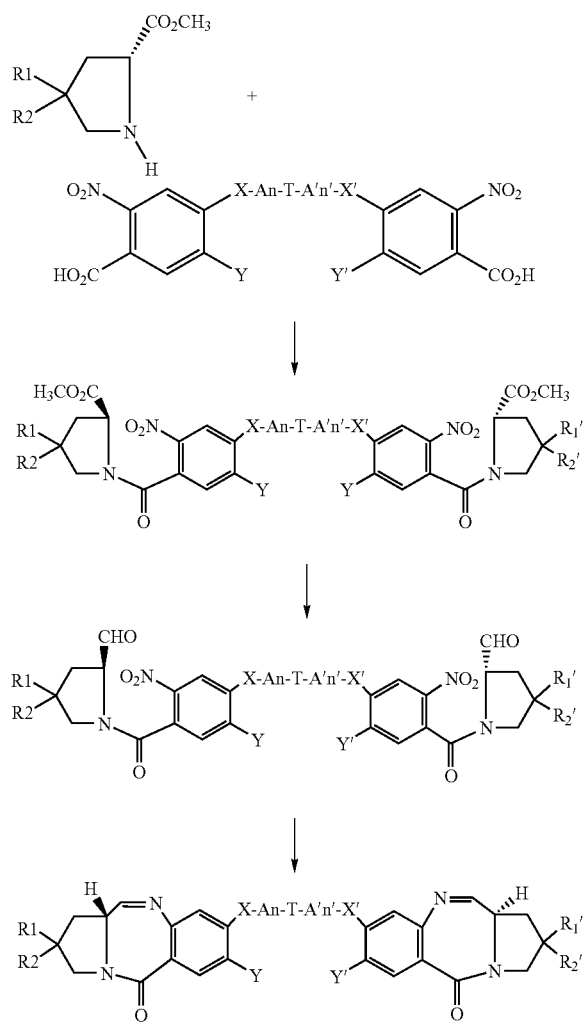

The above reactions can be carried out by the skilled person by applying or adapting the methods illustrated in the examples hereinafter.

Further, the process of the invention may also comprise the additional step of isolating the compound of formula (I) and (II). This can be done by the skilled person by any of the known conventional means, such as the recovery methods described above.

The starting products are commercially available or may be obtained by applying or adapting any known methods or those described in the examples.

The synthesis may also be carried out in one pot as a multicomponent reaction.

According to a further object, the present invention concerns a conjugate molecule comprising at least one tomaymycin derivative covalently bonded to a cell binding agent through a linking group. Said conjugate comprises one or more tomaymycin derivative according to the invention exhibiting a linker comprising a linking group, such as —S— or —S—S—. Said linking group covalently links the cell binding agent with the linker of the tomaymycin derivative. According to a preferred aspect, said tomaymycin derivative is of formula (I'):

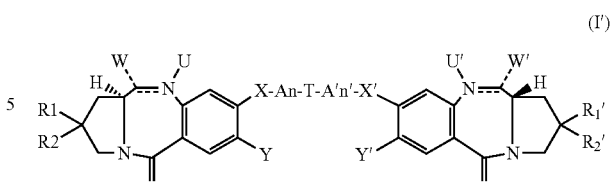

(I')

where

----. represents an optional single bond;
▬▬ represents either a single bond or a double bond
provided that when ▬▬ represents a single bond, U and U', the same or different, independently represent H, and W and W', the same or different, are independently to selected from the group consisting of OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO$_3$—, a sulfonamide such as —NR-SOOR, an amine such as —NRR', optionally cyclic amine such that N10 and C11 are a part of the cycle, a hydroxylamine derivative such as —NROR', an amide such as —NRCOR, an azido such as —N$_3$, a cyano, a halo, a trialkyl or triarylphosphonium, an aminoacid-derived group; Preferably W and W' are the same or different and are OH, OMe, OEt, NHCONH$_2$, SMe;
and when ▬▬ represents a double bond, U and U' are absent and W and W' represent H;
R1, R2, R1', R2' are the same or different and independently chosen from Halide or Alkyl optionally substituted by one or more Hal, CN, NRR', CF$_3$, OR, Aryl, Het, S(O)$_q$R, or R1 and R2 and R1' and R2' form together a double bond containing group =B and =B' respectively.

Preferably, R1 and R2 and R1' and R2' form together a double bond containing group =B and =B' respectively.

B and B' are the same or different and independently chosen from Alkenyl being optionally substituted by one or more Hal, CN, NRR', CF$_3$, OR, Aryl, Het, S(O)$_q$R or B and B' represent an oxygen atom.

Preferably, B=B'.
More preferably, B=B'=CH$_2$ or =CH—CH$_3$,
X, X' are the same or different and independently chosen from one or more —O—, —NR—, —(C=O)—, —S(O)$_q$—.
Preferably, X=X'.
More preferably, X=X'=O.
A, A' are the same or different and independently chosen from Alkyl or Alkenyl, each being optionally containing an oxygen, a nitrogen or a sulfur atom and optionally substituted by one or more Hal, CN, NRR', CF$_3$, OR, S(O)$_q$R, Aryl, Het, Alkyl, Alkenyl.
Preferably, A=A'.
More preferably, A=A'=linear unsubstituted alkyl.
Y, Y' are the same or different and independently chosen from H, OR;
Preferably, Y=Y'.
More preferably, Y=Y'=OAlkyl, more preferably OMethyl.
T is -Alkyl-, —NR—, —O—, —S(O)$_q$—, or a 4 to 10-membered aryl, cycloalkyl, heterocyclic or heteroaryl, each being optionally substituted by one or more Hal, CN, NRR', $CF_3$, R, OR, $S(O)_qR$, and substituted by one or more linker.

Preferably, T is a 4 to 10-membered aryl or heteroaryl, more preferably phenyl or pyridyl substituted by one or more linker(s).

Said linker comprises a linking group. Suitable linking groups are well known in the art and include thiol, sulfide, disulfide groups, thioether groups, acid labile groups, photolabile groups, peptidase labile groups and esterase labile groups. Preferred are disulfide groups and thioether groups.

When the linking group is a thiol-, sulfide or disulfide-containing group, the side chain carrying the thiol or disulfide group can be linear or branched, aromatic or heterocyclic. One of ordinary skill in the art can readily identify suitable side chains. Preferably, said linker is of formula:

-G-D-(Z)p-S—Z' where
G is a single or double bond, —O—, —S— or —NR—;
D is a single bond or -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F—;
where E and F are the same or different and are independently chosen from linear or branched —($OCH_2CH_2$)$_i$Alkyl($OCH_2CH_2$)$_j$—, -Alkyl($OCH_2CH_2$)$_i$-Alkyl-, —($OCH_2CH_2$)$_i$—, —($OCH_2CH_2$)$_i$Cycloalkyl($OCH_2CH_2$)$_j$—, —($OCH_2CH_2$)$_i$Heterocyclic($OCH_2CH_2$)$_j$—, —($OCH_2CH_2$)$_i$Aryl($OCH_2CH_2$)$_j$—, —($OCH_2CH_2$)$_i$Heteroaryl($OCH_2CH_2$)$_j$—, -Alkyl-($OCH_2CH_2$)$_i$Alkyl($OCH_2CH_2$)$_j$—, -Alkyl-($OCH_2CH_2$)$_i$—, -Alkyl-($OCH_2CH_2$)$_i$Cycloalkyl($OCH_2CH_2$)$_j$—, -Alkyl($OCH_2CH_2$)$_i$Heterocyclic($OCH_2CH_2$)$_j$—, -Alkyl-($OCH_2CH_2$)$_i$Aryl($OCH_2CH_2$)$_j$—, -Alkyl($OCH_2CH_2$)$_i$Heteroaryl($OCH_2CH_2$)$_j$—, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;
where i and j, identical or different are integers and independently chosen from 0, 1 to 2000;
Z is linear or branched -Alkyl-;
p is 0 or 1;
Z' represents H, a thiol protecting group such as COR, $R_{20}$ or $SR_{20}$, wherein $R_{20}$ represents H, methyl, Alkyl, optionally substituted Cycloalkyl, aryl, heteroaryl or heterocyclic, provided that when Z' is H, said compound is in equilibrium with the corresponding compound formed by intramolecular cyclisation resulting from addition of the thiol group —SH on the imine bond —NH= of one of the PBD moieties.
n, n', equal or different are 0 or 1, with m=m' and n=n'.
q is 0, 1 or 2.
R, R' are equal or different and independently chosen from H, Alkyl, Aryl, each being optionally substituted by Hal, CN, NRR', $CF_3$, R, OR, $S(O)_qR$, Aryl, Het;
or their pharmaceutically acceptable salts, hydrates, or hydrated salts, or the polymorphic crystalline structures of these compounds or their optical isomers, racemates, diastereomers or enantiomers,
said derivative being covalently bonded to a cell binding agent through said linker.

The present invention refers to following preferred embodiments or any combination of any of them:
G is a single bond or —O— or —NR—;
G is —O—;
D is a single bond or -E-, -E-NR—, -E-NR—CO—, -E-CO—, —CO-E-;
D is -E-, -E-NR—CO—, —CO-E-, -E-CO—;
D is -E-NR—CO—;
D is -E-NR—CO—;
E is linear or branched -Alkyl-, —($OCH_2CH_2$)$_i$— or -Alkyl-heterocyclic;
E is linear or branched -Alkyl-;
Z is —($CH_2$)$_2$—$C(CH_3)_2$—;
p is 0 or 1;
Z' is H or $SR_{20}$, wherein $R_{20}$ represents Alkyl, aryl, heterocyclic or heteroaryl;
Z' is H or $SR_{20}$, wherein $R_{20}$ represents Alkyl.

Specific examples of the thiol-, sulfide- or disulfide-containing linkers include
—($CR_{13}R_{14}$)$_t$($CR_{15}R_{16}$)$_u$($OCH_2CH_2$)$_y$SZ', —($CR_{13}R_{14}$)$_t$($CR_{17}$=$CR_{18}$)($CR_{15}R_{16}$)$_y$($OCH_2CH_2$)$_y$SZ', —($CR_{13}R_{14}$)$_t$($NR_{19}CO$)($CR_{15}R_{16}$)$_u$($OCH_2CH_2$)$_y$ SZ', —($CR_{13}R_{14}$)$_t$(OCO)($R_{15}R_{16}$)$_u$($OCH_2CH_2$)$_y$SZ', —($CR_{13}R_{14}$)$_t$(CO)($CR_{15}R_{16}$)$_u$($OCH_2CH_2$)$_y$SZ', —($CR_{13}R_{14}$)$_t$($CONR_{19}$)($CR_{15}R_{16}$)$_u$($OCH_2CH_2$)$_y$SZ', —($CR_{13}R_{14}$)$_t$-phenyl-CO($CR_{15}R_{16}$)$_u$SZ', —($CR_{13}R_{14}$)$_t$-furyl-CO($CR_{15}R_{16}$)$_u$SZ', —($CR_{13}R_{14}$)$_t$-oxazolyl-CO($CR_{15}R_{16}$)$_u$SZ', —($CR_{13}R_{14}$)$_t$-thiazolyl-CO($CR_{15}R_{16}$)$_u$SZ', —($CR_{13}R_{14}$)$_t$-thienyl-CO($CR_{15}R_{16}$)$_u$SZ', —($CR_{13}R_{14}$)$_t$-imidazolyl-CO($CR_{15}R_{16}$)$_u$SZ', —($CR_{13}R_{14}$)$_t$-morpholino-CO($CR_{15}R_{16}$)$_u$SZ', —($CR_{13}R_{14}$)$_t$piperazino-CO($CR_{15}R_{16}$)$_u$SZ', —($CR_{13}R_{14}$)$_t$—N-methylpiperazino-CO($CR_{15}R_{16}$)$_u$SZ',
—($CR_{13}R_{14}$)$_t$-phenyl-QSZ', —($CR_{13}R_{14}$)$_t$-furyl-QSZ', —($CR_{13}R_{14}$)$_t$-oxazolyl-QSZ', —($CR_{13}R_{14}$)$_t$-thiazolyl-QSZ', —($CR_{13}R_{14}$)$_t$-thienyl-QSZ', —($CR_{13}R_{14}$)$_t$-imidazolyl-QSZ', —($CR_{13}R_{14}$)$_t$-morpholino-QSZ', —($CR_{13}R_{14}$)$_t$-piperazino-QSZ', —($CR_{13}R_{14}$)$_t$—N-methylpiperazino-QSZ', or
—O($CR_{13}R_{14}$)$_t$($CR_{15}R_{16}$)$_u$($OCH_2CH_2$)$_y$SZ', —O($CR_{13}R_{14}$)$_t$($NR_{19}CO$)($CR_{15}R_{16}$)$_u$($OCH_2CH_2$)$_y$SZ', —O($CR_{13}R_{14}$)$_t$($CR_{17}$=$CR_{18}$)($CR_{15}R_{16}$)$_t$ ($OCH_2CH_2$)$_y$SZ', —O-phenyl-QSZ', —O-furyl-QSZ', —O-oxazolyl-Q SZ', —O-thiazolyl-QSZ', —O-thienyl-QSZ', —O-imidazolyl-QSZ', —O-morpholino-QSZ', —O-piperazino-QSZ', —O—N-methylpiperazino-QSZ',
—OCO($CR_{13}R_{14}$)$_t$($NR_{19}CO$)$_v$($CR_{15}R_{16}$)$_u$ ($OCH_2CH_2$)$_y$ SZ', —OCO—($CR_{13}R_{14}$)$_t$ ($CR_{17}$=$CR_{18}$)($CR_{15}R_{16}$)$_u$ ($OCH_2CH_2$)$_y$SZ', —OCONR$_{12}$($CR_{13}R_{14}$)$_t$($CR_{15}R_{16}$)$_u$ ($OCH_2CH_2$)$_y$SZ', —OCO-phenyl-QSZ', —OCO-furyl-QSZ', —OCO-oxazolyl-QSZ', —OCO-thiazolyl-QSZ', —OCO-thienyl-QSZ', —OCO-imidazolyl-QSZ', —OCO-morpholino-QSZ', —OCO-piperazino-QSZ', —OCO—N-methylpiperazino-QSZ', or
—CO($CR_{13}R_{14}$)$_t$($CR_{15}R_{16}$)$_u$ ($OCH_2CH_2$)$_y$ SZ', —CO—($CR_{13}R_{14}$)$_t$ ($CR_{17}$=$CR_{18}$)($CR_{15}R_{16}$)$_u$($OCH_2CH_2$)$_y$SZ', —CONR$_{12}$($CR_{13}R_{14}$)$_t$($CR_{15}R_{16}$)$_u$ ($OCH_2CH_2$)$_y$SZ', —CO-phenyl-QSZ', —CO-furyl-QSZ', —CO-oxazolyl-QSZ', —CO-thiazolyl-QSZ', —CO-thienyl-QSZ', —CO-imidazolyl-QSZ', —CO-morpholino-QSZ', —CO-piperazino-QSZ', —CO-piperidino-QSZ', —CO—N-methylpiperazino-QSZ',
—NR$_{19}$($CR_{13}R_{14}$)$_t$($CR_{15}R_{16}$)$_u$($OCH_2CH_2$)$_y$SZ', —NR$_{19}$CO($CR_{13}R_{14}$)$_t$($CR_{15}R_{16}$)$_u$($OCH_2CH_2$)$_y$SZ', —NR$_{19}$($CR_{13}R_{14}$)$_t$ ($CR_{17}$=$CR_{18}$)($CR_{15}R_{16}$)$_t$ ($OCH_2CH_2$)$_y$SZ', —NR$_{19}$CO($CR_{13}R_{14}$)$_t$ ($CR_{17}$=$CR_{18}$)($CR_{15}R_{16}$)$_t$ ($OCH_2CH_2$)$_y$SZ', —NR$_{19}$CONR$_{12}$($CR_{13}R_{14}$)$_t$($CR_{15}R_{16}$)$_u$ ($OCH_2CH_2$)$_y$SZ', —NR$_{19}$CONR$_{12}$($CR_{13}R_{14}$)$_t$ ($CR_{17}$=$CR_{18}$)($CR_{15}R_{16}$)$_t$ ($OCH_2CH_2$)$_y$SZ', —NR$_{19}$CO-phenyl-QSZ', —NR$_{19}$CO-furyl-QSZ', —NR$_{19}$CO-oxazolyl-QSZ', —NR$_{19}$CO-thiazolyl-QSZ', —NR$_{19}$CO-thienyl-QSZ', —NR$_{19}$CO-imidazolyl-QSZ', —NR$_{19}$CO-morpholino-QSZ', —NR$_{19}$CO-piperazino-QSZ', —NR$_{19}$CO-piperidino-QSZ', —NR$_{19}$CO—N-methylpiperazino-QSZ', —NR$_{19}$-phenyl-QSZ', —NR$_{19}$-furyl-QSZ', —NR$_{19}$-oxazolyl-QSZ', —NR$_{19}$-thiazolyl-QSZ', —NR$_{19}$-thienyl-QSZ', —NR$_{19}$-imidazolyl-QSZ', —NR$_{19}$-morpholino-QSZ', —NR$_{19}$-piperazino-QSZ', —NR$_{19}$-piperidino-QSZ', —NR$_{19}$—N-methylpiperazino-QSZ', —NR$_{19}$CO—NR$_{12}$-phenyl-QSZ', —NR$_{19}$CO—NR$_{12}$-oxazolyl-QSZ', —NR$_{19}$CO—NR$_{12}$-thiazolyl-QSZ', —NR$_{19}$CO—NR$_{12}$-thienyl-QSZ', —NR$_{19}$CO—NR$_{12}$-piperidino-QSZ',
—S(O)$_q$(CR$_{13}$R$_{14}$)$_t$(CR$_{15}$R$_{16}$)$_u$(OCH$_2$CH$_2$)$_y$SZ', —S(O)$_q$(CR$_{13}$R$_{14}$)$_t$(CR$_{17}$=CR$_{18}$)(CR$_{15}$R$_{16}$)$_t$(OCH$_2$CH$_2$)$_y$SZ', —SCONR$_{12}$(CR$_{13}$R$_{14}$)$_t$(CR$_{15}$R$_{16}$)$_u$ (OCH$_2$CH$_2$)$_y$SZ', —SCO-morpholino-QSZ', —SCO-piperazino-QSZ', —SCO-piperidino-QSZ', and —SCO—N-methylpiperazino-QSZ', wherein:

Z' is H, a thiol protecting group such as COR, R$_{20}$' or SR$_{20}$' wherein R$_{20}$' represents alkyl, aryl, heterocyclic, or heteroaryl;

wherein Q is a direct link or a linear alkyl or branched alkyl having from 1-10 carbon atoms or a polyethylene glycol spacer with 2 to 20 repeating ethylene oxy units;

R$_{19}$ and R$_{12}$ are the same or different and are linear alkyl, branched alkyl or cyclic alkyl having from 1 to 10 carbon atoms, or simple or substituted aryl or heterocyclic, and R$_{12}$ can in addition be H, R$_{13}$, R$_{14}$, R$_{15}$ and R$_{16}$ are the same or different and are H or a linear or branched alkyl having from 1 to 4 carbon atoms, R$_{17}$, and R$_{18}$ are H or alkyl, u is an integer from 1 to 10 and can also be 0, t is an integer from 1 to 10 and can also be 0, y is an integer from 1 to 20 and can also be 0.

According to this object, representative compounds of formula (I') are:

8,8'-{5-[3-(4-methyl-4-methyldisulfanyl-pentanoylamino) propyloxy]-1,3-benzenediylbis(methylenoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methylenoxy)]-bis[(S)-2-methylene-7-methoxy-1,2,3,11a-tetrahydro-5H-pyrrolo[2,1-c][1,4]benzodiazepin-5-one]

8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one]

8,8'-[5-(N-4-methyldithio-4,4-dimethylbutanoyl)-amino-1,3-benzenediylbis(methylenoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-mercapto-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-methyldithio-2,2-dimethylethyl) amino-1,3-benzenediyl(methylenoxy)]-bis[7-methoxy-2-methylene-1,2,3,11a-tetrahydro-5H-pyrrolo[2,1-c][1,4] benzodiazepin-5-one]

8,8'-[(4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(4-(4-methyl-4-methyldisulfanyl)-pentanamido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

as well as the corresponding mercapto derivatives, or their pharmaceutically acceptable salts, hydrates, or hydrated salts, or the polymorphic crystalline structures of these compounds or their optical isomers, racemates, diastereomers or enantiomers.

Cell binding agents may be of any kind and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance. More specific examples of cell binding agents that can be used include: monoclonal antibodies; chimeric antibodies; humanized antibodies; fully human antibodies; single chain antibodies; fragments of antibodies such as Fab, Fab', F(ab')$_2$ and F$_v$ {Parham, 131 *J. Immunol.* 2895-2902 (1983); Spring et al, 113 *J. Immunol.* 470-478 (1974); Nisonoff et al, 89 *Arch. Biochem. Biophys.* 230-244 (1960)}; interferons; peptides; lymphokines such as IL-2, IL-3, IL-4, IL-6; hormones such as insulin, TRH (thyrotropin releasing hormones), MSH (melanocyte-stimulating hormone), steroid hormones, such as androgens and estrogens; growth factors and colony-stimulating factors such as EGF, TGFα, insulin like growth factor (IGF-I, IGF-II) G-CSF, M-CSF and GM-CSF {Burgess, 5 *Immunology Today* 155-158 (1984)}; vitamins, such as folate and transferrin {O'Keefe et al, 260 *J. Biol. Chem.* 932-937 (1985)}.

The expression "cell binding agent" included herein also includes modified cell binding agents, wherein said cell binding agent is modified by a modifying agent to improve the reactivity of said cell binding agent towards the linking group of the linker of the tomaymycin derivative. Said modifying agents include N-sulfosuccinimidyl-4-(5-nitro-2-pyridyldithio)butanoate (SSNPB), Succinimidyl 4-[N-maleimidomethyl)cyclohexane-1-carboxylate (SMCC), 4-(2-pyridyldithio)butanoic acid N-hydroxysuccinimide ester (SPDB), and so on as discussed below.

Monoclonal antibody technology permits the production of extremely selective cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of the appropriate cell binding agent is a matter of choice that depends upon the particular cell population that is to be targeted, but in general monoclonal antibodies are preferred if an appropriate one is available.

For example, the monoclonal antibody MY9 is a murine IgG$_1$ antibody that binds specifically to the CD33 Antigen {J. D. Griffin et al 8 *Leukemia Res.,* 521 (1984)} and can be used if the target cells express CD33 as in the disease of acute myelogenous leukemia (AML). Similarly, the monoclonal antibody anti-B4 is a murine IgG$_1$, that binds to the CD19 antigen on B cells {Nadler et al, 131 *J. Immunol.* 244-250 (1983)} and can be used if the target cells are B cells or diseased cells that express this antigen such as in non-Hodgkin's lymphoma or chronic lymphoblastic leukemia. As stated above, the MY9 and anti-B4 antibodies may be murine, chimeric, humanized or fully human.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

The conjugate molecules of the invention may be formed using any techniques. The tomaymycin derivatives of the invention may be linked to an antibody or other cell binding agent via an acid labile linker, or by a photolabile linker. The derivatives can be condensed with a peptide having a suitable sequence and subsequently linked to a cell binding agent to produce a peptidase labile linker. The conjugates can be prepared to contain a primary hydroxyl group, which can be succinylated and linked to a cell binding agent to produce a conjugate that can be cleaved by intracellular esterases to liberate free derivative. Preferably, the derivatives are synthesized to contain a free or protected thiol group, and then one or more disulfide or thiol-containing derivatives are each covalently linked to the cell binding agent via a disulfide bond or a thioether link.

Numerous methods of conjugation are taught in U.S. Pat. Nos. 5,416,064 and 5,475,092. The tomaymycin derivatives can be modified to yield a free amino group and then linked to an antibody or other cell binding agent via an acid labile linker or a photolabile linker. The tomaymycin derivatives with a free amino or carboxyl group can be condensed with a peptide and subsequently linked to a cell binding agent to produce a peptidase labile linker. The tomaymycin derivatives with a free hydroxyl group on the linker can be succinylated and linked to a cell binding agent to produce a conjugate that can be cleaved by intracellular esterases to liberate free drug. Most preferably, the tomaymycin derivatives are treated to create a free or protected thiol group, and then the disulfide- or thiol-containing tomaymycin dimers are linked to the cell binding agent via disulfide bonds.

Representative conjugates of the invention are antibody-tomaymycin derivative, antibody fragment-tomaymycin derivative epidermal growth factor (EGF)-tomaymycin derivative, melanocyte stimulating hormone (MSH)-tomaymycin derivative, thyroid stimulating hormone (TSH)-tomaymycin derivative, estrogen-tomaymycin derivative, estrogen analogue-tomaymycin derivative, androgen-tomaymycin derivative, androgen analogue-tomaymycin derivative, and folate-tomaymycin derivative.

Tomaymycin derivative conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate, N-succinimidyl 4-(2-pyridyldithio)pentanoate (SPP), 4-succinimidyl-oxycarbonyl-α-methyl-α-(2-pyridyldithio)-toluene (SMPT), N-succinimidyl-3-(2-pyridyldithio)butyrate (SDPB), succinimidyl pyridyl-dithiopropionate (SPDP), 4-(2-pyridyldithio)butanoic acid N-hydroxsuccinimide ester (SPDB), succinimidyl 4-[N-maleimidomethyl]cyclohexane-1-carboxylate (SMCC), N-sulfosuccinimidyl-3-(2-(5-nitro-pyridyldithio) butyrate (SSNPB), 2-iminothiolane, or S-acetylsuccinic anhydride by known methods. See, Carlsson et al, 173 *Biochem. J.* 723-737 (1978); Blattler et al, 24 *Biochem.* 1517-1524 (1985); Lambert et al, 22 *Biochem.* 3913-3920 (1983); Klotz et al, 96 *Arch. Biochem. Biophys.* 605 (1962); and Liu et al, 18 *Biochem.* 690 (1979), Blakey and Thorpe, 1 *Antibody, Immunoconjugates & Radio-pharmaceuticals,* 1-16 (1988), Worrell et al 1 *Anti-Cancer Drug Design* 179-184 (1986). The free or protected thiol-containing cell binding agent thus derived is then reacted with a disulfide- or thiol-containing tomaymycin derivative to produce conjugates. The conjugates can be purified by HPLC or by gel filtration.

Preferably, monoclonal antibody- or cell binding agent-tomaymycin derivative conjugates are those that are joined via a disulfide bond, as discussed above, that are capable of delivering tomaymycin derivatives. Such cell binding conjugates are prepared by known methods such as by modifying monoclonal antibodies with succinimidyl pyridyl-dithiopropionate (SPDP) (Carlsson et al, 173 *Biochem. J.* 723-737 (1978)). The resulting thiopyridyl group is then displaced by treatment with thiol-containing tomaymycin derivatives to produce disulfide linked conjugates. Alternatively, in the case of the aryldithio-tomaymycin derivatives, the formation of the cell binding conjugate is effected by direct displacement of the aryl-thiol of the tomaymycin derivative by sulfhydryl groups previously introduced into antibody molecules. Conjugates containing 1 to 10 tomaymycin derivative drugs linked via a disulfide bridge are readily prepared by either method.

More specifically, a solution of the dithio-nitropyridyl modified antibody at a concentration of 2.5 mg/ml in 0.05 M potassium phosphate buffer, at pH 7.5 containing 2 mM EDTA is treated with the thiol-containing tomaymycin derivative (1.3 molar eq./dithiopyridyl group). The release of thio-nitropyridine from the modified antibody is monitored spectrophotometrically at 325 nm and is complete in about 16 hours. The antibody-tomaymycin derivative conjugate is purified and freed of unreacted drug and other low molecular weight material by gel filtration through a column of Sephadex G-25 or Sephacryl S300. The number of tomaymycin derivative moieties bound per antibody molecule can be determined by measuring the ratio of the absorbance at 230 nm and 275 nm. An average of 1-10 tomaymycin derivative molecules/antibody molecule can be linked via disulfide bonds by this method.

The effect of conjugation on binding affinity towards the antigen-expressing cells can be determined using the methods previously described by Liu et al., 93 Proc. Natl. Acad. Sci. 8618-8623 (1996). Cytotoxicity of the tomaymycin derivatives and their antibody conjugates to cell lines can be measured by back-extrapolation of cell proliferation curves as described in Goldmacher et al, 135 *J. Immunol.* 3648-3651 (1985). Cytotoxicity of these compounds to adherent cell lines can be determined by clonogenic assays as described in Goldmacher et al, 102 *J. Cell Biol.* 1312-1319 (1986).

Representative conjugates of the invention are conjugates of tomaymycin derivatives with antibodies, antibody fragments, epidermal growth factor (EGF), melanocyte stimulating hormone (MSH), thyroid stimulating hormone (TSH), estrogen, estrogen analogs, androgen, and androgen analogs.

Representative examples of the preparation of various conjugates of derivatives and cell binding agents are described below.

Disulfide linkers: For example, the monoclonal antibody MY9 is a murine $IgG_1$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine $IgG_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

The antibody or other cell binding agent is modified with N-succinimidyl-3-pyridyldithio propionate as previously described {J. Carlsson, H. Drevin & R. Axen, *Biochem. J.,* 173:723 (1978)} to introduce, on the average, 4 pyridyldithio groups per antibody molecule. The modified antibody is reacted with the thiol-containing derivative to produce a disulfide-linked conjugate.

Alternatively, the conjugates may be prepared by application and/or adaptation of the method disclosed in WO2004/103272, whose teaching is included herein by reference.

Thioether linkers: Thiol-containing derivatives of the present invention can be linked to antibodies and other cell binding agents via a thioether link as previously described (U.S. Pat. No. 5,208,020). The antibody or other cell binding agent can be modified with the commercially available compound such as N-succinimidyl 4-(maleimidomethyl)cyclohexanecarboxylate (SMCC), N-succinimidyl-4-(N-maleimidomethyl)-cyclohexane-1-carboxy-(6-amido-caproate), which is a "long chain" analog of SMCC (LC-SMCC), These crosslinking reagents form non-cleavable linkers derived from maleimido-based moieties.

Crosslinking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromo-acetamido)propionate (SBAP). These crosslinking reagents form non-cleavable linkers derived from haloacetyl-based moieties.

Acid-Labile Linkers: Amino group-containing derivatives of the present invention can be linked to antibodies and other cell binding agents via an acid labile linker as previously described {W. A. Blattler et al, *Biochemistry* 24, 1517-1524 (1985); U.S. Pat. Nos. 4,542,225, 4,569,789, 4,618,492, 4,764,368}.

Similarly, an hydrazido group-containing derivative of the present invention can be linked to the carbohydrate portion of antibodies and other cell binding agents via an acid labile hydrazone linker {for examples of hydrazone linkers see B. C. Laguzza et al, *J. Med. Chem.,* 32, 548-555 (1989); R. S. Greenfield et al, *Cancer Res.,* 50, 6600-6607 (1990)}.

Photo-Labile Linkers: Amine group containing derivatives of the present invention may be linked to antibodies and other cell binding agents via a photolabile linker as previously described {P. Senter et al, *Photochemistry and Photobiology,* 42, 231-237 (1985); U.S. Pat. No. 4,625,014}.

Peptidase-Labile Linkers: Amine group containing derivatives of the present invention may also be linked to cell binding agents via peptide spacers. It has been previously shown that short peptide spacers between drugs and macromolecular protein carriers are stable in serum but are readily hydrolyzed by intracellular peptidases {A. Trouet et al, *Proc. Natl. Acad. Sci.,* 79, 626-629 (1982)}. The amino group containing derivatives may be condensed with peptides using condensing agents such as 1-ethyl-3-(3-dimethylamino-propyl)carbodiimide-HCl (EDC-HCl) to give a peptide derivative that can be linked to cell binding agents.

Esterase-Labile Linkers: Derivatives of the present invention bearing a hydroxy alkyl group may be succinylated with succinic anhydride and then linked to a cell binding agent to produce a conjugate that can be cleaved by intracellular esterases to liberate free drug. {For examples see E. Aboud-Pirak et al, *Biochem Pharmacol.,* 38, 641-648 (1989)}.

The conjugates made by the above methods can be purified by standard chromatography techniques such as size-exclusion, adsorption chromatography including, but not limited to, ion exchange, hydrophobic interaction chromatography, affinity chromatography, chromatography on ceramic hydroxyapatite or on Porapak, or by HPLC. Purification by dialysis or diafiltration may also be used.

Preferably, conjugates between monoclonal antibodies or cell binding agents and derivatives of the present invention are those that are joined via a disulfide bond, as discussed above. Such cell binding conjugates are prepared by known methods such as modifying monoclonal antibodies with succinimidyl pyridyl-dithiopropionate (SPDP) {Carlsson et al, 173 Biochem. J. 723-737 (1978)}. The resulting thiopyridyl group is then displaced by treatment with thiol containing derivative to produce disulfide linked conjugates. Conjugates containing 1 to 10 derivatives linked via a disulfide bridge are readily prepared by this method. Conjugation by this method is fully described in U.S. Pat. No. 5,585,499, which is incorporated by reference.

According to a preferred aspect, the cell binding agent is an antibody, in particular a monoclonal antibody.

According to another preferred aspect, the cell binding agent is an antigen specific antibody fragment, such as sFV, Fab, Fab', or $F(ab')_2$.

According to a further object, the present invention also concerns pharmaceutical compositions comprising a conjugate molecule of the invention or a compound of formula (I) as defined above together with a pharmaceutically acceptable carrier.

According to a further object, the present invention also concerns a method of killing or inhibiting growth of cells, preferably selected cell populations comprising contacting target cells or tissue containing target cells with an effective amount of the pharmaceutical composition according to the invention.

The selected cell population are those cancerous and/or proliferative cells.

According to a further object, the present invention also concerns a method for treatment, preferably selective treatment, of cancer comprising administering an effective amount of the pharmaceutical composition according to the invention to a patient in need thereof.

According to the present invention, "selective treatment of cancer" refers to killing cancerous and/or proliferative cells substantially without killing normal and/or non-proliferative cells.

According to a further object, the present invention also concerns the use of a conjugate molecule of the invention or a compound of formula (I) as defined above for the preparation of a medicament for treating cancer.

The method for inhibiting the growth of selected cell populations can be practiced in vitro, in vivo, or ex vivo.

Examples of in vitro uses include treatments of cell cultures in order to kill all cells except for desired variants that do not express the target antigen; or to kill variants that express undesired antigen.

The conditions of non-clinical in vitro use are readily determined by the skilled artisan.

Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD).

Clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels or as a lyophilized solid that can be redissolved in sterile water for injection. Examples of suitable protocols of conjugate administration are as follows. Conjugates are given weekly for 6 weeks as an i.v. bolus. Bolus doses are given in 50 to 400 ml of normal saline to which human serum albumin (e.g. 0.5 to 1 mL of a concentrated solution of human serum albumin, 100 mg/mL) can be added. Dosages will be about 50 µg to 10 mg/kg of body weight per week, i.v. (range of 10 µg to 100 mg/kg per injection). Six weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; bacterial infection; and parasite infections, such as giardiasis, amoebiasis, schistosomiasis, and others as determined by one skilled in the art.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I) or conjugate, which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in preventing or treating the herein referred pathological condition.

According to the invention, the term "patient", or "patient in need thereof", is intended for an animal or a human being affected or likely to be affected with the herein referred pathological condition. Preferably, the patient is human.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well known in the pharmaceutical art, for example, as described in Remington: The Science and Practice of Pharmacy, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples.

EXPERIMENTAL PART

Method A1: High Pressure Liquid Chromatography-Mass Spectrometry (LCMS)

A Micronmass MassLynx software is used and the analysis is performed on a Agilent 1100 series HPLC with a THERMO Hypersil Gold C18 3 µm column (50×3 mm) using gradient elution with a mixture of (A) acetonitrile and (B) water/0.1% formic acid (gradient: 5% A:95% B up to 95% A:5% B over 5 minutes, 95% A:5% B for 0.5 minutes, 95% A:5% B down to 5% A:95% B over 1 minute, 5% A:95% B for 0.5 minutes) with a 0.8 mL/minute flow rate; Waters-Micromass Platform I, Platform II or ZQ spectrometer with Electrospray (positive and negative ionisation); in line Diode Array (190-490 nm); auxiliary detector Sedere (France) Model SEDEX 65 Evaporative Light Scattering (ELS) detector.

Method A2: High Pressure Liquid Chromatography-Mass Spectrometry (LCMS)

A Micromass MassLynx software is used and the analysis is performed on a Waters Alliance HPLC with a WATERS XBridge C18 3.5 µm column (100×3 mm) using gradient elution with a mixture of (A) methanol and (B) water/0.1% formic acid (gradient: 5% A:95% B up to 95% A:5% B over 10 minutes, 95% A:5% B down to 5% A:95% B over 1 minute, 5% A:95% B for 2 minutes) with a 1.1 mL/minute flow rate; Waters-Micromass Platform II spectrometer with Electrospray (positive and negative ionisation); in line Diode Array (190-500 nm); auxiliary detector Sedere (France) Model SEDEX 85 Evaporative Light Scattering (ELS) detector.

Method A3: High Pressure Liquid Chromatography-Mass Spectrometry (LCMS)

A Micromass MassLynx software is used and the analysis is performed on a Agilent 1100 series HPLC with a XBridge C18 2.5 µm column (50×3 mm) using gradient elution with a mixture of (A) acetonitrile and (B) water/0.1% formic acid (gradient: 5% A:95% B up to 100% A over 5 minutes, 100% A for 0.5 minutes, 100% A down to 5% A:95% B over 1 minute, 5% A:95% B for 0.5 minutes) with a 1.1 mL/minute flow rate; Waters-Micromass ZQ spectrometer with Electrospray; in line Diode Array (210-254 nm)

Method B: High Pressure Liquid Chromatography (HPLC) Purification

HPLC purification was performed on a Macherey Nagel Nucleodur C18 Gravity 5 µM column (21×100 mm, catalogue number 762101), eluting with a mixture of (A) acetonitrile and (B) water (gradient: 5% A:95% B for 5 minutes, 5% A:95% B up to 100% A over 20 minutes, 100% A for 8 minutes, 100% A to 5% A:95% B over 1 minute, 5% A:95% B for 11 minutes) with a 15 mL/minute flow rate (Method B1) or 20 mL/minute (Method B2).

Method C: Electron Ionisation (EI) Mass Spectra

EI mass spectra were recorded using a Finnigan SSQ 7000 mass spectrometer (EI mode: 70 eV, source temperature=150° C., direct introduction)

Method D: Chemical Ionisation (CI) Mass Spectra

CI mass spectra were recorded using a Finnigan SSQ 7000 mass spectrometer (ammonia)

Method E: $^1$H Nuclear Magnetic Resonance (NMR) Spectra $^1$H NMR spectra were recorded on either a Bruker Avance Drx-500, A Bruker Avance Drx-400 or A Bruker Avance DRX-300 spectrometer.

Method F: High Pressure Liquid Chromatography (HPLC) Purification

HPLC purification was performed on a Macherey Nagel VP 250/40 mm NUCLEODUR GRAVITY 100-10 C18 (catalog number 762250), eluting with a mixture of (A) acetonitrile and (B) water/HCOONH$_4$ 0.01M/NH$_4$OH pH9-10 (gradient: 10% A:90% B for 3 minutes, 10% A:90% B up to 95% A:5% B over 37 minutes, 95% A:5% B for 8 minutes, 95% A:5% B to 10% A:90% B over 1 minute, 10% A:90% B for 1 minute ) with a 70 mL/minute flow rate.

Method G1: High Pressure Liquid Chromatography-Mass Spectrometry (LCMS)

A Micromass MassLynx software is used and the analysis is performed on a Acquity HPLC with a Acquity HPLC BEH C18 1.7 µm column (2.1×100 mm) using gradient elution with a mixture of (A) acetonitrile and (B) water/0.1% formic acid (gradient: 5% A:95% B up to 95% A:5% B over 4.7 minutes, 95% A:5% B down to 5% A:95% B over 0.5 minute, 5% A:95% B for 0.8 minutes) with a 1.1 mL/minute flow rate; Quattro Premier spectrometer with Electrospray; in line Diode Array (210-400 nm).

Method G2: High Pressure Liquid Chromatography-Mass Spectrometry (LCMS)

A Micromass MassLynx software is used and the analysis is performed on a Acquity HPLC with a Acquity UPLC BEH C18 1.7 µm column (2.1×100 mm) using gradient elution with a mixture of (A) acetonitrile and (B) water/0.1% formic acid (gradient: 5% A:95% B up to 95% A:5% B over 10 minutes, 95% A:5% B down to 5% A:95% B over 1 minutes, 5% A:95% B for 2 minutes) with a 0.6 mL/minute flow rate; Quattro Premier spectrometer with Electrospray; in line Diode Array (210-400 nm).

Method H: High Pressure Liquid Chromatography (HPLC) Purification Method

HPLC purification was performed on a Varian HPLC using a Kromasil 16 µm C18 column (250×21.2 mm, PN A0490-250x212, Lot. No. DT0259, SN 9772196), eluting with a mixture of (A) water and (B) acetonitrile with a 20 mL/minute flow rate. The collection size was 80 seconds. Mass spectra of the compounds were obtained on a Bruker Esquire 3000 instrument. NMR spectra were recorded on a Bruker Avance spectrometer operating at 400 MHz.

Gradients for Eluting the Column:

1. Purification of 8,8'-[5-(N-4-methyldithio-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one]

55% A:45% B for 8 minutes, 55% A:45% B to 50% A:50% B over 14 minutes, 50% A:50% B to 10% A:90% B over 4 minutes, 10% A:90% B for 5 minutes, 10% A:90% B to 55% A:45% B over 1 minute, 55% A:45% B for 3 minutes.

2. Purification of 8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one]

60% A:40% B for 4 minutes, 60% A:40% B to 55% A:45% B over 5 minutes, 55% A:45% B for 4 minutes, 55% A:45% B to 50% A:50% B over 13 minutes, 50% A:50% B to 10% A:90% B over 10 seconds, 10% A:90% B for 5 minutes, 10% A:90% B to 60% A:40% B over 10 seconds, 60% A:40% B for 3 minutes.

3. Purification of 8,8'-[5-(N-methyl-N-(2-methyldithio-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

60% A:40% B for 8 minutes, 60% A:40% B to 45% A:55% B over 16 minutes, 45% A:55% B to 10% A:90% B over 2 minutes, 10% A:90% B for 5 minutes, 10% A:90% B to 60% A:40% B over 1 minute, 60% A:40% B for 3 minutes.

4. Purification of 8,8'-[5-(N-methyl-N-(2-mercapto-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

65% A:35% B to 60% A:40% B over 8 minutes, 60% A:40% B to 50% A:50% B over 19 minutes, 50% A:50% B to 10% A:90% B over 10 seconds, 10% A:90% B for 5 minutes, 10% A:90% B to 65% A:35% B over 10 seconds, 65% A:35% B for 3 minutes.

EXAMPLE 1

8,8'-[1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

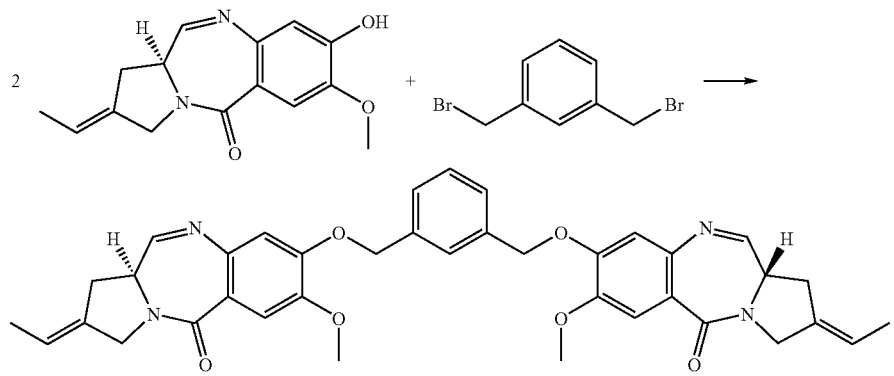

Potassium carbonate (22.8 mg), α,α'-dibromo-m-xylene (7.3 mg) and potassium iodide (9.1 mg) were added to a stirred solution of pre-tomaymycin (15 mg) in dimethylformamide (0.5 mL). The reaction was stirred for 20 h at 30° C.

Solids were filtered off, washed twice with dimethylformamide (0.2 mL) then discarded. Water (0.4 mL) was added to the combined dimethylformamide solution and the resulting solution was injected for HPLC purification according to method B1. The appropriate fractions were combined and concentrated by centrifugal evaporation over a Jouan Model RC10.10. apparatus to afford 8,8'-[1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] as a white powder (3.33 mg):

LC/MS (Method A1, Platform II): ES: m/z=647 MH$^+$ Retention time=3.53 minutes $^1$H N.M.R. (500 MHz, CDCl$_3$-d1, δ in ppm): 1.75 (d, J=7.0 Hz, 6H); 2.96 (m, 4H); 3.89 (m, 2H) 3.96 (s, 6H); 4.27 (s broad, 4H); 5.17 (d, J=12.5 Hz, 2H); 5.23 (d, J=12.5 Hz, 2H) 5.60 (m, 2H); 6.85 (s, 2H); from 7.36 to 7.43 (m, 3H); 7.51 (s broad, 1H); 7.53 (s, 2H); 7.63 (d, J=4.5 Hz, 2H).

EXAMPLE 2

8,8'-[5-methoxy-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

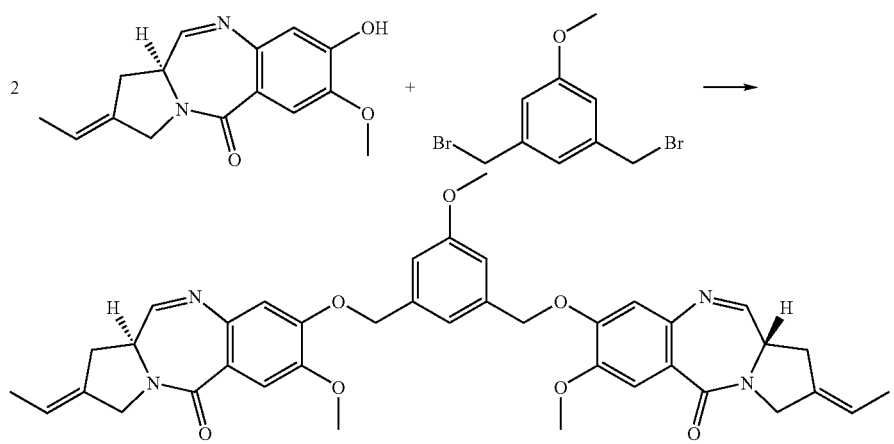

8,8'-[5-methoxy-1,3-benzenediylbis(methylenoxy)]-bis [(S)-2-eth-(E)-ylidene-7-methoxy-1,2,3,11a-tetrahydro-5H-pyrrolo[2,1-c][1,4]benzodiazepin-5-one] may be prepared following the procedure for the preparation of 8,8'-[1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] (Example 1), starting with 1,3-bis-bromomethyl-5-methoxy-benzene:

LC/MS (Method A1, Platform II): ES: m/z=677 MH$^+$ Retention time=4.17 minutes $^1$H N.M.R. (300 MHz, CDCl$_3$-d1, δ in ppm): 1.75 (d, J=7.0 Hz, 6H); 2.96 (m, 4H) 3.81 (s, 3H); 3.89 (m, 2H); 3.96 (s, 6H); 4.26 (s broad, 4H); 5.14 (d, J=12.5 Hz, 2H); 5.21 (d, J=12.5 Hz, 2H); 5.60 (m, 2H); 6.82 (s, 2H); 6.95 (s broad, 2H); 7.07 (s broad, 1H); 7.53 (s, 2H); 7.63 (d, J=4.5 Hz, 2H).

1,3-bis-bromomethyl-5-methoxy-benzene may be prepared as follows:

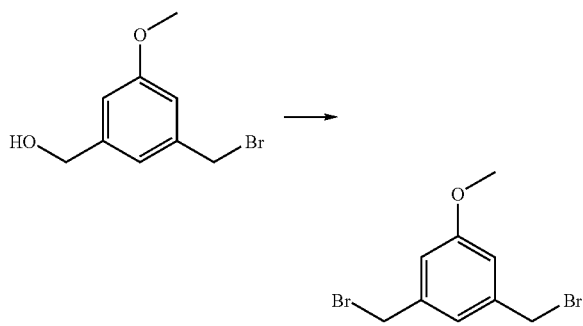

Carbon tetrabromide (663 mg) was added to a stirred solution of 1-bromomethyl-3-hydroxymethyl-5-methoxy-benzene (420 mg) in anhydrous dichloromethane (10 mL) under argon. After cooling the resulting solution at 0° C., a solution of triphenylphosphine (500 mg) in anhydrous dichloromethane (10 mL) was added dropwise. The reaction mixture was stirred at room temperature for 20 h and then concentrated in vacuo to a residue. The residue was purified by silica gel chromatography (Merck SuperVarioFlash 30 g column, Si60 15-40 μm, eluted with dichloromethane/heptane, 40:60) to give 1,3-bis-bromomethyl-5-methoxy-benzene (170 mg):

EI (Method C): m/z=292 M$^{+m/z=}$213 [M–Br]$^{+m/z=}$134 [213–Br]$^+$.

1H N.M.R. (400 MHz, DMSO-d6, δ in ppm): 3.77 (s, 3H); 4.65 (s, 4H); 6.98 (s broad, 2H); 7.10 (s broad, 1H)

1-bromomethyl-3-hydroxymethyl-5-methoxy-benzene may be prepared as follows:

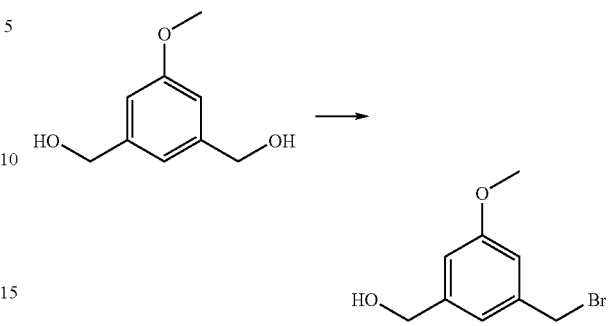

Carbon tetrabromide (3.47 g) was added to a stirred solution of 1,3-dihydroxymethyl-5-methoxy-benzene (800 mg) in anhydrous dichloromethane (16 mL) under argon. After cooling the resulting solution at 0° C., a solution of triphenylphosphine (2.68 g) in anhydrous dichloromethane (16 mL) was added dropwise. The reaction mixture was stirred at room temperature for 20 h and then concentrated in vacuo to a residue. The residue was purified by silica gel chromatography (Merck SuperVarioPrep 90 g column, Si60 15-40 μm, eluted with methanol/dichloromethane, 4:96) to give 1-bromomethyl-3-hydroxymethyl-5-methoxy-benzene (420 mg):

EI (Method C): m/z=230 M$^{+m/z=}$151 [M–Br]$^+$

1H N.M.R. (400 MHz, DMSO-d6, δ in ppm): 3.75 (s, 3H); 4.46 (d broad, J=5.5 Hz, 2H) 4.65 (s, 2H); 5.22 (t broad, J=5.5 Hz, 1H); 6.83 (s broad, 1H); 6.88 (s broad, 1H) 6.97 (s broad, 1H)

EXAMPLE 3

8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

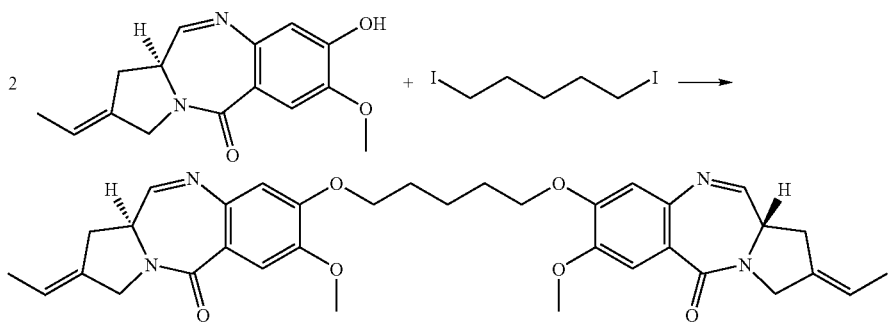

Potassium carbonate (22.8 mg) and 1,5-diiodopentane (8.2 μL) were added to a stirred solution of pre-tomaymycin (15 mg) in dimethylformamide (0.5 mL). The reaction was stirred for 20 h at room temperature and an additional portion of potassium carbonate (8 mg) was added. The reaction was stirred for another 20 h at room temperature.

Solids were filtered off and the dimethylformamide solution was injected for HPLC purification according to method B2. The appropriate fractions were combined and concentrated by centrifugal evaporation over a Jouan Model RC10.10. apparatus to afford 8,8'-[1,5-pentanediylbis(oxy)]- bis[(S)-2-eth-(E)-ylidene-7-methoxy-1,2,3,11a-tetrahydro-5H-pyrrolo[2,1-c][1,4]benzodiazepin-5-one] as a white powder (4 mg):

LC/MS (Method A2): ES: m/z=613 MH+ Retention time=9.04 minutes

1H N.M.R. (500 MHz, CDCl$_3$-d1, δ in ppm): 1.66 (m partially masked, 2H); 1.75 (d broad, J=7.0 Hz, 6H); 1.96 (m, 4H); 2.97 (d broad, J=7.0 Hz, 4H); 3.89 (m, 2H); 3.94 (s, 6H); 4.06 (m, 2H); 4.13 (m, 2H); 4.26 (s broad, 4H); 5.60 (m, 2H); 6.80 (s, 2H); 7.50 (s, 2H); 7.66 (d, J=4.5 Hz, 2H)

EXAMPLE 4

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one]

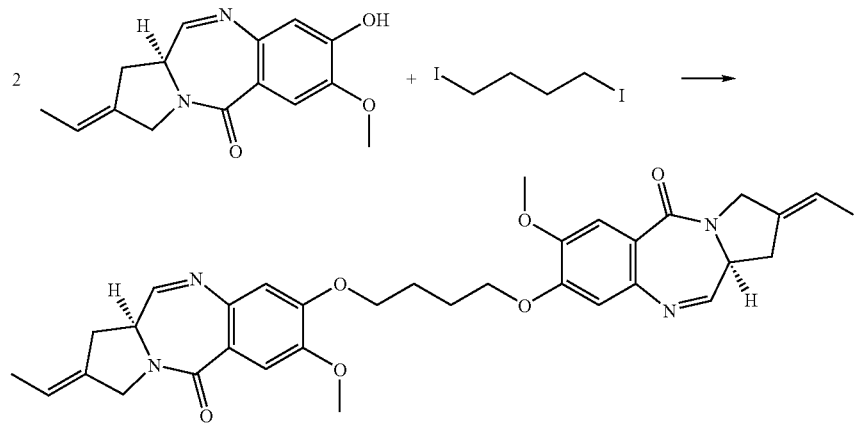

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one] may be prepared following the procedure for the preparation of 8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one] (Example 3), starting with 1,4-diiodobutane:

LC/MS (Method A1, Platform II): ES: m/z=599 MH+ m/z=318.5 (M+H+ K)$^{2+}$/2 Retention time=3.23 minutes $^1$H N.M.R. (500 MHz, CDCl$_3$-d1, δ in ppm): 1.75 (d broad, J=7.0 Hz, 6H); 2.10 (m, 4H); 2.98 (d broad, J=7.0 Hz, 4H); 3.90 (m, 2H); 3.93 (s, 6H); 4.11 (m, 2H); 4.20 (m, 2H); 4.27 (s broad, 4H); 5.60 (m, 2H); 6.82 (s, 2H); 7.50 (s, 2H); 7.66 (d, J=4.5 Hz, 2H)

EXAMPLE 5

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

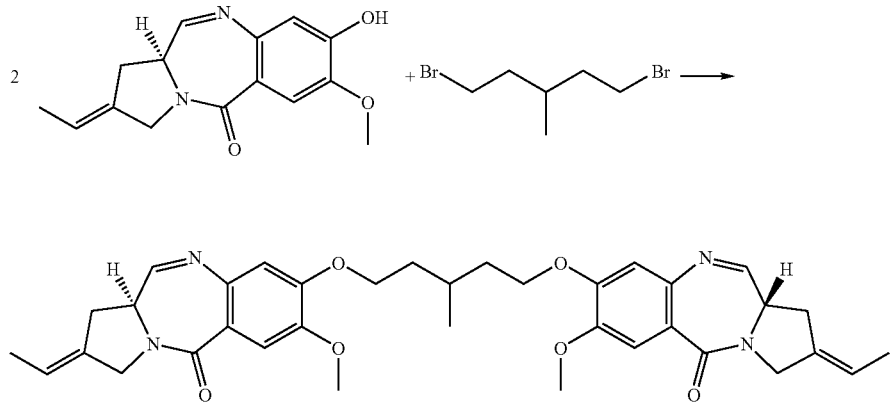

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one] may be prepared following the procedure for the preparation of 8,8'-[1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] (Example 1), starting with 1,5-dibromo-3-methylpentane:

LC/MS (Method A1, Platform II): ES: m/z=627 MH⁺ Retention time=3.92 minutes

EXAMPLE 6

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

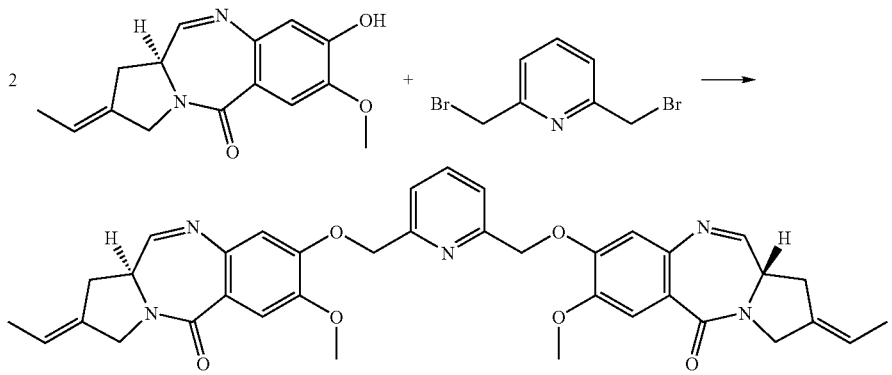

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one] may be prepared following the procedure for the preparation of 8,8'-[1,3-benzene-diylbis(methylenoxy)]-bis[(S)-2-eth-(E)-ylidene-7-methoxy-1,2,3,11a-tetrahydro-5H-pyrrolo[2,1-c][1,4]benzodiazepin-5-one] (Example 1), starting with 2,6-bis-bromomethyl-pyridine:

LC/MS (Method A1, ZQ): ES: m/z=648 MH⁺ Retention time=3.21 minutes

¹H N.M.R. (400 MHz, CDCl₃-d1, δ in ppm): 1.75 (d broad, J=6.5 Hz, 6H); from 2.94 to 2.99 (m, 4H); 3.90 (m, 2H); 3.99 (s, 6H); 4.27 (s broad, 4H); 5.32 (s, 4H); 5.60 (m, 2H); 6.86 (s, 2H); 7.48 (d, J=8.0 Hz, 2H); 7.56 (s, 2H); 7.64 (d, J=4.5 Hz, 2H); 7.74 (t, J=8.0 Hz, 1H).

EXAMPLE 7

8,8'-[4-(3-tert-butoxycarbonylaminopropyloxy)-2,6-pyridinediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] May be Prepared as Follows

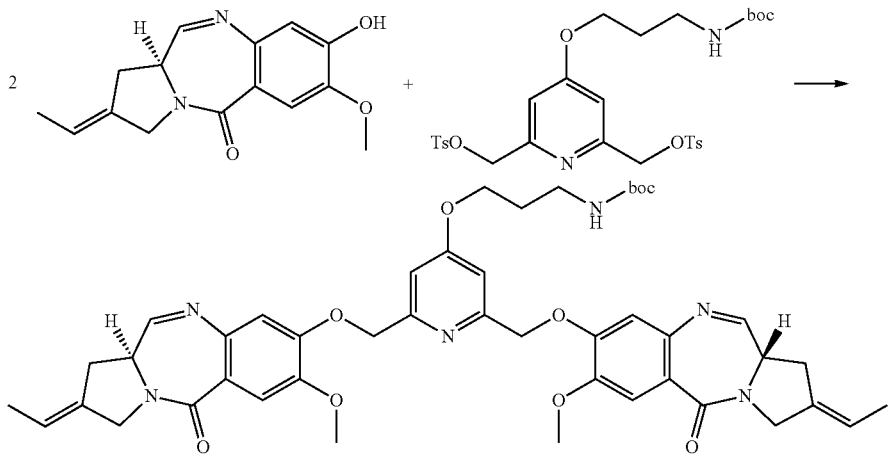

To a stirred solution of pre-tomaymycin (30 mg) in dimethylformamide (0.5 mL), were added potassium carbonate (45.7 mg), a solution of 4-(3-tert-butoxycarbonylamino-propoxy)-2,6-bis-(tosyloxymethyl)-pyridine (41 mg) in dimethylformamide (0.5 mL) and potassium iodide (18.3 mg). The reaction was stirred for 20 h at 30° C. Solids were filtered off and washed with dimethylformamide (0.2 mL). Water (0.5 mL) was added to the combined dimethylformamide solution and formic acid was added until complete dissolution of the precipitate. The resulting solution was injected for HPLC purification according to method B1. The appropriate fractions were combined and concentrated by centrifugal evaporation over a Jouan Model RC10.10. apparatus to afford 8,8'-[4-(3-tert-butoxycarbonylaminopropyloxy)-2,6-pyridine-diylbis(methylenoxy)]-bis[(S)-2-eth-(E)-ylidene-7-methoxy-1,2,3,11a-tetrahydro-5H-pyrrolo[2,1-c][1,4]benzodiazepin-5-one] (8.3 mg).

| LC/MS (Method A1, Platform I): | | |
|---|---|---|
| ES: | m/z = 857 | MH$^+$ + 2H$_2$O |
| | m/z = 839 | MH$^+$ + H$_2$O |
| | m/z = 821 | MH$^+$ |
| | m/z = 721 | [M-C$_5$O$_2$H$_8$] + H$^+$ |

Retention time = 3.67 minutes $^1$H N.M.R. (500 MHz, CD3CO$_2$D-d4, δ in ppm): 1.41 (s, 9H); 1.71 (d, J=6.5 Hz, 6H); 2.08 (m, 2H); 2.95 (m, 4H); 3.34 (m, 2H); 3.90 (s, 6H); 4.06 (m, 2H); 4.18 (m, 2H) from 4.24 to 4.36 (m, 4H); 4.43 (t, J=6.0 Hz, 2H); 5.50 (s broad, 4H); 5.61 (m, 2H); from 6.80 to 7.70 (m very broad, 2H); 6.95 (s broad, 2H); from 7.48 to 7.58 (m, 4H).

4-(3-tert-butoxycarbonylamino-propoxy)-2,6-bis-(tosyloxymethyl)-pyridine may be prepared as follows:

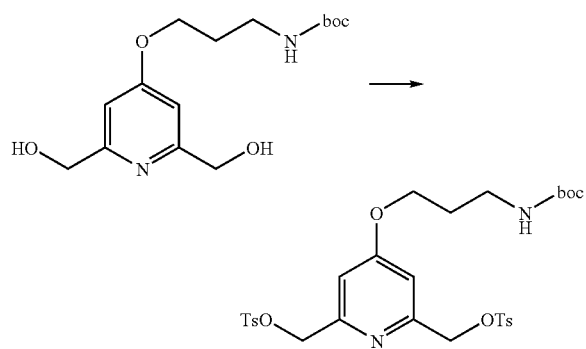

To a precooled (0° C.) solution of 4-(3-tert-butoxycarbonylamino-propoxy)-2,6-bis-(hydroxymethyl)-pyridine (76 mg) in dichloromethane (0.7 mL), was added a solution of potassium hydroxide (30 mg) in water (0.3 mL). Tosyl chloride (93.7 mg) was added, and the resulting heterogenous mixture was shaken vigorously for 1 h and then washed into separatory funnel using dichloromethane and water. The layers were separated, and the aqueous layer was extracted three times with dichloromethane. The combined organic solutions were dried over magnesium sulfate, and concentrated in vacuo to a residue. The residue was purified by silica gel chromatography (Interchrom Puriflash 10 g column, SiOH 15-35 μm), using gradient elution with a mixture of heptane (A) and ethyl acetate (B) (gradient: 90% A:10% B up to 50% A:50% B) to give 4-(3-tert-butoxycarbonylamino-propoxy)-2,6-bis-(tosyloxymethyl)pyridine (56 mg):

LC/MS (Method A1, Platform I): ES: m/z=621 MH$^+$Retention time=4.90 minutes 4-(3-tert-butoxycarbonylamino-propoxy)-2,6-bis-(hydroxymethyl)-pyridine may be prepared as follows:

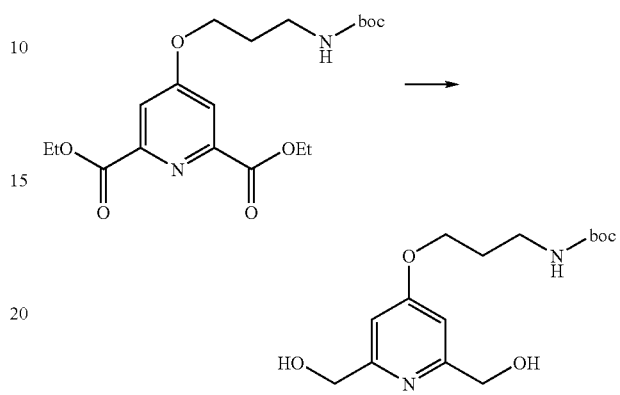

To a solution of 4-(3-tert-butoxycarbonylamino-propoxy)-pyridine-2,6-dicarboxylic acid diethyl ester (150 mg) in absolute ethanol (5 mL) was added sodium borohydride (43 mg) and calcium chloride (128 mg). After stirring for 4 h, hydrogen evolution ceased, and reaction was quenched with water. Solvent was evaporated under reduced pressure. The residue was then washed into separatory funnel using dichloromethane and water. The layers were separated, and the aqueous layer was extracted three times with dichloromethane. The combined organic solutions were dried over magnesium sulphate, and concentrated in vacuo to give 4-(3-tert-butoxycarbonylamino-propoxy)-2,6-bis-(hydroxymethyl)pyridine (80 mg):

LC/MS (Method A1, ZQ): ES m/z=313 MH$^+$Retention time=1.90 minutes $^1$H N.M.R. (400 MHz, DMSO-d6, δ in ppm): 1.37 (s, 9H); 1.84 (m, 2H); 3.08 (q, J=6.5 Hz, 2H) 4.05 (t, J=6.5 Hz, 2H); 4.45 (d, J=6.0 Hz, 4H); 5.32 (t, J=6.0 Hz, 2H) 6.84 (s, 2H) 6.90 (t broad, J=6.5 Hz, 1H).

4-(3-tert-butoxycarbonylamino-propoxy)-pyridine-2,6-dicarboxylic acid diethyl ester may be prepared as follows:

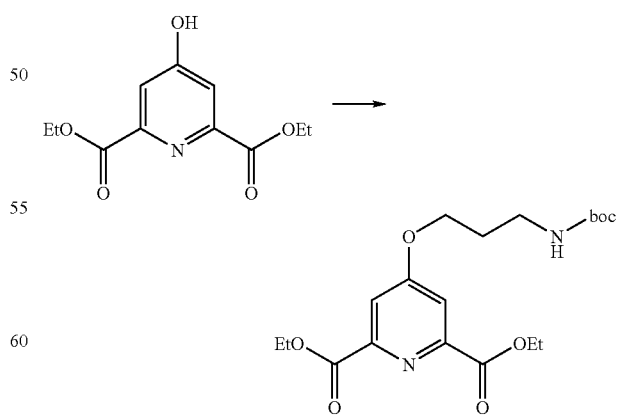

The diethyl ester of chelidamic acid (Scrimin, P.; Tecilla, P.; Tonellato, U.; Vendrame, T. *J. Org. Chem.* 1989, 54, 5988) (150 mg) was dissolved in dry dimethylformamide (2 mL).

3-(tert-Butoxy-amino)-propyl bromide (164 mg) and potassium carbonate (130 mg) were added. The resulting mixture was stirred for 15 h at 70° C. The reaction was quenched with a saturated ammonium chloride aqueous solution and then washed into separatory funnel using ethyl acetate. The layers were separated, and the aqueous layer was extracted 3 times with ethyl acetate. The combined organic solutions were dried over magnesium sulfate, and concentrated in vacuo to a residue. The residue was purified by silica gel chromatography (Merck SuperVarioFlash 30 g column, Si60 15-40 μm), using gradient elution with a mixture of heptane (A) and ethyl acetate (B) (gradient: 60% A:40% B up to 50% A:50% B) to give 4-(3-tert-butoxycarbonylamino-propoxy)-pyridine-2,6-dicarboxylic acid diethyl ester (150 mg):

CI (Method D): m/z=397 MH⁺

$^1$H N.M.R. (400 MHz, DMSO-d6, δ in ppm): 1.34 (t, J=7.0 Hz, 6H); 1.36 (s, 9H); 1.86 (m, 2H); 3.10 (q, J=6.5 Hz, 2H); 4.21 (t, J=6.5 Hz, 2H); 4.37 (q, J=7.0 Hz, 4H); 6.89 (m broad, 1H); 7.71 (s, 2H)

EXAMPLE 8

8,8'-[5-(3-aminopropyloxy)-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] May be Prepared as Follows To a stirred solution of pre-tomaymycin (21 mg) in dimethylformamide (0.7 mL), were added potassium carbonate (32 mg), 1-(3-allyloxycarbonylamino-propyloxy)-3,5-bis-(bromomethyl)-benzene (16.2 mg) and potassium iodide (12.8 mg). The reaction was stirred for 20 h at 30° C. Solids were filtered off, washed twice with dimethylformamide (0.2 mL) then discarded. Water (0.5 mL) was added to the combined dimethylformamide solution and the resulting precipitate was filtered off, washed with water and dried by centrifugal evaporation over a Jouan Model RC10.10 apparatus. To the crude compound (27 mg) dissolved in dimethylformamide (0.8 mL), tetrakis(triphenylphosphine) palladium (2 mg), triphenylphosphine (0.9 mg) and pyrrolidine (5.6 μL) were added. After stirring for 15 h at 30° C., tetrakis(triphenylphosphine) palladium (2 mg), triphenylphosphine (1 mg) and pyrrolidine (2.8 μL) were added and the reaction mixture was stirred at room temperature for another 15 h. Water (0.4 mL) was added to the dimethylformamide solution and formic acid was added until complete dissolution of the precipitate. The resulting solution was injected for HPLC purification according to method B1. The appropriate fractions were combined and concentrated by centrifugal evaporation over a Jouan Model RC10.10. apparatus to afford 8,8'-[5-(3-aminopropyloxy)-1,3-benzenediylbis-(methylenoxy)]-bis[(S)-2-eth-(E)-ylidene-7-methoxy-1,2,3,11a-tetrahydro-5H-pyrrolo[2,1-c][1,4]benzodiazepin-5-one] (0.2 mg).

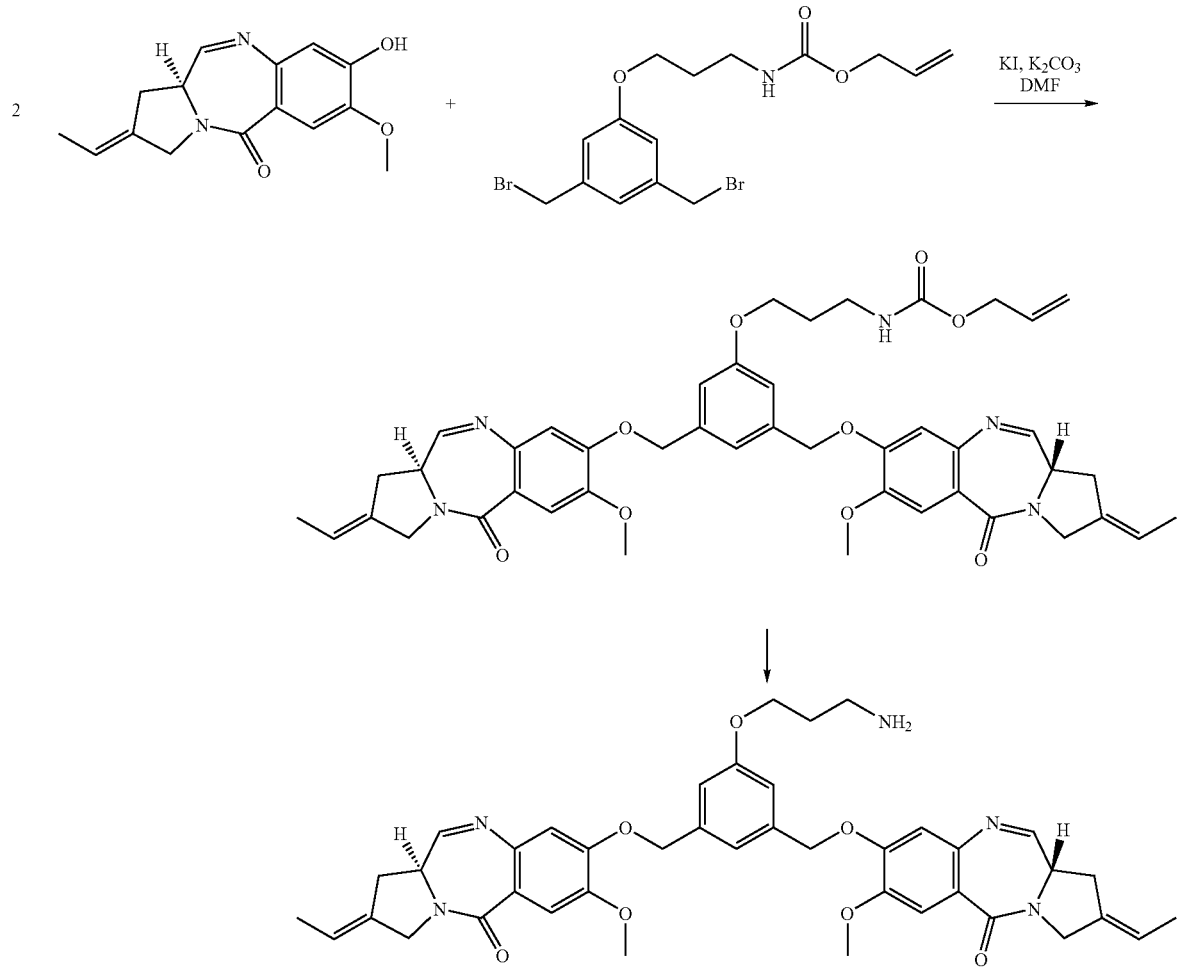

LC/MS (Method A1, Platform II): ES: m/z=800 MH+Retention time=2.84 minutes 1-(3-allyloxycarbonylamino-propyloxy)-3,5-bis-(bromomethyl)-benzene may be prepared as follows:

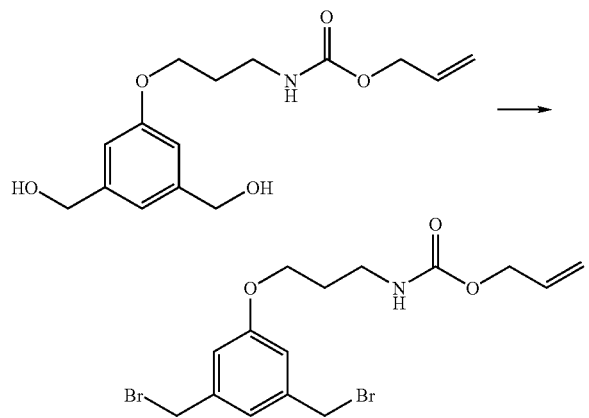

To a suspension of 1-(3-allyloxycarbonylamino-propyloxy)-3,5-bis-(hydroxy-methyl)-benzene (70 mg) in dichloromethane (3 mL) were added carbon tetrabromide (248 mg) and a solution of triphenylphosphine (199 mg) in dichloromethane (2 mL). After refluxing for 3 h, the reaction mixture was purified by silica gel chromatography (Merck SuperVarioFlash 25 g column, Si60 15-40 µm), eluted with dichloromethane to give 1-(3-allyloxycarbonylamino-propyloxy)-3,5-bis-(bromomethyl)-benzene (52 mg):

LC/MS (Method A1, Platform II): ES m/z=420 MH+Retention time=4.50 minutes

¹H N.M.R. (400 MHz, DMSO-d6, δ in ppm): 1.85 (m, 2H); 3.15 (q, J=6.5 Hz, 2H) 3.99 (t, J=6.5 Hz, 2H); 4.46 (d broad, J=5.5 Hz, 2H); 4.65 (s, 4H); 5.16 (d broad, J=11.0 Hz, 1H) 5.26 (d broad, J=17.5 Hz, 1H); 5.90 (m, 1H); 6.96 (d, J=1.5 Hz, 2H); 7.09 (t, J=1.5 Hz, 1H); 7.29 (t broad, J=6.5 Hz, 1H).

1-(3-allyloxycarbonylamino-propyloxy)-3,5-bis-(hydroxymethyl)-benzene may be prepared as follows:

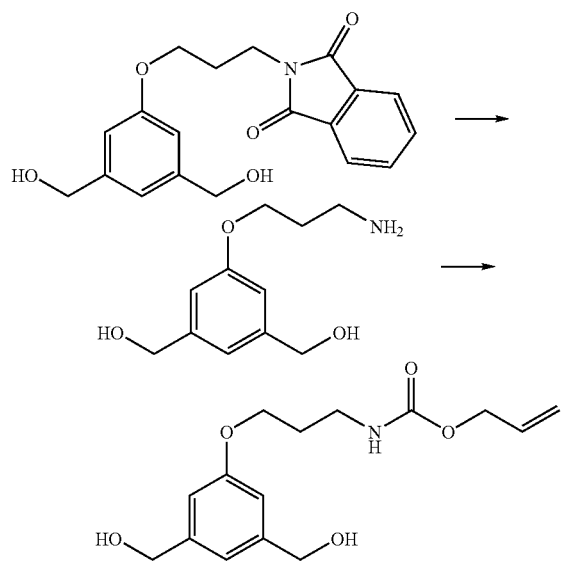

5-(3-Phthalimido-propyloxy)-1,3-bis-(hydroxymethyl)-benzene (1.45 g) was dissolved in a mixture of dichloromethane and ethanol (25 mL, 25:75). Hydrazine hydrate (0.62 mL) was added and the reaction mixture was refluxed for 1 h. The solvent was removed in vacuo and the residue dissolved in dichloromethane. The insoluble residue was filtered off and purified by silica gel chromatography (Merck SuperVarioPrep 70 g column, Si60 15-40 µm), eluted with methanol/dichloromethane, 20:80 then ammonium hydroxide/methanol/dichloromethane, 0.5:25:75 to give 1-(3-amino-propyloxy)-3,5-bis-(hydroxy-methyl)-benzene (1 g) suitable for further transformation.

A sample of 1-(3-amino-propyloxy)-3,5-bis-(hydroxymethyl)-benzene (100 mg) was dissolved in methanol (5 mL). To the cooled solution (0° C.) was added a solution of sodium carbonate (120 mg) in water (5 mL) and allyl chloroformate (42 µL). After stirring for 30 minutes at 0° C., the reaction mixture was steered at room temperature for another 15 h. Solvent was removed in vacuo The residue was then washed into separatory funnel using ethyl acetate and water. The layers were separated, and the aqueous layer was extracted twice with ethyl acetate. The combined organic solutions were dried over magnesium sulphate, and concentrated in vacuo to give 5-(3-allyloxycarbonylamino-propyloxy)-2,6-bis-(hydroxymethyl)benzene (75 mg):

EI (Method C): m/z=295 M$^{+m/z}$=142 (M–C$_8$H$_9$O$_3$)$^{+m/z}$=41 C$_3$H$_5^+$ ¹H N.M.R. (300 MHz, DMSO-d6, δ in ppm): 1.85 (m, 2H); 3.14 (q, J=6.5 Hz, 2H); 3.96 (t, J=6.5 Hz, 2H); from 4.41 to 4.48 (m, 6H); 5.11 (t partially masked, J=5.5 Hz, 2H); 5.16 (qd, J=1.5 et 10.5 Hz, 1H); 5.26 (qd, J=1.5 et 17.0 Hz, 1H); 5.90 (m, 1H); 6.72 (s broad, 2H); 6.83 (s broad, 1H); 7.26 (t broad, J=6.5 Hz, 1H)

5-(3-phthalimido-propyloxy)-1,3-bis-(hydroxymethyl)-benzene may be prepared as follows:

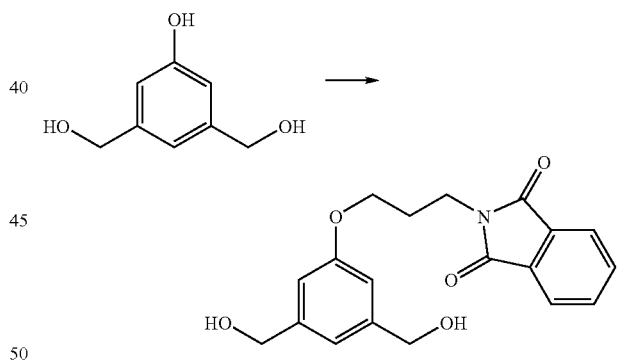

3,5-Bis-hydroxymethylphenol (Felder, D.; Gutierrez Nava, M.; del Pilar Carreon, M.; Eckert, J. F.; Luccisano, M.; Schall, C.; Masson, P.; Gallani, J. L.; Heinrich, B.; Guillon, D.; Nierengarten, J. F. Helv. Chimica Acta 2002, 85, 288) (2.35 g), N-(3-bromo-propyl)-phthalimide (4.49 g) and potassium carbonate (10.53 g) were mixed in acetonitrile (25 mL) and refluxed for 12 h. The reaction mixture was cooled to room temperature and the solvent removed under reduced pressure. The residue was redissolved in dichloromethane and the insoluble residue filtered off. The filtrate was washed with water, dried over magnesium sulfate, and concentrated in vacuo to a residue. The residue was purified by silica gel chromatography (Merck SuperVarioPrep 90 g column, Si60 15-40 µm), eluted with methanol/dichloromethane, 4:96 to give 5-(3-phthalimido-propyloxy)-1,3-bis-(hydroxymethyl)benzene (1.45 g):

LC/MS (Method A1, Platform II): ES m/z=342 MH+m/z=324 (MH+−H₂O) Retention time=2.90 minutes ¹H N.M.R. (300 MHz, DMSO-d6, δ in ppm): 2.05 (m, 2H); 3.76 (t, J=6.5 Hz, 2H); 3.99 (t, J=6.5 Hz, 2H); 4.40 (d, J=5.5 Hz, 4H); 5.09 (t, J=5.5 Hz, 2H); 6.59 (s broad, 2H); 6.82 (s broad, 1H); from 7.80 to 7.90 (m, 4H)

EXAMPLE 9

8,8'-[5-(N-methyl-3-tert-butoxycarbonylaminopropyl)-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] May be Prepared as Follows

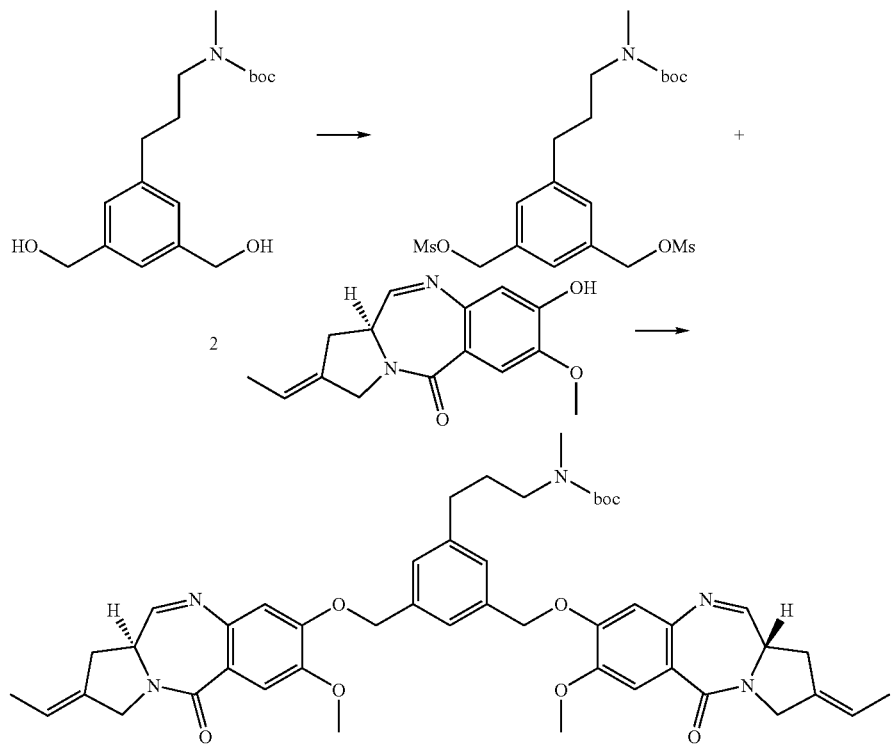

To a cooled (0° C.) solution of 5-(N-methyl-3-tert-butoxycarbonylaminopropyl)-1,3-bis-(hydroxymethyl)-benzene (50 mg) and triethylamine (113 μL) in dichloromethane (2 mL), was added methanesulfonyl chloride (26 μL). After 30 minutes, the reaction mixture was washed twice with water and the resulting dichloromethane solution was dried over magnesium sulfate, and concentrated in vacuo to a viscous oil (50.3 mg). A solution of pre-tomaymycin (15 mg) in dimethylformamide (0.5 mL) was added to a mixture of the crude compound (13 mg), potassium carbonate (23 mg) and potassium iodide (9 mg). The reaction mixture was stirred for 20 h at 30° C. Another sample of the crude compound was added (6 mg), and the reaction mixture was stirred for another 20 h at 30° C. Solids were filtered off, washed with dimethylformamide (0.2 mL) then discarded. Water (0.4 mL), one drop of formic acid and another water (1.5 mL) were added to the combined dimethylformamide solution.

A sample of the resulting suspension (2 mL) was filtered and the resulting solid was dried under vacuo to give 8,8'-[5-(N-methyl-3-tert-butoxycarbonylaminopropyl)-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one] (3.1 mg):

LC/MS (Method A1, Platform II): ES: m/z=818 MH+ Retention time=4.11 minutes 5-(N-methyl-3-tert-butoxycarbonylaminopropyl)-1,3-bis-(hydroxymethyl)-benzene may be prepared as follows:

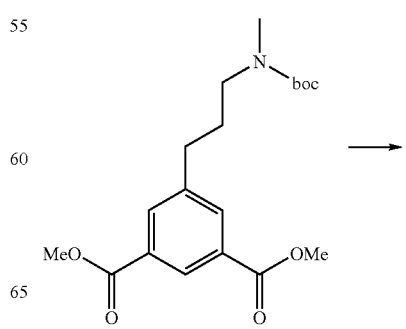

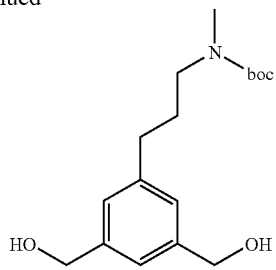

To a cooled solution (−5° C.) of 5-(N-methyl-3-tert-butoxycarbonylaminopropyl)-benzene-1,3-dicarboxylic acid diethyl ester (100 mg) in tetrahydrofuran (2 mL) was slowly added a 1M solution of lithium aluminium hydride in diethyl ether (0.55 mL). 10 minutes after the end of the addition, sodium sulfate decahydrate was added until gas evolution ceased. The solid was filtered off, washed twice with ethyl acetate and the combined organic solutions were concentrated in vacuo to give 5-(N-methyl-3-tert-butoxycarbonylaminopropyl)-1,3-bis-(hydroxymethyl)-benzene (66.8 mg) as a viscous oil:

CI (Method D): m/z=327 $MNH_4^{+m/z=}310$ $MH^{+m/z=}271$ $(MNH_4^+ - C_4H_8)$ $^1$H N.M.R. (300 MHz, DMSO-d6, δ in ppm): 1.37 (s broad, 9H); 1.75 (m, 2H); from 2.45 to 2.54 (m masked, 2H); 2.77 (s, 3H); 3.18 (t, J=7.0 Hz, 2H); 4.45 (d, J=5.5 Hz, 4H); 5.08 (t, J=5.5 Hz, 2H); 7.00 (s broad, 2H); 7.08 (s broad, 1H)

5-(N-methyl-3-tert-butoxycarbonylaminopropyl)-benzene-1,3-dicarboxylic acid diethyl ester may be prepared as follows:

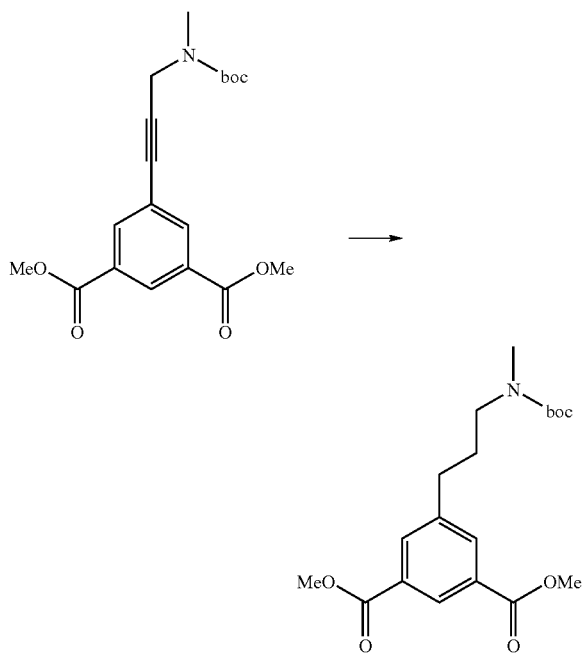

To a solution of 5-(N-methyl-3-tert-butoxycarbonylaminopropyn-1-yl)-benzene-1,3-dicarboxylic acid diethyl ester (890 mg) in methanol (10 mL) was added palladium 10% on carbon (89 mg) and the solution was stirred at room temperature under an hydrogen atmosphere (1 bar) for 18 h. The solid was filtered off and solvent was removed in vacuo to afford 5-(N-methyl-3-tert-butoxycarbonylaminopropyl)-benzene-1,3-dicarboxylic acid diethyl ester (767 mg) as a yellow oil:

EI (Method C): m/z=365 $M^+$. m/z=309 $(M-C_4H_8)^+$. m/z=265 $(m/z=309-CO_2)^+$. m/z=57 $C_4H_9^{+m/z=}44$ $C_2H_6N^+$ $^1$H N.M.R. (400 MHz, DMSO-d6, δ in ppm): 1.32 (s broad, 9H); 1.79 (m, 2H); 2.70 (t, J=7.0 Hz, 2H); 2.76 (s, 3H); 3.16 (m, 2H); 3.87 (s, 6H); 8.06 (d, J=2.0 Hz, 2H) 8.32 (t, J=2.0 Hz, 1H)

5-(N-methyl-3-tert-butoxycarbonylaminopropyn-1-yl)-benzene-1,3-dicarboxylic acid diethyl ester may be prepared as follows:

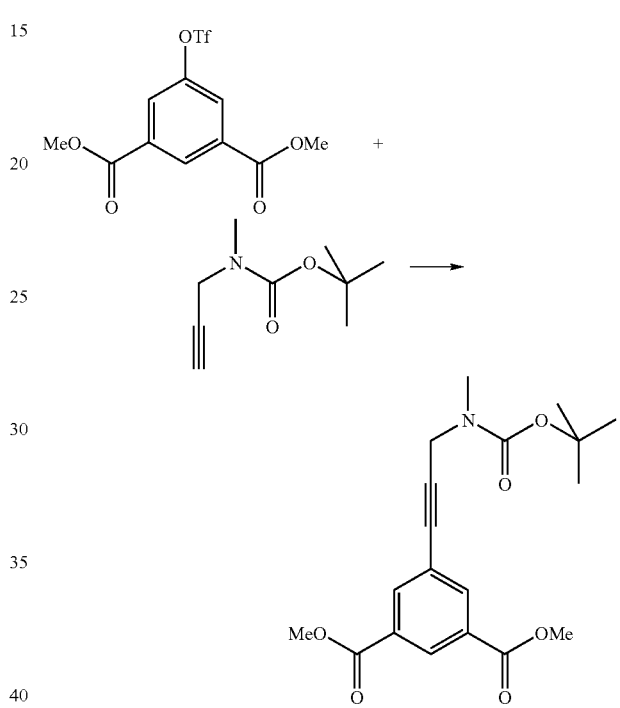

5-Trifluoromethanesulfonyloxy-isophthalic acid dimethyl ester (Bodwell, G. J. Fleming, J. J.; Mannion, M. R.; Miller, D. O. *J. Org. Chem.* 2000, 65 (17), 5360) (1 g) was dissolved in 2 mL of acetonitrile. N-Methyl-N-tert-butoxycarbonyl-propargylamine (Bradbury, B. J.; Baumgold, J.; Jacobsen, K. A. *J. Med. Chem.* 1990, 33 (2), 741) (643 mg), bis(triphenylphosphine)palladium chloride (205 mg), copper iodide (56 mg) and triethylamine (591 mg) were added. The resultant mixture was stirred for 15 h at room temperature. The solvent was removed by evaporation under reduced pressure and the residue was then washed into separatory funnel using ethyl acetate and water. The layers were separated, and the aqueous layer was extracted once with ethyl acetate. The combined organic solutions were washed with a saturated sodium chloride aqueous solution, dried over magnesium sijlphate, and concentrated in vacuo to a residue. The residue was purified by silica gel chromatography (Biotage FLASH 40+M 100 g column, SiOH 32-63 µm, eluted with ethyl acetate/heptane, 20:80) to give 5-(N-methyl-3-tert-butoxycarbonylaminopropyn-1-yl)-benzene-1,3-dicarboxylic acid diethyl ester (896 mg):

$^1$H N.M.R. (300 MHz, DMSO-d6, δ in ppm): 1.43 (s, 9H); 2.90 (s, 3H); 3.90 (s, 6H) 4.30 (s, 2H); 8.16 (d, J=1.5 Hz, 2H); 8.42 (t, J=1.5 Hz, 1H)

EXAMPLE 10

8,8'-{5-[3-(4-methyl-4-methyldisulfanyl-pentanoy-lamino)propyloxy]-1,3-benzenediylbis(methyl-enoxy)}-bis[(S)-2-eth-(E)-ylidene-7-methoxy-1,2,3,11a-tetrahydro-5H-pyrrolo[2,1-c][1,4]benzodiazepin-5-one] May be Prepared as Follows

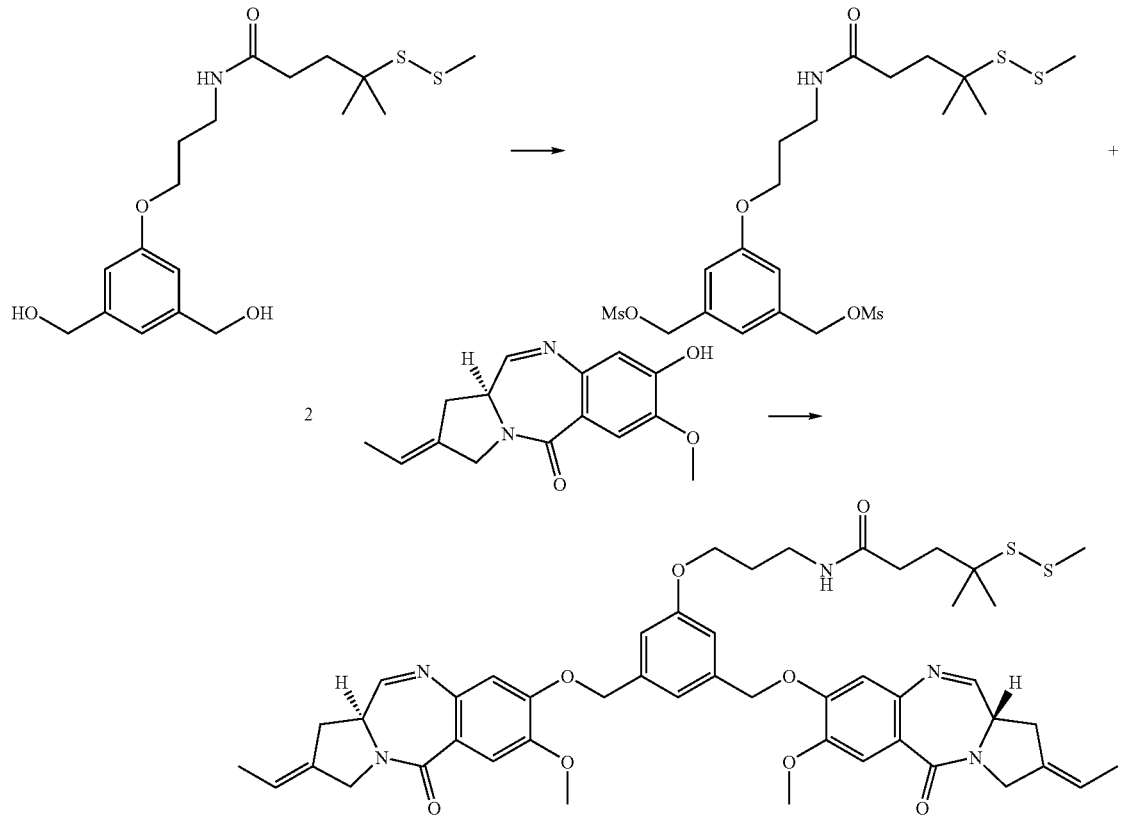

To a cooled (0° C.) solution of 1-[3-(4-methyl-4-methyldisulfanyl-pentanoylamino)-propyloxy]-3,5-bis-(hydroxymethyl)-benzene (45 mg) and triethylamine (49 µL) in dichloromethane (1.5 mL), was added methanesulfonyl chloride (19 µL). After 30 minutes, the reaction mixture was washed twice with water and the resulting dichloromethane solution was dried over magnesium sulfate, and concentrated in vacuo to a viscous oil (39 mg).

To a solution of pre-tomaymycin (26 mg) in dimethylformamide (0.9 mL) was added potassium carbonate (40 mg), potassium iodide (16 mg) and a sample of the crude compound (31 mg). The reaction mixture was stirred for 20 h at 30° C. Another sample of the crude compound was added (6 mg), and the reaction mixture was stirred for another 20 h at 30° C. Solids were filtered off, washed with dimethylformamide (0.3 mL) then discarded. Water (1.6 mL) was added to the combined dimethylformamide solution and the resulting solid was filtered, washed with water and dried in vacuo to give a residue. The residue was purified by silica gel chromatography (Interchrom Puriflash 2 g column, SiOH 15-35 µm, eluted with dichloromethane/methanol, 95:5) then another purification by silica gel chromatography (Chromabond OH 2 g column, 45 µm, eluted with dichloromethane to give 8,8'-{5-[3-(4-methyl-4-methyldisulfanylpentanoyl-amino) propyloxy]-1,3-benzenediylbis(methylenoxy)}-bis[(S)-2-eth-(E)-ylidene-7-methoxy-1,2,3,11a-tetrahydro-5H-pyrrolo[2,1-c][1,4]benzo-diazepin-5-one] (0.2 mg):

LC/MS (Method A1, Platform I): ES: m/z=896 MH$^+$ Retention time=4.09 minutes $^1$H N.M.R. (500 MHz, CDCl3-d1, δ in ppm): 1.29 (s, 6H); 1.75 (d, J=6.5 Hz, 6H); from 1.92 to 2.03 (m, 4H); 2.28 (m, 2H); 2.39 (s, 3H); 2.97 (m, 4H); 3.45 (q, J=6.0 Hz, 2H); 3.89 (q, J=5.5 Hz, 2H); 3.96 (s, 6H) 4.04 (t, J=5.0 Hz, 2H); 4.27 (s broad, 4H) 5.14 (d, J=12.5 Hz, 2H) 5.20 (d, J=12.5 Hz, 2H) 5.60 (m, 2H) 5.84 (t broad, J=6.0 Hz, 1H); 6.83 (s, 2H) 6.94 (s, 2H); 7.09 (s, 1H) 7.53 (s, 2H) 7.64 (d, J=5.0 Hz, 2H).

1-[3-(4-methyl-4-methyldisulfanyl-pentanoylamino)-propyloxy]-3,5-bis-(hydroxymethyl)-benzene

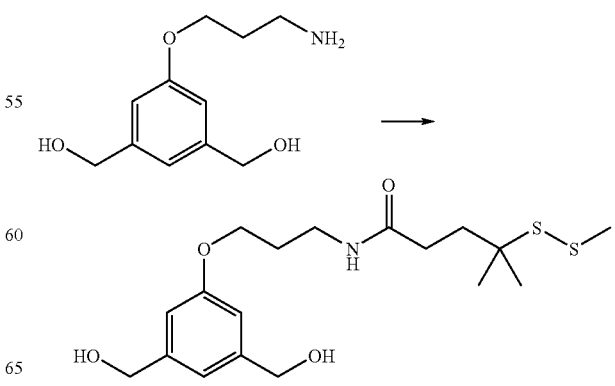

To a solution of 1-(3-amino-propyloxy)-3,5-bis-(hydroxymethyl)-benzene (50 mg) in dimethylformamide (1 mL) was added 4-methyl-4-methyldisulfanyl-pentanoic acid (44 mg), N,N'-diisopropylcarbodiimide (35 mL) and 1-hydroxybenzotriazole hydrate (5.8 mg). After 15 h at room temperature, water was added to the reaction mixture and the aqueous solution was extracted twice with ethyl acetate. The combined organic solutions were washed with a saturated sodium chloride aqueous solution, dried over magnesium sulfate and concentrated in vacuo to a residue. The residue was purified by silica gel chromatography (Interchrom Puriflash 5 g column, SiOH 15-35 μm), eluted with methanol/dichloromethane, 5:95 to give 1-[3-(4-methyl-4-methyldisulfanyl-pentanoylamino)-propyloxy]-3,5-bis-(hydroxymethyl)-benzene (48 mg):

LC/MS (Method A1, ZQ): ES m/z=388 MH$^+$Retention time=3.03 minutes $^1$H N.M.R. (300 MHz, DMSO-d6, δ in ppm): 1.24 (s, 6H); from 1.76 to 1.87 (m, 4H) 2.16 (m, 2H); 2.40 (s, 3H); 3.19 (q, J=6.5 Hz, 2H); 3.95 (t, J=6.5 Hz, 2H); 4.44 (d broad, J=5.5 Hz, 4H); 5.12 (d, J=5.5 Hz, 2H); 6.73 (s broad, 2H); 6.83 (s broad, 1H); 7.92 (t broad, J=5.5 Hz, 1H)

EXAMPLE 11

Preparation of Starting Products and/or Intermediates

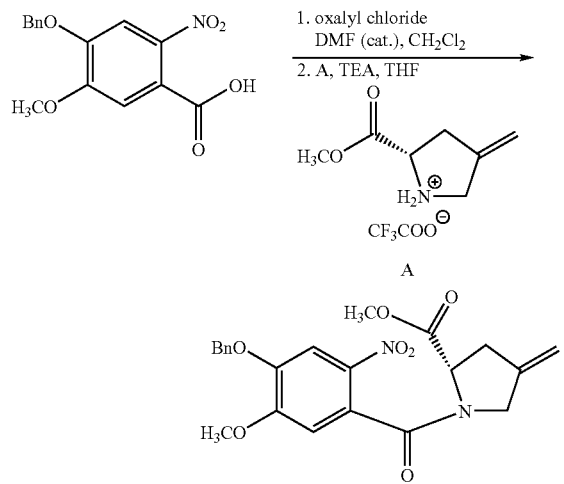

To a solution of 4-benzyloxy-5-methoxy-2-nitrobenzoic acid (4.8 g, 16 mmol) in anhydrous dichloromethane (80 mL) and THF (5 mL) was added oxalyl chloride (2.8 mL, 32 mmol) and DMF (30 μL, 0.38 mmol) at room temperature. Large amounts of bubble formed after the addition of DMF. The mixture was stirred overnight then the solvents were removed by rotary evaporation in vacuo. The residue was co-evaporated one more time by addition of anhydrous dichloromethane to give the acetyl chloride as a yellow solid.

To a solution of 4-methylene-L-proline methyl ester, compound A, (3.95 g, 15.5 mmol) in anhydrous THF (80 mL) was added triethylamine (6.7 mL, 48 mmol) at 0° C. After 2 minutes the above acetyl chloride in anhydrous THF (80 mL) was added quickly in 10 minutes via a cannula at the same temperature. The obtained yellow cloudy solution was stirred at 0~5° C. for 30 minutes then at room temperature for 4 hours. The reaction solution was diluted with ethyl acetate and water. The aqueous layer was extracted with ethyl acetate twice and the combined organic layers were washed with 2% HCl solution and brine, dried over anhydrous magnesium sulfate. It was filtered and the solvents were removed. The residue was purified by flash chromatography (Hexanes/AcOEt, 1:1, 1:1.5) to give (2S)-4-(methylene)-1-[5-methoxy-2-nitro-4-(phenylmethoxy)-benzoyl]-2-pyrrolidinecarboxylic acid methyl ester as a yellow solid (5.6 g, y=85%). $^1$H NMR (400 Hz, CDCl$_3$): the compound appears as a pair of distinct rotamers. δ 7.76 (s, 0.7H), 7.73 (s, 0.3H), 7.43-7.29 (m, 5H), 6.83 (s, 0.7H), 6.80 (s, 0.3H), 5.17 (s, 1.4H), 5.16 (s, 0.6H), 5.10-4.89 (m, 2.7H), 4.57 (d, J=16 Hz, 0.3H), 4.19-4.12 (m, 0.7H), 3.95-3.77 (m, 6.3H), 3.57 (s, 1H), 3.06-2.96 (m, 1H), 2.73-2.62 (m, 1H); $^{13}$C NMR (400 Hz, CDCl$_3$): 171.8, 171.7, 166.5, 166.2, 154.9, 154.4, 148.25, 148.18, 141.7, 141.3, 137.19, 137.13, 135.3, 135.2, 128.7, 128.43, 128.41, 127.5, 127.3, 109.5, 109.1, 109.0, 108.9, 71.3, 60.6, 58.1, 56.7, 56.5, 52.39, 52.37, 52.0, 50.2, 37.1, 35.5; MS (ESI): m/z 449.3 (M+Na)$^+$.

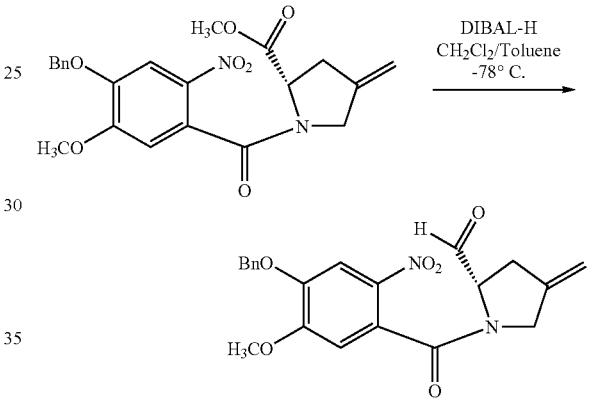

To a solution of the ester (3.15 g, 7.39 mmol) in anhydrous dichloromethane (9 mL) and toluene (27 mL) was added dibal-H (15 mL, 1.0 M in toluene) dropwise via a syringe pump in 30 minutes at −78° C. The mixture was continued to stir at −78° C. for 2 hours and TLC (hexanes/AcOEt, 1:1.5) showed all the starting material consumed. The reaction was quenched with methanol (0.3 mL, 7.4 mmol) at −78° C. and 5% HCl (20 mL) was added followed by addition of AcOEt (50 mL). The dry ice/acetone bath was removed and the mixture was warmed to 0° C. and stirred for 15 minutes. The aqueous layer was extracted with AcOEt twice and the combined organic layers were washed with cold 5% HCl and brine, dried over anhydrous sodium sulfate. It was filtered through celite and the solvents were removed. The residue was purified by flash chromatography (Hexanes/AcOEt, 1:1, 1:1.5, 1:2, 1:3, 1:5, 100% AcOEt) to give (2S)-4-(methylene)-1-[5-methoxy-2-nitro-4-(phenylmethoxy)benzoyl]-2-pyrrolidinecarboxaldehyde as a fluffy yellow solid (2.69 g, y=92%). $^1$H NMR (400 Hz, CDCl$_3$): the compound appears as a pair of distinct rotamers. δ 9.75 (s, 0.7H), 9.32 (s, 0.3H), 7.76 (s, 0.7H), 7.69 (s, 0.3H), 7.45-7.31 (m, 5H), 6.85 (s, 0.7H), 6.80 (s, 0.3H), 5.19-4.82 (m, 4.7H), 4.56 (d, J=16 Hz, 0.3H), 4.14-3.79 (m, 5H), 2.99-2.68 (m, 2H); $^{13}$C NMR (400 Hz, CDCl$_3$): 198.3, 197.1, 167.1, 155.0, 154.6, 148.4, 141.3, 140.4, 137.2, 135.2, 128.7, 128.5, 128.4, 127.5, 126.9, 126.6, 109.8, 109.4, 109.3, 109.2, 109.1, 71.3, 66.6, 64.3, 56.7, 56.6, 52.2, 50.6, 33.2, 31.9; MS (ESI): m/z 419.2 (M+Na)$^+$.

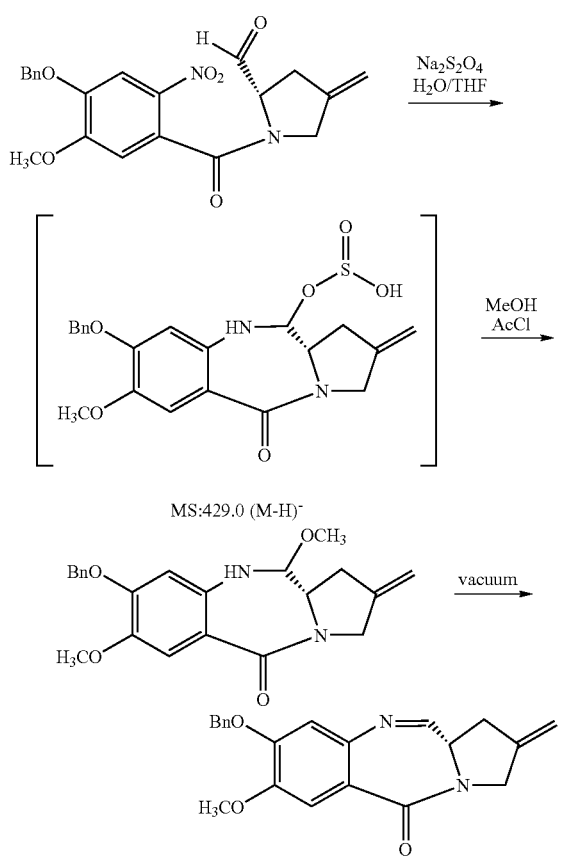

Procedure 1: To a solution of (2S)-4-(methylene)-1-[5-methoxy-2-nitro-4-(phenylmethoxy)benzoyl]-2-pyrrolidinecarboxaldehyde (1.0 equivalent) in THF/H$_2$O (v/v, 1.7:1, 0.03 M) was added sodium hydrosulfite (5~8 equivalent) in portions within 2 minutes at room temperature. The mixture was further stirred for 6~20 hours and monitored by TLC (hexanes/AcOEt 1:2 and CH$_2$Cl$_2$/MeOH 5:1). After the aldehyde was almost consumed, the reaction was quenched with methanol (about same volume as THF used). The solvents were removed by rotary evaporation in vacuo (temperature <40° C.) and the remainder solid was put on high vacuum to make it completely dry. The solid was suspended in anhydrous methanol (0.03 M) and AcCl (8~10 equivalent) was added dropwise at room temperature. After stirred for 15 minutes, the cloudy solution was filtered and the solid was washed with anhydrous methanol. The clear yellow filtrate was stirred at room temperature for 1 to 2 hours and was quenched with saturated sodium bicarbonate. After most of the methanol was removed by rotary evaporation, the remainder was diluted with dichloromethane and water. The aqueous layer was extracted with AcOEt. The combined organic layers were dried over anhydrous sodium sulfate and filtered. The solvents were removed and the residue was purified by flash chromatography (hexanes/AcOEt, 1:3, 1:5) to give (11aS)-7-methoxy-2-methylene-8-(phenylmethoxy)-1,2,3,11a-tetrahydro-5H-pyrrolo[2,1-c][1,4]benzodiazepin-5-one in 70% to 85% yield. The NMR spectra are consistent with the literature reported. MS (ESI): m/z 371.2 (M+Na)$^+$. MS (ESI, with CH$_3$OH): m/z 403.3 (M+CH$_3$OH+Na)$^+$. MS (ESI, with H$_2$O): m/z 389.2 (M+H$_2$O+Na)$^+$.

Procedure 2: To a solution of (2S -4-(methylene)-1-[5-methoxy-2-nitro-4-(phenylmethoxy)benzoyl]-2-pyrrolidinecarboxaldehyde (1.0 equivalent) in MeOH/H$_2$O (v/v, 3.2:1, 0.03 M) was added sodium hydrosulfite (6~8 equivalent) in portions within 2 minutes at room temperature, followed by addition of sodium hydrosulfate (0.5~1.0 equivalent). The mixture was further stirred for 12~20 hours and monitored by TLC (hexanes/AcOEt 1:2 and CH$_2$Cl$_2$/MeOH 5:1). After the intermediate [MS (ESI): 459.0 (M–H)$^-$] was almost consumed, the reaction was quenched with saturated sodium bicarbonate to pH 5~6. The solvents were removed by rotary evaporation in vacuo (temperature <40° C.) and the remainder solid was put on high vacuum to make it completely dry. The solid was suspended in anhydrous methanol (0.03 M) and AcCl (8~10 equivalent) was added dropwise at room temperature. After stirred for 15 minutes, the cloudy solution was filtered and the solid was washed with anhydrous methanol. The clear yellow filtrate was stirred at room temperature for 1 to 2 hours and was quenched with saturated sodium bicarbonate. After most of the methanol was removed by rotary evaporation, the remainder was diluted with dichloromethane and water. The aqueous layer was extracted with AcOEt. The combined organic layers were dried over anhydrous sodium sulfate and filtered. The solvents were removed and the residue was purified by flash chromatography (hexanes/AcOEt, 1:3, 1:5) to give (11aS)-7-methoxy-2-methylene-8-(phenylmethoxy)-1,2,3,11a-tetrahydro-5H-pyrrolo[2,1-c][1,4]benzodiazepin-5-one in 65% to 80% yield.

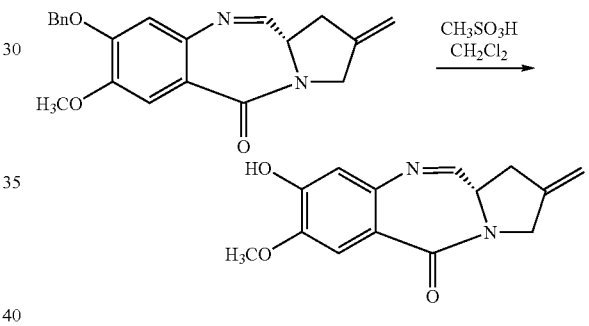

To a solution of the starting material (98 mg, 0.28 mmol) in anhydrous dichloromethane (2 mL) was added a freshly mixed solution of methanesulfonic acid (2 mL) in anhydrous dichloromethane (4 mL) at room temperature. The mixture was stirred at room temperature for 1.5 hours and was poured on ice (~30 g), quenched with saturated NaHCO$_3$ and diluted with dichloromethane. The aqueous layer was extracted with dichloromethane once and the combined organic layers were dried over anhydrous sodium sulfate, filtered and the solvents were removed. The residue was purified by flash chromatography (CH$_2$Cl$_2$/MeOH, 15:1) to give the product as a yellow solid (29 mg). The above aqueous layer was stirred at room temperature overnight and extracted with dichloromethane and AcOEt subsequently. The combined dichloromethane and AcOEt were dried over anhydrous sodium sulfate, filtered and the solvents were removed to give (11aS)-8-hydroxy-7-methoxy-2-methylene-1,2,3,11a-tetrahydro-5H-pyrrolo[2,1-c][1,4]benzodiazepin-5-one (25 mg). The total yield is 74%. $^1$H NMR (400 Hz, CDCl$_3$): δ 7.65 (d, J=4.8 Hz, 1H), 7.48 (s, 1H), 6.87 (s, 1H), 6.35 (bs, 1H), 5.17 (t, J=1.6 Hz, 1H), 5.14 (7, J=1.6 Hz, 1H), 4.26 (s, 2H), 3.93 (s, 3H), 3.87-3.83 (m, 1H), 3.12-3.05 (m, 1H), 2.91 (d, J=16 Hz, 1H); MS (ESI): m/z 281.0 (M+Na)$^+$. MS (ESI, with water): m/z 258.9 (M+H)$^+$, m/z 299.1 (M+H$_2$O+Na)$^+$.

EXAMPLE 12

8,8'-[5-acetylthiomethyl-1,3-benzenediylbis(methylenoxy)]-bis[(S)-2-methylene-7-methoxy-1,2,3,11a-tetrahydro-5H-pyrrolo[2,1-c][1,4]benzodiazepin-5-one]

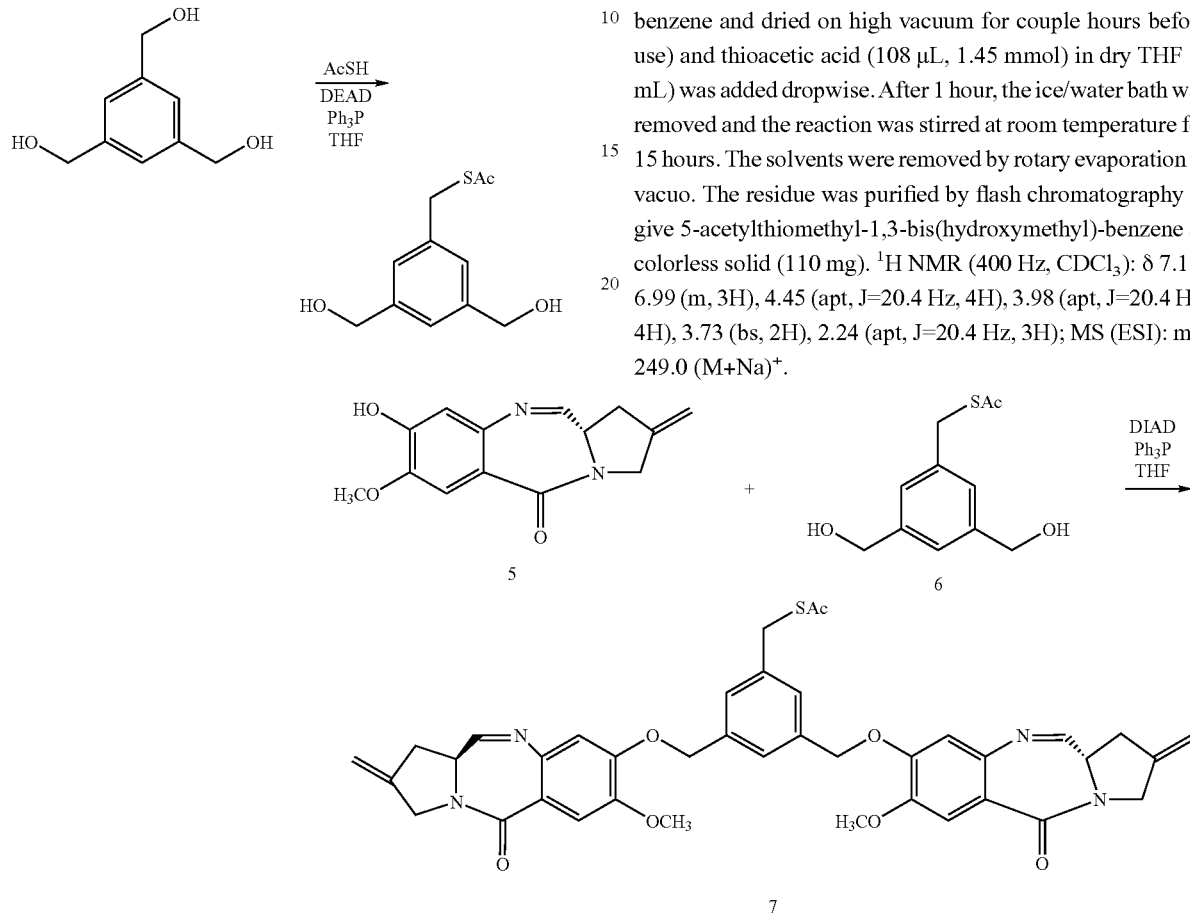

To a solution of triphenylphosphine (577 mg, 2.2 mmol) in anhydrous THF (5 mL) was added diethyl azodicarboxylate (2.2 M in toluene, 791 µL, 1.7 mmol) dropwise at 0° C. After stirred at 0° C. for 50 minutes, a solution of 1,3,5-tri(hydroxymethyl)benzene (269 mg, 1.6 mmol, prepared by reduction of trimethyl 1,3,5-benzenetricarboxylate with lithium aluminum hydride in THF, co-evaporated with dry benzene and dried on high vacuum for couple hours before use) and thioacetic acid (108 µL, 1.45 mmol) in dry THF (4 mL) was added dropwise. After 1 hour, the ice/water bath was removed and the reaction was stirred at room temperature for 15 hours. The solvents were removed by rotary evaporation in vacuo. The residue was purified by flash chromatography to give 5-acetylthiomethyl-1,3-bis(hydroxymethyl)-benzene as colorless solid (110 mg). $^1$H NMR (400 Hz, CDCl$_3$): δ 7.13-6.99 (m, 3H), 4.45 (apt, J=20.4 Hz, 4H), 3.98 (apt, J=20.4 Hz, 4H), 3.73 (bs, 2H), 2.24 (apt, J=20.4 Hz, 3H); MS (ESI): m/z 249.0 (M+Na)$^+$.

To a solution of triphenylphosphine (28 mg, 0.1 mmol) in anhydrous THF (0.3 mL) was added disopropyl azodicarboxylate (19 µL, 0.09 mmol) dropwise at 0° C. After stirred at 0° C. for 35 minutes, a solution of (11aS)-8-hydroxy-7-methoxy-2-methylene-1,2,3,11a-tetrahydro-5H-pyrrolo[2,1-c][1,4]benzodiazepin-5-one, compound 5, (18 mg, 0.07 mmol, co-evaporated with dry benzene and dried on high vacuum for couple hours before use) in dry THF (0.2 mL) was added. The mixture was continued to stir for 10 minutes before 5-acetylthiomethyl-1,3-bis(hydroxymethyl)-benzene, compound 6, (6.6 mg, 0.03 mmol, co-evaporated with dry benzene and dried on high vacuum for couple hours before use) in dry THF (0.2 mL) was added. The reaction mixture was allowed to stir at 0° C. for 35 minutes. The ice/water bath was removed and the solution was stirred at room temperature for 21 hours. The solvents were removed by rotary evaporation in vacuo. The residue was purified by flash chromatography to furnish the crude product which was further purified by preparative HPLC (C18 column, CH$_3$CN/H$_2$O) to give 0.7 mg of 8,8'-[5-acetylthiomethyl-1,3-benzenediylbis(methylenoxy)]-bis[(S)-2-methylene-7-methoxy-1,2,3,11a-tetrahydro-5H-pyrrolo[2,1-c][1,4]benzodiazepin-5-one], compound 7. MS (ESI, with H$_2$O): m/z 765.3 (M+2H$_2$O+Na)$^+$, 747.3 (M+H$_2$O+Na)$^+$, 729.2 (M+Na)$^+$, 707.3 (M+H)$^+$, 663.2 (M−Ac)$^-$.

EXAMPLE 13
Bis-{2-[(S)-2-methylene-7-methoxy-5-oxo-1,3,11a-tetrahydro-5H-pyrrolo[2,1-c][1,4]benzodiazepin-8-yloxy]-ethyl}-carbamic acid tert-butyl ester
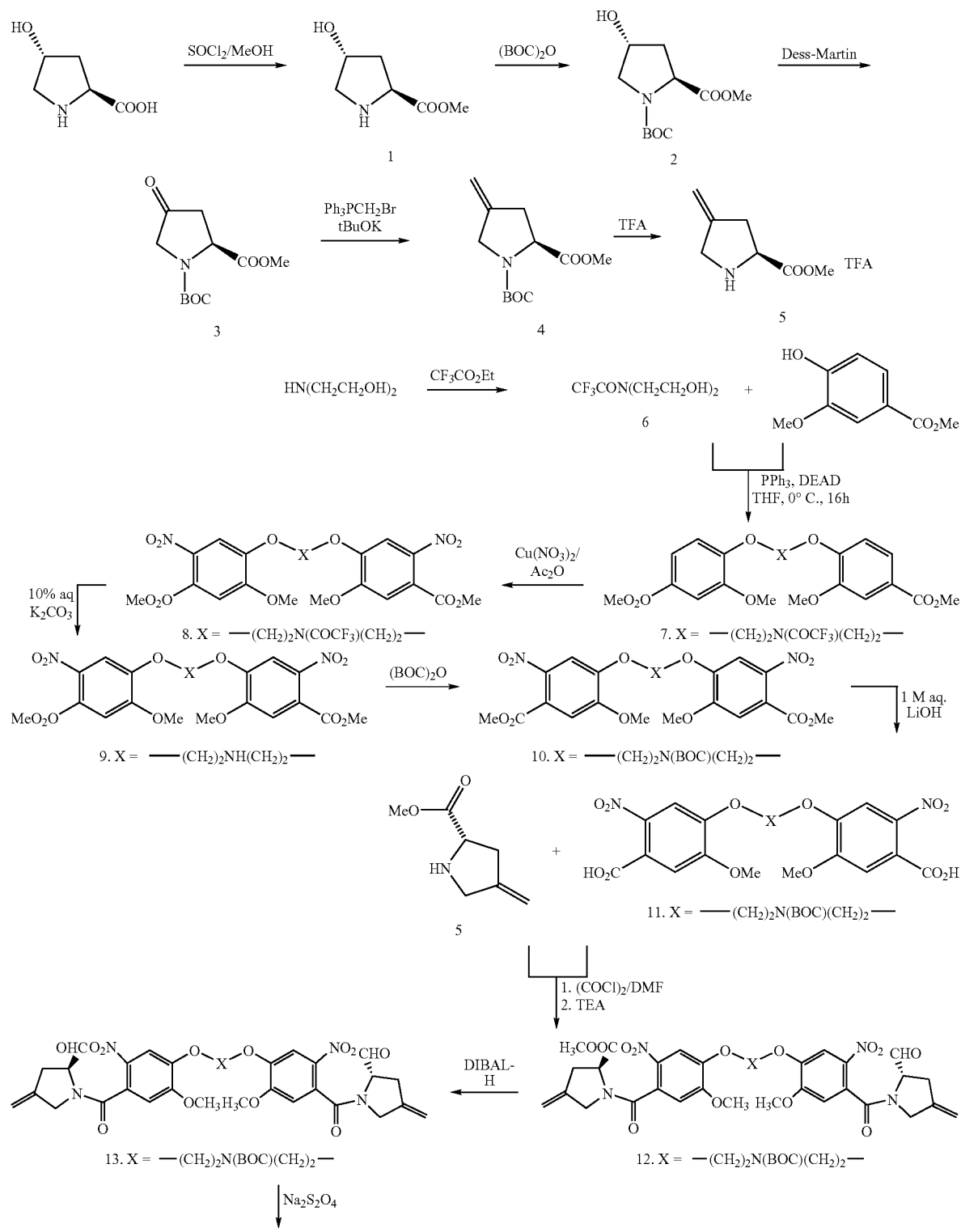
Scheme 1

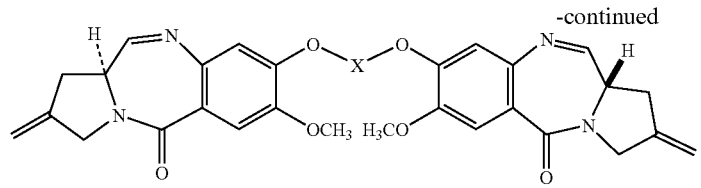

-continued

14. X = —(CH$_2$)$_2$N(BOC)(CH$_2$)$_2$—

Compound 1. Thionyl chloride (5.6 mL, 76.3 mmol) was added dropwise to dry methanol (76 mL) at −20° C., following by addition of trans-4-hydroxy-L-proline (5.0 g, 38.1 mmol). The resulting mixture was allowed to warm to rt and stirred for 20 h. The solvent was removed under reduced pressure, and the residue was further dried under high vacuum to provide trans-4-hydroxy-L-proline methyl ester 1 as a white solid: $^1$HNMR (300 MHz, DMSO-d$_6$) δ 2.18-2.23 (m, 2H), 3.06 (m, 1H), 3.32-3.36 (m, 2H), 3.76 (s, 3H), 4.42 (br. s, 1H), 4.48 (dd, J=5.4, 8.1 Hz, 1H), 5.56 (br. s, 1H); EIMS m/z 146 ([M]$^+$+1).

Compound 2. To a solution of trans-4-hydroxy-L-proline methyl ester 1 (4.48 g, 30.9 mmol) and sodium bicarbonate (1.56 g, 18.5 mmol) in anhydrous DMF (42 mL) was added solution of (BOC)$_2$O in DMF (20 mL) at 0° C. under argon. After stirring for an overnight at rt, the reaction was quenched by the addition of 100 mL H$_2$O at 0° C., and extracted with EtOAc (4×80 mL). The combined organic layer was washed with brine (100 mL), dried (MgSO$_4$), filtered and concentrated with rotavapor. The residue was purified by flash chromatography (silica gel, 1:1 hexanes/EtOAc) to give N—BOC protected trans-4-hydroxy-L-proline methyl ester 2 as colorless oil: $^1$HNMR (300 MHz, CDCl$_3$, rotamers) δ 1.38 and 1.43 (2×s, 9H), 2.04-2.07 (m, 1H), 2.23-2.27 (m, 2H), 3.54-3.63 (m, 2H), 3.70 (s, 3H), 4.34-4.38 (m, 1H), 4.46 (br. s, 1H).

Compound 3. (Franco Manfre, Jean-Marc Kern, and Jean-Francois Biellmann *J. Org. Chem.* 1992, 57, 2060-2065). N—BOC protected trans-4-hydroxy-L-proline methyl ester compound 2 (3.24 g, 13.2 mmol) was dissolved in CH$_2$Cl$_2$ (132 mL) and cooled to 0° C. Pyridine and Dess-Martin periodinane were added and stirring was continued until TLC showed no SM left. The reaction mixture was diluted with CH$_2$Cl$_2$, washed with 10% aq. Na$_2$S$_2$O$_3$ (3×50 mL), 1N aq. HCl (50 mL), sat. aq. NaHCO$_3$ (50 mL), brine (50 mL), dried over MgSO$_4$, filtered and concentrated. Purification of the residue by flash chromatography (silica gel, 7:3 hexanes/EtOAc) gave N—BOC protected 4-oxo-L-proline methyl ester 3 as light yellow oil: $^1$HNMR (300 MHz, CDCl$_3$, rotamers) δ 1.44 (s, 9H), 2.53-2.57 (m, 1H), 2.85-2.96 (m, 1H), 3.72 and 3.74 (2×s, 3H), 3.85-3.87 (m, 2H), 4.67-4.77 (m, 1H).

Compound 4. (Kuei-Ying Lin, Mark Matteucci U.S. Pat. No. 5,414,077) A solution of potassium-t-butoxide (2.51 g, 22.3 mmol) in anhydrous THF (40 mL) was added to a suspension of methyltriphenylphosphonium bromide (7.99 g, 22.3 mmol) in THF (40 mL) at 0° C. The resulting yellow ylide suspension was stirred at 0° C. for 2 h before the addition of the solution of N—BOC protected 4-oxo-L-proline methyl ester 3 (2.72 g, 11.2 mmol) in THF (32 mL). After stirring at rt for 1 h, the reaction mixture was diluted with EtOAc (100 mL), washed with H$_2$O (80 mL), brine (80 mL), dried (MgSO$_4$), and concentrated. Purification of the residue by flash chromatography (silica gel, 9:1 hexanes/EtOAc) yielded N—BOC protected 4-methylene-L-proline methyl ester, compound 4, as colorless oil: $^1$HNMR (300 MHz, CDCl$_3$, rotamers) δ 1.40 and 1.45 (2×s, 9H), 2.58-2.62 (m, 1H), 2.88-2.98 (m, 1H), 3.69 and 3.70 (2×s, 3H), 4.03-4.06 (m, 2H), 4.36-4.49 (m, 1H), 4.97-4.99 (m, 2H); EIMS m/z 264 ([M]$^+$+Na).

Compound 5. N—BOC protected 4-methylene-L-proline methyl ester, compound 4, (0.8 g, 3.31 mmol) was dissolved in CH$_2$Cl$_2$ (6.5 mL) and cooled to 0° C. A solution of trifluoroacetic acid (6.5 mL) in CH$_2$Cl$_2$ (6.5 mL) was added dropwise and the resulting mixture was stirred at rt for 1.5 h. After removal of volatile solvents with rotavapor, the brown residue was dissolved in 10 mL H$_2$O, washed with Et$_2$O (3×5 mL). Aqueous solution was concentrated, which was further dried under high vacuum to yield 4-methylene-L-proline methyl ester 5 as TFA salt: $^1$HNMR (300 MHz, CDCl$_3$, rotamers) δ 2.83-2.87 (m, 1H), 3.05-3.11 (m, 1H), 3.80 and 3.81 (2×s, 3H), 4.00-4.10 (m, 2H), 4.55 (dd, J=5.7, 5.7 Hz, 1H), 5.17-5.21 (m, 2H); $^{13}$CNMR δ 34.0, 49.1, 53.8, 59.3, 111.7, 137.6, 169.8; EIMS m/z 142 ([M]$^+$+1).

Compound 6. (Kamal, A.; et al *J. Med. Chem.* 2002, 45, 4679-4688) Diethanolamine (3.57 g, 34 mmol) was dissolved in methanol (20 mL) and treated with Et$_3$N (4.7 mL, 34 mmol) and ethyl trifluoroacetate (4.90 g, 34 mmol) for 20 h at rt, followed by adding another 1 mL CF$_3$COOEt. After another 20 h, removal of volatile solvents under high vacuum yielded N-trifluoroacetyl-diethanolamine compound 6 as light yellow oil, which was used without further purification.

Compound 7. Diethyl azodicarboxylate (7.66 g, 44 mmol) was added dropwise to a stirred solution of methyl vanillate (7.30 g, 40.1 mmol) and triphenylphosphine (15.67 g, 59.7 mmol) in anhydrous THF (57 mL) at 0° C., and the resulting mixture was stirred for 1 h at this temperature followed by addition of a solution of N-trifluoroacetyl-diethanolamine 6 (7.30 g, 40.1 mmol) in anhydrous THF (20 mL). After stirring for an overnight at rt, the reaction was quenched with H$_2$O (100 mL), and extracted with Et$_2$O (3×80 mL). The combined Et$_2$O layers were washed with brine (100 mL), dried (MgSO$_4$), and concentrated. Purification of the residue by flash chromatography (silica gel, 8:2 to 7:3 hexanes/EtOAc) yielded N-trifluorocetyl-N,N-di[2-(4-methoxycarbonyl-2-methoxy-phenoxy)ethyl]amine, compound 7, as a white solid: $^1$HNMR (300 MHz, CDCl$_3$) δ 3.81 (s, 3H), 3.84 (s, 3H), 3.87 (s, 3H), 3.88 (s, 3H), 4.04-4.08 (m, 4H), 4.28-4.32 (m, 4H), 6.84 and 6.85 (2×d, J=6.3 Hz, 2H), 7.50 and 7.51 (2×d, J=1.5 Hz, 2H), 7.61 (dd, J=1.5, 6.3 Hz, 2H).

Compound 8. Solid Cu(NO$_3$)$_2$.xH$_2$O (2.33 g, 12.41 mmol) was added to a stirred solution of N-trifluorocetyl-N,N-di[2-(4-methoxycarbonyl-2-methoxy-phenoxy)ethyl]amine 7 (2.62 g, 4.96 mmol) in acetic anhydride (50 mL) at 0° C. The reaction mixture was stirred at 0° C. for 1 h and rt for 2 h, then poured into 200 mL ice-water. Stirring was continued for another 1 h. The resulting yellow precipitate was collected by filtration. Further purification with flash chromatography (silica gel, 6:4 hexanes/EtOAc) yielded N-trifluorocetyl-N,N-di[2-(4-methoxycarbonyl-2-methoxy-5-nitro-phenyloxy)ethyl]amine, compound 8, as light yellow solid: $^1$HNMR (300 MHz, CDCl$_3$) δ 3.86 (s, 3H), 3.88 (s, 3H), 3.886 (s, 3H), 3.890 (s, 3H), 4.04-4.09 (m, 4H), 4.30-4.35 (m, 4H), 6.98 and 6.99 (2×s, 2H), 7.37 and 7.40 (2×s, 2H).

Compound 9. A solution of N-trifluorocetyl-N,N-di[2-(4-methoxycarbonyl-2-methoxy-5-nitro-phenyloxy)ethyl]amine 8 (2.58 g, 4.16 mmol) in THF-MeOH (1:2, 48 mL) was treated with 10% aq. K$_2$CO$_3$ (16 mL) at rt for 12 h. After removal of volatile with rotavapor, the residue was diluted with 100 mL H$_2$O, extracted with EtOAc (3×100 mL). The combined EtOAc layers were washed with brine (100 mL), dried (MgSO$_4$), and concentrated yielding N,N-di[2-(4-methoxycarbonyl-2-methoxy-5-nitro-phenyloxy)ethyl]amine, compound 9, at yellow solid, which was used without further purification: $^1$HNMR (300 MHz, CDCl$_3$) δ 3.17 (t, J=3.9 Hz, 4H), 3.89 (s, 6H), 3.93 (s, 6H), 4.19 (t, J=3.9 Hz, 4H), 7.05 (s, 2H), 7.47 (s, 2H).

Compound 10. N,N-di[2-(4-methoxycarbonyl-2-methoxy-5-nitrophenyl-oxy)ethyl]amine, compound 9, (crude, 4.16 mmol) and NaHCO$_3$ (210 mg, 2.50 mmol) was suspended in THF, and treated with (BOC)$_2$O (999 mg, 4.58 mmol) at 0° C. and stirring was continued at rt for 3 h. After removal of THF, the residue was partitioned between H$_2$O and EtOAc (100/100 mL). Aqueous layer was further extracted with EtOAc (2×50 mL). The combined EtOAc layers were washed with brine (80 mL), dried (MgSO$_4$), and concentrated. Purification of the residue by flash chromatography (silica gel, 6:4 hexanes/EtOAc) yielded N-tert-butoxycarbonyl-N,N-d i[2-(4-methoxycarbonyl-2-methoxy-5-nitro-phenyloxy)ethyl]amine, compound 10, as light yellow solid: $^1$HNMR (300 MHz, CDCl$_3$) δ 1.44 (s, 9H), 3.77 (m, 4H), 3.83, 3.86 and 3.87 (3×s, 12H), 4.20 and 4.26 (2×t, J=3.9 Hz, 4H), 6.97 and 6.99 (2×s, 2H), 7.36 and 7.40 (2×s, 2H); EIMS m/z 646 ([M]$^+$+Na).

Compound 11. N-tert-butoxycarbonyl-N,N-di[2-(4-methoxycarbonyl-2-methoxy-5-nitro-phenyloxy)ethyl]amine, compound 10 (2.11 g, 3.39 mmol) was suspended in THF-MeOH—H$_2$O (3:1:1, 65 mL) and treated with 1M aq. LiOH (14 mL) at rt for 3 h. After removal of volatile solvents, the residue was diluted with H$_2$O (25 mL). The resulting aqueous solution was acidified to pH~1 with concentrate HCl. The precipitated N-tert-butoxycarbonyl-N,N-d[2-(4-carboxy-2-methoxy-5-nitro-phenyloxy)ethyl]amine, compound 11, was collected by filtration, washed with H$_2$O, and further dried under high vacuum: $^1$HNMR (300 MHz, CDCl$_3$, rotamers) δ 1.39 (s, 9H), 3.70 (m, 4H), 3.88 and 3.89 (2×s, 6H), 4.29 (m, 4H), 7.29 and 7.31 (2×s, 2H), 7.63 (s, 2H), 13.60 (br. s, 2H); $^{13}$CNMR 527.8, 46.2 and 46.6, 56.3 and 56.4, 67.2, 79.2, 107.9 and 108.0, 111.3, 141.4 and 141.5, 149.1, 151.7, 154.5, 165.9; HRMS m/z calcd for C$_{25}$H$_{29}$N$_3$O$_{14}$Na 618.1547, found 618.1552 ([M]$^+$+Na).

Compound 12. A catalytic amount of DMF (2 drops) was added to a solution of N-tert-butoxycarbonyl-N,N-d[2-(4-carboxy-2-methoxy-5-nitro-phenyloxy)ethyl]amine 11 (194 mg, 0.33 mmol) and oxalyl chloride (72.7 µL, 0.81 mmol) in anhydrous THF (6.5 mL) and the resulting mixture was stirred at rt for an overnight. Excess THF and oxalyl chloride was removed with rotavapor. The actyl chloride was resuspended in fresh THF (4 mL) and was added dropwise to a solution of 4-methylene-L-proline methyl ester 5 (206.7 mg, 0.81 mmol), Et$_3$N (0.19 mL, 1.39 mmol), and H$_2$O (0.4 mL) in THF (1 mL) at 0° C. under argon atmosphere. The reaction mixture was allowed to warm to rt and stirring was continued for 2 h. After removal of THF, the residue was partitioned between H$_2$O and EtOAc (10/10 mL). The aqueous layer was further extracted with EtOAc (2×8 mL). The combined organic layers were washed with brine (10 mL), dried (MgSO$_4$) and concentrated. Purification of the residue by flash chromatography (silica gel, 2:8 hexanes/EtOAc) yielded bis{2-[5-methoxy-2-nitro-4-[(S)-4-methylene-2-methoxycarbonyl-1-pyrrolidinylcarbonyl]-phenyloxy]-ethyl}-carbamic acid tert-butyl ester 12 as light yellow oil (rotamers): $^1$HNMR (300 MHz, CDCl$_3$, rotamers) δ 1.46 (s, 9H), 2.68-2.75 (m, 2H), 2.99-3.10 (m, 2H), 3.60-4.28 (m, 24H), 4.56-5.12 (m, 6H), 6.78-6.83 (m, 2H), 7.63-7.71 (m, 2H); EIMS m/z 864 ([M]$^+$+Na).

Compound 13. To a vigorously stirred solution of bis{2-[5-methoxy-2-nitro-4-[(S)-4-methylene-2-methoxycarbonyl-1-pyrrolidinylcarbonyl]phenyloxy]-ethyl}-carbamic acid tert-butyl ester 12 (100 mg, 0.12 mmol) in anhydrous toluene (2.4 mL) was added dropwise solution of DIBAL-H (480 µL of a 1M solution in toluene) at −78° C. under argon atmosphere. After the mixture was stirred for an additional 45 min, excess reagent was decomposed by addition of five drops of methanol followed by 5% HCl (4 mL). The resulting mixture was allowed to warm to 0° C. Layers were separated and the aqueous layer was further extracted with CH$_2$Cl$_2$ (3×3 mL). Combined organic layers were washed with brine, dried (MgSO$_4$) and concentrated. Purification of the residue by flash chromatography (silica gel, 95:5 CHCl$_3$/MeOH) yielded bis{2-[5-methoxy-2-nitro-4-[(S)-4-methylene-2-formyl-1-pyrrolidinylcarbonyl]phenyloxy]-ethyl}-carbamic acid tert-butyl ester 13 as light yellow oil (84 mg, 91%).

Compound 14. A mixture of bis{2-[5-methoxy-2-nitro-4-[(S)-4-methylene-2-formyl-1-pyrrolidinylcarbonyl]phenyloxy]-ethyl}-carbamic acid tert-butyl ester 13 (180 mg, 0.23 mmol), Na$_2$S$_2$O$_4$ (1.84 mmol, 8 equiv), 3.5 mL THF, and 2.2 mL H$_2$O was stirred at rt for 20 h. Solvents were removed under high vacuum. The residue was re-suspended in MeOH (30 mL), and AcCl was added dropwise until pH~2. The resulting mixture was stirred at rt for 1 h. The reaction was work-up by removing most of MeOH, then diluted with EtOAc (25 mL). The EtOAc solution was washed with sat. aq. NaHCO$_3$, brine, dried (MgSO$_4$), and concentrated. Purification of the residue by flash chromatography (silica gel, 97:3 CHCl$_3$/MeOH) yielded bis-{2-[(S)-2-methylene-7-methoxy-5-oxo-1,3,11a-tetrahydro-5H-pyrrolo[2,1-c][1,4]benzodiazepin-8-yloxy]-ethyl}-carbamic acid tert-butyl ester 14 as white solid (86 mg, 50%).

EXAMPLE 14

(11aS)-7-(5-bromopentyloxy)-2-methylene-1,2,3,11a-tetrahydro-5H-pyrrolo[2,1-c][1,4]benzodiazepin-5-one

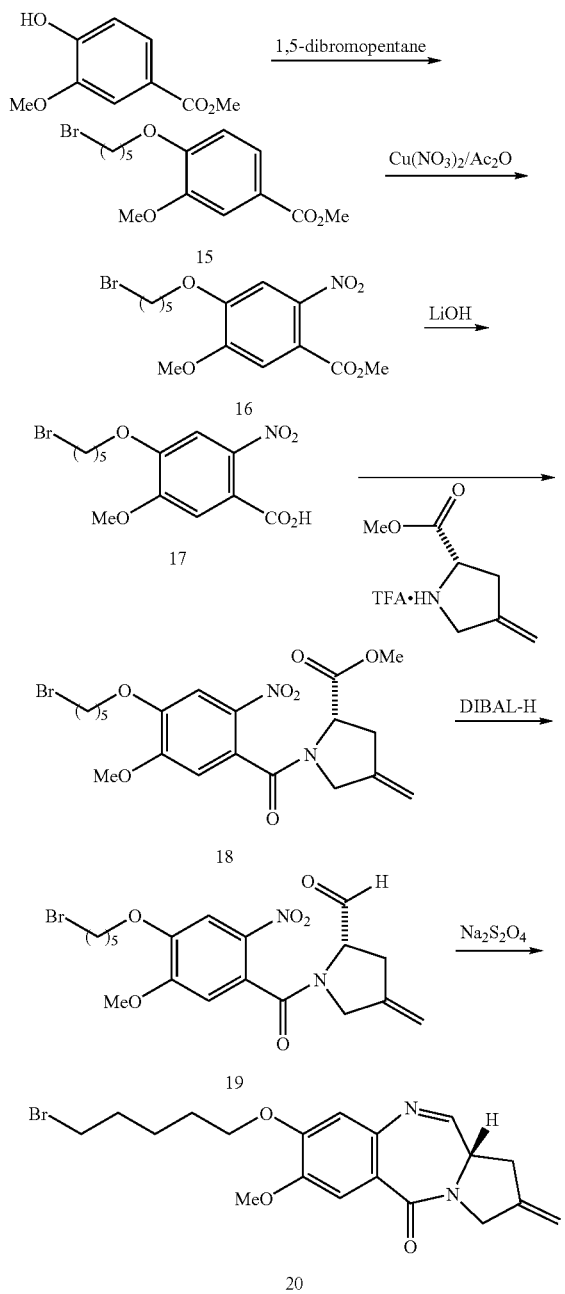

Compound 15. To a solution of methyl vanillate (9.109 g, 50 mmol) in acetone (200 mL) were added K₂CO₃ (27.64 g, 200 mmol) and 1,5-dibromopentane (20.4 mL, 150 mmol). The resulting mixture was heated to reflux. After 6 h, TLC showed no starting material left. The mixture was cooled to rt, and the solid was removed by filtration. The filtrate was concentrated. Purification by flash chromatography (silica gel, 8:2 hexanes/EtOAc) afforded 4-(5-bromopentyloxy)-3-methoxy-benzoic acid methyl ester 15 as white solid (13.65 g, 82%): ¹HNMR (300 MHz, CDCl₃) δ 1.60-1.66 (m, 2H), 1.85-1.97 (m, 4H), 3.42 (t, J=5.0 Hz, 2H), 3.87 (s, 3H), 3.89 (s, 3H), 4.06 (t, J=5.0 Hz, 2H), 6.85 (d, J=6.3 Hz, 1H), 7.52 (d, J=1.5 Hz, 1H), 7.63 (dd, J=6.3, 1.5 Hz, 1H); EIMS m/z 353 and 355 ([M]⁺+Na).

Compound 16. Solid Cu(NO₃)₂.xH₂O (3.64 g, 19.42 mmol) was added to a stirred solution of 4-(5-bromopentyloxy)-3-methoxy-benzoic acid methyl ester 15 (5.36 g, 16.18 mmol) in acetic anhydride (81 mL) at 0° C. The reaction mixture was stirred at 0° C. for 1 h and rt for 2 h, then poured into 200 mL ice-water. Stirring was continued for another 1 h. The resulting yellow precipitate was collected by filtration and washed with water. Further dried under high vacuum yielded 4-(5-bromopentyloxy)-5-methoxy-2-nitro-benzoic acid methyl ester compound 16 as light yellow solid (5.98 g), which was used directly to the next step: ¹HNMR (300 MHz, CDCl₃) δ 1.59-1.70 (m, 2H), 1.85-1.98 (m, 4H), 3.43 (t, J=5.1 Hz, 2H), 3.89 (s, 3H), 3.94 (s, 3H), 4.08 (t, J=4.8 Hz, 2H), 7.05 (s, 1H), 7.42 (s, 1H). EIMS m/z 398 and 400 ([M]⁺+Na).

Compound 17. 4-(5-Bromopentyloxy)-5-methoxy-2-nitro-benzoic acid methyl ester 16 (5.98 g, 15.9 mmol) was suspended in THF-MeOH—H₂O (3:1:1, 157 mL) and treated with 1M aq. LiOH (31 mL) at rt for 5 h. After removal of volatile solvents, the residue was diluted with H₂O (70 mL). The resulting aqueous solution was acidified to pH~2 with concentrate HCl. The precipitated 4-(5-bromopentyloxy)-5-methoxy-2-nitro-benzoic acid 17 was collected by filtration, washed with H₂O, and further dried under high vacuum (5.47 g): ¹HNMR (300 MHz, CDCl₃) δ 1.64-1.68 (m, 2H), 1.87-1.98 (m, 4H), 3.43 (t, J=4.8 Hz, 2H), 4.08 (s, 3H), 4.10 (t, J=5.1 Hz, 2H), 7.21 (s, 1H), 7.35 (s, 1H), 13.60 (br. s, 1H); EIMS m/z 384 and 386 ([M]⁺+Na).

Compound 18. A catalytic amount of DMF (2 drops) was added to a solution of 4-(5-bromopentyloxy)-5-methoxy-2-nitro-benzoic acid 17 (270 mg, 0.74 mmol) and oxalyl chloride (80 μL, 0.89 mmol) in anhydrous THF (7.5 mL) and the resulting mixture was stirred at rt for an overnight. Excess THF and oxalyl chloride were removed with rotavapor. The acetyl chloride was resuspended in fresh THF (6 mL) and was added dropwise to a solution of 4-methylene-L-proline methyl ester 5 (228 mg, 0.89 mmol), Et₃N (0.32 mL, 2.31 mmol), and H₂O (0.15 mL) in THF (1.5 mL) at 0° C. under argon atmosphere. The reaction mixture was allowed to warm to rt and stirring was continued for 4 h. After removal of THF, the residue was partitioned between H₂O and EtOAc (20/20 mL). The aqueous layer was further extracted with EtOAc (3×10 mL). The combined organic layers were washed with brine (20 mL), dried (MgSO₄) and concentrated. Purification of the residue by flash chromatography (silica gel, 6:4 hexanes/EtOAc) yielded 1-[4-(5-bromopentyloxy)-5-methoxy-2-nitro-benzoyl]-4-methylene-L-proline methyl ester 18 as light yellow oil (rotamers): ¹HNMR (300 MHz, CDCl₃, rotamers) δ 1.62-1.68 (m, 2H), 1.86-1.98 (m, 4H), 2.64-2.75 (m, 1H), 2.99-3.08 (m, 1H), 3.43 (t, J=5.1 Hz, 2H), 3.59-3.96 (m, 7H), 4.05-4.21 (m, 3H), 4.57-4.61 and 4.90-5.12 (m, 3H), 6.80 and 6.83 (2 s, 1H), 7.64 and 7.67 (2 s, 1H); EIMS m/z 507 and 509 ([M]⁺+Na).

Compound 19. To a vigorously stirred solution of 1-[4-(5-bromopentyloxy)-5-methoxy-2-nitro-benzoyl]-4-methylene-L-proline methyl ester 18 (61 mg, 0.12 mmol) in anhydrous toluene —CH$_2$Cl$_2$ (3:1, 2.5 mL) was added dropwise solution of DIBAL-H (188 µL of a 1M solution in toluene) at −78° C. under argon atmosphere. After the mixture was stirred for an additional 45 min, excess reagent was decomposed by addition of three drops of methanol followed by 5% HCl (2 mL). The resulting mixture was allowed to warm to 0° C. Layers were separated and the aqueous layer was further extracted with CH$_2$Cl$_2$ (3×2 mL). Combined organic layers were washed with brine, and dried (MgSO$_4$) and concentrated. Purification of the residue by flash chromatography (silica gel, 1:1 hexanes/EtOAc) yielded (S)-1-[4-(5-bromopentyloxy)-5-methoxy-2-nitro-benzoyl]-4-methylene-2-pyrrolidinecarboxaldehyde 19 as light yellow oil (44 mg, 80%).

Compound 20. A mixture of (S)-1-[4-(5-bromopentyloxy)-5-methoxy-2-nitro-benzoyl]-4-methylene-2-pyrrolidinecarboxaldehyde 19 (43.7 mg, 0.096 mmol), Na$_2$S$_2$O$_4$ (0.58 mmol, 6 equiv), 1.5 mL THF, and 0.9 mL H$_2$O was stirred at rt for 18 h. Solvents were removed under high vacuum. The residue was re-suspended in MeOH (6 mL), and AcCl was added dropwise until pH~2. The resulting mixture was stirred at rt for 1 h. The reaction was work-up by removing most of MeOH, then diluted with EtOAc (20 mL). The EtOAc solution was washed with sat. aq. NaHCO$_3$, brine, and dried (MgSO$_4$) and concentrated. Purification of the residue by flash chromatography (silica gel, 98:2 CHCl$_3$/MeOH) yielded (11aS)-7-(5-bromopentyloxy)-2-methylene-1,2,3,11a-tetrahydro-5H-pyrrolo[2,1-c][1,4]benzodiazepin-5-one 20 as light yellow oil (31 mg, 74%): $^1$HNMR (300 MHz, CDCl$_3$) δ 1.58-1.66 (m, 2H), 1.84-1.99 (m, 4H), 2.91-2.95 (m, 1H), 3.08-3.14 (m, 1H), 3.42 (t, J=5.1 Hz, 2H), 3.93 (s, 3H), 3.87-4.27 (m, 5H), 5.15 (br s, 1H), 5.18 (br s, 1H), 6.84 (s, 1H), 7.49 (s, 1H), 7.71 (d, J=4.0 Hz, 1H); EIMS m/z 429 and 431 ([M]$^+$+Na).

Compound 20 can then be coupled to a PBD moiety prepared as in example 11 to form a compound of the invention.

EXAMPLE 15

8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzo-diazepin-5-one]

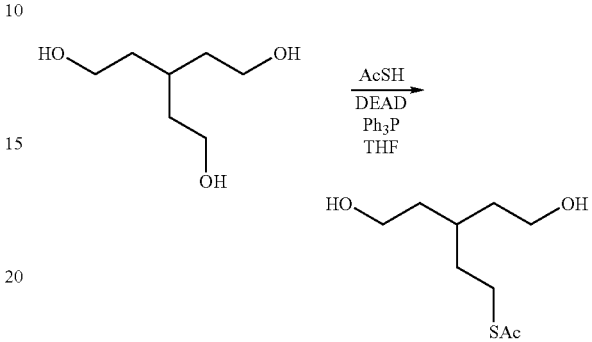

To a solution of triphenylphosphine (1.77 g, 6.8 mmol) in anhydrous THF (15 mL) was added diethyl azodicarboxylate (2.2 M in toluene, 2.4 mL, 5.4 mmol) dropwise at 0° C. After stirred at 0° C. for 55 minutes, a solution of 3-(2-hydroxyethyl)pentane-1,5-diol (740 mg, 5 mmol) and thioacetic acid (335 µL, 4.5 mmol) in dry THF (7 mL) was added dropwise. After 1 hour the ice/water bath was removed and the reaction was stirred at room temperature for 16 hours. The solvents were removed by rotary evaporation in vacuo. The residue was purified by flash chromatography (CHCl$_3$/MeOH, 20:1, 15:1, 10:1, 4:1) to give 3-(2-acetylthioethyl)pentane-1,5-diol as white solid (350 mg) and recovered starting material triol (406 mg). $^1$H NMR (400 Hz, CDCl$_3$): δ 3.65-3.63 (m, 4H), 3.45 (bs, 2H), 2.84-2.80 (m, 2H), 2.28 (s, 3H), 1.73-1.67 (m, 1H), 1.55-1.49 (m, 6H). MS (ESI): m/z 229.0 (M+Na)$^+$.

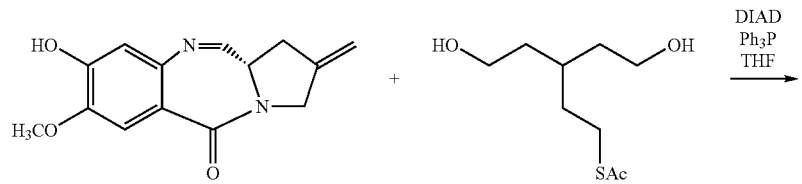

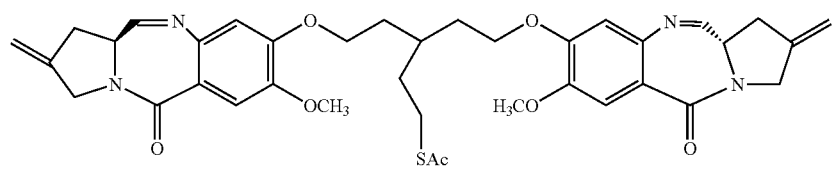

To a solution of triphenylphosphine (53 mg, 0.2 mmol) in anhydrous THF (0.4 mL) was added disopropyl azodicarboxylate (36 μL, 0.17 mmol) dropwise at 0° C. After stirred at 0° C. for 25 minutes, a solution of (11aS)-8-hydroxy-7-methoxy-2-methylene-1,2,3,11a-tetrahydro-5H-pyrrolo[2,1-c][1,4]benzodiazepin-5-one, the PBD monomer, (38 mg, 0.14 mmol, co-evaporated with dry benzene and dried on high vacuum for couple hours before use) in dry THF (0.2 mL) was added. The mixture was continued to stir for 10 minutes before the thioacetate compound (12 mg, 0.058 mmol, co-evaporated with dry benzene and dried on high vacuum for couple hours before use) in dry THF (0.2 mL) was added. The reaction mixture was allowed to stir at 0° C. for 35 minutes. The ice/water bath was removed and the solution was stirred at room temperature for 12 hours. The solvents were removed by rotary evaporation in vacuo. The residue was purified by flash chromatography (CHCl$_3$/MeOH, 100:1, 50:1, 25:1, 20:1) to furnish 8,8'-[3-(2-acetylthioethyl)-1,5-pentanediyl-bis(oxy)]-bis[(S)-2-methylene-7-methoxy-1,2,3,11a-tetrahydro-5H-pyrrolo[2,1-c][1,4]benzodiazepin-5-one] (19 mg, y=47%). $^1$H NMR (400 Hz, CDCl$_3$): δ 7.66 (d, J=4.4 Hz, 2H), 7.46 (s, 2H), 6.78 (s, 2H), 5.17 (s, 2H), 5.14 (s, 2H), 4.26 (s, 4H), 4.17-4.09 (m, 4H), 3.88 (s, 6H), 3.87-3.83 (m, 2H), 3.13-3.06 (m, 2H), 2.94-2.90 (m, 4H), 2.29 (s, 3H), 1.95 (bs, 3H), 1.68 (bs, 4H). MS (ESI, with H$_2$O): m/z 745.3 (M+2H$_2$O+Na)$^+$, 727.3 (M+H$_2$O+Na)$^+$, 709.2 (M+Na)$^+$.

EXAMPLE 16

8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one] May be Prepared as Follows

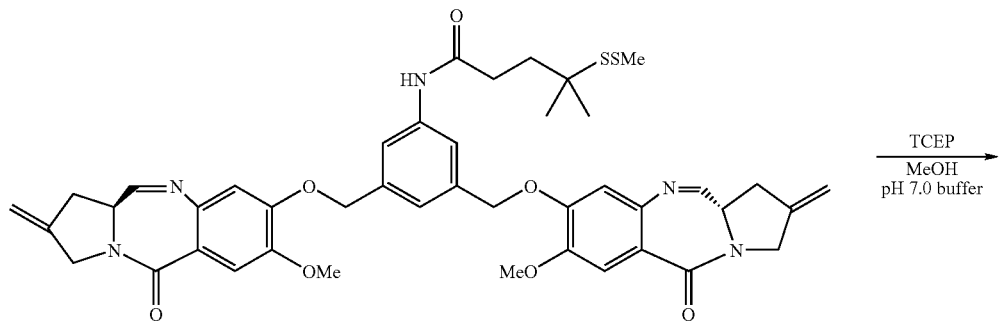

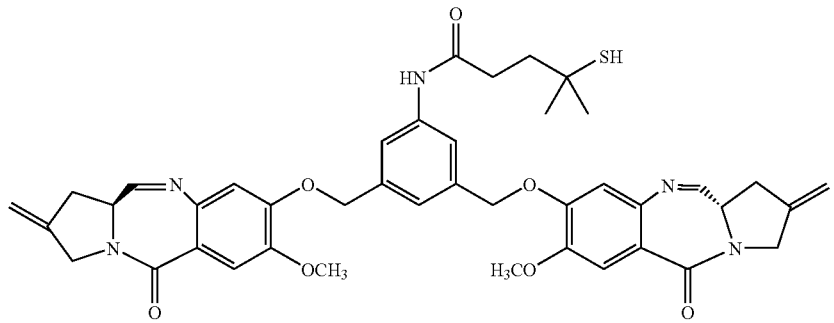

To a suspension of Tris(2-carboxyethyl)phosphine hydrochloride (TCEP, 52 mg, 0.18 mmol) in water (0.3 mL) was added saturated sodium bicarbonate (~0.6 mL) dropwise to adjust the pH to 6~7. A phosphate buffer (pH 7.0, 10 mM, $Na_2HPO_4/H_3PO_4$, 0.5 mL) was then added to it. This obtained TCEP solution was added to a mixture of 8,8'-[5-(N-4-methyldithio-4,4-dimethylbutanoyl)-amino-1,3-benzenediylbis(methylenoxy)]-bis[7-methoxy-2-methylene-1,2,3,11a-tetrahydro-5H-pyrrolo[2,1-c][1,4]benzodiazepin-5-one] (29 mg, 0.036 mmol) in methanol (2.2 mL) and stirred at room temperature for 3 hours. The reaction was quenched with a phosphate buffer (pH 6.5) and extracted with dichloromethane. The combined organic layers were washed with brine, dried over anhydrous sodium sulfate, filtered and the solvents were removed under reduced pressure to give a white solid. The solid was dissolved in dichloromethane/MeOH (2:1) and evaporated again. Dichloromethane was added and evaporated. The residue was high vacuumed and purified by reverse phase C18 column {$CH_3CN/H_2O$, the solid was dissolved in $CH_3CN/H_2O$ (3:1, 2 mL) and stirred for 30 minutes before loading on column} to furnish 8,8'-[5-(N-4-mercapto-4,4-dimethylbutanoate)-amino-1,3-benzenediylbis (methylenoxy)]-bis[7-methoxy-2-methylene-1,2,3,11a-tetrahydro-5H-pyrrolo[2,1-c][1,4]benzodiazepin-5-one] (11 mg) as a white solid (method H).

MS (ESI): m/z=786.3 $MNa^+$ m/z=804.2 $MNa^+ + H_2O$ 8,8'-[5-(N-4-methyldithio-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one] May be Prepared as Follows:

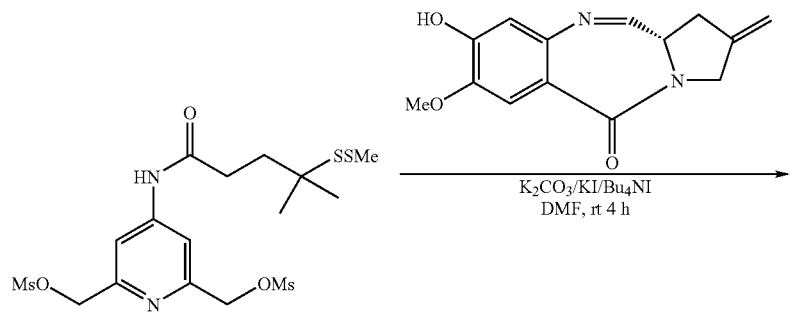

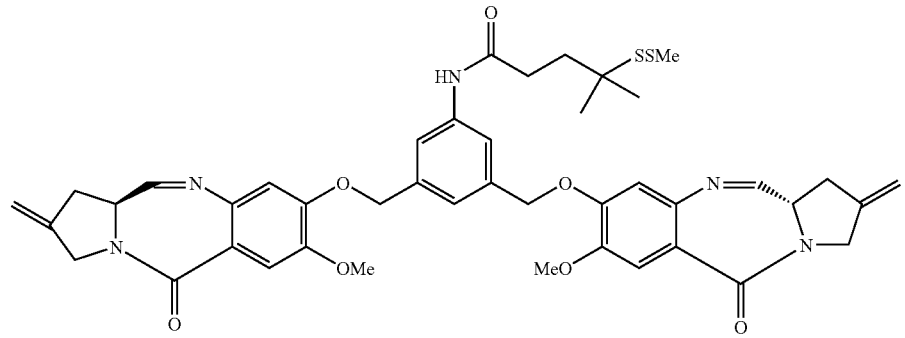

To a solution of 5-(N-4-methyldithio-4,4-dimethylbutanoyl)-amino-1,3-bis-(mesyloxymethyl)-benzene (89 mg, 0.18 mmol) dissolved in anhydrous DMF (2 mL) was added 8-hydroxy-7-methoxy-2-methylene-1,2,3,11a-tetrahydro-5H-pyrrolo[2,1-c][1,4]benzodiazepin-5-one (93 mg, 0.36 mmol), potassium carbonate powder (100 mg, 0.72 mmol), potassium iodide powder (15 mg, 0.09 mmol) and tetrabutylammonium iodide (13 mg, 0.036 mmol) at room temperature. After the mixture was stirred for one hour, a second portion of 8-hydroxy-7-methoxy-2-methylene-1,2,3,11a-tetrahydro-5H-pyrrolo[2,1-c][1,4]benzodiazepin-5-one was added (22 mg, 0.085 mmol). The solution continued to stir at room temperature for another 3 hours. The reaction was then quenched with water and diluted with dichloromethane. The organic layer was separated and the aqueous layer was extracted with dichloromethane. The combined organic layers were washed with brine, dried over anhydrous sodium sulfate. It was filtered and the filtrate was evaporated under reduced pressure followed by high vacuum to remove the residual DMF. The residue was then purified by reverse phase C18 column ($CH_3CN/H_2O$) to furnish 8,8'-[5-(N-4-methyldithio-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one] (29 mg) as a white solid (method H).

MS (ESI): m/z=832.2 $MNa^+$ m/z=850.2 $MNa^+$+$H_2O$ $^1$H NMR (400 Hz, $CDCl_3$-d1, in δ ppm): 7.67 (bs, 2H), 7.58-7.26 (m, 5H), 6.82 (s, 2H), 5.21-5.14 (m, 8H), 4.30 (s, 4H), 4.02-3.88 (m, 9H), 3.16-3.10 (m, 2H), 2.97-2.93 (m, 2H), 2.45-2.40 (m, 5H), 2.09-2.03 (m, 2H), 1.34 (s, 6H)

5-(N-4-methyldithio-4,4-dimethylbutanoyl)amino-1,3-bis-(mesyloxymethyl)-benzene may be prepared as follows:

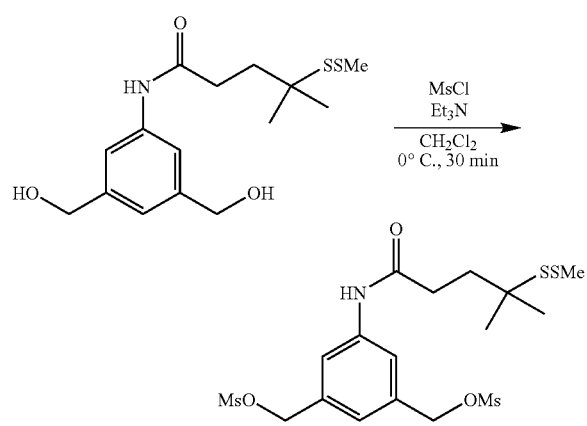

To a suspension of 5-(N-4-methyldithio-4,4-dimethylbutanoyl)-amino-1,3-bis-(hydroxymethyl)-benzene (329 mg, 1.0 mmol) in anhydrous dichloromethane (7 mL) was added triethylamine (348 μL, 2.5 mmol) followed by methanesulfonyl chloride (193 μL, 2.5 mmol) dropwise over 10 minutes at −2° C. The solution was stirred at 0° C. for another 30 minutes and was then quenched with a mixture of ice and water. The mixture was extracted with cold dichloromethane and the combined dichloromethane layers were washed with cold water, dried over anhydrous sodium sulfate. It was filtered and the filtrate was evaporated by rotary evaporation in vacuo. The residue was quickly purified by a short silica gel column (Dichloromethane/Hexanes/Ethylacetate, 1:2:4) to furnish 5-(N-4-methyldithio-4,4-dimethylbutanoyl)-amino-1,3-bis-(mesyloxymethyl)-benzene as a colorless oil (410 mg).

MS (ESI): m/z=508.0 $MNa^+$ m/z=483.9 M−H m/z=519.9 M−H+$2H_2O$ 5-(N-4-methyldithio-4,4-dimethylbutanoyl)-amino-1,3-bis-(hydroxymethyl)-benzene may be prepared as follows:

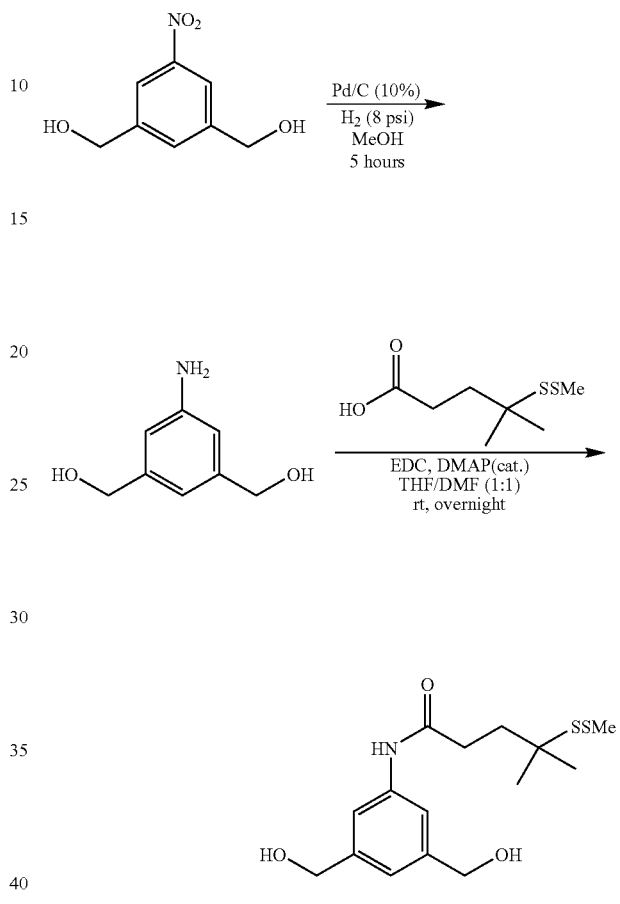

To a solution of 5-Nitro-m-xylene-α,α'-diol (890 mg, 5.4 mmol) in methanol (50 mL) was added Pd/C (10%, 287 mg). A hydrogen atmosphere was introduced and the mixture was hydrogenated under pressure ($H_2$, 5~8 psi) for 5 hours at room temperature. The solution was filtered through celite and the filtrate was evaporated by rotary evaporation in vacuo to give 5-amino-m-xylene-α,α'-diol, which was then dissolved in THF (10 mL)/DMF (15 ml). 4-methyldithio-4,4-dimethyl butanoic acid (1.05 g, 5.4 mmol) dissolved in THF (5 ml) was added at room temperature followed by the addition of 1-(3-dimethylaminopropyl)-3-ethylcarbodiimide hydrochloride (2.1 g, 10.8 mmol) and 4-dimethylamino pyridine (66 mg, 0.54 mmol). The obtained mixture was stirred at room temperature overnight then quenched with 10% ammonium chloride, extracted with ethylacetate, washed and dried. It was filtered and the solvents were removed by rotary evaporation in vacuo. The residue was purified by flash chromatography ($CH_2Cl_2$/MeOH, 15:1, 10:1, 7:1) to furnish 5-(N-4-methyldithio-4,4-dimethylbutanoyl)-amino-1,3-bis-(hydroxymethyl)-benzene as a white solid (729 mg).

MS (ESI): m/z=352.1 $MNa^+$ $^1$H NMR (400 Hz, $CDCl_3$-d1, in δ ppm): 7.47 (s, 2H), 7.10 (s, 1H), 4.58 (s, 4H), 2.52-2.47 (m, 2H), 2.42 (s, 3H), 2.02-1.98 (m, 2H), 1.34 (s, 6H).

EXAMPLE 17

8,8'-[5-(N-methyl-N-(2-mercapto-2,2-dimethylethyl) amino-1,3-benzenediyl(methylenoxy)]-bis[7-methoxy-2-methylene-1,2,3,11a-tetrahydro-5H-pyrrolo[2,1-c][1,4]benzodiazepin-5-one] May be Prepared as Follows

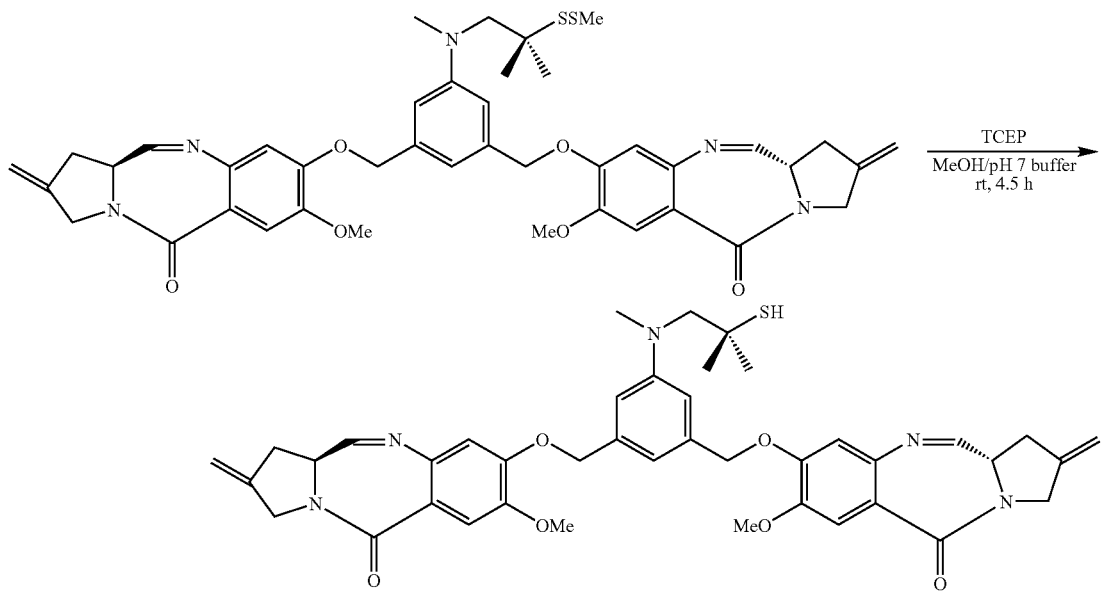

To a suspension of Tris(2-carboxyethyl)phosphine hydrochloride (TCEP, 64 mg, 0.22 mmol) in water (0.05 mL) was added saturated sodium bicarbonate (~0.7 mL) dropwise to adjust the pH to 6~7. A phosphate buffer (pH 7.0, 10 mM, Na$_2$HPO$_4$/H$_3$PO$_4$, 0.8 mL) was then added to it. This obtained TCEP solution was added to a mixture of 8,8'-[5-(N-methyl-N-(2-methyldithio-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one] (35 mg, 0.045 mmol) in methanol (5 mL) and stirred at room temperature for 4.5 hours. The reaction was quenched with a phosphate buffer (pH 6.5) and extracted with dichloromethane. The combined organic layers were washed with brine, dried over anhydrous sodium sulfate, filtered and the solvents were removed under reduced pressure to give a white solid. The solid was dissolved in dichloromethane/MeOH (2:1) and evaporated again. Dichloromethane was added and evaporated. The residue was high vacuumed and purified by reverse phase C18 column {CH$_3$CN/H$_2$O, the solid was dissolved in CH$_3$CN/H$_2$O (3:1, 2 mL) and stirred for 30 minutes before loading on column} to furnish 8,8'-[5-(N-methyl-N-(2-mercapto-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one] (10.5 mg, y=32%) as a white solid (method H).

MS (ESI): m/z=758.2 MNa$^+$ m/z=776.2 MNa$^+$+H$_2$O m/z=794.3 MNa$^+$+2H$_2$O 8,8'-[5-(N-methyl-N-(2-methyldithio-2,2-dimethylethyl) amino-1,3-benzenediyl(methylenoxy)]-bis[7-methoxy-2-methylene-1,2,3,11a-tetrahydro-5H-pyrrolo[2,1-c][1,4]benzodiazepin-5-one] may be prepared as follows:

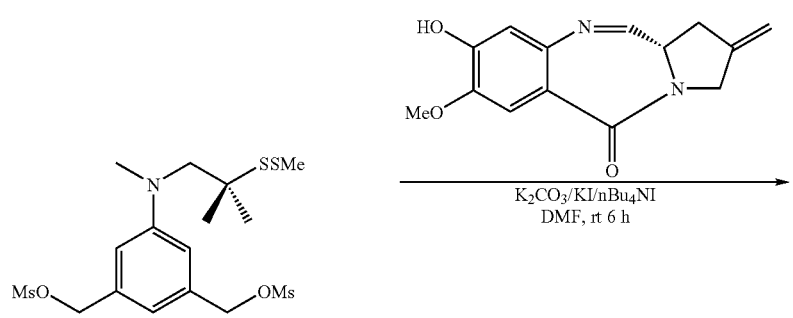

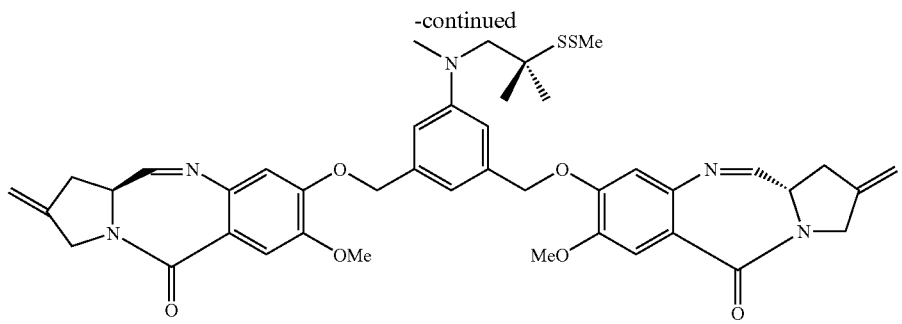

To a solution of 5-(N-methyl-N-(2-methyldithio-2,2-dimethylethyl)amino-1,3-bis-(mesyloxymethyl)-benzene (105 mg, 0.23 mmol) in anhydrous DMF (2.5 mL) was added 8-hydroxy-7-methoxy-2-methylene-1,2,3,11a-tetrahydro-5H-pyrrolo[2,1-c][1,4]benzodiazepin-5-one (119 mg, 0.46 mmol), potassium carbonate powder (127 mg, 0.92 mmol), potassium iodide powder (20 mg, 0.12 mmol) and tetrabutylammonium iodide (17 mg, 0.046 mmol) at room temperature. After the mixture was stirred for 1.5 hours, the second portion of 8-hydroxy-7-methoxy-2-methylene-1,2,3,11a-tetrahydro-5H-pyrrolo[2,1-c][1,4]benzodiazepin-5-one was added (23 mg, 0.089 mmol). The solution continued to stir at room temperature for 4.5 hours. The reaction was then quenched with water and diluted with dichloromethane. The organic layer was separated and the aqueous layer was extracted with dichloromethane. The combined organic layers were washed with brine, and dried over anhydrous sodium sulfate. The solution was filtered and the filtrate was evaporated under reduced pressure, then submitted to high vacuum to remove the residual DMF. The residue was suspended in $CH_3CN/H_2O$ (10:1) and filtered. The filtrate was evaporated and the crude product was purified by reverse phase C18 column ($CH_3CN/H_2O$) to furnish 8,8'-[5-(N-methyl-N-(2-methyldithio-2,2-dimethylethyl)-amino-1,3-benzenediyl (methylenoxy)]-bis[7-methoxy-2-methylene-1,2,3,11a-tetrahydro-5H-pyrrolo[2,1-c][1,4]benzodiazepin-5-one] (39 mg) as a white solid (method H).

MS (ESI): m/z=804.2 $MNa^+$ m/z=822.2 $MNa^+ + H_2O$ m/z=840.2 $MNa^+ + 2H_2O$ $^1$H NMR (400 Hz, $CDCl_3$-d1, in δ ppm): 7.64 (bs, 2H), 7.50 (s, 2H), 6.83-6.76 (m, 5H), 5.18-5.10 (m, 8H), 4.27 (s, 4H), 3.95 (s, 6H), 3.90-3.84 (m, 3H), 3.51 (s, 2H), 3.13-3.07 (m, 2H), 3.01 (s, 3H), 2.94-2.90 (m, 2H), 2.41 (s, 3H), 1.30 (s, 6H)

5-(N-methyl-N-(2-methyldithio-2,2-dimethylethyl) amino-1,3-bis-(mesyloxymethyl)-benzene may be prepared as follows:

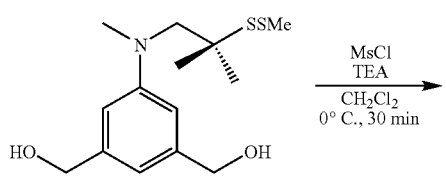

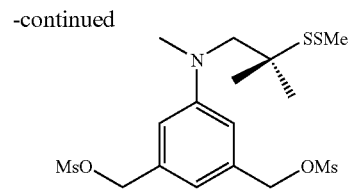

To a solution of 5-(N-methyl-N-(2-methyldithio-2,2-dimethylethyl)amino-1,3-bis-(hydroxymethyl)-benzene (135 mg, 0.45 mmol) in anhydrous dichloromethane (3 mL) was added triethylamine (153 μL, 1.1 mmol) followed by methanesulfonyl chloride (87 μL, 1.1 mmol) dropwise over 10 minutes at −2° C. The solution was stirred at 0° C. for another 30 minutes and was then quenched with ice/water. The mixture was extracted with cold dichloromethane and the combined dichloromethane layers were washed with cold water, and dried over anhydrous sodium sulfate. It was then filtered and the filtrate was evaporated by rotary evaporation in vacuo. The residue was purified by a preparative TLC plate (hexanes/ethylacetate, 1:1.5) to furnish 5-(N-methyl-N-(2-methyldithio-2,2-dimethylethyl)amino-1,3-bis-(mesyloxymethyl)-benzene as a colorless oil (105 mg)

MS (ESI): m/z=480.0 $MNa^+$ 5-(N-methyl-N-(2-methyldithio-2,2-dimethylethyl) amino-1,3-bis-(hydroxymethyl)-benzene may be prepared as follows:

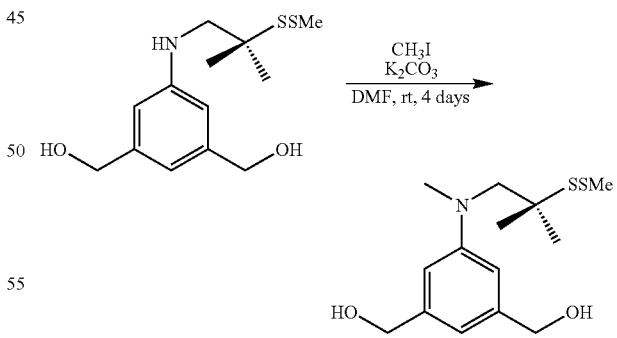

To a solution of 5-(N-(2-methyldithio-2,2-dimethylethyl) amino-1,3-bis-(hydroxymethyl)-benzene (226 mg, 0.78 mmol) in DMF (4 mL) was added iodomethane (149 μL, 2.4 mmol) followed by potassium carbonate powder (108 mg, 0.78 mmol). After stirring at room temperature for 4 days the mixture was quenched with saturated ammonium chloride and then diluted with dichloromethane. The organic layer was separated and the aqueous layer was extracted with dichloromethane. The combined organic layers were washed with brine, dried over anhydrous sodium sulfate. The solution was filtered and the filtrate was evaporated under reduced pressure. The residue was purified by flash chromatography (hexanes/ethylacetate, 1:2) to furnish 5-(N-methyl-N-(2-methyldithio-2,2-dimethylethyl)amino-1,3-bis-(hydroxymethyl)-benzene as colorless foam (152 mg)

MS (ESI): m/z=324.1 MNa+

$^1$H NMR (400 Hz, CDCl$_3$-d1, in δ ppm): 6.70 (s, 2H), 6.66 (s, 1H), 4.06 (s, 4H), 3.54 (s, 2H), 3.04 (s, 3H), 2.46 (s, 3H), 1.37 (s, 6H)

5-(N-(2-methyldithio-2,2-dimethylethyl)amino-1,3-bis-(hydroxymethyl)-benzene may be prepared as follows:

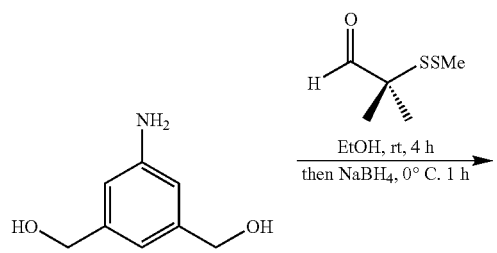

dride (220 mg, 5.8 mmol) was added. The mixture continued to stir at 0° C. for one hour and then was quenched with cold 5% hydrochloric acid and diluted with dichloromethane. Saturated sodium bicarbonate was added to make the solution slightly basic. The organic layer was separated and the aqueous layer was extracted with dichloromethane. The combined organic layers were washed with brine, dried over anhydrous sodium sulfate. The solution was filtered and the filtrate was evaporated under reduced pressure. The residue was purified by flash chromatography (CH$_2$Cl$_2$/MeOH, 15:1, 10:1) to furnish 5-(N-(2-methyldithio-2,2-dimethylethyl)amino-1,3-bis-(hydroxymethyl)-benzene as colorless oil (832 mg)

MS (ESI): m/z=310.0 MNa+

EXAMPLE 18

8,8'-[(4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] May be Prepared as Follows

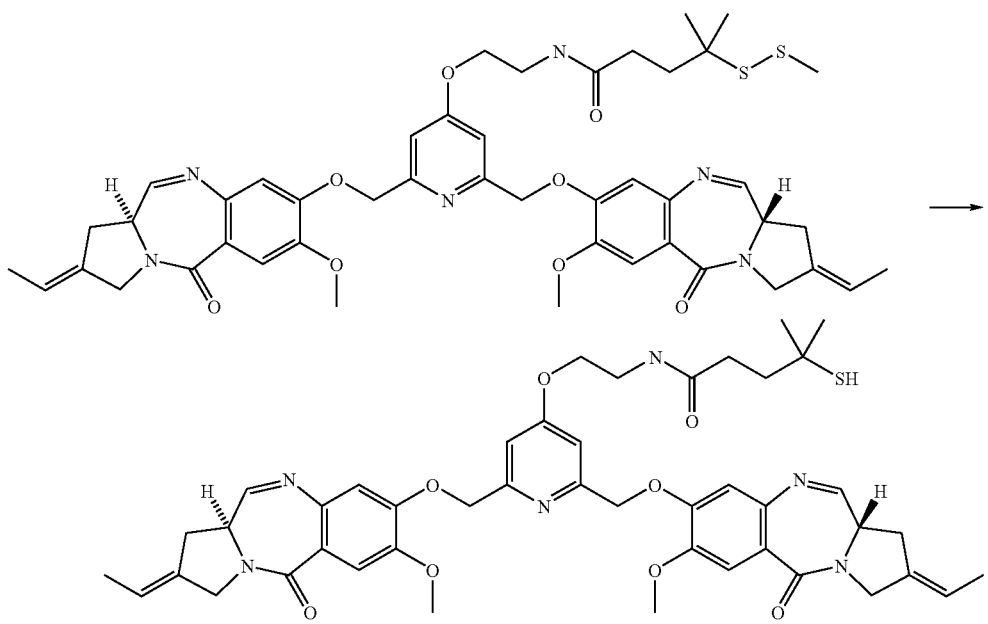

-continued

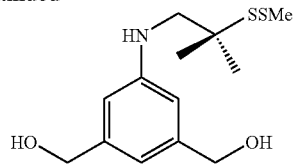

To a solution of 5-amino-1,3-bis-hydroxylmethyl-benzene (765 mg, 5 mmol) in absolute ethanol (25 mL) was added 2-(methyldithio)-isobutylaldehyde (751 mg, 5 mmol). After stirring at room temperature for 4 hours the solution was cooled to 0° C. with an ice/water bath and sodium borohy- To a solution of 8,8'-[(4-(2-(4-methyl-4-methyldisulfanyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] (60 mg) in methanol (1.6 mL) was added DMF (0.2 mL) and a solution of tris(2-carboxyethyl)phosphine hydrochloride (48 mg) in water 0.2 mL. The reaction mixture was stirred for 18 h at room temperature and the solvent was removed in vacuo to give a residue that was purified by silica gel chromatography (Merck SuperVarioFlash 10 g column, Si60 15-40 µm), using gradient elution with a mixture of methanol (A)/dichloromethane/acetonitrile 9:1 (B), (gradient: 100% B down to 10% A:90% B) to give 8,8'-[(4-(2-(4-mercapto-4-methyl)-pentanamido-ethoxy)-pyridin-2,6-dimethyl)-dioxy]-bis[(S)-

87
2-eth-(E)-ylidene-7-dimethoxy-1,2,3,11a-tetrahydro-pyrrolo[2,1-c][1,4]benzodiazepin-5-one] (17 mg):
LC/MS (Method A1, ZQ): ES: m/z=855 MH$^+$+H$_2$O m/z=837 MH$^+$ Retention time=3.70 minutes
88
8,8'-[(4-(2-(4-methyl-4-methyldisulfanyl)-pentanamidoethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared as follows:
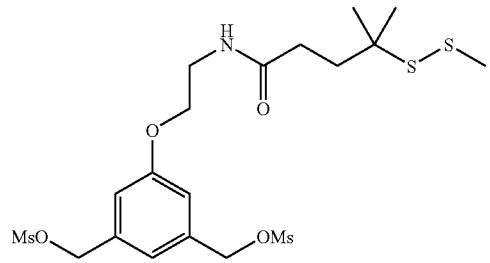
+
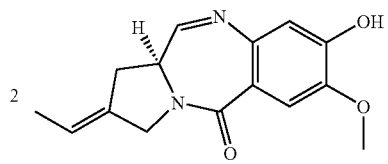
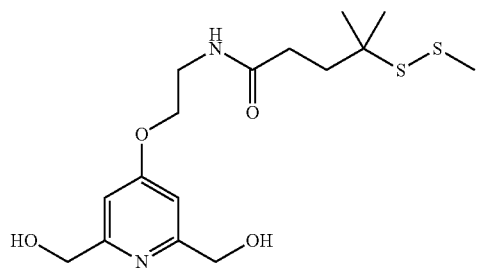
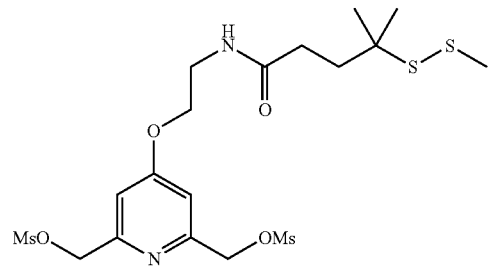
+
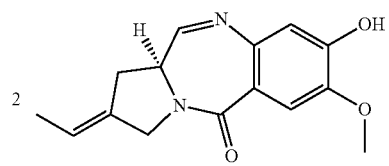

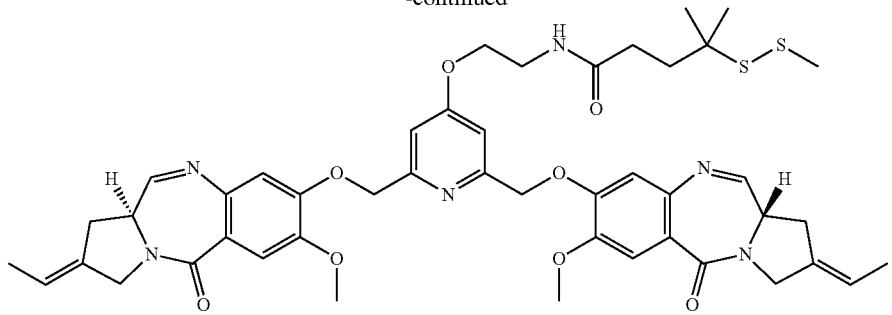

To a cooled (0° C.) solution of 4-(2-(4-methyl-4-methyldisulfanyl)-pentanamido-ethoxy)-2,6-bis-(hydroxymethyl)-pyridine (360 mg) and triethylamine (810 μL) in dichloromethane (4 mL), was added a solution of methanesulfonyl chloride (298 μL) in dichloromethane (4 mL). After 2 hours, water was added. The layers were separated, and the aqueous layer was extracted twice dichloromethane. The combined organic solutions were dried over magnesium sulfate, and concentrated in vacuo to a residue. The residue was purified by silica gel chromatography (Interchrom Puriflash 20 g column, SiOH 15-35 μm), using gradient elution with a mixture of methanol (A)/dichloromethane (B), (gradient: 100% B down to 3% A:97% B) to give 280 mg of mesylate compound.

To a solution of pre-tomaymycin (120 mg) in dimethylformamide (4 mL) was added potassium carbonate (244 mg), potassium iodide (147 mg) and a sample of the mesylate compound (137 mg). The reaction mixture was stirred for 20 h at 30° C. Water (20 mL) was added and the resulting solid was filtered, washed with water and dried in vacuo to give a residue. The residue was purified by silica gel chromatography (Interchrom Puriflash 20 g column, SiOH 15-35 μm), using gradient elution with a mixture of methanol (A)/dichloromethane (B), (gradient: 100% B down to 6% A:94% B) to give crude compound, which was dissolved in water/acetonitrile 1:1 then concentrated in vacuo to give 8,8'-[(4-(2-(4-methyl-4-methyldisulfanyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] (120 mg):

LC/MS (Method A1, ZQ): ES: m/z=919 MH$^+$+2H$_2$O m/z=901 MH$^+$+H$_2$O m/z=883 MH$^+$Retention time=3.82 minutes $^1$H N.M.R. (500 MHz, CDCl3-d1, δ in ppm): δ=1.28 (s, 6H); 1.75 (d, J=6.5 Hz, 6H); 1.94 (m, 2H); 2.29 (m, 2H); 2.39 (s, 3H); 2.97 (m, 4H); from 3.50 to 4.20 (m, 6H); 4.00 (s, 6H); 4.27 (s, 4H); 5.27 (m, 4H); 5.61 (m, 2H); 5.87 (t broad, J=5.5 Hz, 1H); 6.83 (s, 2H); 6.97 (s, 2H); 7.55 (s, 2H) 7.64 (d, J=4.5 Hz, 2H).

4-(2-(4-methyl-4-methyldisulfanyl)-pentanamido-ethoxy)-2,6-bis-(hydroxymethyl)-pyridine may be prepared as follows:

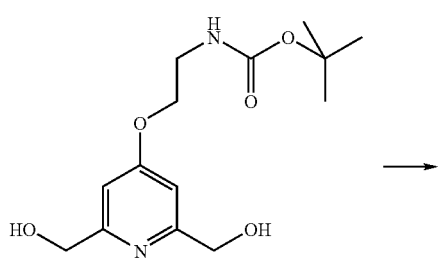

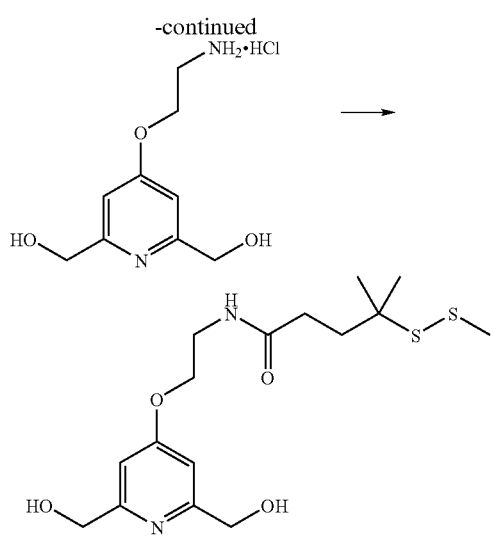

To a solution of 4-(2-tert-butoxycarbonylamino-ethoxy)-2,6-bis-(hydroxymethyl)-pyridine (656 mg) in dioxane (3.5 mL) was added a solution of hydrochloric acid 4N in dioxane (5.5 mL). After 20 h at room temperature, the reaction mixture was concentrated in vacuo to a residue (603 mg).

To a solution of a sample of the previous residue (150 mg) in dimethylformamide (3.5 mL) was added triethylamine (267 μL), 4-methyl-4-methyldisulfanyl-pentanoic acid (149 mg), N,N'-diisopropylcarbodiimide (119 μL) and 1-hydroxybenzotriazole hydrate (49 mg). After 15 h at room temperature, water was added to the reaction mixture and the aqueous solution was extracted three times with ethyl acetate. The combined organic solutions were washed with a saturated sodium chloride aqueous solution, dried over magnesium sulfate and concentrated in vacuo to a residue. The residue was purified by silica gel chromatography (Interchrom Puriflash 20 g column, SiOH 15-35 μm), using gradient elution with a mixture of methanol (A)/dichloromethane (B), (gradient: 100% B down to 10% A:90% B) to give 4-(2-(4-methyl-4-methyldisulfanyl)-pentanamido-ethoxy)-2,6-bis-(hydroxymethyl)-pyridine (81 mg):

LC/MS (Method A3): ES m/z=375 MH$^+$m/z=156 C$_7$H$_{10}$NO$_3$$^+$Retention time=2.2 minutes $^1$H N.M.R. (400 MHz, DMSO-d6, δ in ppm): δ=1.22 (s, 6H); 1.79 (m, 2H); 2.19 (m, 2H); 2.39 (s, 3H); 3.43 (q, J=5.5 Hz, 2H); 4.06 (t, J=5.5 Hz, 2H); 4.45 (d broad, J=6.0 Hz, 4H); 5.33 (d, J=6.0 Hz, 2H); 6.84 (s, 2H); 8.13 (t broad, J=5.5 Hz, 1H).

4-(2-tert-butoxycarbonylamino-ethoxy)-2,6-bis-(hydroxymethyl)-pyridine

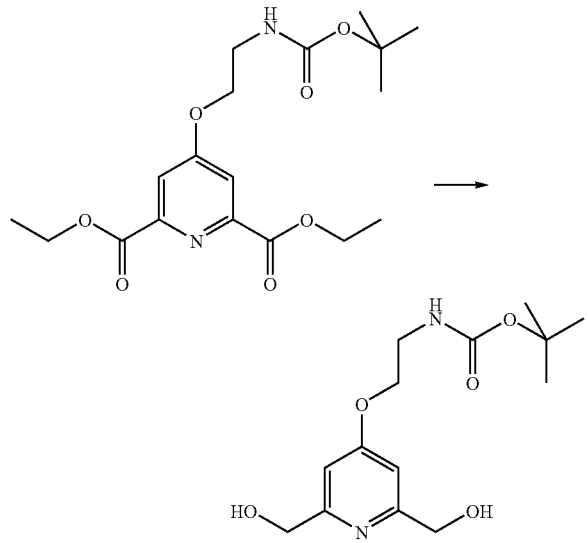

4-(2-tert-butoxycarbonylamino-ethoxy)-2,6-bis-(hydroxymethyl)-pyridine may be prepared following the procedure for the preparation of 4-(3-tert-butoxycarbonylaminopropoxy)-2,6-bis-(hydroxymethyl)pyridine, starting with 4-(2-tert-Butoxycarbonylamino-ethoxy)-pyridine-2,6-dicarboxylic acid diethyl ester:

LC/MS (Method A3): ES m/z=299 MH$^+$m/z=156 $C_7H_{10}NO_3^+$ Retention time=1.7 minutes $^1$H N.M.R. (300 MHz, DMSO-d6, δ in ppm): δ=1.39 (s, 9H); 3.32 (m partially masked, 2H); 4.03 (t, J=6.0 Hz, 2H); 4.46 (d, J=6.0 Hz, 4H); 5.30 (t, J=6.0 Hz, 2H); 6.83 (s, 2H); 7.00 (t broad, J=6.0 Hz, 1H).

4-(2-tert-Butoxycarbonylamino-ethoxy)-pyridine-2,6-dicarboxylic acid diethyl ester

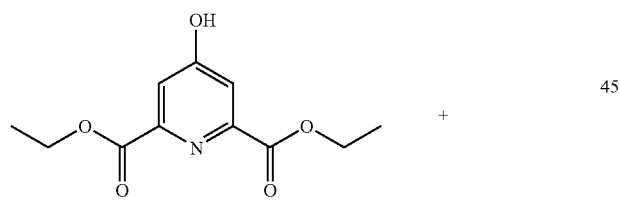

4-(2-tert-Butoxycarbonylamino-ethoxy)-pyridine-2,6-dicarboxylic acid diethyl ester may be prepared following the procedure for the preparation of 4-(3-tert-butoxycarbonylamino-propoxy)-pyridine-2,6-dicarboxylic acid diethyl ester, using 2-tert-butoxycarbonylamino-ethyl bromide:

LC/MS (Method A3): ES m/z=383 MH$^+$m/z=240 $C_{11}H_{14}NO_5^+$ Retention time=3.6 minutes $^1$H N.M.R. (300 MHz, DMSO-d6, δ in ppm): δ=1.23 (t, J=7.0 Hz, 6H); 1.37 (s, 9H); 3.33 (m partially masked, 2H); 4.22 (t, J=5.5 Hz, 2H); 4.38 (q, J=7.0 Hz, 4H); 7.01 (t broad, J=5.5 Hz, 1H); 7.71 (s, 2H).

EXAMPLE 19

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydropyrrolo[2,1-c][1,4]benzodiazepin-5-one]

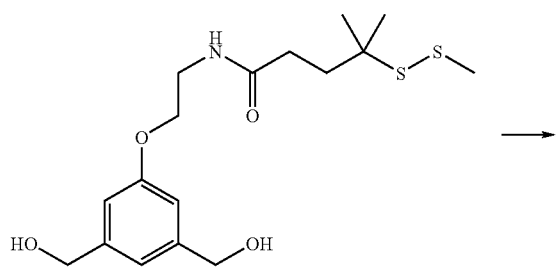

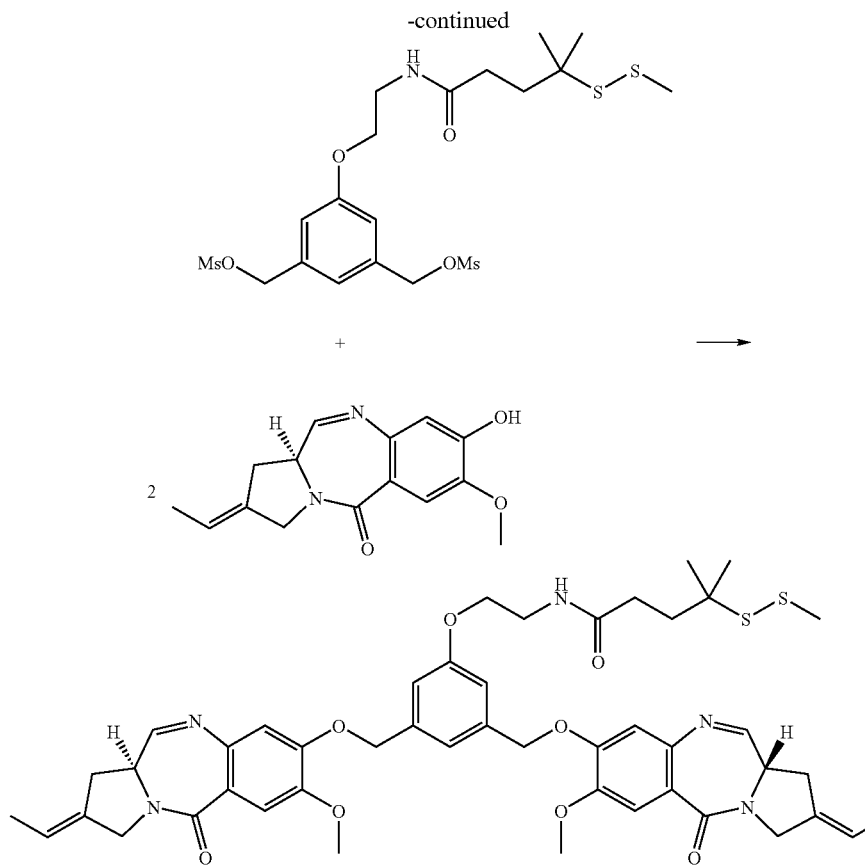

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(2-(4-methyl-4-methyldisulfanyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], starting with 1-(2-(4-methyl-4-methyldisulfanyl)-pentanamido-ethoxy)-3,5-bis-(hydroxymethyl)-benzene:

LC/MS (Method A1, Platform 1): ES: m/z=882 MH$^+$ Retention time=4.13 minutes $^1$H N.M.R. (500 MHz, CDCl3-d1, δ in ppm): 1.30 (s, 6H); 1.75 (d, J=6.5 Hz, 6H); 1.96 (m, 2H); 2.31 (m, 2H); 2.40 (s, 3H); 2.97 (m, 4H); 3.66 (m, 2H); 3.89 (m, 2H); 3.97 (s, 6H) 4.04 (t, J=5.5 Hz, 2H) 4.27 (s broad, 4H); 5.14 (d, J=12.5 Hz, 2H); 5.19 (d, J=12.5 Hz, 2H); 5.61 (m, 2H) 5.93 (t, J=6.0 Hz, 1H); 6.82 (s, 2H); 6.94 (s broad, 2H) 7.09 (s broad, 1H); 7.53 (s, 2H); 7.64 (d, J=4.5 Hz, 2H).

1-(2-(4-methyl-4-methyldisulfanyl)-pentanamido-ethoxy)-3,5-bis-(hydroxymethyl)-benzene

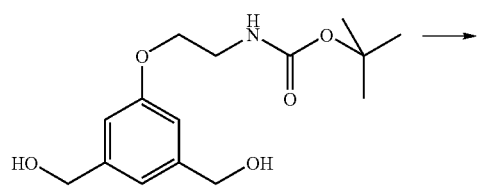

1-(2-(4-methyl-4-methyldisulfanyl)-pentanamido-ethoxy)-3,5-bis-(hydroxymethyl)-benzene may be prepared following the procedure for the preparation of 4-(2-(4-methyl-4-methyldisulfanyl)-pentanamido-ethoxy)-2,6-bis-(hydroxymethyl)-pyridine, using 1-(2-tert-butoxycarbonylamino-ethoxy)-3,5-bis-(hydroxymethyl)-benzene:

$^1$H N.M.R. (400 MHz, CDCl3-d1, δ in ppm): δ=1.22 (s, 6H); 1.80 (m, 2H); 2.20 (m, 2H); 2.39 (s, 3H); 3.40 (q, J=6.0 Hz, 2H); 3.95 (t, J=6.0 Hz, 2H); 4.44 (d, J=6.0 Hz, 4H); 5.11 (t broad, J=6.0 Hz, 2H); 6.73 (s broad, 2H); 6.84 (s broad, 1H); 8.09 (t broad, 1H).

1-(2-tert-butoxycarbonylamino-ethoxy)-3,5-bis-(hydroxymethyl)-benzene

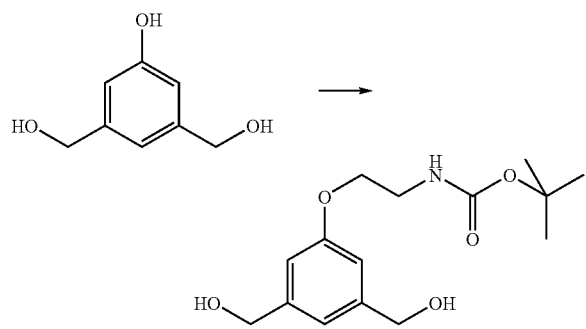

1-(2-tert-butoxycarbonylamino-ethoxy)-3,5-bis-(hydroxymethyl)-benzene may be prepared following the procedure for the preparation of 5-(3-phthalimido-propoxy)-1,3-bis-(hydroxymethyl)-benzene, using 2-tert-butoxycarbonylamino-ethyl bromide:

LC/MS (Method A3): ES m/z=298 MH⁺ m/z=242 (M+2H−tBu)⁺ m/z=224 (m/z=242−H$_2$O)⁺ m/z=206 (m/z=224−H$_2$O)⁺ m/z=162 (m/z=206−CO$_2$)⁺ Retention time=2.7 minutes $^1$H N.M.R. (500 MHz, DMSO-d6, δ in ppm): δ=1.39 (s, 9H); 3.28 (q, J=6.0 Hz, 2H); 3.91 (t, J=6.0 Hz, 2H); 4.44 (d, J=6.0 Hz, 4H); 5.14 (t, J=6.0 Hz, 2H); 6.72 (s broad, 2H) 6.83 (s broad, 1H) 7.01 (t broad, J=7.0 Hz, 1H).

EXAMPLE 20

8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]
May be Prepared as Follows

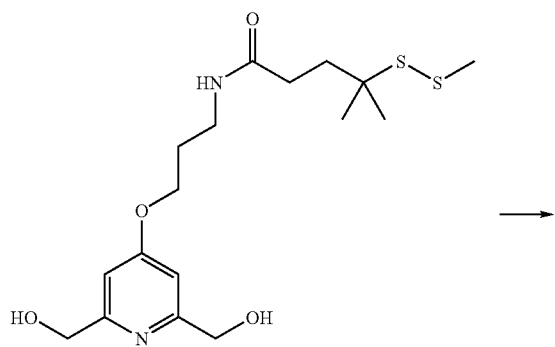

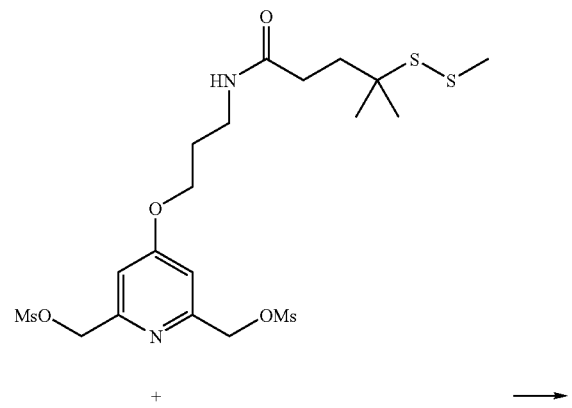

+

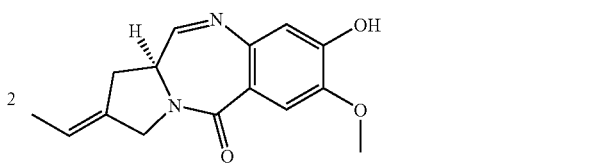

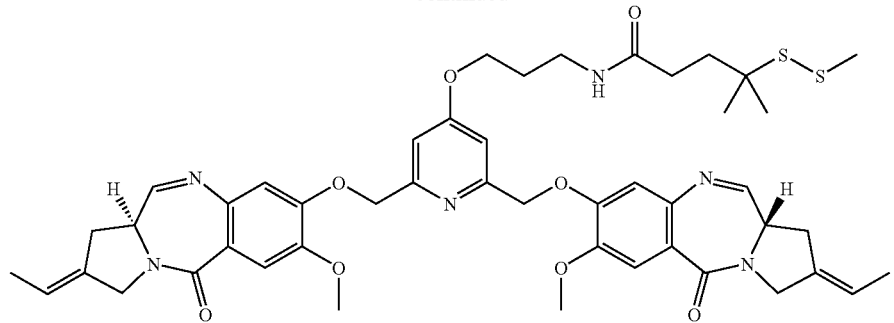

To a cooled (0° C.) solution of 4-(3-(4-methyl-4-methyldisulfanyl)-pentanamido-propoxy)-2,6-bis-(hydroxymethyl)-pyridine (55 mg) and triethylamine (99 μL) in dichloromethane (2 mL), was added methanesulfonyl chloride (36 μL). After 30 minutes, water was added. The layers were separated, and the aqueous layer was extracted twice with dichloromethane. The combined organic solutions were dried over magnesium sulfate, and concentrated in vacuo to a residue (95 mg).

To a stirred solution of pre-tomaymycin (50 mg) in dimethylformamide (0.75 mL), were added potassium carbonate (114 mg), a solution of the previous residue (55 mg) in dimethylformamide (1 mL) and potassium iodide (46 mg). The reaction was stirred for 20 h at 30° C. Solids were filtered off and washed with dimethylformamide. Water was added to the combined dimethylformamide solution and formic acid was added until complete dissolution of the precipitate. The resulting solution was injected for HPLC purification according to method B. The appropriate fractions were combined and concentrated by centrifugal evaporation over a Jouan Model RC10.10. apparatus to afford 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] (13.5 mg).

LC/MS (Method A3): ES m/z=897 MH$^+$m/z=664 (M–C$_{10}$H$_{20}$NOS$_2$+2H)$^+$m/z=234 C$_{10}$H$_{20}$NOS$_2$$^+$Retention time=3.7 minutes $^1$H N.M.R. (500 MHz, CD3COOD-d4, δ in ppm): δ=1.25 (s, 6H); from 1.60 to 2.20 (m partially masked, 10H) 2.35 (m, 5H); from 2.80 to 4.44 (m, 14H); 3.91 (s, 6H) 5.40 (s, 4H); 5.62 (m, 2H) from 6.83 to 7.95 (m, 8H).

4-(3-(4-methyl-4-methyldisulfanyl)-pentanamido-propoxy)-2,6-bis-(hydroxymethyl)-pyridine

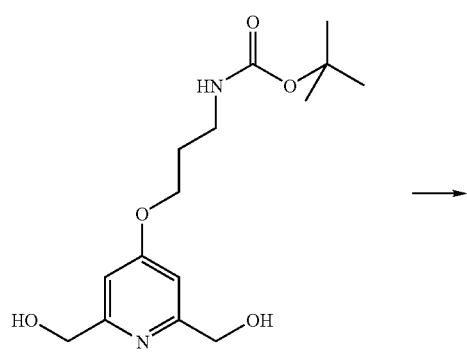

4-(3-(4-methyl-4-methyldisulfanyl)-pentanamido-propoxy)-2,6-bis-(hydroxymethyl)-pyridine may be prepared following the procedure for the preparation of 4-(2-(4-methyl-4-methyldisulfanyl)-pentanamido-ethoxy)-2,6-bis-(hydroxymethyl)-pyridine, using 4-(3-tert-butoxycarbonylamino-propoxy)-2,6-bis-(hydroxymethyl)-pyridine LC/MS (Method A3): ES m/z=389 MH$^+$m/z=234 (M–C$_7$H$_8$NO$_3$)$^+$m/z=156 C$_7$H$_{10}$NO$_3$$^+$Retention time=2.3 minutes The thiol (SH) derivative deriving from compound of example 20 is in equilibrium with the compound of formula:
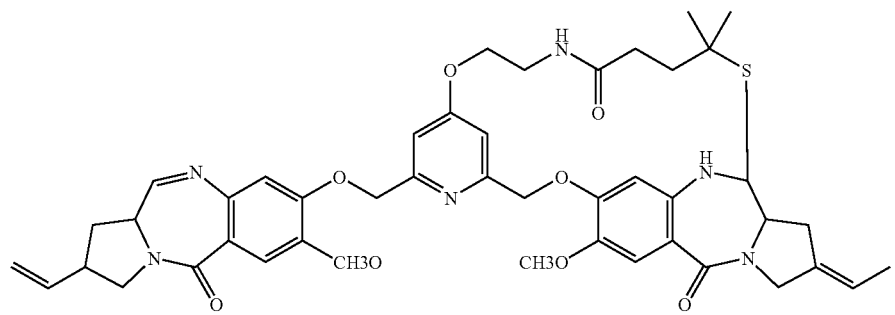
EXAMPLE 21
8,8'-[(4-(4-(4-methyl-4-methyldisulfanyl)-pentana-mido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]
20
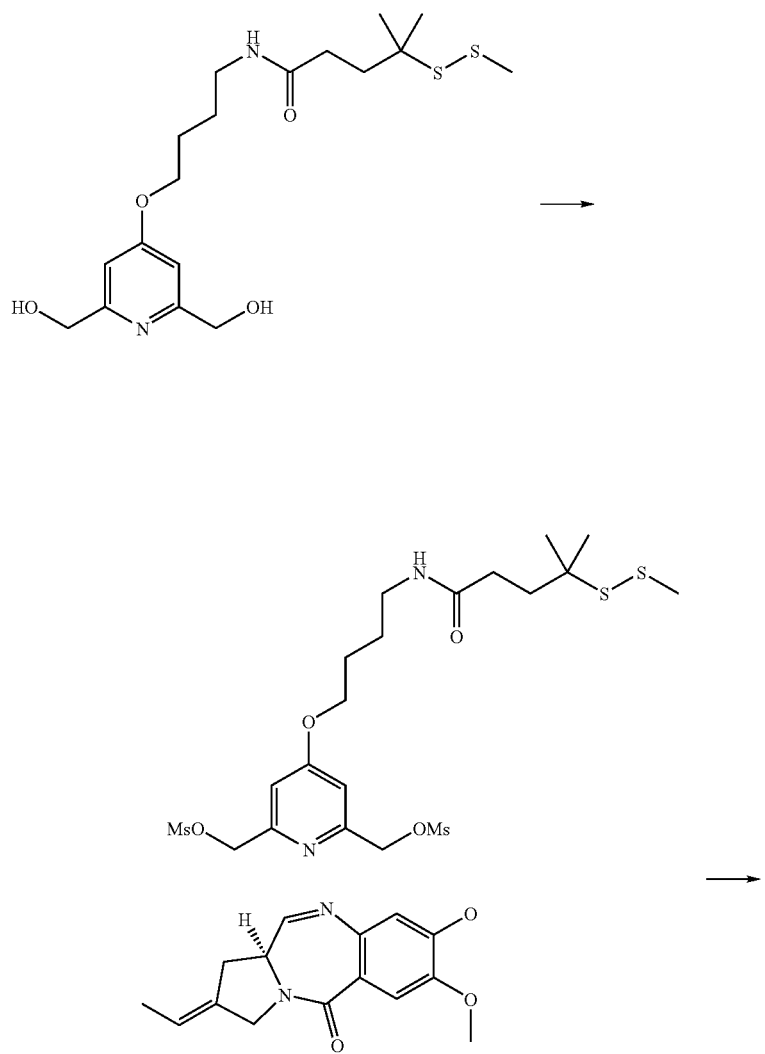

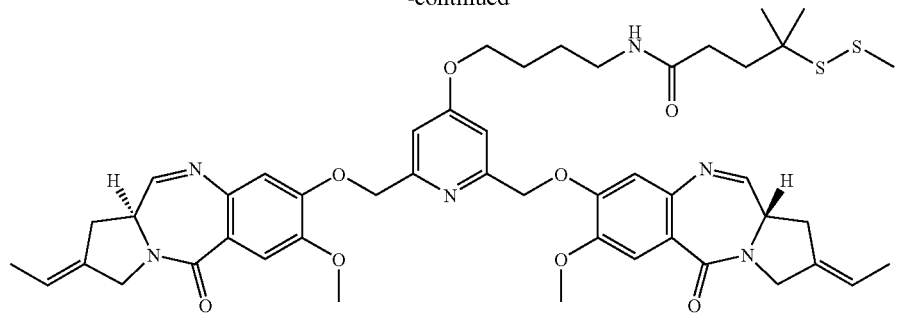

8,8'-[(4-(4-(4-methyl-4-methyldisulfanyl)-pentanamido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 4-(4-(4-methyl-4-methyldisulfanyl)-pentanamido-butoxy)-2,6-bis-(hydroxymethyl)-pyridine:

LC/MS (Method A1, Platform II): ES: m/z=947 MH$^+$+2H$_2$O m/z=929 MH$^+$+H$_2$O m/z=911 MH$^+$Retention time=3.74 minutes $^1$H N.M.R. (500 MHz, CD3COOD-d4, δ in ppm): δ=1.26 (s, 6H); from 1.59 to 1.76 (m, 8H); from 1.81 to 1.94 (m, 4H) 2.35 (m, 5H); from 2.80 to 4.40 (m, 14H); 3.92 (s, 6H); 5.39 (m, 4H); 5.50 (m, 2H) from 6.72 to 7.95 (m, 8H).

4-(4-(4-methyl-4-methyldisulfanyl)-pentanamido-butoxy)-2,6-bis-(hydroxymethyl)-pyridine 4-(4-(4-methyl-4-methyldisulfanyl)-pentanamido-butoxy)-2,6-bis-(hydroxymethyl)-pyridine may be prepared following the procedure for the preparation of 4-(2-(4-methyl-4-methyldisulfanyl)-pentanamido-ethoxy)-2,6-bis-(hydroxymethyl)-pyridine, using 4-(4-tert-Butoxycarbonylamino-butoxy)-2,6-bis-(hydroxymethyl)-pyridine LC/MS (Method A3): ES m/z=403 MH$^+$m/z=248 (M−C$_7$H$_8$NO$_3$)$^+$m/z=156 C$_7$H$_{10}$NO$_3^+$Retention time=2.3 minutes 4-(4-tert-Butoxycarbonylamino-butoxy)-2,6-bis-(hydroxymethyl)-pyridine

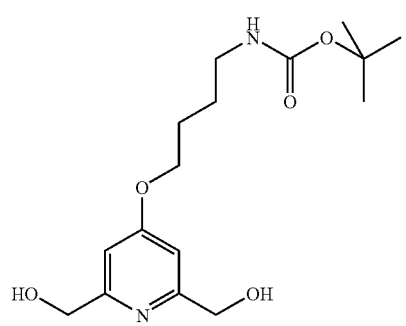

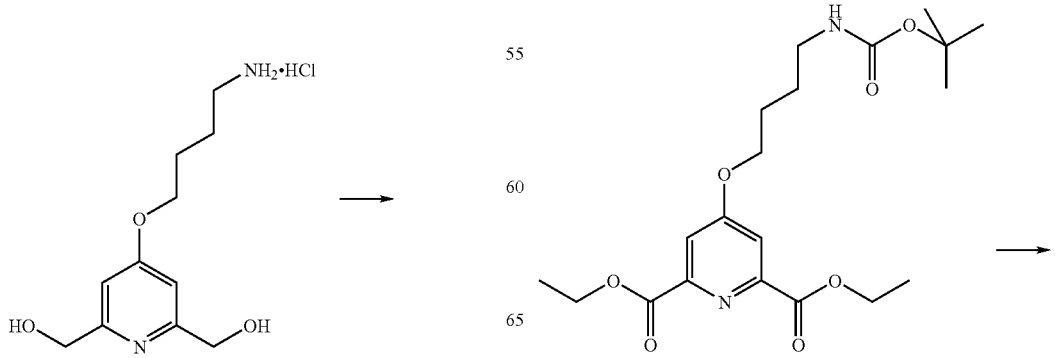

103

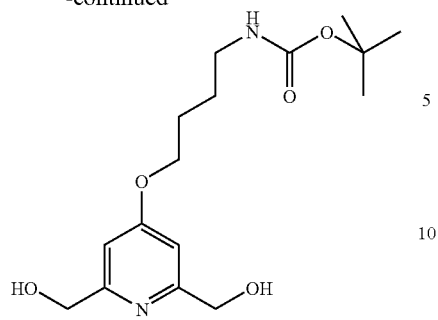

4-(4-tert-Butoxycarbonylamino-butoxy)-2,6-bis-(hydroxymethyl)-pyridine may be prepared following the procedure for the preparation of 4-(3-tert-butoxycarbonylamino-propoxy)-2,6-bis-(hydroxymethyl)pyridine, starting with 4-(4-tert-Butoxycarbonylamino-butoxy)-pyridine-2,6-dicarboxylic acid diethyl ester:

LC/MS (Method A3): ES m/z=411 MH⁺ m/z=355 (M+2H−tBu)⁺ m/z=240 $C_{11}H_{14}NO_5^+$ Retention time=3.9 minutes 4-(4-tert-Butoxycarbonylamino-butoxy)-pyridine-2,6-dicarboxylic acid diethyl ester

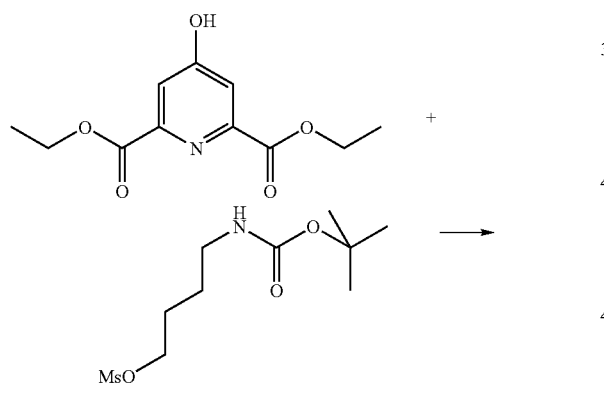

104

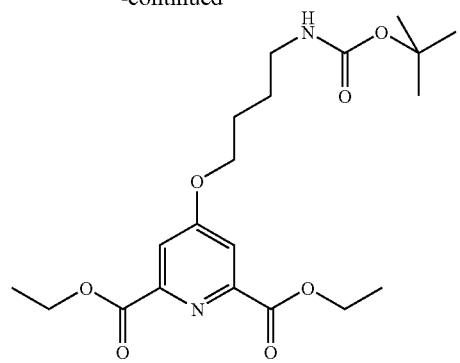

4-(4-tert-Butoxycarbonylamino-butoxy)-pyridine-2,6-dicarboxylic acid diethyl ester may be prepared following the procedure for the preparation of 4-(3-tert-butoxycarbonylamino-propoxy)-pyridine-2,6-dicarboxylic acid diethyl ester, using methane sulfonic acid 4-tert-butoxycarbonylamino-butyl ester (Cazenave Gassiot, A.; Charton, J.; Girault-Mizzi, S.; Gilleron, P.; Debreu-Fontaine, M-A.; Sergheraert, C.; Melnyk, P. *Bioorg. Med. Chem. Lett.* 2005, 15(21), 4828):

LC/MS (Method A3): ES m/z=327 MH⁺ m/z=271 (M+2H−tBu)⁺ m/z=156 $C_7H_{10}NO_3^+$ Retention time=2.0 minutes

EXAMPLE 22

8,8'-[(4-(3-[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

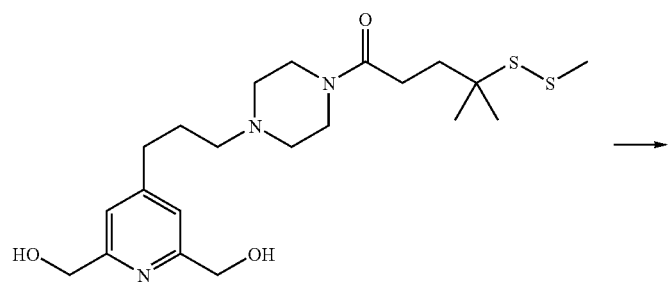

-continued

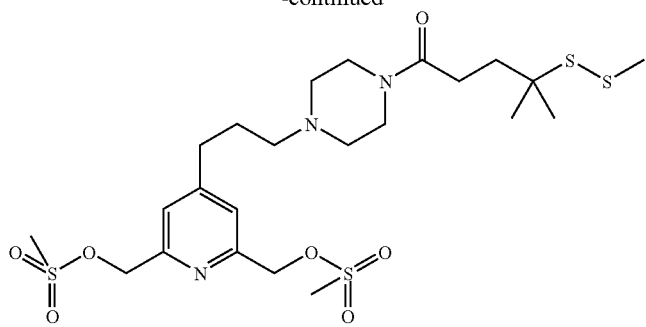

+

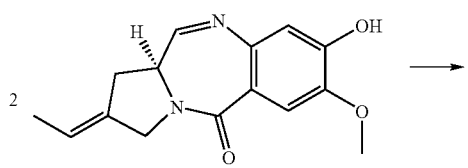

→

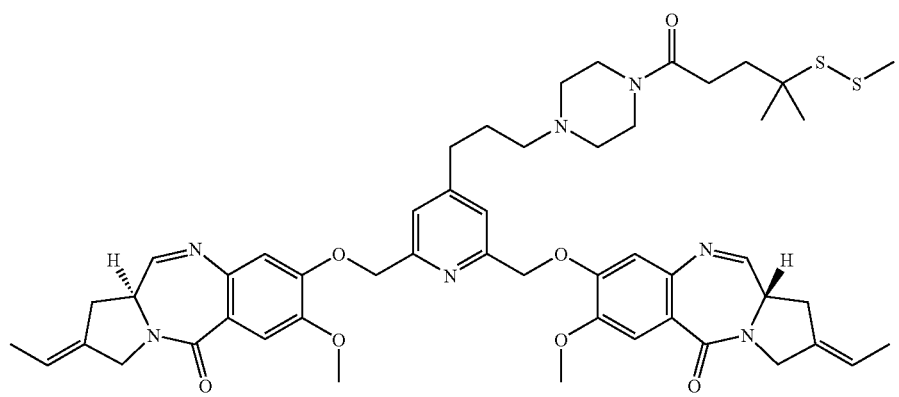

8,8'-[(4-(3-[4-(4-methyl-4-methyldisulfanyl-pentanoyl)-piperazin-1-yl]-propyl)-pyridin-2,6-dimethyl)-dioxy]-bis [(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 4-(3-[4-(4-methyl-4-methyldisulfanyl-pentanoyl)-piperazin-1-yl]-propyl)-2,6-bis-(hydroxymethyl)-pyridine:

LC/MS (Method A1, Platform II): ES: m/z=950 MH$^+$ Retention time=3.32 minutes $^1$H N.M.R. (500 MHz, CDCl3, δ in ppm): δ=1.32 (s, 6H); 1.76 (d, J=6.5 Hz, 6H) 1.80 (m, 2H); 1.94 (m, 2H) from 2.27 to 2.46 (m, 11H) 2.67 (m, 2H); 2.97 (m, 4H); from 3.40 to 3.70 (m, 4H) 3.90 (m, 2H); 4.00 (s, 6H) 4.27 (s broad, 4H); 5.29 (s broad, 4H); 5.60 (q broad, J=6.5 Hz, 2H); 6.86 (s, 2H); 7.30 (s, 2H); 7.56 (s, 2H) 7.65 (d, J=4.5 Hz, 2H).

4-(3-[4-(4-methyl-4-methyldisulfanyl-pentanoyl)-piperazin-1-yl]-propyl)-2,6-bis-(hydroxymethyl)-pyridine may be prepared as follows

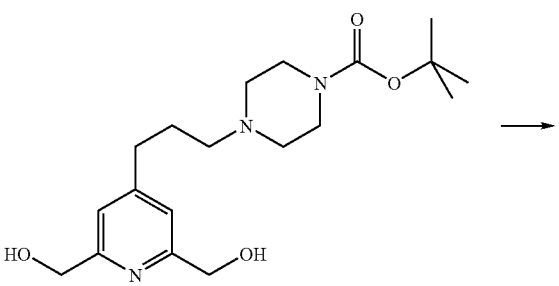

→

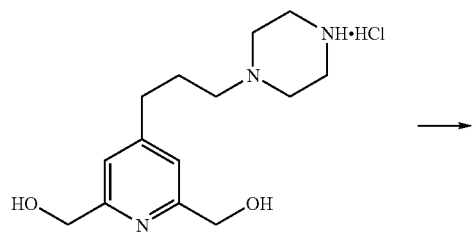

→

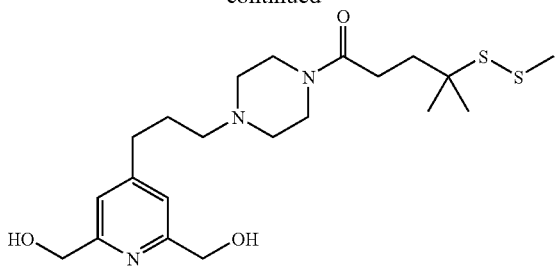

To a solution of 4-(3-(4-tert-Butoxycarbonyl-piperazin-1-yl)-propyl)-2,6-bis-(hydroxymethyl)-pyridine (610 mg) in dioxane (10 mL) was added a solution of hydrochloric acid 4N in dioxane (2.5 mL). After 4h at room temperature, the reaction mixture was concentrated in vacuo to a residue (560 mg).

To a solution of a sample of the previous residue (160 mg) in dimethylformamide (2.5 mL) was added N,N-diisopropylethylamine (181 μL), 4-methyl-4-methyldisulfanyl-pentanoic acid (158 mg), N,N'-diisopropyl-carbodiimide (88 μL) and 1-hydroxybenzotriazole hydrate (15 mg). After 15 h at room temperature, solids were filtered off and the dimethylformamide solution was injected for HPLC purification according to method F. The appropriate fractions were combined and concentrated by freeze-drying to afford 4-(3-[4-(4-methyl-4-methyldisulfanyl-pentanoyl)-piperazin-1-yl]-propyl)-2,6-bis-(hydroxymethyl)-pyridine (105 mg):

LC/MS (Method A3): ES m/z=442 MH$^+$ m/z=266 (M+2H–C$_7$H$_{13}$OS$_2$)$^+$ Retention time=2.3 minutes $^1$H N.M.R. (400 MHz, DMSO-d6, δ in ppm): δ=1.27 (s, 6H); from 1.70 to 1.83 (m, 4H) from 2.25 to 2.39 (m, 8H); 2.40 (s, 3H); 2.63 (m, 2H); 3.43 (m, 4H); 4.49 (s, 4H) 5.28 (m broad, 2H); 7.18 (s, 2H)

4-(3-(4-tert-Butoxycarbonyl-piperazin-1-yl)-propyl)-2,6-bis-(hydroxymethyl)-pyridine 4-(3-(4-tert-Butoxycarbonyl-piperazin-1-yl)-propyl)-2,6-bis-(hydroxymethyl)-pyridine may be prepared following the procedure for the preparation of 4-(3-tert-butoxycarbonylamino-propoxy)-2,6-bis-(hydroxymethyl)pyridine, starting with 4-[3-(4-tert-Butoxycarbonyl-piperazin-1-yl)-propyl]-pyridine-2,6-dicarboxylic acid diethyl ester:

LC/MS (Method A3): ES m/z=366 MH$^+$ m/z=310 (M+2H–tBu)$^+$ m/z=266 (M+2H–CO$_2$tBu)$^+$ Retention time=0.5 minutes $^1$H N.M.R. (400 MHz, DMSO-d6, δ in ppm): δ=1.39 (s, 9H); 1.73 (m, 2H); 2.29 (m, 6H); 2.61 (m, 2H); 3.30 (m partially masked, 4H); 4.49 (d, J=6.0 Hz, 4H); 5.30 (t broad, J=6.0 Hz, 2H); 7.18 (s, 2H).

4-[3-(4-tert-Butoxycarbonyl-piperazin-1-yl)-propyl]-pyridine-2,6-dicarboxylic acid diethyl ester

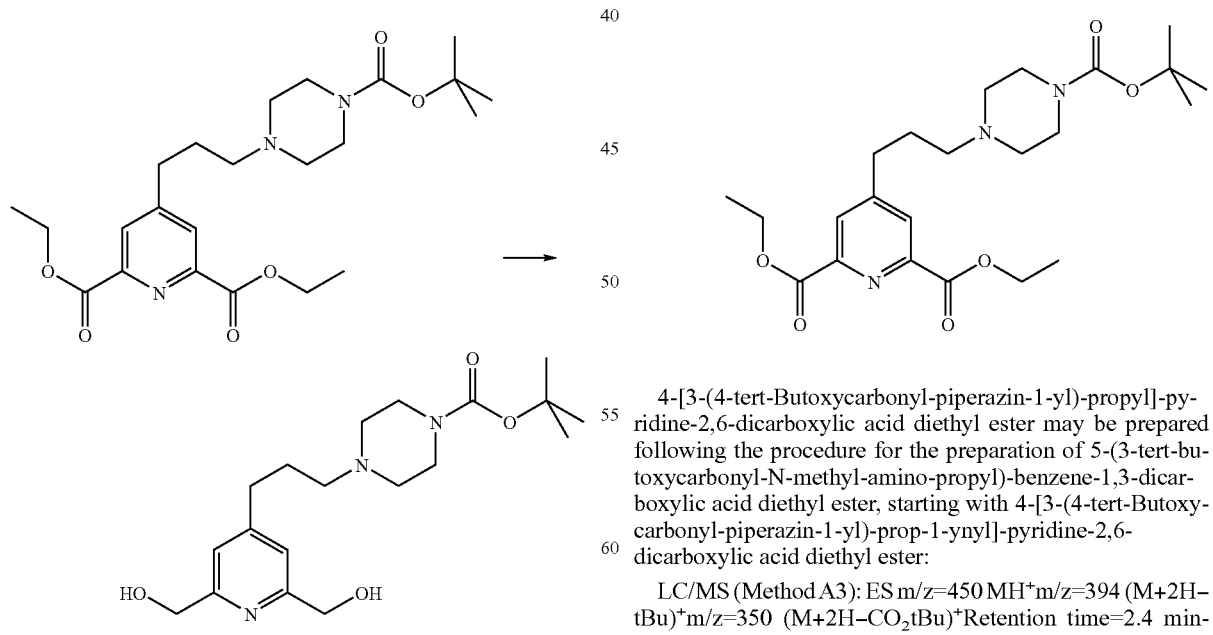

4-[3-(4-tert-Butoxycarbonyl-piperazin-1-yl)-propyl]-pyridine-2,6-dicarboxylic acid diethyl ester may be prepared following the procedure for the preparation of 5-(3-tert-butoxycarbonyl-N-methyl-amino-propyl)-benzene-1,3-dicarboxylic acid diethyl ester, starting with 4-[3-(4-tert-Butoxycarbonyl-piperazin-1-yl)-prop-1-ynyl]-pyridine-2,6-dicarboxylic acid diethyl ester:

LC/MS (Method A3): ES m/z=450 MH$^+$ m/z=394 (M+2H–tBu)$^+$ m/z=350 (M+2H–CO$_2$tBu)$^+$ Retention time=2.4 minutes $^1$H N.M.R. (400 MHz, DMSO-d6, δ in ppm): δ=1.35 (t, J=7.0 Hz, 6H); 1.39 (s, 9H) 1.79 (m, 2H); 2.27 (m, 6H); 2.80 (m, 2H) 3.29 (m, 4H); 4.39 (q, J=7.0 Hz, 4H) 8.12 (s, 2H).

109

4-[3-(4-tert-Butoxycarbonyl-piperazin-1-yl)-prop-1-ynyl]-pyridine-2,6-dicarboxylic acid diethyl ester

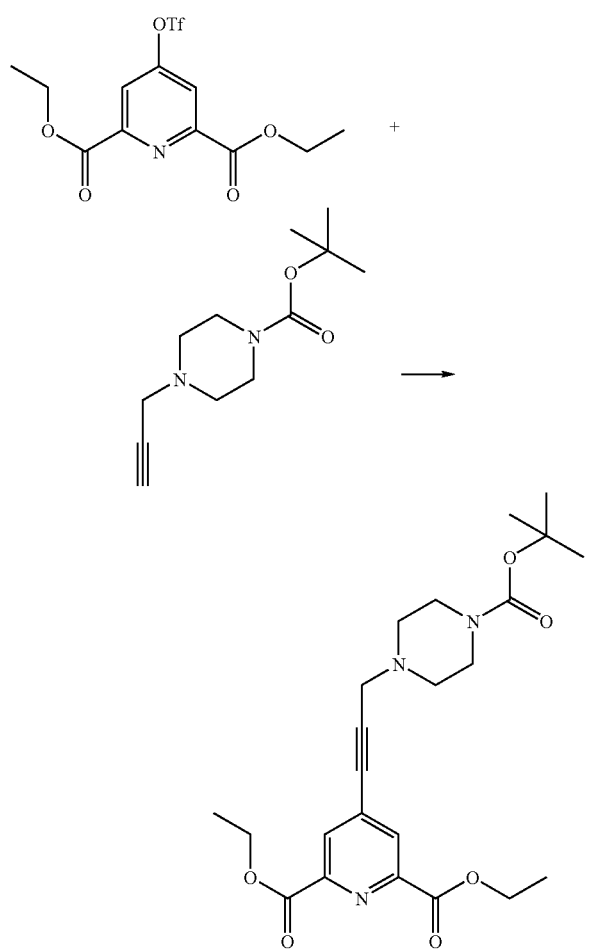

4-[3-(4-tert-Butoxycarbonyl-piperazin-1-yl)-prop-1-ynyl]-pyridine-2,6-dicarboxylic acid diethyl ester may be prepared following the procedure for the preparation of 5-(3-tert-butoxycarbonyl-N-methyl-amino-propyn-1-yl)-benzene-1,3-dicarboxylic acid diethyl ester, starting with 4-trifluoromethanesulfonyloxy-pyridine-2,6-dicarboxylic acid diethyl ester and tert-butyl-4-propargyl-piperazine-1-carboxylate (Zheng, H.; Weiner, L. M.; Bar-Am, O.; Epsztejn, S.; Cabantchik, Z. I.; Warshawsky, A.; Youdim, M. B. H.; and Fridkin, M. *Bioorg. Med. Chem.* 2005, 3, 773)

110

EI (Method C) m/z=445 M$^+$. m/z=388 (M-C$_4$H$_9$)$^+$ m/z=344 (m/z=388-CO$_2$)$^+$ m/z=57 C$_4$H$_9^+$ $^1$H N.M.R. (400 MHz, CDCl3-d1, δ in ppm): δ=1.46 (t, J=7.0 Hz, 6H); 1.48 (s, 9H); 2.60 (m broad, 4H); 3.52 (m broad, 4H); 3.62 (s broad, 2H); 4.49 (q, J=7.0 Hz, 4H); 8.23 (s, 2H).

4-trifluoromethanesulfonyloxy-pyridine-2,6-dicarboxylic acid diethyl ester may be prepared as follows

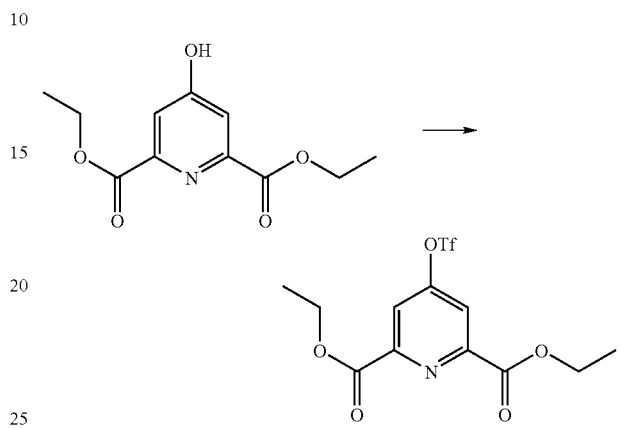

To a cooled (0° C.) solution of chelidamic acid diethyl ester (Chaubet, F.; Nguyen van duong, M.; Gref, A.; Courtieu, J.; Crumbliss, A. L.; Gaudemer, A. *Tetrahedron Lett.* 1990, 31(40), 5729-5732) (3.5 g) in pyridine (35 mL), was added dropwise trifluoromethanesulfonyl chloride (2.6 mL). The reaction was then stirred at room temperature for 3 hours. Water and ethyl acetate were added. The layers were separated, and the aqueous layer was extracted twice ethyl acetate. The combined organic solutions were dried over magnesium sulfate, and concentrated in vacuo to a residue. The residue was purified by silica gel chromatography (Merck SuperVarioPrep 90g column, Si60 15-40μm), eluted with dichloromethane to give 4-trifluoromethanesulfonyloxy-pyridine-2,6-dicarboxylic acid diethyl ester (4.2g).

LC/MS (Method A1, Platform I) ES m/z=372 MH$^+$ Retention time=4.38 minutes

EXAMPLE 23

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

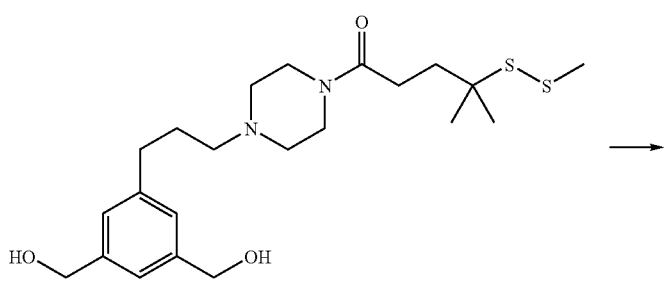

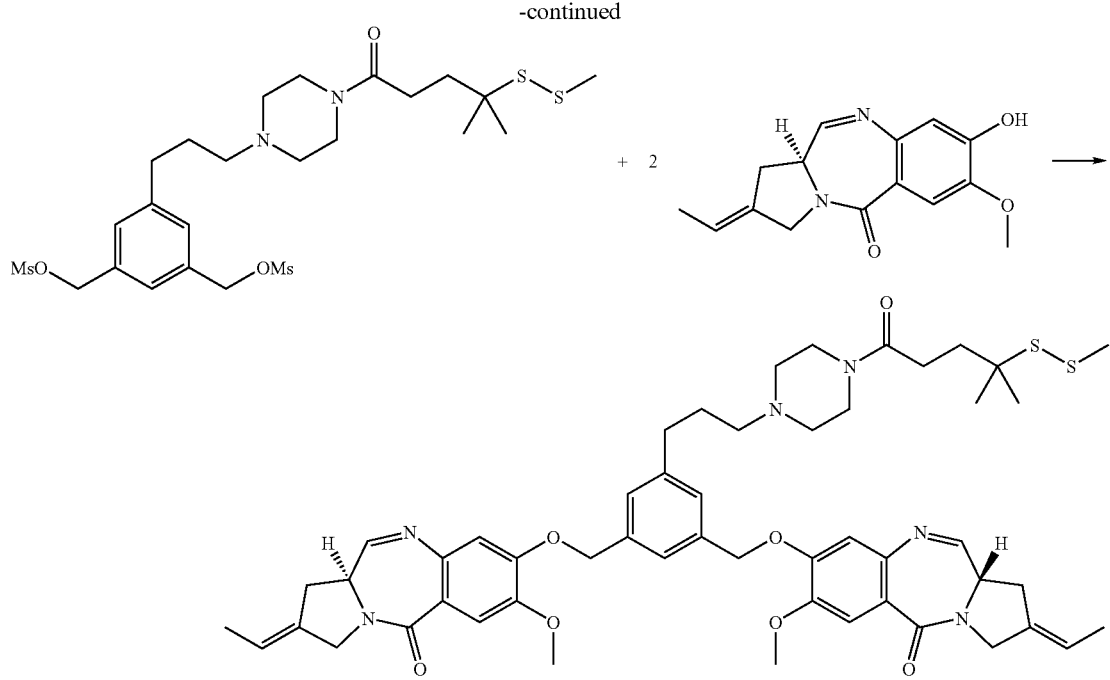

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 1-(3-[4-(4-methyl-4-methyldisulfanyl-pentanoyl)-piperazin-1-yl]-propyl)-3,5-bis-(hydroxymethyl)-benzene:

LC/MS (Method A3): ES m/z=949 MH⁺ m/z=475.3 (M+2H)²⁺/2 Retention time=3.3 minutes 1-(3-[4-(4-methyl-4-methyldisulfanyl-pentanoyl)-piperazin-1-yl]-propyl)-3,5-bis-(hydroxymethyl)-benzene

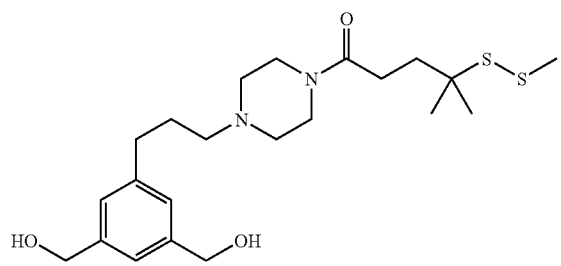

1-(3-[4-(4-methyl-4-methyldisulfanyl-pentanoyl)-piperazin-1-yl]-propyl)-3,5-bis-(hydroxymethyl)-benzene may be prepared following the procedure for the preparation of 4-(3-[4-(4-methyl-4-methyldisulfanyl-pentanoyl)-piperazin-1-yl]-propyl)-2,6-bis-(hydroxymethyl)-pyridine, starting with 1-(3-(4-tert-Butoxycarbonyl-piperazin-1-yl)-propyl)-3,5-bis-(hydroxymethyl)-benzene:

LC/MS (Method A3): ES m/z=441 MH⁺ Retention time=2.4 minutes

¹H N.M.R. (400 MHz, DMSO-d6, δ in ppm): δ=1.26 (s, 6H); 1.71 (m, 2H); 1.79 (m, 2H); from 2.22 to 2.40 (m, 8H); 2.39 (s, 3H); 2.58 (m, 2H); 3.44 (m, 4H); 4.45 (d, J=6.0 Hz, 4H); 5.09 (t, J=6.0 Hz, 2H); 7.00 (s broad, 2H); 7.08 (s broad, 1H).

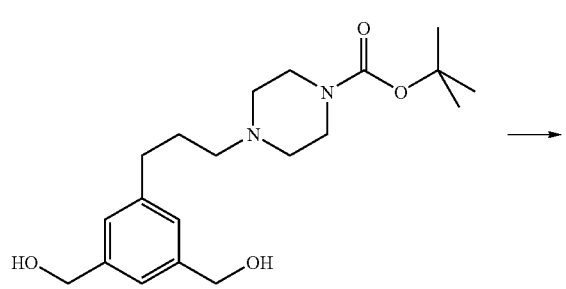

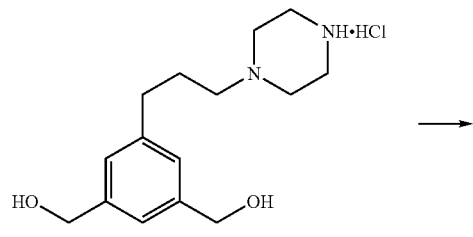

1-(3-(4-tert-Butoxycarbonyl-piperazin-1-yl)-propyl)-3,5-bis-(hydroxymethyl)-benzene

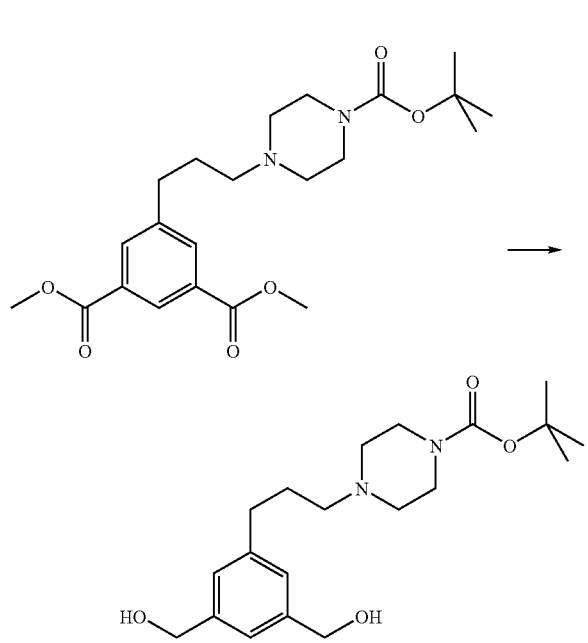

1-(3-(4-tert-Butoxycarbonyl-piperazin-1-yl)-propyl)-3,5-bis-(hydroxymethyl)-benzene may be prepared following the procedure for the preparation of 5-(3-tert-butoxycarbonyl-N-methyl-amino-propyl)-1,3-bis-(hydroxymethyl)-benzene, starting with 5-[3-(4-tert-Butoxycarbonyl-piperazin-1-yl)-propyl]-isophthalic acid dimethyl ester:

LC/MS (Method A3): ES m/z=365 MH$^+$ m/z=309 (M+2H−tBu)$^+$ Retention time=2.0 minutes $^1$H N.M.R. (300 MHz, DMSO-d6, δ in ppm): δ=1.39 (s, 9H); 1.71 (m, 2H); 2.28 (m, 6H) 2.57 (m, 2H); 3.29 (m partially masked, 4H); 4.44 (d, J=6.0 Hz, 4H); 5.08 (t, J=6.0 Hz, 2H); 7.00 (s broad, 2H); 7.08 (s broad, 1H).

5-[3-(4-tert-Butoxycarbonyl-piperazin-1-yl)-propyl]-isophthalic acid dimethyl ester

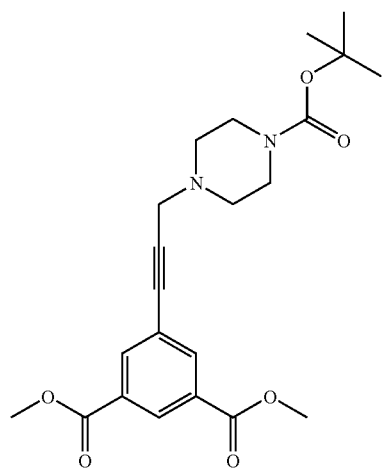

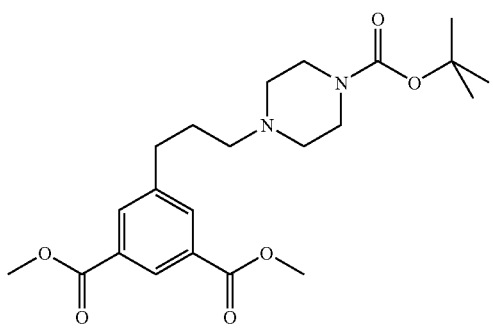

5-[3-(4-tert-Butoxycarbonyl-piperazin-1-yl)-propyl]-isophthalic acid dimethyl ester may be prepared following the procedure for the preparation of 5-(3-tert-butoxycarbonyl-N-methyl-amino-propyl)-benzene-1,3-dicarboxylic acid diethyl ester, starting with 5-[3-(4-tert-Butoxycarbonyl-piperazin-1-yl)-prop-1-ynyl]-isophthalic acid dimethyl ester:

LC/MS (Method A3): ES m/z=421 MH$^+$ m/z=365 (M+2H−tBu)$^+$ m/z=321 (M+2H−CO$_2$tBu)$^+$ Retention time=2.7 minutes $^1$H N.M.R. (400 MHz, DMSO-d6, δ in ppm): δ=1.39 (s, 9H); 1.74 (m, 2H); 2.28 (m, 6H); 2.75 (m, 2H); 3.30 (m partially masked, 4H); 3.89 (s, 6H); 8.08 (d, J=2.0 Hz, 2H); 8.32 (t, J=2.0 Hz, 1H).

5-[3-(4-tert-Butoxycarbonyl-piperazin-1-yl)-prop-1-ynyl]-isophthalic acid dimethyl ester

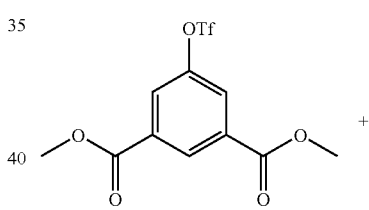

+

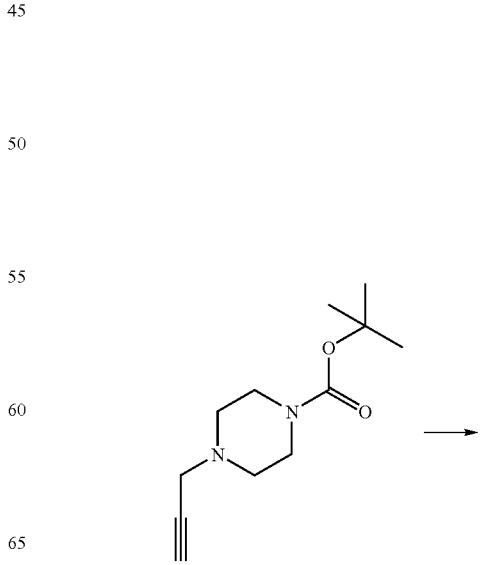

115

-continued

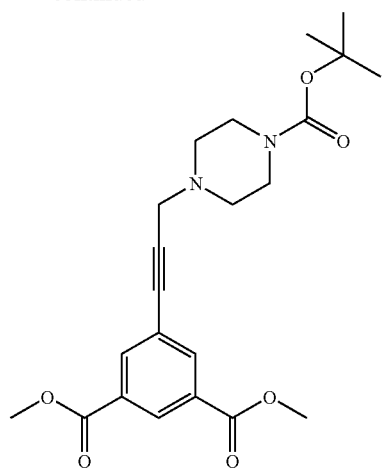

116

5-[3-(4-tert-Butoxycarbonyl-piperazin-1-yl)-prop-1-ynyl]-isophthalic acid dimethyl ester may be prepared following the procedure for the preparation of 5-(3-tert-butoxy-carbonyl-N-methyl-amino-propyn-1-yl)-benzene-1,3-dicarboxylic acid diethyl ester, starting with tert-butyl-4-propargyl-piperazine-1-carboxylate LC/MS (Method A3): ES m/z=417 MH$^+$m/z=361 (M+2H–tBu)$^+$m/z=317 (M+2H–CO$_2$tBu)$^+$Retention time=3.1 minutes $^1$H N.M.R. (400 MHz, DMSO-d6, δ in ppm): δ=1.40 (s, 9H); 2.50 (m masked, 4H) 3.35 (m, 4H); 3.61 (s, 2H); 3.90 (s, 6H); 8.14 (s broad, 2H); 8.40 (s broad, 1H).

EXAMPLE 24

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

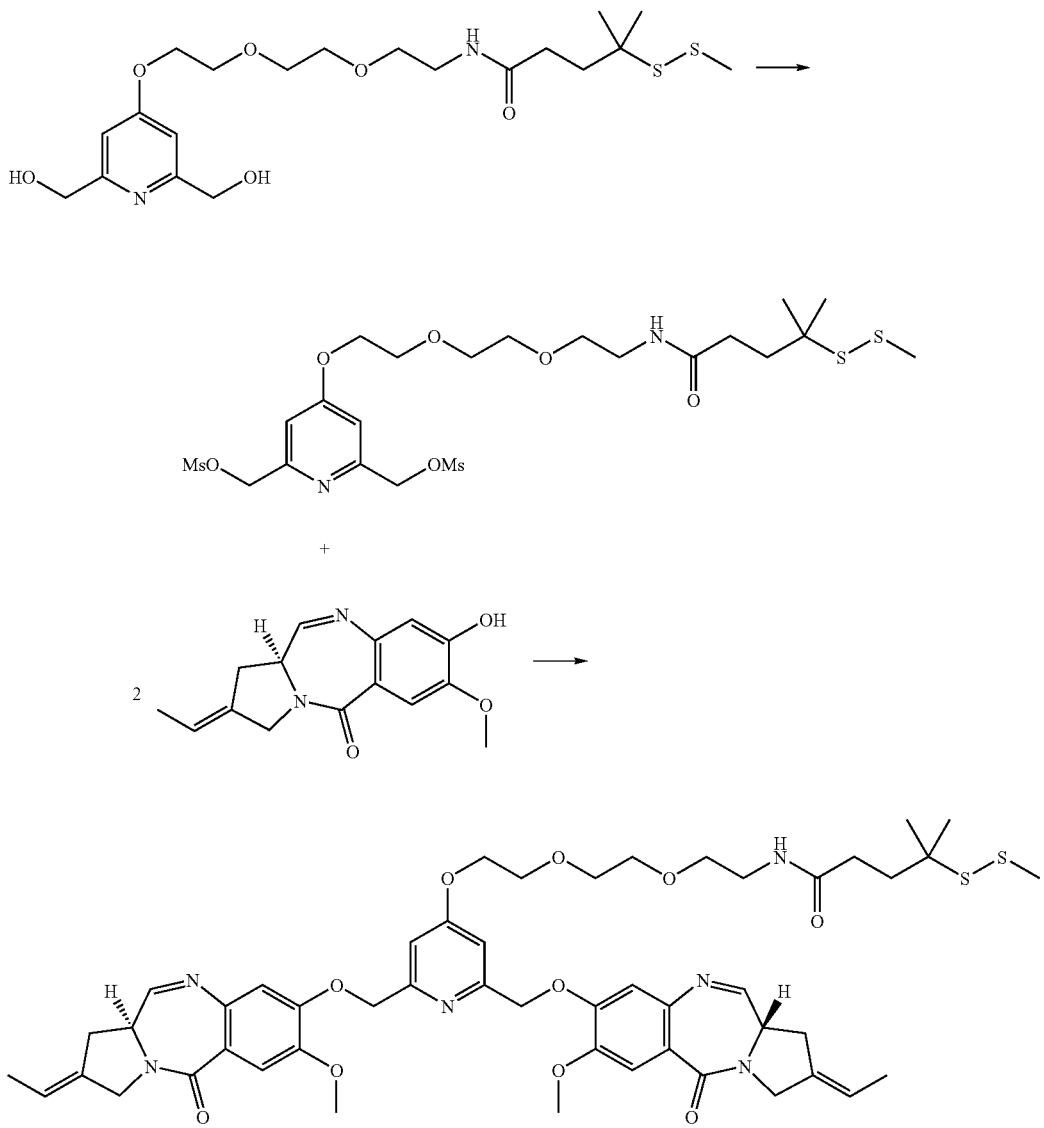

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 4-(2-{2-[2-(4-methyl-4-methyldisulfanyl-pentanoylamino)-ethoxy]-ethoxy}-ethoxy)-2,6-bis-(hydroxymethyl)-pyridine:

LC/MS (Method A3): ES m/z=971 MH$^{+m/z=}$486.3 (M+2H)$^{2+}$/2 Retention time=3.60 minutes $^1$H N.M.R. (500 MHz, CDCl3-d1, δ in ppm): δ=1.28 (s, 6H); 1.76 (d, J=6.5 Hz, 6H); 1.94 (m, 2H); 2.26 (m, 2H); 2.40 (s, 3H); 2.98 (m, 4H); from 3.36 to 3.95 (m, 12H); 4.00 (s, 6H); 4.18 (m, 2H); 4.28 (s broad, 4H); 5.27 (m, 4H); 5.61 (m, 2H); 5.97 (m broad, 1H); 6.84 (s, 2H); 7.01 (s broad, 2H); 7.56 (s, 2H); 7.64 (d, J=4.5 Hz, 2H).

4-(2-{2-[2-(4-methyl-4-methyldisulfanyl-pentanoylamino)-ethoxy]-ethoxy}-ethoxy)-2,6-bis-(hydroxymethyl)-pyridine

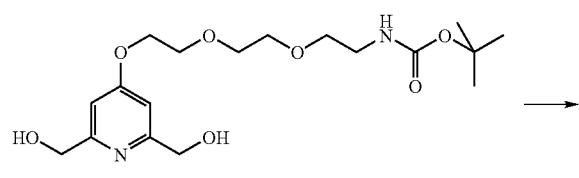

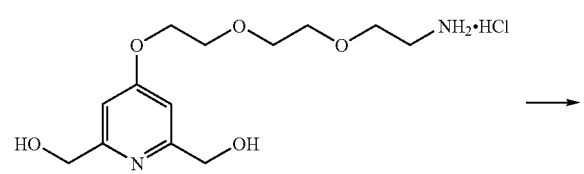

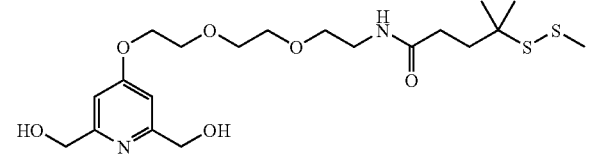

4-(2-{2-[2-(4-methyl-4-methyldisulfanyl-pentanoylamino)-ethoxy]-ethoxy}-ethoxy)-2,6-bis-(hydroxymethyl)-pyridine may be prepared following the procedure for the preparation of 4-(3-[4-(4-methyl-4-methyldisulfanyl-pentanoyl)-piperazin-1-yl]-propyl)-2,6-bis-(hydroxymethyl)-pyridine, starting with 4-(2-{2-[2-tert-butoxycarbonylamino-ethoxy]-ethoxy}-ethoxy)-2,6-bis-(hydroxymethyl)-pyridine LC/MS (Method A3): ES m/z=463 MH$^+$Retention time=2.3 minutes $^1$H N.M.R. (400 MHz, DMSO-d6, δ in ppm): δ=1.22 (s, 6H); 1.79 (m, 2H); 2.15 (m, 2H); 2.39 (s, 3H); 3.18 (q, J=6.0 Hz, 2H); 3.40 (t, J=6.0 Hz, 2H); 3.52 (m, 2H); 3.60 (m, 2H); 3.76 (m, 2H); 4.18 (m, 2H); 4.45 (s, 4H); 5.32 (m broad, 2H); 6.85 (s, 2H); 7.90 (t broad, J=6.0 Hz, 1H).

4-(2-{2-[2-tert-butoxycarbonylamino-ethoxy]-ethoxy}-ethoxy)-2,6-bis-(hydroxymethyl)-pyridine

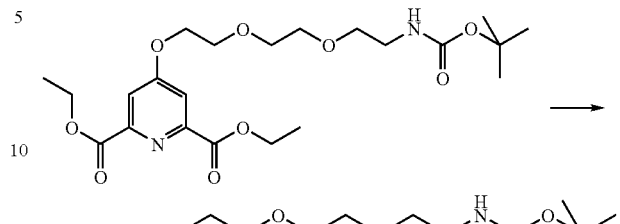

4-(2-{2-[2-tert-butoxycarbonylamino-ethoxy]-ethoxy}-ethoxy)-2,6-bis-(hydroxymethyl)-pyridine may be prepared following the procedure for the preparation of 4-(3-tert-butoxycarbonylamino-propoxy)-2,6-bis-(hydroxymethyl)pyridine, starting with 4-(2-{2-[2-tert-butoxycarbonylamino-ethoxy]-ethoxy}-ethoxy)-pyridine-2,6-dicarboxylic acid diethyl ester:

LC/MS (Method A3): ES m/z=387 MH$^+$m/z=331 (M+2H−tBu)$^+$Retention time=2.0 minutes $^1$H N.M.R. (400 MHz, DMSO-d6, δ in ppm): δ=1.37 (s, 9H); 3.07 (q, J=6.0 Hz, 2H); 3.39 (t, J=6.0 Hz, 2H); 3.51 (m, 2H); 3.59 (m, 2H); 3.73 (m, 2H); 4.18 (m, 2H); 4.45 (d, J=6.0 Hz, 4H); 5.31 (t, J=6.0 Hz, 2H); 6.73 (t broad, J=6.0 Hz, 1H) 6.85 (s, 2H).

4-(2-{2-[2-tert-butoxycarbonylamino-ethoxy]-ethoxy}-ethoxy)-pyridine-2,6-dicarboxylic acid diethyl ester may be prepared as follows:

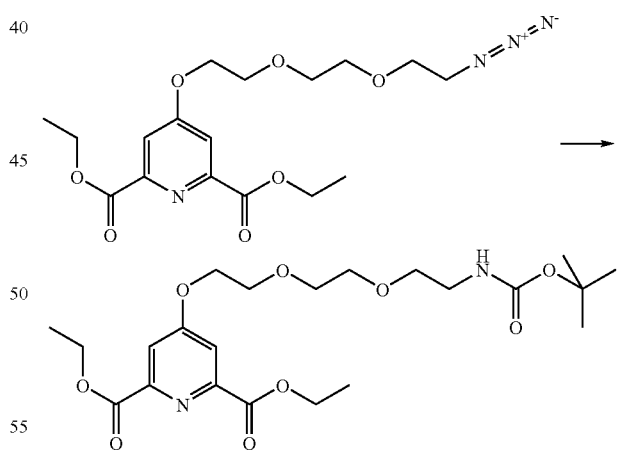

To a solution of 4-(2-{2-[2-azido-ethoxy]-ethoxy}-ethoxy)-pyridine-2,6-dicarboxylic acid diethyl ester (Roy, B. C.; Santos, M.; Mallik, S.; D. Campiglia, A. D. *J. Org. Chem.* 2003, 68(10), 3999) (900 mg) in ethyl acetate (18 mL) were added di-tert-butyl-dicarbonate (545mg) and palladium 10% on carbon (73 mg). The solution was stirred at room temperature under an hydrogen atmosphere (2 bar) for 18h. The solid was filtered off and solvent was removed in vacuo to a residue. The residue was purified by silica gel chromatography (Analogix Super Flash SiO$_2$ SF25-34g), using gradient elution with a mixture of dichloromethane (A) and methanol (B) (gradient: 100% A down to 97.5% A:2.5% B) to give 4-(2-{2-[2-tert-butoxycarbonylamino-ethoxy]-ethoxy}-ethoxy)-pyridine-2,6-dicarboxylic acid diethyl ester (760mg):

LC/MS (MethodA3): ES m/z=471 MH⁺ m/z=415 (M+2H−tBu)⁺ m/z=371 (M+2H−CO₂tBu)⁺ Retention time=3.6 minutes ¹H N.M.R. (300 MHz, DMSO-d6, δ in ppm): δ=1.32 (t, J=7.0 Hz, 6H); 1.36 (s, 9H); 3.04 (q, J=6.0 Hz, 2H); 3.38 (t, J=6.0 Hz, 2H); 3.51 (m, 2H); 3.59 (m, 2H); 3.79 (m, 2H); 4.25 (m masked, 2H); 4.29 (q, J=7.0 Hz, 4H); 6.70 (t broad, J=6.0 Hz, 1H); 7.73 (s, 2H)

EXAMPLE 25

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

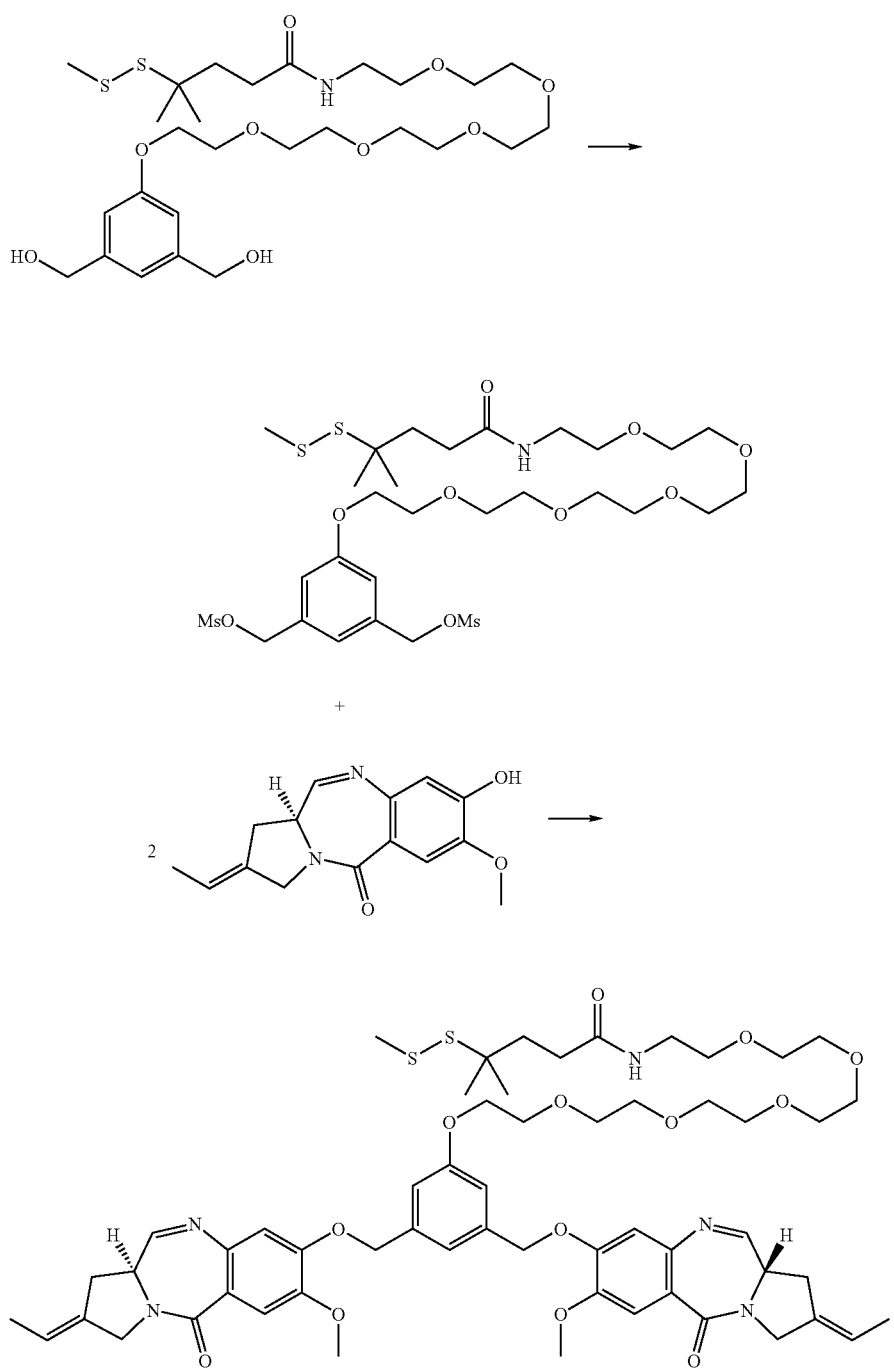

121

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-3,5-bis-(hydroxymethyl)-benzene:

LC/MS (Method A1, Platform II): ES: m/z=1102 MH$^+$Retention time=4.49 minutes $^1$H N.M.R. (500 MHz, CDCl3-d1, δ in ppm): δ=1.30 (s, 6H) 1.75 (d, J=6.5 Hz, 6H); 1.95 (m, 2H); 2.28 (m, 2H); 2.41 (s, 3H); 2.97 (m, 4H); from 3.33 to 3.96 (m, 24H); 3.96 (s, 6H); 4.12 (m, 2H) 4.27 (s broad, 4H); from 5.07 to 5.24 (m, 4H); 5.60 (m, 2H); 6.21 (m broad, 1H) 6.81 (s, 2H); 6.96 (s, 2H); 7.07 (s, 1H); 7.51 (s, 2H); 7.65 (d, J=4.5 Hz, 2H).

1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-3,5-bis-(hydroxymethyl)-benzene

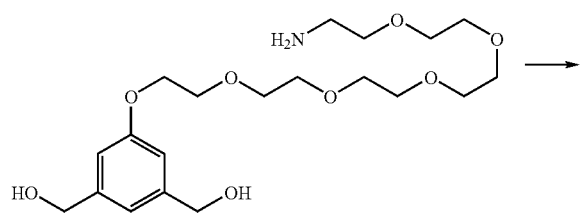

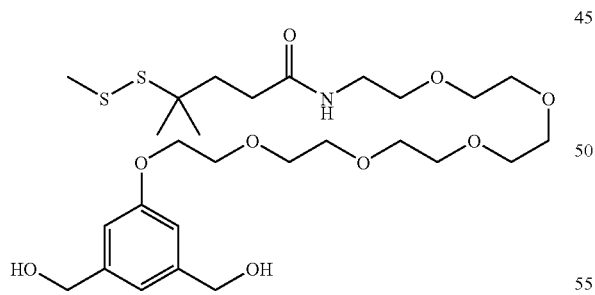

1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-3,5-bis-(hydroxymethyl)-benzene may be prepared following the procedure for the preparation of 1-(3-(4-methyl-4-methyldisulfanyl)-pentanamido-propoxy)-3,5-bis-(hydroxymethyl)-benzene, starting with 1-(2-{2-[2-(2-{2-[2-amino-ethoxy]-ethoxy}-ethoxy)-ethoxy]-ethoxy}-ethoxy)-3,5-bis-(hydroxymethyl)-benzene:

LC/MS (Method G1): ES m/z=594 MH$^+$Retention time=1.9 minutes.

122

1-(2-{2-[2-(2-{2-[2-amino-ethoxy]-ethoxy}-ethoxy)-ethoxy]-ethoxy}-ethoxy)-3,5-bis-(hydroxymethyl)-benzene may be prepared as follows:

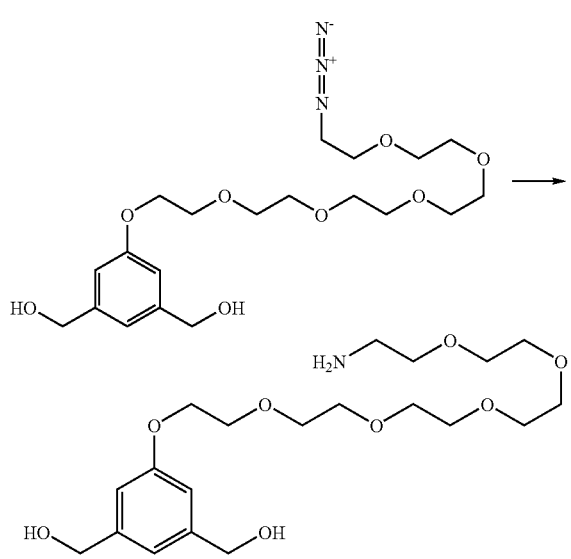

To a solution of 1-(2-{2-[2-(2-{2-[2-azido-ethoxy]-ethoxy}-ethoxy)-ethoxy]-ethoxy}-ethoxy)-3,5-bis-(hydroxymethyl)-benzene (540 mg) in THF (5.5 mL) were added triphenylphosphine (320 mg) and water (22 µL). The solution was stirred at room temperature for 18h and solvent was removed in vacuo to a residue. The residue was purified by silica gel chromatography (Merck SuperVarioFlash 30g column, Si60 15-40µm, eluted with dichloromethane/methanol 95:5, then dichloromethane/methanol/NH$_4$OH 75:25:2.5 to give 1-(2-{2-[2-(2-{2-[2-amino-ethoxy]-ethoxy}-ethoxy)-ethoxy]-ethoxy}-ethoxy)-3,5-bis-(hydroxymethyl)-benzene (430 mg):

LC/MS (Method A3): ES: m/z=418 MH$^+$Retention time=1.3 and 1.7 minutes 1-(2-{2-[2-(2-{2-[2-azido-ethoxy]-ethoxy}-ethoxy)-ethoxy]-ethoxy}-ethoxy)-3,5-bis-(hydroxymethyl)-benzene may be prepared as follows:

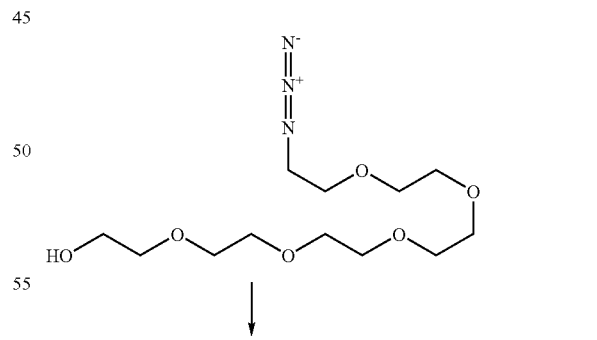

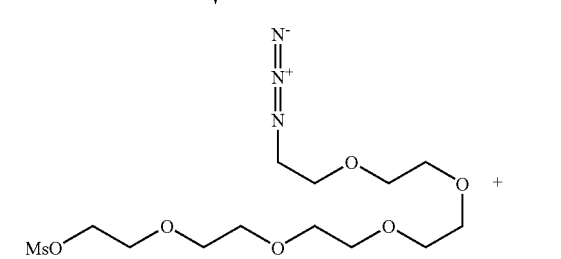

123

-continued

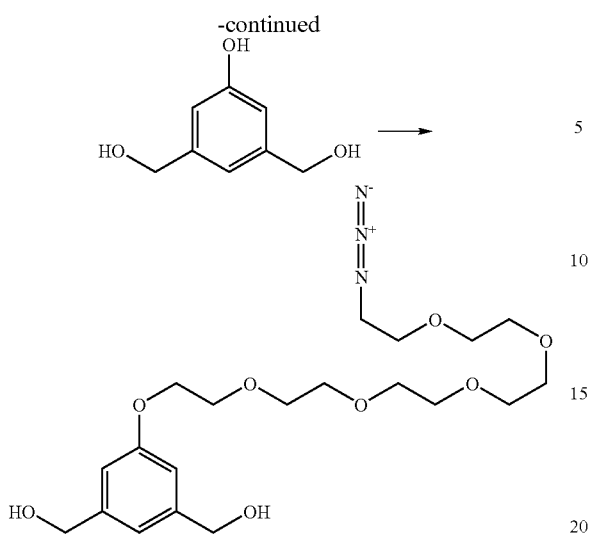

To a cooled (0° C.) solution of 2-[2-(2-{2-[2-(2-Azido-ethoxy)-ethoxy]-ethoxy}-ethoxy)-ethoxy]-ethanol (1.6 g) and triethylamine (1.45 mL) in dichloromethane (40 mL), was added methanesulfonyl chloride (617 μL). After 1 hour, water was added. The layers were separated and the organic layer was dried over magnesium sulfate, and concentrated in vacuo to a residue (1.83 g).

A sample of the residue (1.4 g), 3,5-bis-hydroxymethylphenol (510 mg) and potassium carbonate (686 mg) were mixed in dimethylformamide (8 mL) and heated at 70° C. for 15h. The reaction mixture was cooled to room temperature, water was added and the aqueous solution was extracted three times with ethyl acetate. The combined organic solutions were washed with a saturated sodium chloride aqueous solution, dried over magnesium sulfate and concentrated in vacuo to a residue. The residue was purified by silica gel chromatography (Merck SuperVarioPrep 70g column, Si60 15-40μm), eluted with a mixture of methanol (A)/dichloromethane (B), (gradient: 2% A:98% B to 10% A:90% B) to give 1-(2-{2-[2-(2-{2-[2-azido-ethoxy]-ethoxy}-ethoxy)-ethoxy]-ethoxy}-ethoxy)-3,5-bis-(hydroxymethyl)-benzene (540 mg):

CI (Method D): m/z=461 MNH$_4^+$

2-[2-(2-{2-[2-(2-Azido-ethoxy)-ethoxy]-ethoxy}-ethoxy)-ethoxy]-ethanol may be prepared as follows:

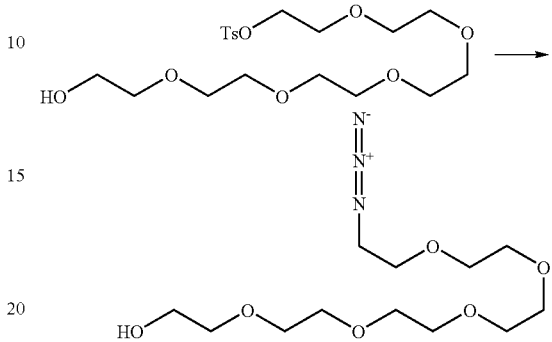

To a solution of 2-[2-(2-{2-[2-(2-tosyloxy-ethoxy)-ethoxy]-ethoxy}-ethoxy)-ethoxy]-ethanol (Loiseau, F. A.; Hii, K. K.; Hill, A. M. *J. Org. Chem.* 2004, 69, 639) (4.5 g) in dimethylformamide (30 mL), was added sodium azide (0.89 g). The solution was stirred at 70° C. for 18h and solvent was then removed in vacuo to a residue. Dichloromethane was added and the resulting precipitate was filtered off. The organic layer was concentrated in vacuo to give 2-[2-(2-{2-[2-(2-Azido-ethoxy)-ethoxy]-ethoxy}-ethoxy)-ethoxy]-ethanol (3.1 g):

CI (Method D): m/z=325 MNH$_4^+$

EXAMPLE 26

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

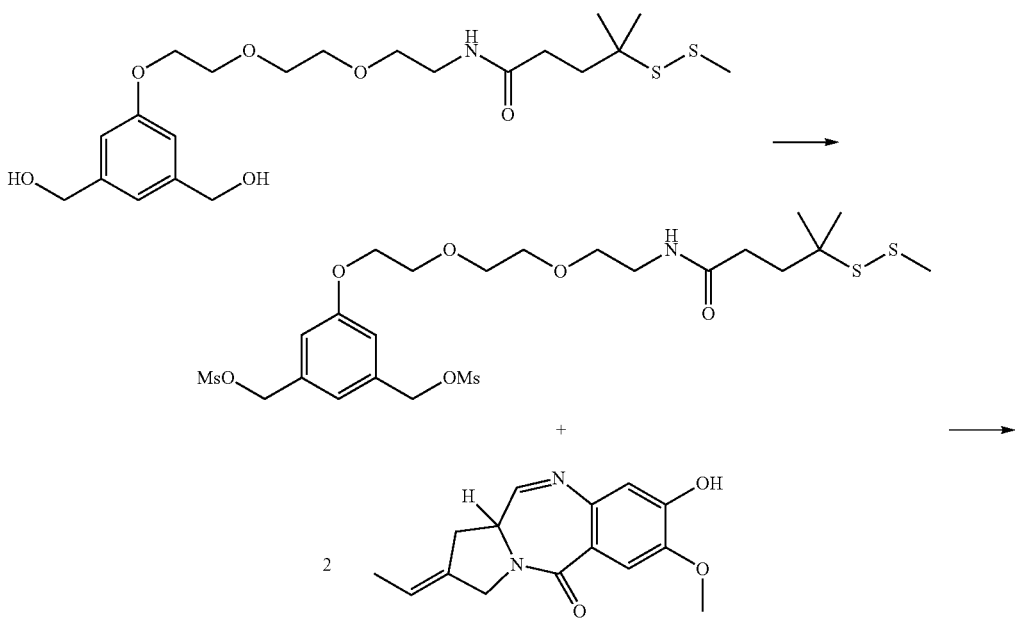

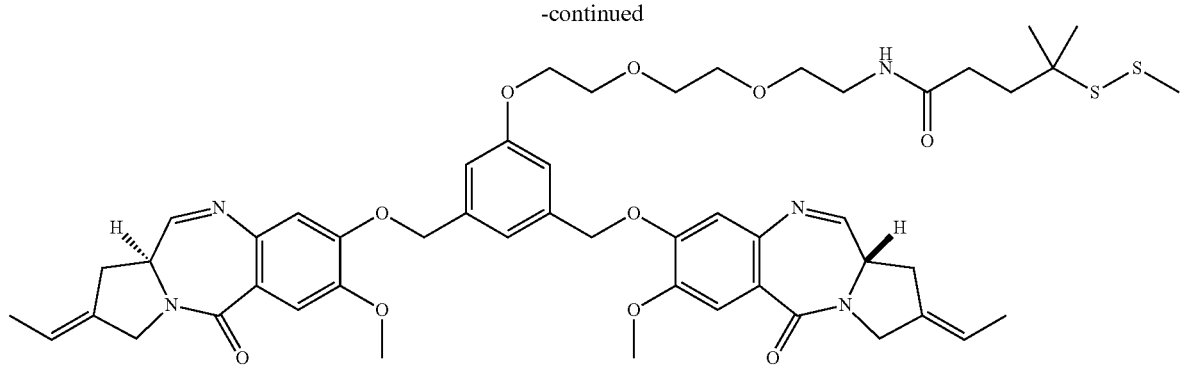

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 1-(2-{2-[2-(4-methyl-4-methyldisulfanyl-pentanoylamino)-ethoxy]-ethoxy}-ethoxy)-3,5-bis-(hydroxymethyl)-benzene:

LC/MS (Method A1, Platform II): ES: m/z=970 MH$^+$Retention time=3.89 minutes $^1$H N.M.R. (500 MHz, CDCl3-d1, δ in ppm): δ=1.27 (s, 6H); 1.75 (d, J=6.5 Hz, 6H); 1.94 (m, 2H); 2.26 (m, 2H); 2.40 (s, 3H); 2.98 (m, 4H); from 3.35 to 3.92 (m, 12H); 3.96 (s, 6H); 4.15 (m, 2H); 4.28 (s broad, 4H) from 5.10 to 5.23 (m, 4H) 5.60 (q broad, J=6.5 Hz, 2H); 6.05 (t broad, J=6.0 Hz, 1H) 6.81 (s, 2H); 6.98 (s, 2H) 7.09 (s, 1H); 7.53 (s, 2H); 7.64 (d, J=4.5 Hz, 2H).

1-(2-{2-[2-(4-methyl-4-methyldisulfanyl-pentanoylamino)-ethoxy]-ethoxy}-ethoxy)-3,5-bis-(hydroxymethyl)-benzene

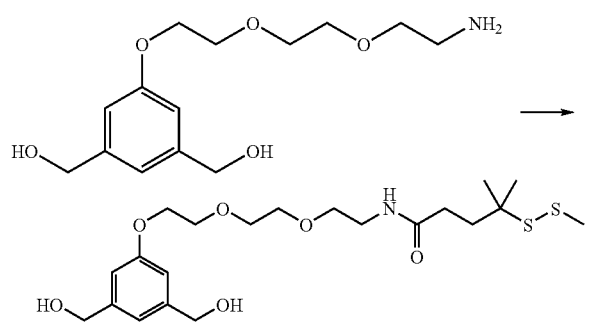

1-(2-{2-[2-(4-methyl-4-methyldisulfanyl-pentanoylamino)-ethoxy]-ethoxy}-ethoxy)-3,5-bis-(hydroxymethyl)-benzene may be prepared following the procedure for the preparation of 1-(3-(4-methyl-4-methyldisulfanyl)-pentanamido-propoxy)-3,5-bis-(hydroxymethyl)-benzene, starting with 1-(2-{2-[2-amino-ethoxy]-ethoxy}-ethoxy)-3,5-bis-(hydroxymethyl)-benzene:

LC/MS (Method A3): ES: m/z=462 MH$^+$m/z=444 (M+H–H$_2$O)$^+$Retention time=3.0 minutes 1-(2-{2-[2-amino-ethoxy]-ethoxy}-ethoxy)-3,5-bis-(hydroxymethyl)-benzene

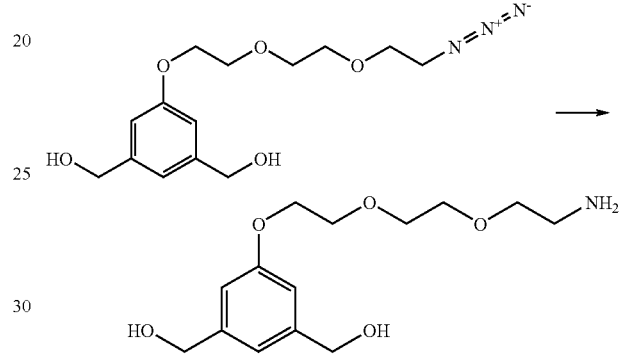

1-(2-{2-[2-amino-ethoxy]-ethoxy}-ethoxy)-3,5-bis-(hydroxymethyl)-benzene may be prepared following the procedure for the preparation of 1-(2-{2-[2-(2-{2-[2-amino-ethoxy]-ethoxy}-ethoxy)-ethoxy]-ethoxy}-ethoxy)-3,5-bis-(hydroxymethyl)-benzene, starting with 1-(2-{2-[2-azido-ethoxy]-ethoxy}-ethoxy)-3,5-bis-(hydroxymethyl)-benzene: LC/MS (Method A3): ES: m/z=286 MH$^+$m/z=268 (M+H–H$_2$O)$^+$Retention time=0.8 minutes 1-(2-{2-[2-azido-ethoxy]-ethoxy}-ethoxy)-3,5-bis-(hydroxymethyl)-benzene Azido

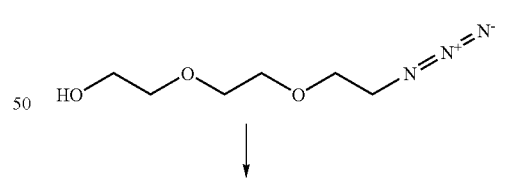

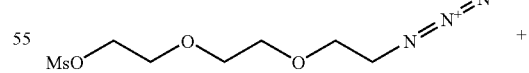

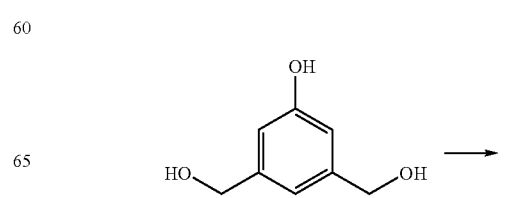

127

-continued

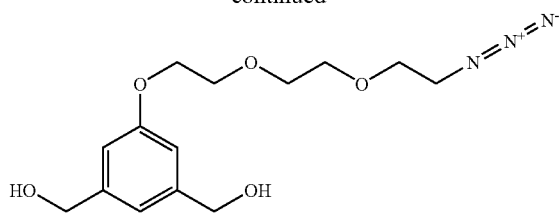

1-(2-{2-[2-azido-ethoxy]-ethoxy}-ethoxy)-3,5-bis-(hydroxymethyl)-benzene may be prepared following the procedure for the preparation of 1-(2-{2-[2-(2-{2-[2-azido-ethoxy]-ethoxy}-ethoxy)-ethoxy]-ethoxy}-ethoxy)-3,5-bis-(hydroxymethyl)-benzene, starting with 2-[2-(2-Azido-ethoxy)-ethoxy]-ethanol (Roy, B. C; Santos, M.; Mallik, S. Campiglia, A. D. *J. Org. Chem.* 2003, 68(10), 3999):

CI (MethodD) m/z=329 $MNH_4^+$.

EXAMPLE 27

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

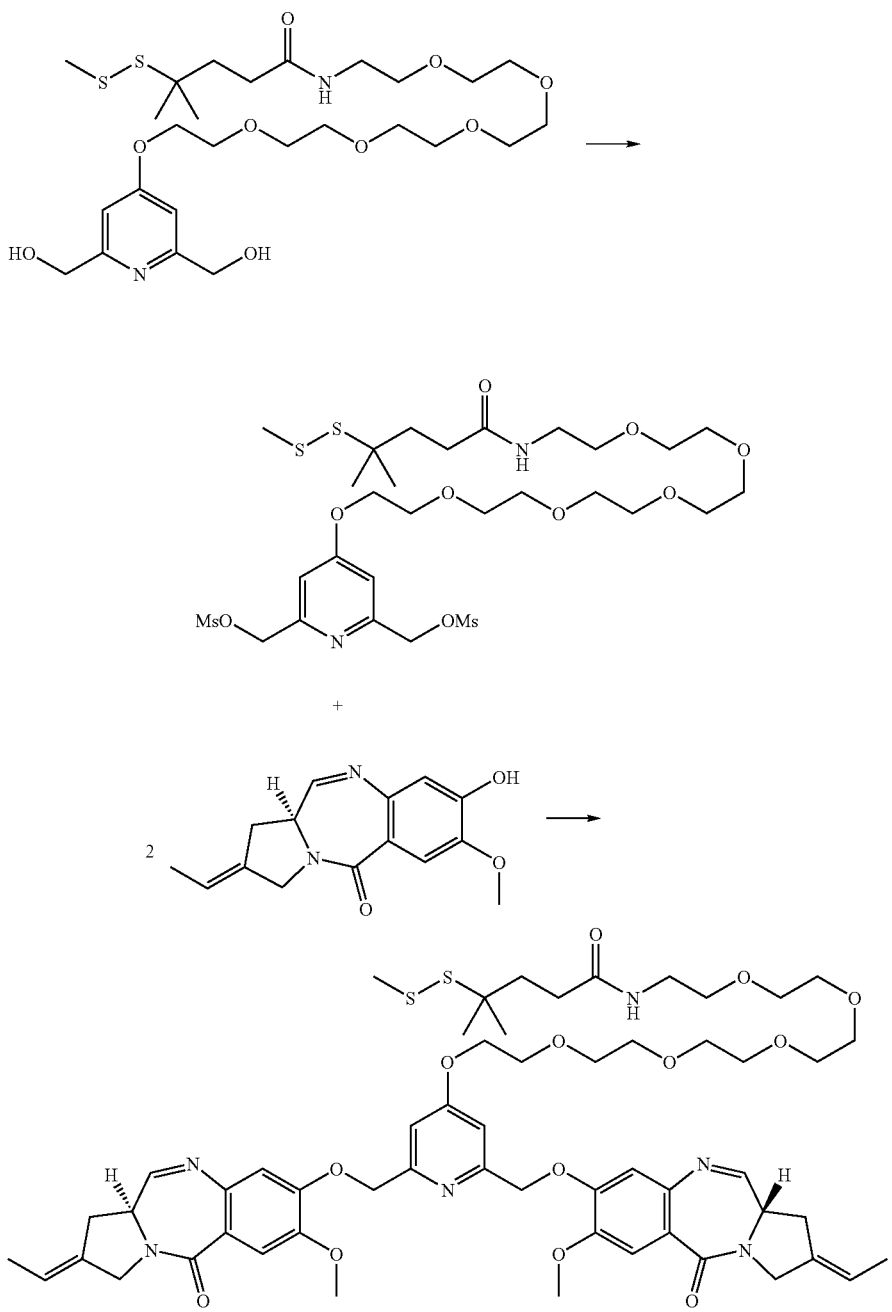

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-2,6-bis-(hydroxymethyl)-pyridine:

LC/MS (Method A3): ES: m/z=1103 MH$^+$ m/z=552 (M+2H)$^{2+}$/2 Retention time=3.7 minutes $^1$H N.M.R. (500 MHz, CDCl3-d1, δ in ppm): δ=1.29 (s, 6H); 1.75 (d, J=6.5 Hz, 6H); 1.94 (m, 2H); 2.28 (m, 2H); 2.40 (s, 3H); 2.97 (m, 4H); from 3.33 to 3.95 (m, 24H); 3.99 (s, 6H); 4.18 (m, 2H); 4.28 (s broad, 4H); 5.27 (m, 4H); 5.60 (m, 2H); 6.19 (m broad, 1H); 6.82 (s, 2H); 7.00 (s broad, 2H); 7.55 (s, 2H); 7.64 (d, J=4.5 Hz, 2H).

4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-2,6-bis-(hydroxymethyl)-pyridine

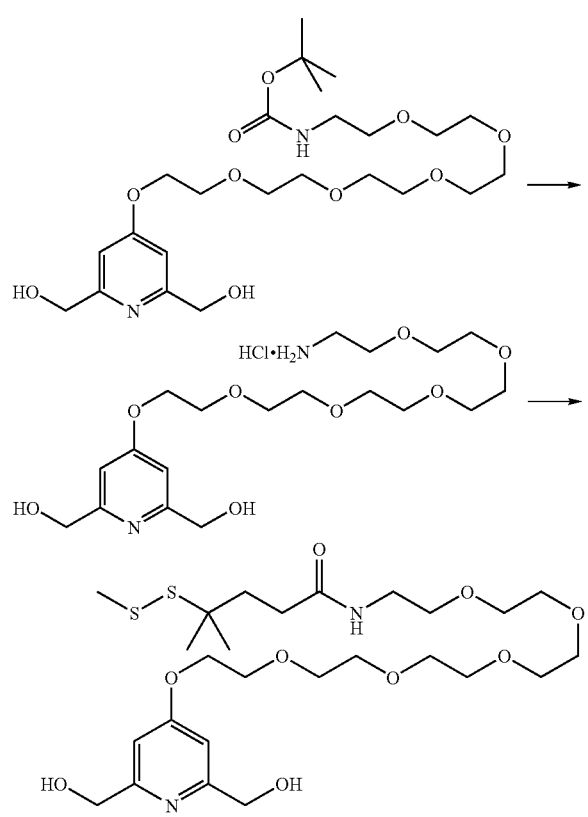

4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-2,6-bis-(hydroxymethyl)-pyridine may be prepared following the procedure for the preparation of 4-(3-[4-(4-methyl-4-methyldisulfanyl-pentanoyl)-piperazin-1-yl]-propyl)-2,6-bis-(hydroxymethyl)-pyridine, starting with 4-(2-{2-[2-(2-{2-[2-tert-butoxycarbonylamino-ethoxy]-ethoxy}-ethoxy)-ethoxy]-ethoxy}-ethoxy)-2,6-bis-(hydroxymethyl)-pyridine:

LC/MS (Method A3): ES: m/z=596 MH$^+$ Retention time=2.4 minutes 4-(2-{2-[2-(2-{2-[2-tert-butoxycarbonylamino-ethoxy]-ethoxy}-ethoxy)-ethoxy]-ethoxy}-ethoxy)-2,6-bis-(hydroxymethyl)-pyridine

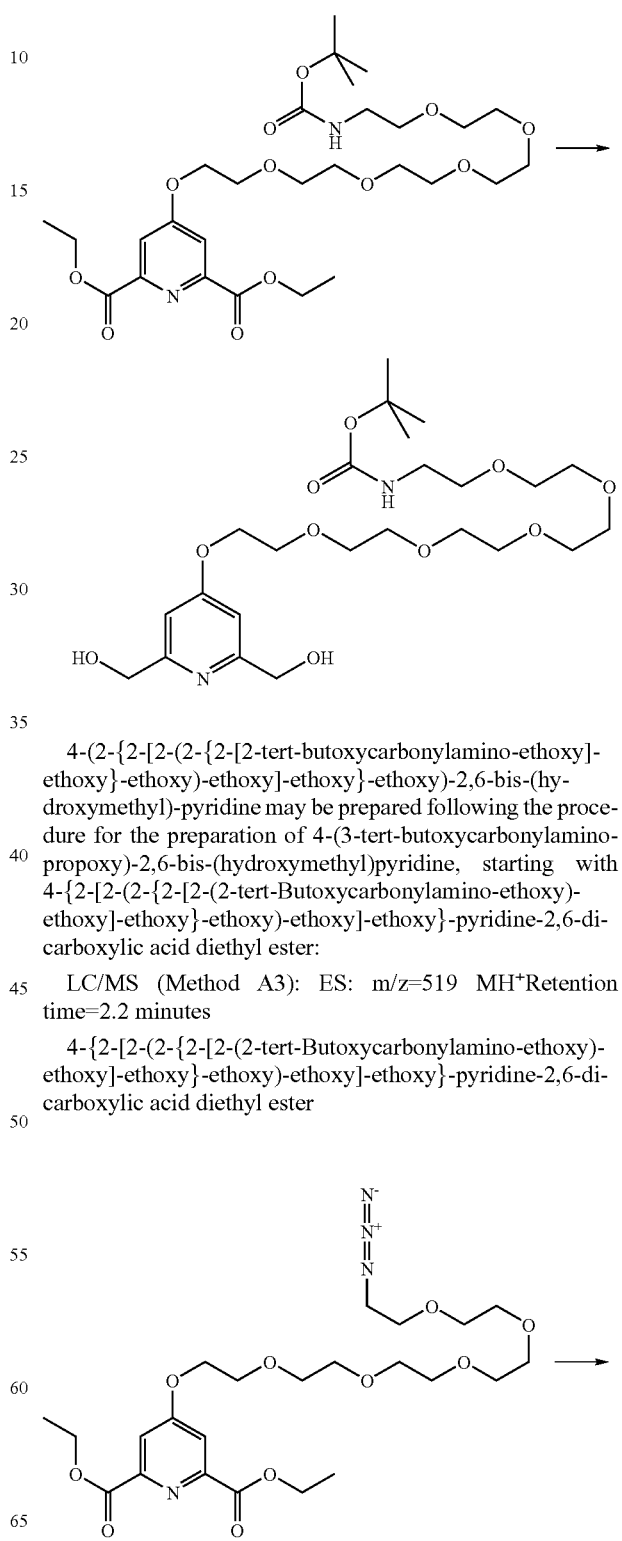

4-(2-{2-[2-(2-{2-[2-tert-butoxycarbonylamino-ethoxy]-ethoxy}-ethoxy)-ethoxy]-ethoxy}-ethoxy)-2,6-bis-(hydroxymethyl)-pyridine may be prepared following the procedure for the preparation of 4-(3-tert-butoxycarbonylamino-propoxy)-2,6-bis-(hydroxymethyl)pyridine, starting with 4-{2-[2-(2-{2-[2-(2-tert-Butoxycarbonylamino-ethoxy)-ethoxy]-ethoxy}-ethoxy)-ethoxy]-ethoxy}-pyridine-2,6-dicarboxylic acid diethyl ester:

LC/MS (Method A3): ES: m/z=519 MH$^+$ Retention time=2.2 minutes

4-{2-[2-(2-{2-[2-(2-tert-Butoxycarbonylamino-ethoxy)-ethoxy]-ethoxy}-ethoxy)-ethoxy]-ethoxy}-pyridine-2,6-dicarboxylic acid diethyl ester

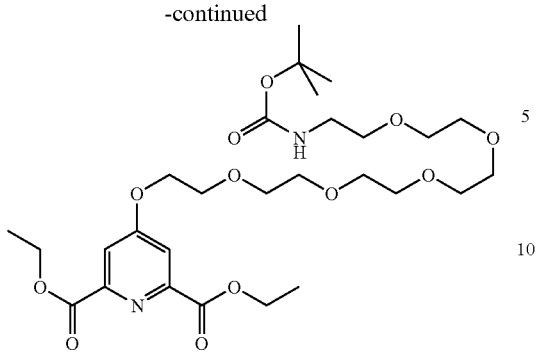

4-{2-[2-(2-{2-[2-(2-tert-Butoxycarbonylamino-ethoxy)-ethoxy]-ethoxy}-ethoxy)-ethoxy]-ethoxy}-pyridine-2,6-dicarboxylic acid diethyl ester may be prepared following the procedure for the preparation of 4-(2-{2-[2-tert-butoxycarbonylamino-ethoxy]-ethoxy}-ethoxy)-pyridine-2,6-dicarboxylic acid diethyl ester, starting with 4-{2-[2-(2-{2-[2-(2-Azido-ethoxy)-ethoxy]-ethoxy}-ethoxy)-ethoxy]-ethoxy}-pyridine-2,6-dicarboxylic acid diethyl ester:

LC/MS (Method A3): ES: m/z=603 MH$^+$m/z=271 (M+2H−CO$_2$tBu)$^+$Retention time=3.6 minutes 4-{2-[2-(2-{2-[2-(2-Azido-ethoxy)-ethoxy]-ethoxy}-ethoxy)-ethoxy]-ethoxy}-pyridine-2,6-dicarboxylic acid diethyl ester may be prepared as follows:

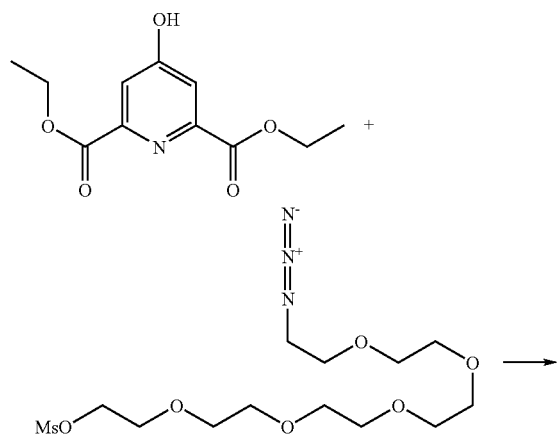

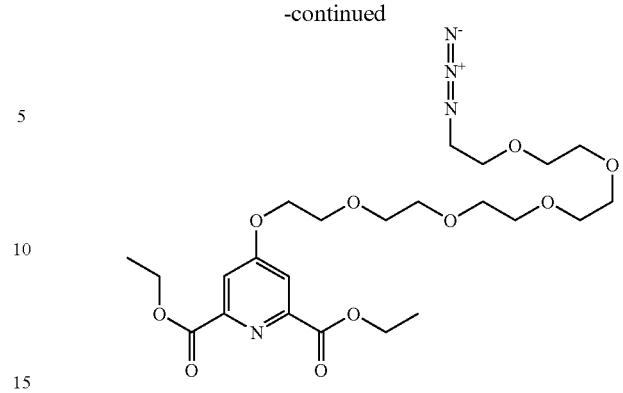

To a solution of chelidamic acid diethyl ester (1.03g) in dimethylformamide (10mL) were added methanesulfonic acid 2-[2-(2-{2-[2-(2-azido-ethoxy)-ethoxy]-ethoxy}-ethoxy)-ethoxy]-ethyl ester (1.82g) and potassium carbonate (893 mg). The resulting mixture was heated at 70° C. for 15h, then was cooled to room temperature. Water was added and the aqueous solution was extracted three times with ethyl acetate. The combined organic solutions were washed with a saturated sodium chloride aqueous solution, dried over magnesium sulfate and concentrated in vacuo to a residue. The residue was purified by silica gel chromatography (Merck SuperVarioPrep 70 g column, Si60 15-40µm), eluted with a mixture of methanol (A)/dichloromethane (B), (gradient: 3% A:97% B to 5% A:95% B) to give 4-{2-[2-(2-{2-[2-(2-Azido-ethoxy)-ethoxy]-ethoxy}-ethoxy)-ethoxy]-ethoxy}-pyridine-2,6-dicarboxylic acid diethyl ester (2.19 g):

LC/MS (Method A3): ES: m/z=529 MH$^+$Retention time=3.4 minutes

EXAMPLE 28

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

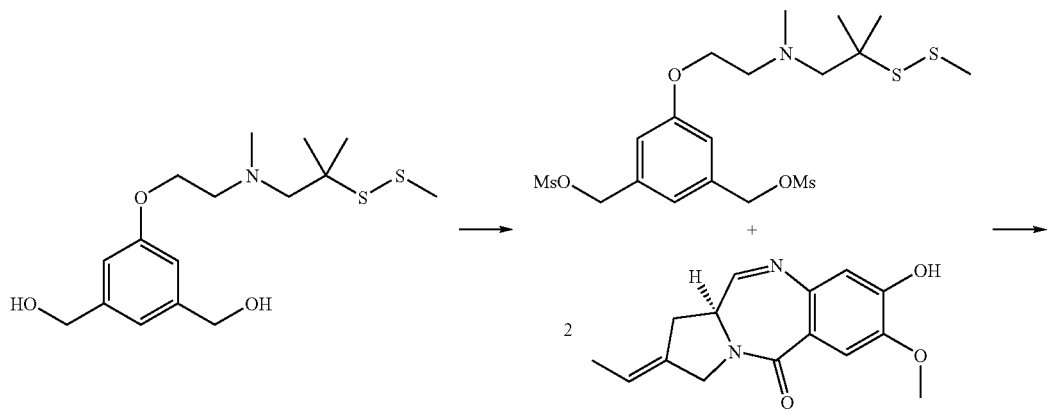

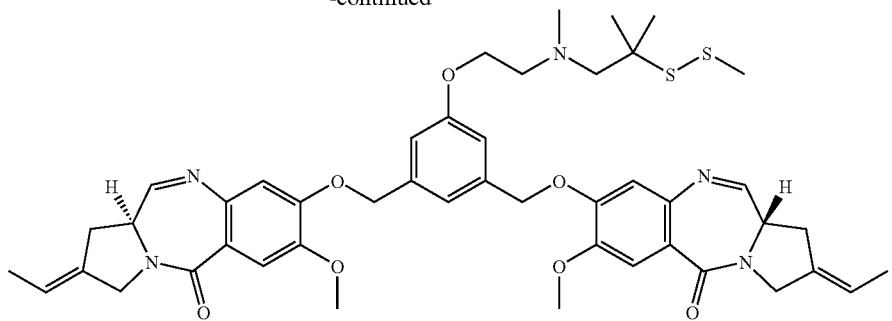

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 1-(2-[methyl-(2-methyl-2-methyldisulfanyl-propyl)-amino]-ethoxy)-3,5-bis-(hydroxymethyl)-benzene:

LC/MS (Method A1, Platform 1): ES: m/z=872 MH$^+$+H$_2$O m/z=854 MH$^+$ Retention time=3.40 minutes $^1$H N.M.R. (500 MHz, CDCl3-d1, δ in ppm): δ=1.31 (s, 6H); 1.75 (d, J=6.5 Hz, 6H); 2.39 (s, 3H); 2.45 (s, 3H); 2.62 (s, 2H); 2.92 (t, J=6.5 Hz, 2H); 2.97 (m, 4H) 3.89 (m, 2H) 3.96 (s, 6H); 4.06 (t, J=6.5 Hz, 2H); 4.26 (s broad, 4H); 5.12 (d, J=12.5 Hz, 2H); 5.19 (d, J=12.5 Hz, 2H); 5.60 (q broad, J=6.5 Hz, 2H); 6.82 (s, 2H); 6.95 (s broad, 2H); 7.06 (s broad, 1H) 7.52 (s, 2H); 7.64 (d, J=4.5 Hz, 2H).

1-(2-[methyl-(2-methyl-2-methyldisulfanyl-propyl)-amino]-ethoxy)-3,5-bis-(hydroxymethyl)-benzene may be prepared as follows:

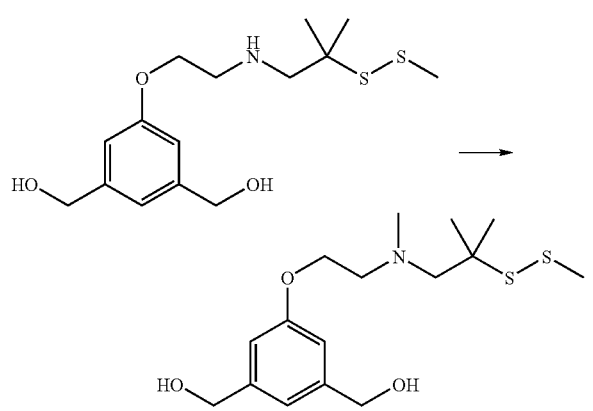

To a cooled (5° C.) suspension of 1-(2-(2-methyl-2-methyldisulfanyl-propyl)-amino-ethoxy)-3,5-bis-(hydroxymethyl)-benzene (280 mg) in formaldehyde (228 μL), was added formic acid (319μL). The resulting mixture was heated at 100° C. for 1h 15nm, then was cooled to room temperature. Water and ice were added, followed by an aqueous solution of sodium hydroxide until pH=12. The resulting aqueous solution was extracted three times with ethyl acetate and the combined organic solutions were dried over magnesium sulfate and concentrated in vacuo to a residue. The residue was purified by silica gel chromatography (Merck SuperVarioFlash 25 g column, Si60 15-40μm), eluted with a mixture of methanol (A)/dichloromethane (B), (gradient: 2% A:98% B to 5% A:95% B) to give 1-(2-[methyl-(2-methyl-2-methyldisulfanyl-propyl)-amino]-ethoxy)-3,5-bis-(hydroxymethyl)-benzene (210 mg):

LC/MS (Method A3): ES: m/z=346 MH$^+$ m/z=212 (M+2H-C$_5$H$_{11}$S$_2$)$^+$m/z=135 C$_5$H$_{11}$S$_2$$^+$ Retention time=2.1 minutes $^1$H N.M.R. (400 MHz, DMSO-d6, δ in ppm): δ=1.27 (s, 6H); 2.39 (s, 3H); 2.40 (s, 3H); 2.60 (s, 2H); 2.85 (t, J=6.0 Hz, 2H); 4.02 (t, J=6.0 Hz, 2H); 4.44 (d, J=6.0 Hz, 4H) 5.10 (t, J=6.0 Hz, 2H); 6.72 (s broad, 2H); 6.82 (s broad, 1H).

1-(2-(2-methyl-2-methyldisulfanyl-propyl)-amino-ethoxy)-3,5-bis-(hydroxymethyl)-benzene may be prepared as follows:

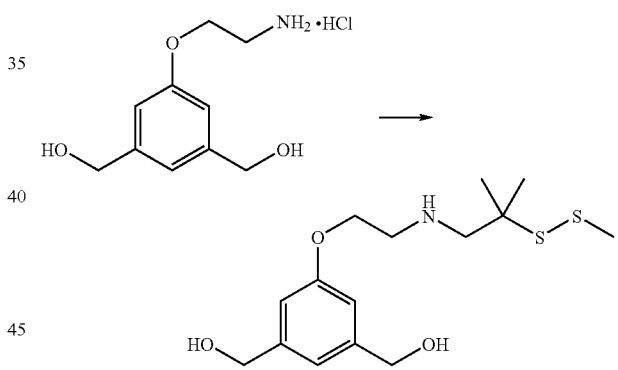

To a suspension of 1-(2-amino-ethoxy)-3,5-bis-(hydroxymethyl)-benzene hydrochloride (900 mg) in tetrahydrofuran (4.5mL) was added triethylamine (1.07mL). After stirring for 15min, 2-(methyldithio)isobutylaldehyde (530 μL) and titanium isopropoxide (1.42 mg) were added and the resulting mixture was stirred at room temperature for 2h. Ethanol (9mL) and sodium cyanoborohydride (242 mg) were added and the new mixture was stirred at room temperature for 18h. Solids were filtered off and the filtrate was concentrated in vacuo to a residue. The residue was then diluted in ethyl acetate and the resulting solids were filtered off. The organic solution was then washed with water and with a saturated sodium chloride aqueous solution, dried over magnesium and concentrated in vacuo to a new residue that was purified by silica gel chromatography (Merck SuperVarioFlash 30g column, Si60 15-40μm), eluted with a mixture of methanol (A)/dichloromethane (B), (gradient: 4% A: 96% B to 10% A:90% B) to give 1-(2-(2-methyl-2-methyldisulfanyl-propyl)-amino-ethoxy)-3,5-bis-(hydroxymethyl)-benzene (290 mg):

¹H N.M.R. (400 MHz, DMSO-d6, δ in ppm): δ=1.27 (s, 6H); 1.82 (m broad, 1H) 2.39 (s, 3H) 2.67 (s, 2H); 2.91 (t, J=6.0 Hz, 2H); 4.00 (t, J=6.0 Hz, 2H); 4.43 (d, J=6.0 Hz, 4H) 5.10 (t, J=6.0 Hz, 2H); 6.73 (s broad, 2H); 6.83 (s broad, 1H).

EXAMPLE 29

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

4-(3-[methyl-(4-methyl-4-methyldisulfanyl-pentanoyl)-amino]-propyl)-2,6-bis-(hydroxymethyl)-pyridine

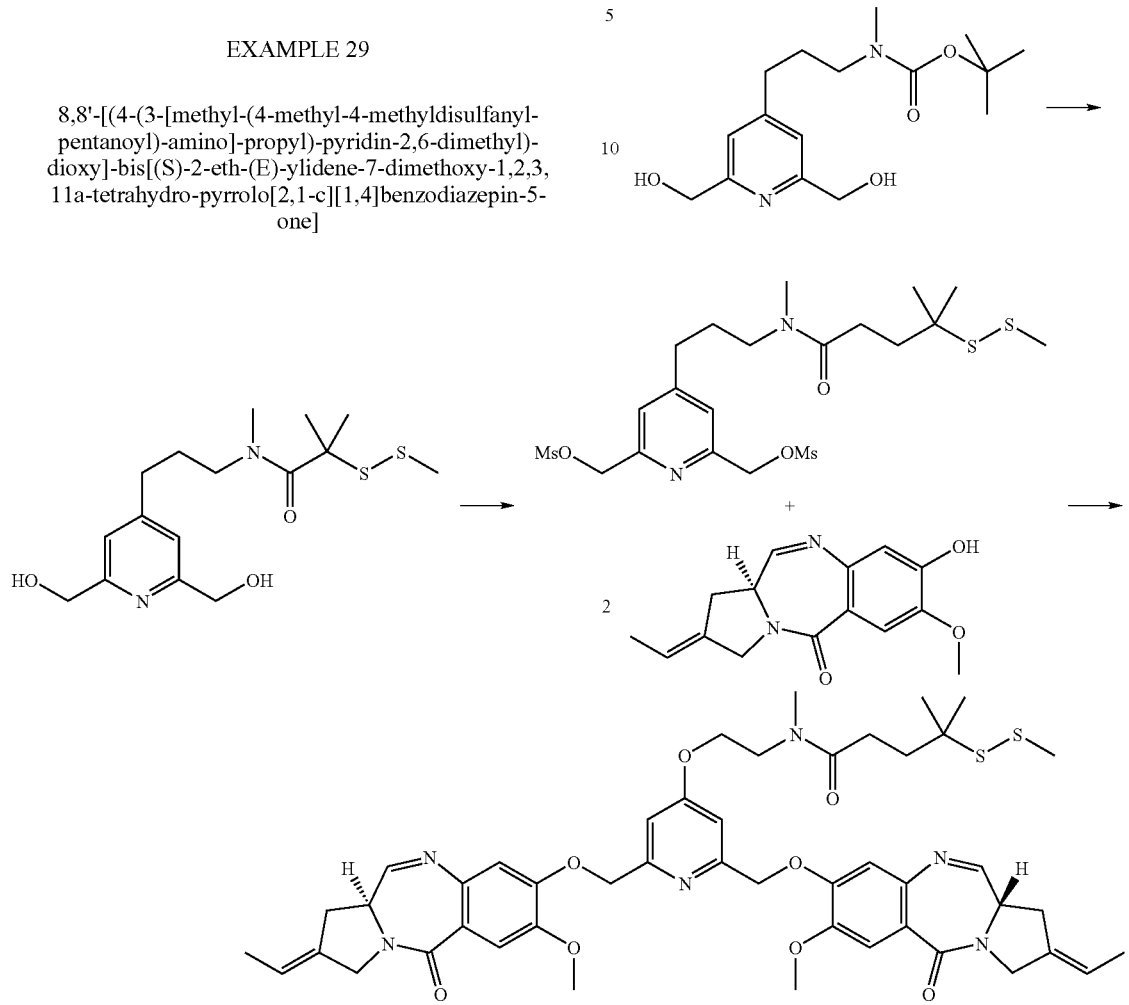

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 4-(3-[methyl-(4-methyl-4-methyldisulfanyl-pentanoyl)-amino]-propyl)-2,6-bis-(hydroxymethyl)-pyridine:

¹H N.M.R. (500 MHz, CDCl3-d1, δ in ppm): δ=1.32 (s, 6H); 1.75 (d, J=6.5 Hz, 6H); 1.94 (m, 4H); from 2.20 to 4.30 (m, 18H); 4.00 (s, 6H); 4.27 (s broad, 4H); from 5.21 to 5.68 (m, 6H); from 6.80 to 7.70 (m, 8H).

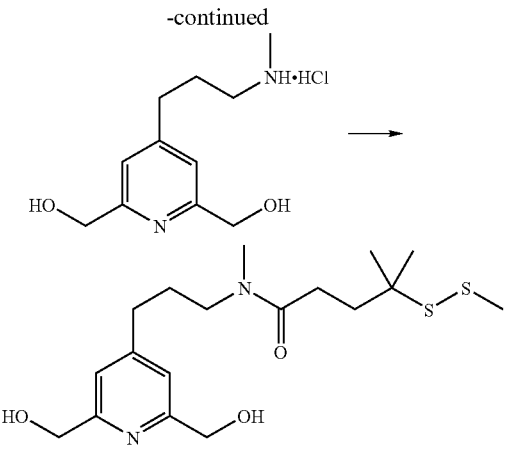

4-(3-[methyl-(4-methyl-4-methyldisulfanyl-pentanoyl)-amino]-propyl)-2,6-bis-(hydroxy methyl)-pyridine may be prepared following the procedure for the preparation of 4-(2-(4-methyl-4-methyldisulfanyl)-pentanamido-ethoxy)-2,6- bis-(hydroxymethyl)-pyridine, using 4-(3-(tert-Butoxycarbonyl-methyl-amino)-propyl)-2,6-bis-(hydroxymethyl)-pyridine:

LC/MS (Method A3): ES: m/z=387 MH+ Retention time=2.5 minutes 4-(3-(tert-Butoxycarbonyl-methyl-amino)-propyl)-2,6-bis-(hydroxymethyl)-pyridine

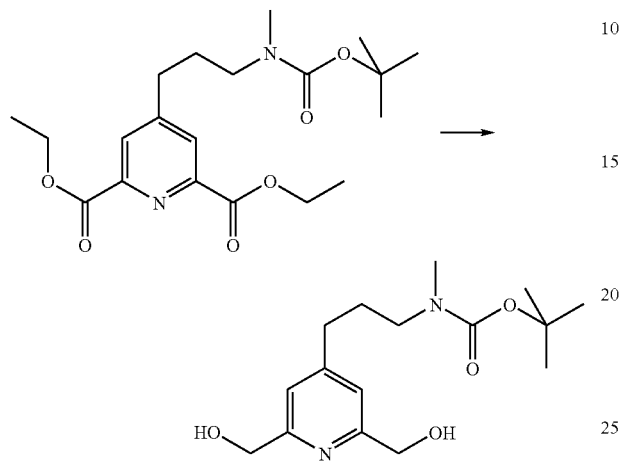

4-(3-(tert-Butoxycarbonyl-methyl-amino)-propyl)-2,6-bis-(hydroxymethyl)-pyridine may be prepared following the procedure for the preparation of 4-(3-tert-butoxycarbonylamino-propoxy)-2,6-bis-(hydroxymethyl)pyridine, using 4-(3-(tert-butoxycarbonyl-methyl-amino)-propyl)-pyridine-2,6-bis-dicarboxylic acid diethyl ester:

CI (Method D) m/z=311 MH+

4-(3-(tert-Butoxycarbonyl-methyl-amino)-propyl)-pyridine-2,6-bis-dicarboxylic acid diethyl ester

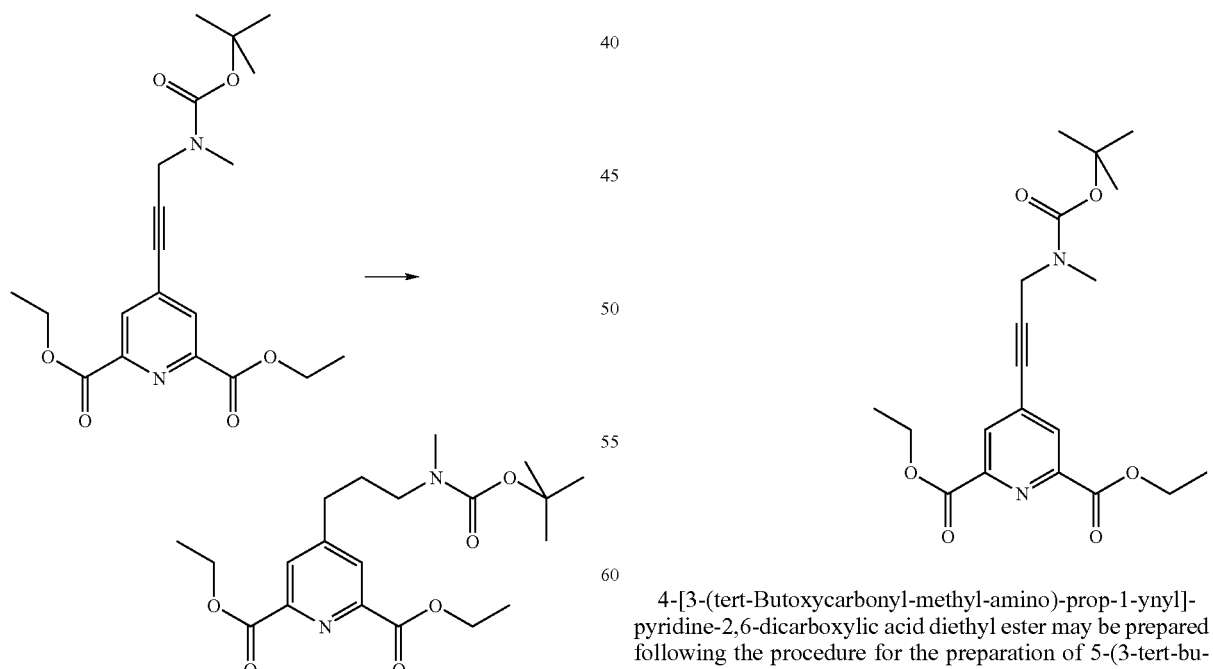

4-(3-(tert-Butoxycarbonyl-methyl-amino)-propyl)-pyridine-2,6-bis-dicarboxylic acid diethyl ester may be prepared following the procedure for the preparation of 5-(3-tert-butoxycarbonyl-N-methyl-amino-propyl)-benzene-1,3-dicarboxylic acid diethyl ester, starting with 4-[3-(tert-Butoxycarbonyl-methyl-amino)-prop-1-ynyl]-pyridine-2,6-dicarboxylic acid diethyl ester:

LC/MS (Method G2): ES: m/z=395 MH+ m/z=339 (M+2H−tBu)+ Retention time=7.5 minutes 4-[3-(tert-Butoxycarbonyl-methyl-amino)-prop-1-ynyl]-pyridine-2,6-dicarboxylic acid diethyl ester

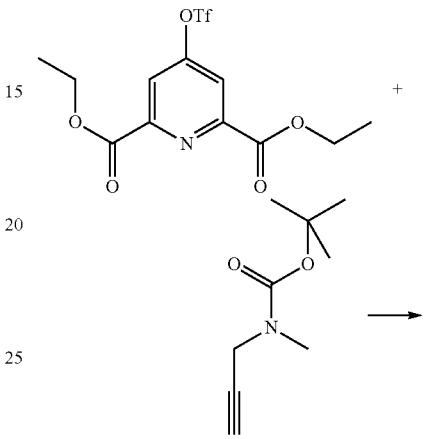

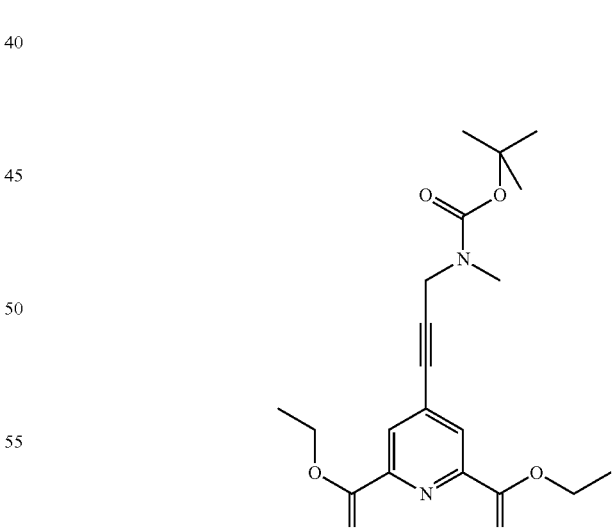

4-[3-(tert-Butoxycarbonyl-methyl-amino)-prop-1-ynyl]-pyridine-2,6-dicarboxylic acid diethyl ester may be prepared following the procedure for the preparation of 5-(3-tert-butoxycarbonyl-N-methyl-amino-propyn-1-yl)-benzene-1,3-dicarboxylic acid diethyl ester, starting with tert-butoxycarbonyl-N-methyl-propargylamine.

CI (Method D) m/z=391 MH+

EXAMPLE 30

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

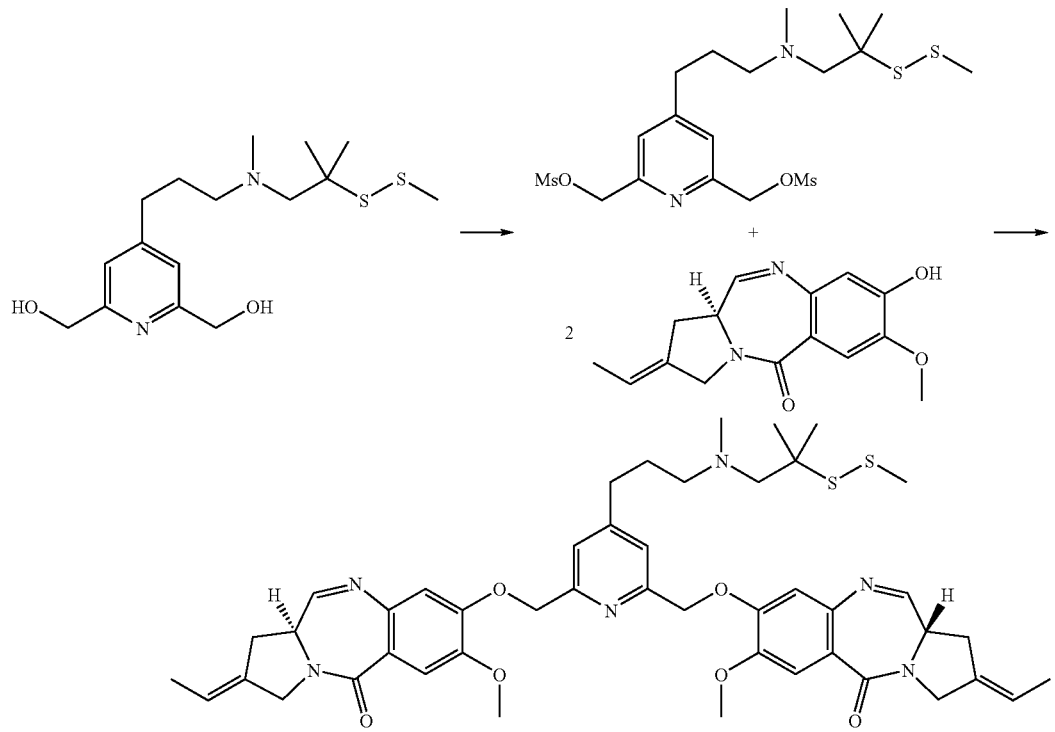

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] may be prepared following the procedure for the preparation of 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one], using 4-{3-[methyl-(2-methyl-2-methyldisulfanyl-propyl)-amino]-propyl}-2,6-bis-(hydroxy methyl)-pyridine:

$^1$H N.M.R. (500 MHz, CDCl3-d1, δ in ppm): δ=1.28 (s, 6H); 1.65 (m partially masked, 2H) 1.75 (d, J=6.5 Hz, 6H); 2.29 (s, 3H); 2.38 (s, 3H); 2.46 (m, 4H); 2.65 (m, 2H) 2.97 (m, 4H); 3.89 (m, 2H); 4.00 (s, 6H); 4.27 (s broad, 4H); 5.29 (s, 4H); 5.60 (q broad, J=6.5 Hz, 2H); 6.86 (s, 2H); 7.30 (s, 2H); 7.55 (s, 2H) 7.64 (d, J=4.5 Hz, 2H).

4-{3-[methyl-(2-methyl-2-methyldisulfanyl-propyl)-amino]-propyl}-2,6-bis-(hydroxy methyl)-pyridine

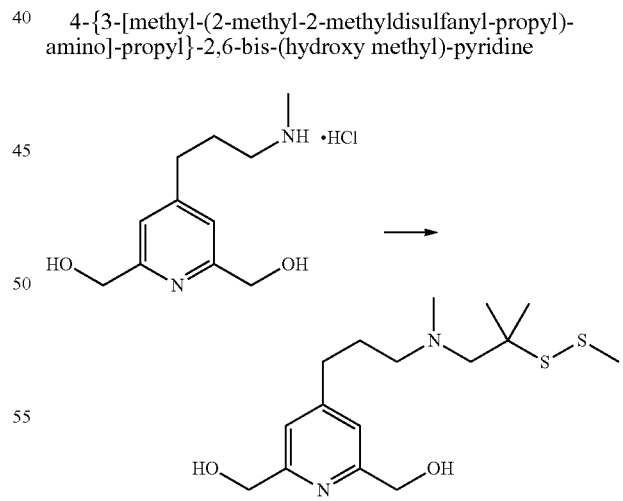

P-34409-034-3

4-{3-[methyl-(2-methyl-2-methyldisulfanyl-propyl)-amino]-propyl}-2,6-bis-(hydroxy methyl)-pyridine may be prepared following the procedure for the preparation of 1-(2-(2-methyl-2-methyldisulfanyl-propyl)-amino-ethoxy)-3,5-bis-(hydroxymethyl)-benzene, using 4-{3-[methyl-amino]-propyl}-2,6-bis-(hydroxy methyl)-pyridine:

LC/MS (Method A1, Platform II): ES m/z=345 MH$^+$Retention time=1.15 minutes

EXAMPLE 31

8,8'-[(1-(4-methyl-4-methyldisulfanyl)-pentana-mido)-benzene-3,5-dimethyl)-dioxy]-bis[(S)-2-eth-(E)-ylidene-7-dimethoxy-1,2,3,11a-tetrahydro-pyr-rolo[2,1-c][1,4]benzodiazepin-5-one] May be Prepared as Follows In the first step, the antibody is reacted with the modifying agent N-sulfosuccinimidyl 5-nitro-2-pyridyldithiobutanoate (SSNPB) to introduce nitropyridyldithio groups. A solution of huC242 antibody at a concentration of 8 mg/mL in an aqueous buffer containing 0.05 M potassium phosphate, 0.05 M sodium chloride and 2 mM ethylenediaminetetra-acetic acid (EDTA), pH 6.5 (65.6 mL) is treated with a 8-fold molar excess of a solution of SSNPB in dimethylacetamide (DMA).

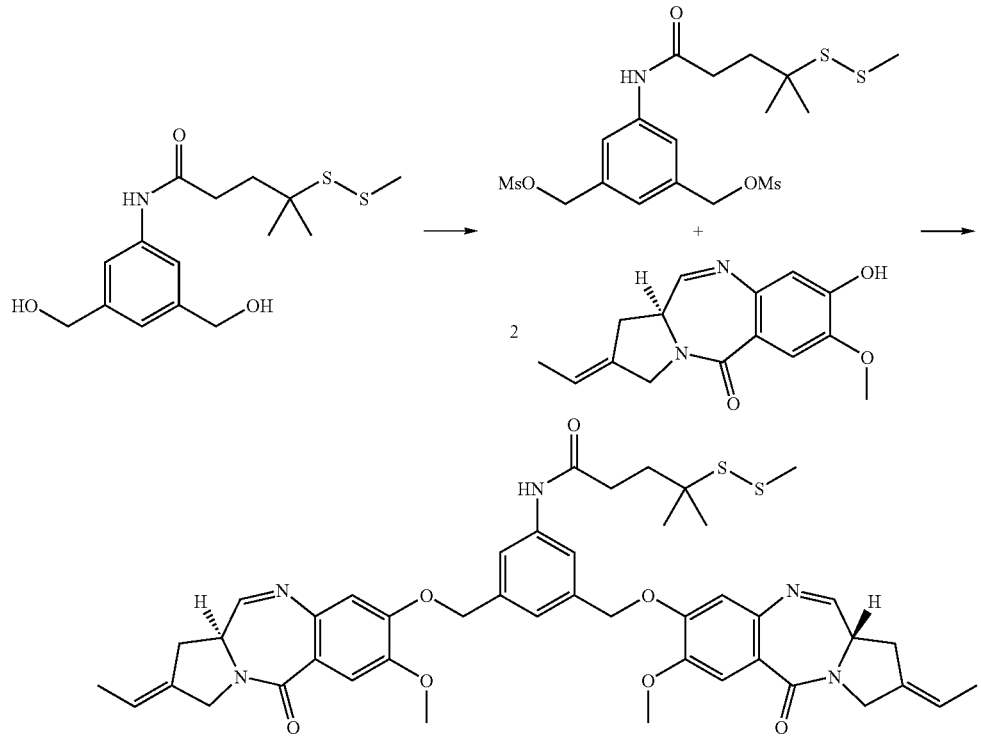

8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzo-diazepin-5-one] may be prepared following the procedure for the preparation of 8,8'-[(4-(2-(4-methyl-4-methyldisulfanyl)-pentanamido-ethoxy)-pyridin-2,6-dimethyl)-dioxy]-bis[(S)-2-eth-(E)-ylidene-7-dimethoxy-1,2,3,11a-tetrahydro-pyr-rolo[2,1-c][1,4]benzodiazepin-5-one], starting with (1-(4-methyl-4-methyldisulfanyl)-pentanamido)-3,5-bis-(hydroxymethyl)-benzene:

LC/MS (Method A1, Platform 1): ES: m/z=838 MH⁺ Retention time=4.11 minutes $^1$H N.M.R. (500 MHz, CDCl3-d1, δ in ppm): δ=1.33 (s, 6H); 1.76 (d, J=6.5 Hz, 6H); 2.03 (m, 2H); 2.43 (s, 3H); 2.46 (m, 2H); 2.97 (m, 4H); 3.89 (m, 2H); 3.95 (s, 6H); 4.27 (s broad, 4H); 5.14 (d, J=12.5 Hz, 2H); 5.19 (d, J=12.5 Hz, 2H); 5.60 (q, J=6.5 Hz, 2H); 6, 81 (s, 2H); from 7.20 to 7.60 (m, 6H); 7.64 (d, J=4.5 Hz, 2H)

The corresponding mercapto derivatives of compounds of examples 19-31 may be prepared by application of the procedure described in example 18.

EXAMPLE A

General Procedure for Conjugate Preparation

Anti-B4 antibody that binds to the CD19 antigen preferentially expressed on the surface of human lymphoma cells is selected for conjugation of tomaymycin derivatives.

The reaction mixture is stirred at room temperature for 90 min. and then loaded on to a Sephadex G25 gel filtration column (50 mm×35.5 mm, column) that has been previously equilibrated into an aqueous buffer containing 0.05 M potassium phosphate, 0.05 M sodium chloride and 2 mM EDTA, pH 7.5. The modified antibody-containing fractions are collected and pooled to yield product. A small aliquot of the modified antibody is treated with dithiothreitol to cleave the nitro-pyridyl disulfide and the released nitro-pyridine-2-thione is assayed spectrophotometrically ($\epsilon_{323nm}$=4,299 M⁻¹ cm⁻¹, $\epsilon_{280nm}$=565 M⁻¹ cm⁻¹ for the compound, and $\epsilon_{280nm}$=217,560 M⁻¹ cm⁻¹ for the antibody). An average of 4 to 6 nitro-pyridyldisulfide molecules are typically linked per molecule of antibody.

The modified antibody is diluted to 2.5 mg/mL in the above buffer at pH 7.5 and then treated with a solution of the tomaymycin derivative in DMA, such that the final concentration of DMA in the buffer is 20%. The conjugation mixture is stirred at room temperature for 16 h. The reaction mixture is purified by passage through a Sephacryl S300 gel filtration column (50 mm×42 cm, column that has been previously equilibrated in a phosphate-buffered saline (PBS) buffer at pH 6.5. Fractions containing monomeric antibody-tomaymycin derivative conjugate are pooled and dialyzed into the PBS buffer. The final conjugate is assayed spectrophotometrically using the extinction coefficients that are determined separately for each tomaymycin derivative.

SPDB-PBD and SMCC-PBD Conjugates of the Compounds of the Invention
huB4-SPDB Compound of Example 16

EXAMPLE A1

Anti-B4 antibody that binds to the CD19 antigen preferentially expressed on the surface of human lymphoma cells is selected for conjugation of tomaymycin derivatives.

The antibody was first modified with 4-(2-pyridyldithio) butanoic acid N-hydroxysuccinimide ester (SPDB) to introduce pyridyldithio groups. A 4.5-fold molar excess of SPDB (0.25 µmol, 81.1 µg) in dimethylacetamide (DMA) (50 µL) was added to a solution of huB4 (8 mg, 0.055 µmol) in aqueous buffer containing 50 mM potassium phosphate, 50 mM sodium chloride and 2 mM ethylenediaminetetra-acetic acid (EDTA), pH 6.5 (0.95 mL). The final protein concentration was 8 mg/mL with 5% DMA in buffer. The modification was allowed to rotate at room temperature for 90 minutes, and was then purified on a Sephadex G25 gel filtration column equilibrated in an aqueous buffer containing 50 mM potassium phosphate, 50 mM sodium chloride and 2 mM EDTA, pH 7.5. A small aliquot of the modified antibody was treated with dithiothreitol (DTT) to cleave the pyridyldisulfide groups. The modified antibody and released pyridine thiol were assayed spectrophotometrically ($\epsilon_{343}$=8,080 M$^{-1}$ cm$^{-1}$ for the released pyridine thiol, $\epsilon_{280}$=5100 M$^{-1}$ cm$^{-1}$ for the modified pyridyldithio groups and $\epsilon_{280}$=222,960 M$^{-1}$ cm$^{-1}$ for antibody). An average of 3.36 pyridyldisulfide molecules per molecule of antibody were linked.

The modified antibody (2.29 mg, 0.016 µmol) was diluted in the above buffer at pH 7.5 (732.8 µL) and DMA (91.6 uL, 10% v/v) and then treated with a solution of 8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one] (Compound of example 16) (0.157 µmol, 0.12 mg) in DMA (91.6 µl, 10% v/v). The final protein concentration was 2.5 mg/mL with 20% DMA in buffer. The conjugation was allowed to rotate at room temperature overnight and then clarified by sedimentation (13,200 RPM for 4 min). The supernatant was then purified on a Sephadex G25 gel filtration column equilibrated in a phosphate-buffered saline (PBS) buffer at pH 6.5. The purified conjugate was dialyzed into PBS pH 6.5 buffer (~1:650 dilution) with four buffer exchanges. The conjugate was clarified through a 0.22 µm syringe filter and assayed spectrophotometrically ($\epsilon_{280}$=7743 M$^{-1}$ cm$^{-1}$, $\epsilon_{318}$=9137 M$^{-1}$ cm$^{-1}$ for the PBD, and $\epsilon_{280}$=222,960 M$^{-1}$ cm$^{-1}$ for antibody). An average of 1.76 PBD molecules (Compound of example 16) per molecule of antibody were linked.

huB4-SMCC Compound of Example 16

EXAMPLE A2

Anti-B4 antibody that binds to the CD19 antigen preferentially expressed on the surface of human lymphoma cells is selected for conjugation of tomaymycin derivatives.

In the first step, the antibody is reacted with the modifying agent Succinimidyl 4-[N-maleimidomethyl]cyclohexane-1-carboxylate (SMCC) to introduce maleimide groups. A solution of huB4 antibody at a concentration of 6 mg/mL in an aqueous buffer containing 0.05 M potassium phosphate, 0.05 M sodium chloride and 2 mM ethylenediaminetetra-acetic acid (EDTA), pH 6.7 (1 mL) is treated with a 6.5-fold molar excess of a solution of SMCC in dimethylacetamide (DMA). The reaction mixture is stirred at room temperature for 90 min. and then loaded on to a Sephadex G25 gel filtration column (NAP10) that has been previously equilibrated into an aqueous buffer containing 0.10 M N-(2-hydroxyethyl)-piperazine-N'-2-ethanesulfonic acid (HEPES), pH 8.0. The modified antibody-containing fractions are collected and pooled to yield product. A small aliquot of the modified antibody is treated with β-mercapto ethanol for 10 min followed by addition of 5,5'-dithiobis-2-nitrobenzoic acid (DTNB) to assay remaining thiol ($\epsilon_{412nm}$=14,150 M$^{-1}$ cm$^{-1}$ for 5-thio-2-nitro benzoic acid (TNB), and $\epsilon_{280nm}$=222,960 M$^{-1}$ cm$^{-1}$ for the antibody). The amount of thiol consumed in the reaction with maleimide on the antibody (compared to a control without antibody) is equal to the moles of maleimide attached to the antibody (subtractive Ellman's assay). Approximately 3.2 reactive maleimide groups per antibody were linked.

The modified antibody (3 mg, 0.021 µmol) is diluted to 3.0 mg/mL in HEPES buffer at pH 8.0 and then treated with a solution of compound of example 16 in DMA (5 mM), such that the final concentration of DMA in the buffer is 15%. Three molar equivalents of 8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one] (Compound of example 16) were added per linker (9.6 eq. per antibody, 0.202 µmol, 149 µg). The conjugation mixture is stirred at room temperature for 20 h. The reaction mixture is purified by passage through a G25 column (NAP 5) that has been previously equilibrated in 0.05 potassium phosphate (KPi), 0.05 M NaCl, 0.002 M EDTA buffer at pH 6.7. Fractions containing huB4-compound of example 16 conjugate are pooled and dialyzed into the KPi buffer for 3 exchanges (24 hr). The final conjugate (2.2 mg, 2.3 mg/ml) is assayed spectrophotometrically using the extinction coefficients that are determined for compound of example 16 ($\epsilon_{318nm}$=9,137 M$^{-1}$ cm$^{-1}$, $\epsilon_{280nm}$=7,743 M$^{-1}$ cm$^{-1}$) and B4 antibody ($\epsilon_{280nm}$=222,960 M$^{-1}$ cm$^{-1}$). An average of 2.8 PBD molecules (Compound of example 16) per molecule of antibody were linked.

huB4-SPDB Compound of Example 17

EXAMPLE A3

Anti-B4 antibody that binds to the CD19 antigen preferentially expressed on the surface of human lymphoma cells is selected for conjugation of tomaymycin derivatives.

The antibody was first modified with 4-(2-pyridyldithio) butanoic acid N-hydroxysuccinimide ester (SPDB) to introduce pyridyldithio groups. A 4.5-fold molar excess of SPDB (0.124 µmol, 40.6 µg) in DMA (25 µL) was added to solution of huB4 (4 mg, 0.028 µmol) in aqueous buffer containing 50 mM potassium phosphate, 50 mM sodium chloride and 2 mM EDTA, pH 6.5 (0.475 mL). The final protein concentration was 8 mg/mL with 5% DMA in buffer. The modification was allowed to rotate at room temperature for 90 minutes, and then purified on a Sephadex G25 gel filtration column equilibrated in an aqueous buffer containing 50 mM potassium phosphate, 50 mM sodium chloride and 2 mM EDTA, pH 7.5. A small aliquot of the modified antibody was treated with DTT to cleave the pyridyldisulfide groups. The modified antibody and released pyridine thiol were assayed spectrophotometrically ($\epsilon_{343}$=8,080 M$^{-1}$ cm$^{-1}$ for the released pyridine thiol, $\epsilon_{280}$=5100 M$^{-1}$ cm$^{-1}$ for the modified pyridyldithio groups and $\epsilon_{280}$=222,960 M$^{-1}$ cm$^{-1}$ for antibody). An average of 3.31 pyridyldisulfide molecules per molecule of antibody were linked.

The modified antibody (3.06 mg, 0.021 µmol) was diluted in the above buffer at pH 7.5 (0.976 mL) and DMA (122 uL, 10% v/v) and then treated with a solution of 8,8'-[5-(N-methyl-N-(2-mercapto-2,2-dimethylethyl)amino-1,3-benzenediyl (methylenoxy)]-bis[7-methoxy-2-methylene-1,2,3,11a-tetrahydro-5H-pyrrolo[2,1-c][1,4]benzodiazepin-5-one] (Compound of example 17) (0.209 µmol, 0.154 mg) in DMA (122 µl, 10% v/v). The final protein concentration was 2.5 mg/mL with 20% DMA in buffer. The conjugation was allowed to rotate at room temperature overnight and then clarified by sedimentation (13,200 RPM for 4 min). The supernatant was then purified on a Sephadex G25 gel filtration column equilibrated in a PBS buffer at pH 6.5. The purified conjugate was dialyzed into PBS pH 6.5 buffer (~1:1200 dilution) with three buffer exchanges. The conjugate was clarified through a 0.22 µm syringe filter and assayed spectrophotometrically ($\epsilon_{280}$=10736 M$^{-1}$ cm$^{-1}$, $\epsilon_{318}$=12053 M$^{-1}$ cm$^{-1}$ for the PBD, and $\epsilon_{280}$=222,960 M$^{-1}$ cm$^{-1}$ for antibody). An average of 3.05 PBD molecules (compound of example 17) per molecule of antibody were linked.
huB4-SMCC Compound of Example 17

EXAMPLE A4

Anti-B4 antibody that binds to the CD19 antigen preferentially expressed on the surface of human lymphoma cells is selected for conjugation of tomaymycin derivatives.

In the first step, the antibody is reacted with the modifying agent Succinimidyl 4-[N-maleimidomethyl]cyclohexane-1-carboxylate (SMCC) to introduce maleimide groups. A solution of huB4 antibody at a concentration of 6 mg/mL in an aqueous buffer containing 0.05 M potassium phosphate, 0.05 M sodium chloride and 2 mM ethylenediaminetetra-acetic acid (EDTA), pH 6.7 (1 mL) is treated with a 7-fold molar excess of a solution of SMCC in dimethylacetamide (DMA). The reaction mixture is stirred at room temperature for 90 min. and then loaded on to a Sephadex G25 gel filtration column (NAP10) that has been previously equilibrated into an aqueous buffer containing 0.10 M N-(2-hydroxyethyl)-piperazine-N'-2-ethanesulfonic acid (HEPES), pH 8.0. The modified antibody-containing fractions are collected and pooled to yield product. A small aliquot of the modified antibody is treated with β-mercapto ethanol for 10 min followed by addition of 5,5'-dithiobis-2-nitrobenzoic acid (DTNB) to assay remaining thiol ($\epsilon_{412nm}$=14,150 M$^{-1}$ cm$^{-1}$ for 5-thio-2-nitro benzoic acid (TNB), and $\epsilon_{280nm}$=222,960 M$^{-1}$ cm$^{-1}$ for the antibody). The amount of thiol consumed in the reaction with maleimide on the antibody (compared to a control without antibody) is equal to the moles of maleimide attached to the antibody (subtractive Ellman's assay). Approximately 3.7 reactive maleimide groups per antibody were linked.

The modified antibody (4.4 mg, 0.03 mmol) is diluted to 8.7 mg/mL in HEPES buffer at pH 8.0 and then treated with a solution of compound of example 17 in DMA (5.4 mM), such that the final concentration of DMA in the buffer is 20%. Two molar equivalents of 8,8'-[5-(N-methyl-N-(2-mercapto-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one] (Compound of example 17) were added per linker (7.4 eq. per antibody, 0.222 µmol, 164 µg). The conjugation mixture is stirred at room temperature for 20 h. The reaction mixture is purified by passage through a G25 column (NAP 5) that has been previously equilibrated in 0.05 potassium phosphate (KPi), 0.05 M NaCl, 0.002 M EDTA buffer at pH 6.7. Fractions containing huB4-compound of example 17 conjugate are pooled and dialyzed into the KPi buffer for 3 exchanges (24 hr). The final conjugate (2.25 mg, 2.25 mg/ml) is assayed spectrophotometrically using the extinction coefficients that are determined for compound of example 17 ($\epsilon_{318nm}$=12,053 M$^{-1}$ cm$^{-1}$, $\epsilon_{280nm}$=10,736 M$^{-1}$ cm$^{-1}$) and B4 antibody ($\epsilon_{280nm}$=222,960 M$^{-1}$ cm$^{-1}$). An average of 2.8 PBD molecules (Compound of example 17) per molecule of antibody were linked.
huMy9-6-SPDB Compound of Example 16

EXAMPLE A5

The antibody was first modified with 4-(2-pyridyldithio) butanoic acid N-hydroxysuccinimide ester (SPDB) to introduce pyridyldithio groups. A 4.5-fold molar excess SPDB (0.246 µmol, 80.1 µg) in DMA (50 µL) was added to solution of huMy9-6 (8 mg, 0.055 µmol) in aqueous buffer containing 50 mM potassium phosphate, 50 mM sodium chloride and 2 mM EDTA, pH 6.5 (0.950 mL). The final protein concentration was 8 mg/mL with 5% DMA in buffer. The modification was allowed to rotate at room temperature for 90 minutes, and then purified on a Sephadex G25 gel filtration column equilibrated in an aqueous buffer containing 50 mM potassium phosphate, 50 mM sodium chloride and 2 mM EDTA, pH 8.5. A small aliquot of the modified antibody was treated with DTT to cleave the pyridyldisulfide groups. The modified antibody and released pyridine thiol were assayed spectrophotometrically ($\epsilon_{343}$=8,080 M$^{-1}$ cm$^{-1}$ for the released pyridine thiol, $\epsilon_{280}$=5100 M$^{-1}$ cm$^{-1}$ for the modified pyridyldithio groups and $\epsilon_{280}$=206,460 M$^{-1}$ cm$^{-1}$ for antibody). An average of 3.32 pyridyldisulfide molecules per molecule of antibody were linked.

The modified antibody (3.05 mg, 0.0208 µmol) was diluted in the above buffer at pH 8.5 (976 µL) and DMA (122 uL, 10% v/v) and then treated with a solution of 8,8'-[5-(N-4-mercapto-4,4-dimethylbutanoyl)amino-1,3-benzenediylbis (methylenoxy)]-bis[7-methoxy-2-methylene-1,2,3,11a-tetrahydro-5H-pyrrolo[2,1-c][1,4]benzodiazepin-5-one] (Compound of example 16) (0.207 µmol, 0.158 mg) in DMA (122 µl, 10% v/v). The final protein concentration was 2.5 mg/mL with 20% DMA in buffer. The conjugation was allowed to rotate at room temperature overnight and then clarified by sedimentation (13,200 RPM for 4 min). The supernatant was then purified on a Sephadex G25 gel filtration column equilibrated in a PBS buffer at pH 6.5. The purified conjugate was dialyzed into PBS pH 6.5 buffer (~1:600 dilution) with three buffer exchanges. The conjugate was clarified through a 0.22 µm syringe filter and assayed spectrophotometrically ($\epsilon_{280}$=7743 M$^{-1}$ cm$^{-1}$, $\epsilon_{318}$=9137 M$^{-1}$ cm$^{-1}$ for the PBD, and $\epsilon_{280}$=206,460 M$^{-1}$ cm$^{-1}$ for antibody). An average of 2.58 PBD molecules (Compound of example 16) per molecule of antibody were linked.

EXAMPLE B

Binding Assay

The relative binding affinities of the anti-B4 antibody and its tomaymycin conjugate on antigen-expressing Ramos cells is determined using a fluorescence-based assay. The antibody-tomaymycin conjugate and naked antibody at starting concentrations of 1 a 10$^{-7}$ M are added to 96-well round bottom plates and titrated using 3-fold serial dilutions so that there are duplicates for each concentration. Ramos cells are added at 50,000 cells per well to each well containing various concentrations of the antibody or conjugate, as well as to control wells. The plates are incubated on ice for 3 hours. After the incubation period, the cells in the plate are washed, and a fluorescence labeled secondary antibody that binds to a humanized IgG, like anti-B4, is added, and the plates are incubated for 1 hour on ice. The plates are washed again after the incubation period, and the cells are fixed with 1% formaldehyde/PBS solution. The fluorescence in each well of the plates is read using a Becton Dickinson FACSCalibur fluorescence analyzer. Data are plotted as a percent of the maximum fluorescence obtained at the highest concentration of antibody or conjugate.

EXAMPLE C

In Vitro Potency and Specificity of Tomaymycin Derivative or Tomaymycin Derivative Conjugates. General Protocol to be Used Samples of free tomaymycin derivative or tomaymycin derivative conjugate are added to a 96-well flat bottomed tissue culture plate and titrated using serial dilutions ranging from $1 \times 10^{-12}$ M to $3 \times 10^{-7}$ M. Antigen positive tumor cells or antigen negative tumor cells are added to the wells in such a way that there are triplicate samples for each drug concentration for each cell line. The plates are incubated at 37° C. in an atmosphere of 5% $CO_2$ for 4 days.

At the end of the incubation period, 20 µl of the tetrazolium reagent WST-8 (2-(2-methoxy-nitrophenyl)-3-(4-nitrophenyl)-5-(2,4-disulfophenyl)-2-tetrazolium, monosodium salt) is added to each well, and the plates are returned to the incubator for 2 hours. The absorbance in each well of the plates is then measured using the Molecular Devices plate reader at 450 nm. Surviving fraction of cells at each concentration of tomaymycin derivative or conjugate are plotted.

| Compounds | A549 ($IC_{50}$) | KB ($IC_{50}$) | MCF7 ($IC_{50}$) |
| --- | --- | --- | --- |
| Example 5 | $7 \times 10^{-11}$ M | $1 \times 10^{-10}$ M | $1 \times 10^{-10}$ M |
| Example 1 | $<10^{-12}$ M | $<10^{-12}$ M | $<10^{-12}$ M |
| Example 2 | $<10^{-12}$ M | $<10^{-12}$ M | $<10^{-12}$ M |

Figure 1B:
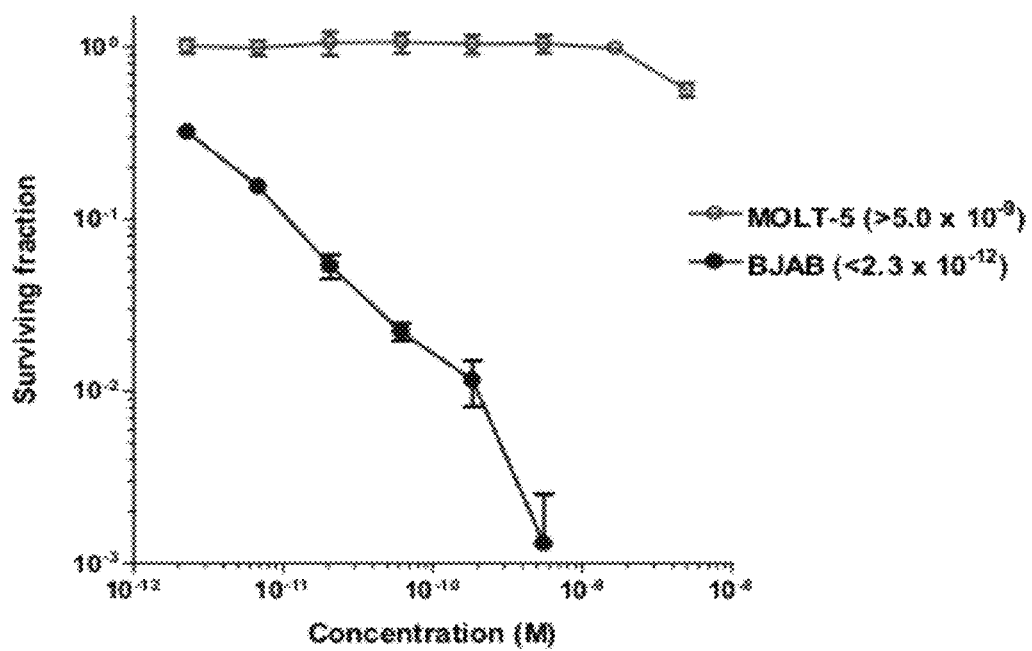
FIG. 1b represents in vitro potency of huB4-SMCC—compound of example 16 towards antigen positive BJAB cells and antigen negative MOLT-4 cells.
Figure 1C:
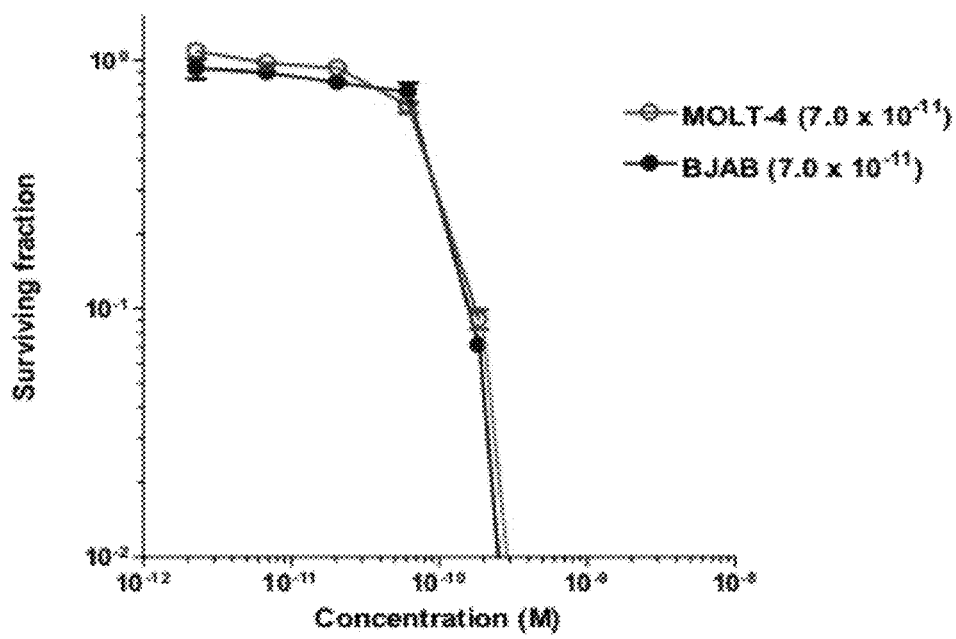
FIG. 1c represents in vitro potency of free compound of example 16 towards BJAB and MOLT-4 cells.
Figure 2A:
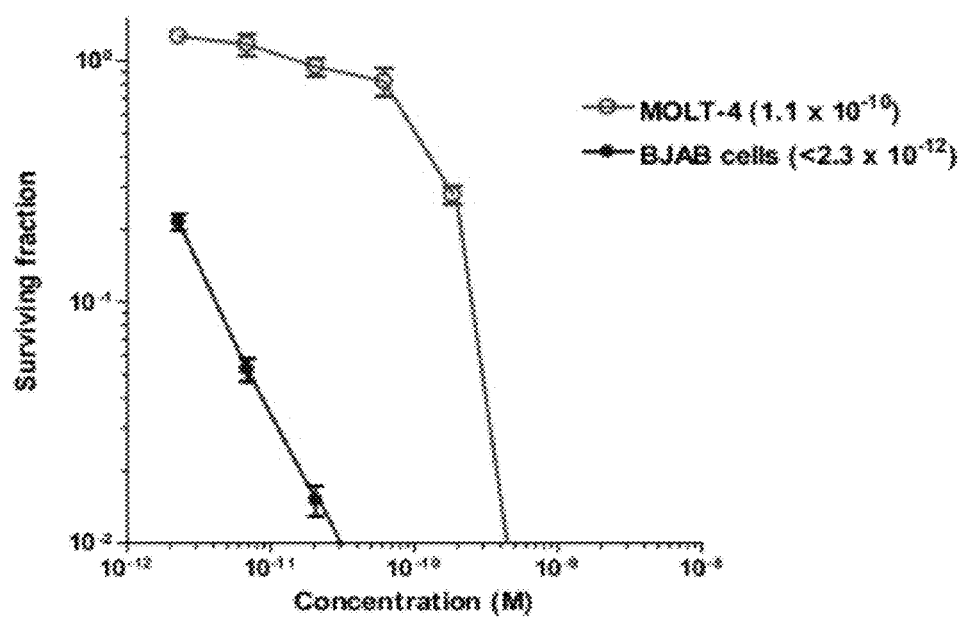
FIG. 2a represents in vitro potency of huB4-SPDB—Compound of example 17 towards antigen positive BJAB cells and antigen negative MOLT-4 cells.
Figure 2B:
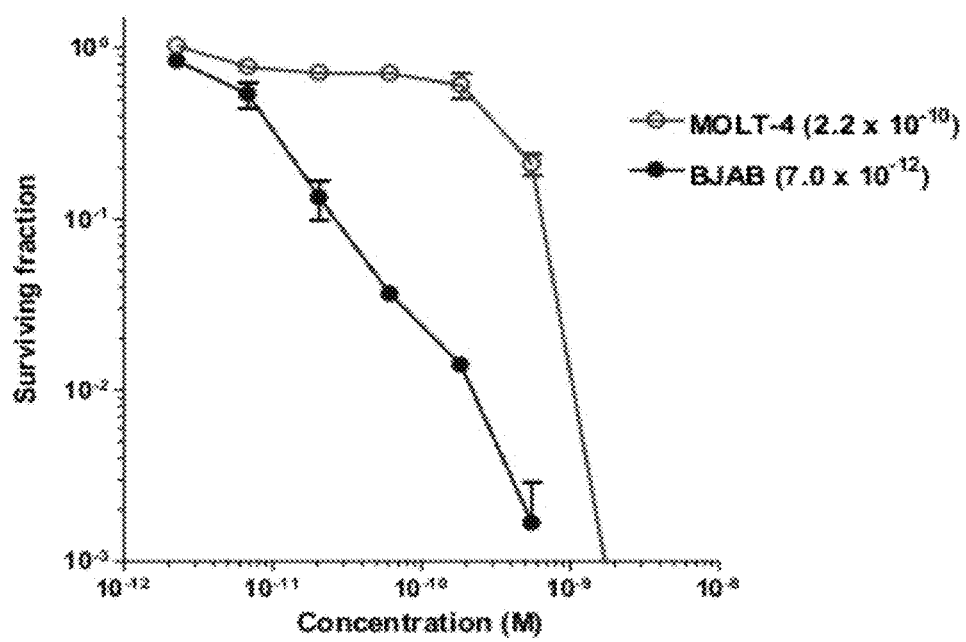
FIG. 2b represents in vitro potency of huB4-SMCC—Compound of example 17 towards antigen positive BJAB cells and antigen negative MOLT-4 cells.
Figure 2C:
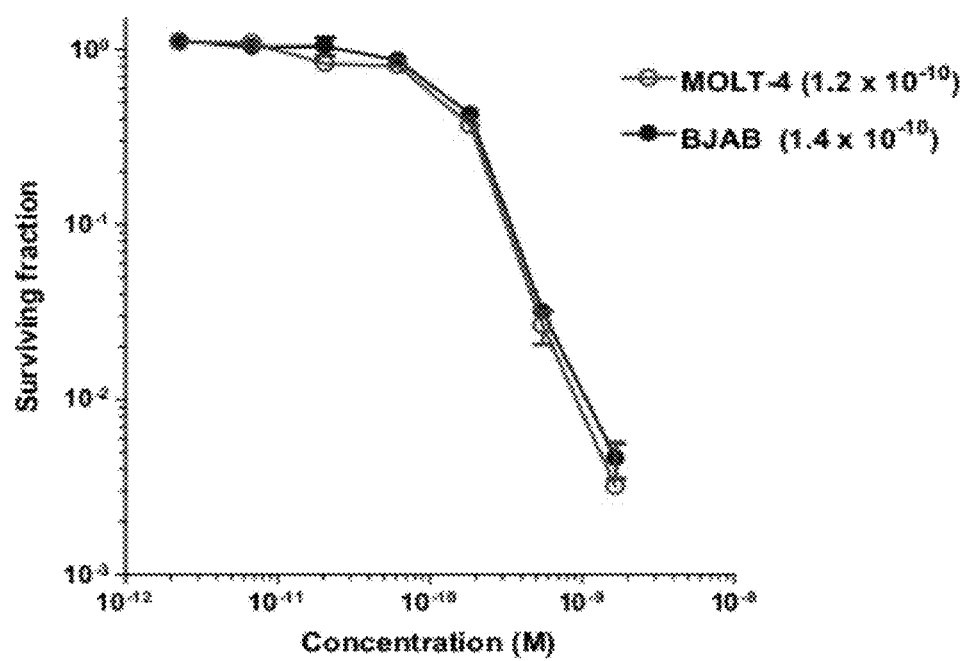
FIG. 2c represents in vitro potency of free compound of example 17 towards BJAB and MOLT-4 cells.
Figure 3A:
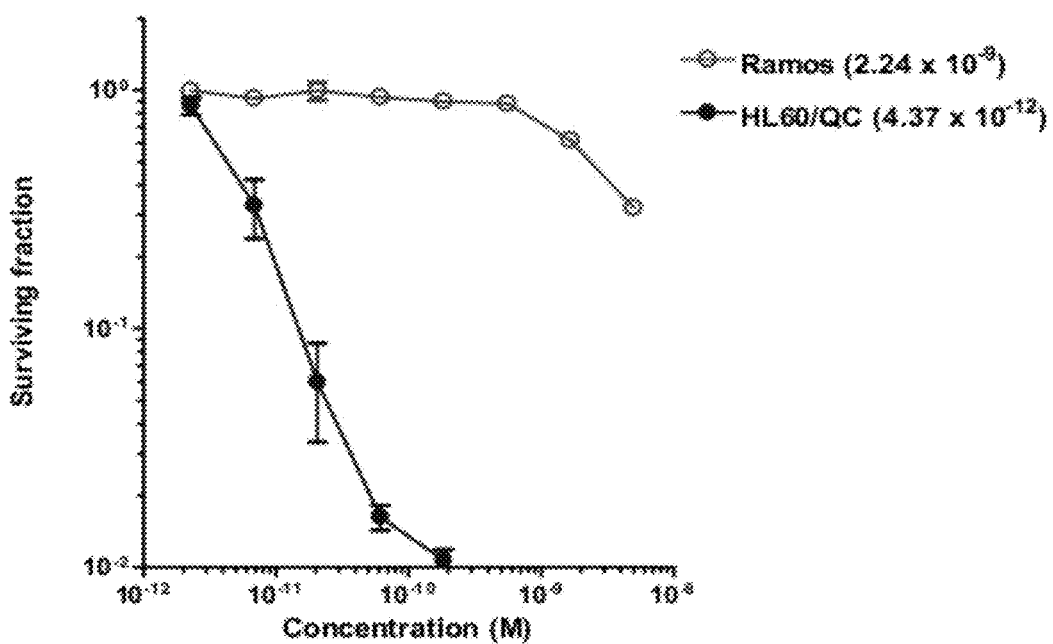
FIG. 3a represents in vitro potency of huMy9-6-SPDB—compound of example 16 towards antigen positive HL60/GC cells and antigen negative Ramos cells.
Figure 3B:
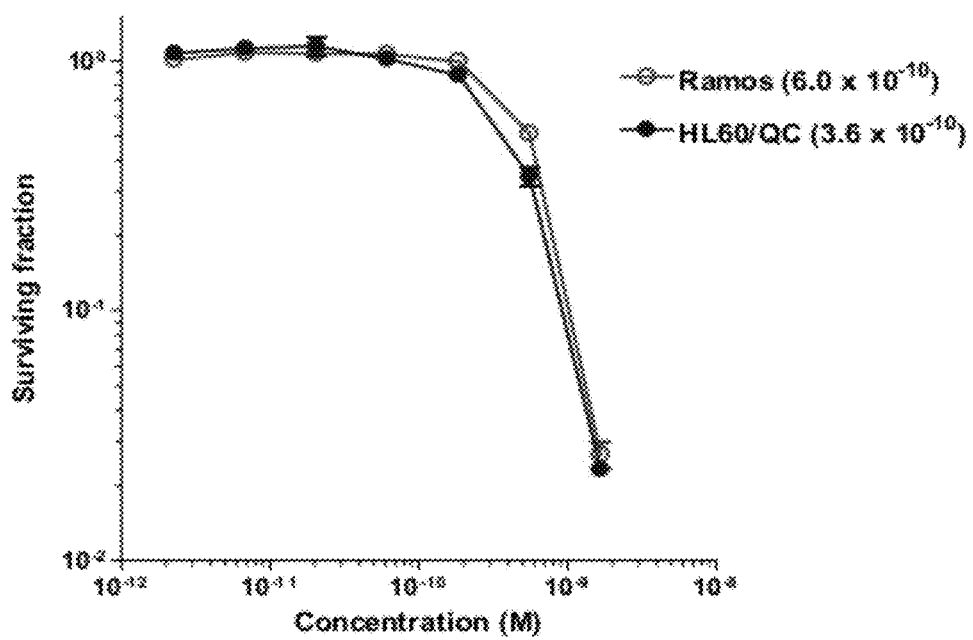
FIG. 3b represents in vitro potency of free compound of example 16 towards HL60/GC and Ramos cells.

The specific cytotoxicity of the compounds vs. the conjugates of the invention against MOLT-4 and BJAB or HL60/GC and Ramos cell lines were tested. Results are illustrated in FIGS. 1*a-c*, 2*a-c* and 3*a-b*.

EXAMPLE D

In Vivo Efficacy of Tomaymycin Derivative or Tomaymycin Derivative Conjugates

The tests can be carried out by application and/or adaptation of the protocol described in WO 2004/103272, with huB4 as the antibody and appropriate antigen positive cell lines, such as Ramos and Rajii Burkitt's Lymphoma cell lines.

What is claimed is:
1. A compound of formula (I)

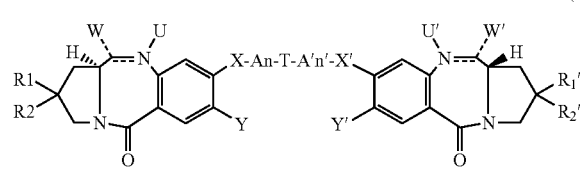

(I)

wherein
---, represents an optional single bond;
▬ represents either a single bond or a double bond;
  provided that when ▬ represents a single bond, U and U', the same or different, independently represent H, and W and W', the same or different, are independently selected from the group consisting of —OH, —OR, —OCOR, —OCOOR, —OCONRR', —NR-CONRR', —OCSNHR, —SH, —SR, —SOR, —SOOR, —$SO_3$, —$OSO_3$, —NRSOOR, $N_3$, a cyano, a halo, a trialkyl and triarylphosphonium;
and when ▬ represents a double bond, U and U' are absent and W and W' represent H;
R1, R2, R1', R2' are the same or different and independently chosen from halide and alkyl optionally substituted by one or more Hal, CN, NRR', $CF_3$, OR, Aryl, Het, $S(O)_qR$; or $R_1$ and $R_2$ and $R_1'$ and $R_2'$ form together a double bond containing group =B and =B' respectively;
B and B' are the same or different and independently represent alkenyl being optionally substituted by one or more Hal, CN, R, $CF_3$, OR, Aryl, Het$S(O)_qR$; or B and B' represent an oxygen atom;
X and X' are the same or different and independently chosen from one or more —O—, —NR—, —(C=O)—, and —$S(O)_q$—;
A and A' are the same or different and independently represent alkyl or alkenyl optionally containing an oxygen, a nitrogen or a sulfur atom and each being optionally substituted by one or more Hal, CN, NRR', $CF_3$, OR, $S(O)_qR$, Aryl, Het, Alkyl, or Alkenyl;
Y and Y' are the same or different and independently chosen from H and OR;
T is —NR—, or a 4 to 10-membered aryl, cycloalkyl, heterocyclic or heteroaryl, each being optionally substituted by one or more Hal, CN, NRR', $CF_3$, R, OR, $S(O)_qR$, or alkyl, and substituted by one more linkers of formula:

-G-D-(Z)*p*-S-Z' wherein
G is a single or double bond, —O—, —S— or —NR—;
D is a single bond or -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F—;
where E and F are the same or different and are independently chosen from linear or branched —($OCH_2CH_2$)$_i$Alkyl($OCH_2CH_2$)$_j$—, -Alkyl($OCH_2CH_2$)$_i$-Alkyl-, —($OCH_2CH_2$)$_i$—, —($OCH_2CH_2$)$_i$Cycloalkyl($OCH_2CH_2$)$_j$—, —($OCH_2CH_2$)$_i$Heterocyclic($OCH_2CH_2$)$_j$—, —($OCH_2CH_2$)$_i$Aryl($OCH_2CH_2$)$_j$—, —($OCH_2$ $CH_2$)$_i$Heteroaryl($OCH_2CH_2$)$_j$—, -Alkyl-($OCH_2CH_2$)$_i$Alkyl($OCH_2CH_2$)$_j$—, -Alkyl-($OCH_2CH_2$)$_i$—, -Alkyl-($OCH_2CH_2$)$_i$Cycloalkyl($OCH_2CH_2$)$_j$—, -Alkyl($OCH_2CH_2$)$_i$Heterocyclic($OCH_2CH_2$)$_j$—, -Alkyl-($OCH_2CH_2$)$_i$Aryl($OCH_2CH_2$)$_j$—, -Alkyl($OCH_2CH_2$)$_i$Heteroaryl($OCH_2CH_2$)$_j$—, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;
i and j, identical or different, are integers and independently chosen from 0, 1 to 2000;
Z is linear or branched -Alkyl-;
p is 0 or 1; and Z' represents H, a thiol protecting group COR, $R_{20}$ or $SR_{20}$, wherein $R_{20}$ represents H, methyl, Alkyl, optionally substituted Cycloalkyl, aryl, heteroaryl or heterocyclic;

n, n', equal or different are 0 or 1;

q is 0, 1 or 2;

R and R' are equal or different and independently chosen from H, Alkyl, Aryl, each being optionally substituted by Hal, CN, NRR', $CF_3$, R, OR, $S(O)_q R$, Aryl, or Het; or pharmaceutically acceptable salt thereof.

2. A compound according to claim 1, wherein n=n'=1.

3. A compound according to claim 1 of formula (II)

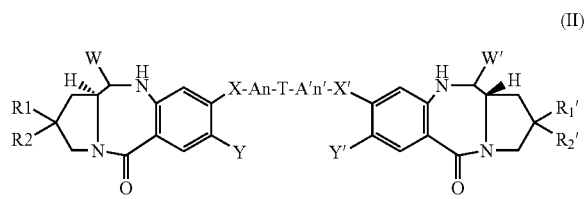

(II)

wherein:

W and W', the same or different, are independently selected from the group consisting of OH, —OR, —OCOR, —OCOOR, —OCONRR', —NRCONRR', —OCSNHR, —SH, —SR, —SOR, —SOOR, —$SO_3$—$OSO_3$, —NRSOOR, $N_3$, a cyano, a halo, a trialkyl and triarylphosphonium; or a pharmaceutically acceptable salt of such compound thereof.

4. A compound according to claim 2 of formula (II)

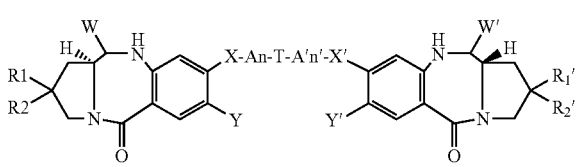

(II)

wherein:

W and W', the same or different, are independently selected from the group consisting of OH, —OR, —OCOR, —OCOOR, —OCONRR', —NRCONRR', —OCSNHR, —SH, —SR, —SOR, —SOOR, —$SO_3^-$, —NRSOOR, a cyano, a halo, a trialkyl and triarylphosphonium; or a pharmaceutically acceptable salt thereof.

5. A compound according to claim 1 of the formula

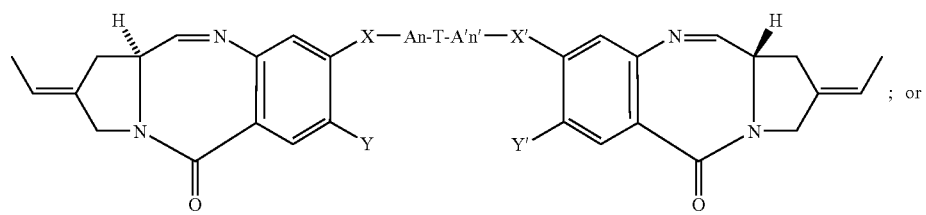

; or a pharmaceutically acceptable salt thereof.

6. A compound according to claim 1 of the formula:

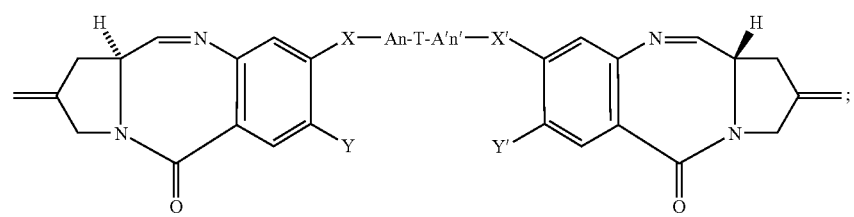

;

or a pharmaceutically acceptable salt.

7. A compound according to claim 1 wherein X=X'; or a pharmaceutically acceptable salt thereof.

8. A compound according to claim 7, wherein X=X'=O; or a pharmaceutically acceptable salt thereof.

9. A compound according to claim 1 wherein A=A'; or a pharmaceutically acceptable salt thereof.

10. A compound according to claim 9 wherein A=A'=linear unsubstituted alkyl; or a pharmaceutically acceptable salt thereof.

11. A compound according to claim 1 wherein Y=Y'; or a pharmaceutically acceptable salt thereof.

12. A compound according to claim 11, wherein Y=Y'=Oalkyl; or a pharmaceutically acceptable salt thereof.

13. A compound according to claim 1 wherein T is a phenyl or pyridyl, each being optionally substituted by one or more Hal, CN, NRR', $CF_3$, R, OR, $S(O)_qR$; or a pharmaceutically acceptable salt thereof.

14. A compound according to claim 2 wherein T is a phenyl or pyridyl, each being optionally substituted by one or more Hal, CN, NRR', $CF_3$, R, OR, $S(O)_qR$; or pharmaceutically acceptable salt.

15. A compound according to claim 1, wherein G is a single bond or —O— or —NR—; or pharmaceutically acceptable salt thereof.

16. A compound according to claim 15, wherein G is —O—; or a pharmaceutically acceptable salt thereof.

17. A compound according to claim 1, wherein D is a single bond or -E-, -E-NR—, -E-CO—, —CO-E-, or -E-NR—CO—; or a pharmaceutically acceptable salt thereof.

18. A compound according to claim 1, wherein D is -E-NR—CO—; or a pharmaceutically acceptable salt thereof.

19. A compound according to claim 1, wherein E is a linear or branched -Alkyl-, —(OCH$_2$CH$_2$)$_t$— or -Alkyl-heterocyclic; or a pharmaceutically acceptable salt thereof.

20. A compound according to claim 1, wherein Z is —(CH$_2$)$_2$—C(CH$_3$)$_2$—; or a pharmaceutically acceptable salt thereof.

21. A compound according to claim 1, wherein p is 1; or a pharmaceutically acceptable salt thereof.

22. A compound according to claim 1, wherein Z' is H or SR$_{20}$, wherein R$_{20}$ represents Alkyl, aryl, heterocyclic or heteroaryl; or a pharmaceutically acceptable salt thereof.

23. A compound of formula (I)

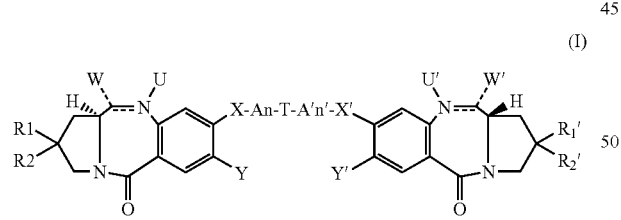

(I)

wherein

----, represents an optional single bond;
▬▬ represents either a single bond or a double bond;
provided that when ▬▬ represents a single bond, U and U', the same or different, independently represent H, and W and W', the same or different, are independently selected from the group consisting of —OH, —OR, —OCOR, —OCOOR, —OCONRR', —NRCONRR', —OCSNHR, —SH, —SR, —SOR, —SOOR, —SO$_3$, —OSO$_3$, —NRSOOR, N$_3$, a cyano, a halo, a trialkyl and triarylphosphonium;
and when ▬▬ represents a double bond, U and U' are absent and W and W' represent H;

R1, R2, R1', R2' are the same or different and independently chosen from halide and alkyl optionally substituted by one or more Hal, CN, NRR', $CF_3$, OR, Aryl, Het, $S(O)_qR$; or R$_1$ and R$_2$ and R$_1$' and R$_2$' form together a double bond containing group =B and =B' respectively;

B and B' are the same or different and independently represent alkenyl being optionally substituted by one or more Hal, CN, R, $CF_3$, OR, Aryl, HetS(O)$_q$R; or B and B' represent an oxygen atom;

X and X' are the same or different and independently chosen from one or more —O—, —NR—, —(C=O)—, and —S(O)$_q$—;

A and A' are the same or different and independently represent alkyl or alkenyl optionally containing an oxygen, a nitrogen or a sulfur atom and each being optionally substituted by one or more Hal, CN, NRR', $CF_3$, OR, $S(O)_qR$, Aryl, Het, Alkyl, or Alkenyl;

Y and Y' are the same or different and independently chosen from H and OR;

T is —NR—, or a 4 to 10-membered aryl, cycloalkyl, heterocyclic or heteroaryl, each being optionally substituted by one or more Hal, CN, NRR', $CF_3$, R, OR, $S(O)_qR$, or alkyl, and substituted by one more linkers;

n, n', equal or different are 0 or 1;

q is 0, 1 or 2;

R and R' are equal or different and independently chosen from H, Alkyl, Aryl, each being optionally substituted by Hal, CN, NRR', $CF_3$, R, OR, $S(O)_qR$, Aryl, or Het;

wherein said one or more linkers is chosen from:

—(CR$_{13}$R$_{14}$)$_t$(CR$_{15}$R$_{16}$)$_u$(OCH$_2$CH$_2$)$_y$SZ', —(CR$_{13}$R$_{14}$)$_t$(CR$_{17}$=CR$_{18}$)(CR$_{15}$R$_{16}$)$_y$(OCH$_2$CH$_2$)$_y$SZ',
—(CR$_{13}$R$_{14}$)$_t$(NR$_{19}$CO)(CR$_{15}$R$_{16}$)$_u$(OCH$_2$CH$_2$)$_y$ SZ',
—(CR$_{13}$R$_{14}$)$_t$(OCO)(R$_{15}$R$_{16}$)$_u$(OCH$_2$CH$_2$)$_y$SZ',
—(CR$_{13}$R$_{14}$)$_t$(CO)(CR$_{15}$R$_{16}$)$_u$(OCH$_2$CH$_2$)$_y$SZ',
—(CR$_{13}$R$_{14}$)$_t$(CONR$_{19}$)(CR$_{15}$R$_{16}$)$_u$(OCH$_2$CH$_2$)$_y$SZ',
—(CR$_{13}$R$_{14}$)$_t$-phenyl-CO(CR$_{15}$R$_{16}$)$_u$SZ', —(CR$_{13}$R$_{14}$)$_t$-furyl-CO(CR$_{15}$R$_{16}$)$_u$SZ', —(CR$_{13}$R$_{14}$)$_t$-oxazolyl-CO(CR$_{15}$R$_{16}$)$_u$SZ',—(CR$_{13}$R$_{14}$)$_t$-thiazolyl-CO(CR$_{15}$R$_{16}$)$_u$SZ', —(CR$_{13}$R$_{14}$)$_t$-thienyl-CO(CR$_{15}$R$_{16}$)$_u$SZ',
—(CR$_{13}$R$_{14}$)$_t$-imidazolyl-CO(CR$_{15}$R$_{16}$)$_u$SZ',
—(CR$_{13}$R$_{14}$)$_t$-morpholino-CO(CR$_{15}$R$_{16}$)$_u$SZ',
—(CR$_{13}$R$_{14}$)$_t$-piperazino-CO(CR$_{15}$R$_{16}$)$_u$SZ',
—(CR$_{13}$R$_{14}$)$_t$-N-methyl-piperazino-CO(CR$_{15}$R$_{16}$)$_u$ SZ',
—(CR$_{13}$R$_{14}$)$_t$-phenyl-QSZ', —(CR$_{13}$R$_{14}$)$_t$-furyl-QSZ', —(CR$_{13}$R$_{14}$)$_t$-oxazolyl-QSZ', —(CR$_{13}$R$_{14}$)$_t$-thiazolyl-QSZ', —(CR$_{13}$R$_{14}$)$_t$-thienyl-QSZ', —(CR$_{13}$R$_{14}$)$_t$-imidazolyl-QSZ', —(CR$_{13}$R$_{14}$)$_t$-morpholino-QSZ', —(CR$_{13}$R$_{14}$)$_t$-piperazino-QSZ', —(CR$_{13}$R$_{14}$)$_t$-N-methylpiperazino-QSZ', or
—O(CR$_{13}$R$_{14}$)$_t$(CR$_{15}$R$_{16}$)$_u$(OCH$_2$CH$_2$)$_y$SZ',
—O(CR$_{13}$R$_{14}$)$_t$(NR$_{19}$CO)(CR$_{15}$R$_{16}$)$_u$(OCH$_2$CH$_2$)$_y$SZ',
—O(CR$_{13}$R$_{14}$)$_t$ (CR$_{17}$=CR$_{18}$)(CR$_{15}$R$_{16}$)$_t$(OCH$_2$CH$_2$)$_y$ SZ', —O-phenyl-QSZ', —O-furyl-QSZ', —O-oxazolyl-QSZ', —O-thiazolyl-QSZ', —O-thienyl-QSZ', —O-imidazolyl-QSZ', —O-morpholino-QSZ', —O-piperazino-QSZ', —O-N-methylpiperazino-QSZ',
—OCO—(CR$_{13}$R$_{14}$)$_t$ (CR$_{17}$=CR$_{18}$)(CR$_{15}$R$_{16}$)$_u$ (OCH$_2$CH$_2$)$_y$SZ', —OCONR$_{12}$(CR$_{13}$R$_{14}$)$_t$(CR$_{15}$R$_{16}$)$_u$ (OCH$_2$CH$_2$)$_y$SZ', —OCO-phenyl-QSZ', —OCO-furyl-QSZ', —OCO-oxazolyl-QSZ', —OCO-thiazolyl-QSZ', —OCO-thienyl-QSZ', —OCO-imidazolyl-QSZ', —OCO-morpholino-QSZ', —OCO-piperazino-QSZ', —OCO—N-methylpiperazino-QSZ', or
—CO(CR$_{13}$R$_{14}$)$_t$(CR$_{15}$R$_{16}$)$_u$ (OCH$_2$CH$_2$)$_y$ SZ', —CO—(CR$_{13}$R$_{14}$)$_t$ (CR$_{17}$=CR$_{18}$)(CR$_{15}$R$_{16}$)$_u$(OCH$_2$CH$_2$)$_y$SZ', —CONR$_{12}$(CR$_{13}$R$_{14}$)$_t$(CR$_{15}$R$_{16}$)$_u$ (OCH$_2$CH$_2$)$_y$SZ',
—CO-phenyl-QSZ', —CO-furyl-QSZ', —CO-oxazolyl-QSZ', —CO-thiazolyl-QSZ', —CO-thienyl-QSZ', —CO-imidazolyl-QSZ', —CO-morpholino-QSZ', —CO-piperazino-QSZ', —CO-piperidino-QSZ', —CO—N-methylpiperazino-QSZ',
—NR$_{19}$(CR$_{13}$R$_{14}$)$_t$(CR$_{15}$R$_{16}$)$_u$(OCH$_2$CH$_2$)$_y$SZ',
—NR$_{19}$CO(CR$_{13}$R$_{14}$)$_t$(CR$_{15}$R$_{16}$)$_u$(OCH$_2$CH$_2$)$_y$SZ',
—NR$_{19}$(CR$_{13}$R$_{14}$)$_t$ (CR$_{17}$=CR$_{18}$)(CR$_{15}$R$_{16}$)$_t$ (OCH$_2$CH$_2$)$_y$SZ', —NR$_{19}$CO(CR$_{13}$R$_{14}$)$_t$ (CR$_{17}$=CR$_{18}$)(CR$_{15}$R$_{16}$)$_t$ (OCH$_2$CH$_2$)$_y$SZ',
—NR$_{19}$CONR$_{12}$(CR$_{13}$R$_{14}$)$_t$(CR$_{15}$R$_{16}$)$_u$ (OCH$_2$CH$_2$)$_y$SZ', —NR$_{19}$CO NR$_{12}$(CR$_{13}$R$_{14}$)$_t$ (CR$_{17}$=CR$_{18}$)(CR$_{15}$R$_{16}$)$_t$ (OCH$_2$CH$_2$)$_y$SZ', —NR$_{19}$CO-phenyl-QSZ',
—NR$_{19}$CO-furyl-QSZ', —NR$_{19}$CO-oxazolyl-QSZ', —NR$_{19}$CO-thiazolyl-QSZ', —NR$_{19}$CO-thienyl-QSZ', —NR$_{19}$CO-imidazolyl-QSZ', —NR$_{19}$CO-morpholino-QSZ', —NR$_{19}$CO-piperazino-QSZ', —NR$_{19}$CO-piperidino-QSZ', —NR$_{19}$CO—N-methylpiperazino-QSZ', —NR$_{19}$-phenyl-QSZ', —NR$_{19}$-furyl-QSZ', —NR$_{19}$-oxazolyl-QSZ', —NR$_{19}$-thiazolyl-QSZ', —NR$_{19}$-thienyl-QSZ', —NR$_{19}$-imidazolyl-QSZ', —NR$_{19}$-morpholino-QSZ', —NR$_{19}$-piperazino-QSZ', —NR$_{19}$-piperidino-QSZ', —NR$_{19}$—N-methylpiperazino-QSZ', —NR$_{19}$CO—NR$_{12}$-phenyl-QSZ', —NR$_{19}$CO—NR$_{12}$-oxazolyl-QSZ', —NR$_{19}$CO—NR$_{12}$-thiazolyl-QSZ', —NR$_{19}$CO—NR$_{12}$-thienyl-QSZ', —NR$_{19}$CO—NR$_{12}$-piperidino-QSZ',
—S(O)$_q$(CR$_{13}$R$_{14}$)$_t$(CR$_{15}$R$_{16}$)$_u$(OCH$_2$CH$_2$)$_y$SZ', —S(O)$_q$ (CR$_{13}$R$_{14}$)$_t$(CR$_{17}$=CR$_{18}$)(CR$_{15}$R$_{16}$)$_t$(OCH$_2$CH$_2$)$_y$SZ',
—SCONR$_{12}$(CR$_{13}$R$_{14}$)$_t$(CR$_{15}$R$_{16}$)$_u$ (OCH$_2$CH$_2$)$_y$SZ',
—SCO-morpholino-QSZ', —SCO-piperazino-QSZ', —SCO-piperidino-QSZ', and —SCO—N-methylpiperazino-QSZ', wherein:

Z' is H, a thiol protective group, R$_{20}$' or SR$_{20}$' wherein R$_{20}$' represents alkyl, aryl, heterocyclic or heteroaryl, wherein Q is a direct link or a linear alkyl or branched alkyl having from 1-10 carbon atoms or a polyethylene glycol spacer with 2 to 20 repeating ethylene oxy units;

R$_{19}$ and R$_{12}$ are the same or different and are linear alkyl, branched alkyl or cyclic alkyl having from 1 to 10 carbon atoms, or simple or substituted aryl or heterocyclic, and R$_{12}$ can in addition be H, R$_{13}$, R$_{14}$, R$_{15}$ and R$_{16}$ are the same or different and are H or a linear or branched alkyl having from 1 to 4 carbon atoms, R$_{17}$ and R$_{18}$ are H or alkyl, u is an integer from 1 to 10 and can also be 0, t is an integer from 1 to 10 and can also be 0, y is an integer from 1 to 20 and can also be 0; or a pharmaceutically acceptable salt thereof.

24. A compound according to claim 1 which is:

8,8'-[1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-methoxy-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[4-(3-tert-butoxycarbonylaminopropyloxy)-2,6-pyridinediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(3-aminopropyloxy)-1,3-benzenediylbis(methyleneoxy)]-bis[(S)-2-eth-(E)-ylidene-7-methoxy-1,2,3,11a-tetrahydro-5H-pyrrolo [2,1-c][1,4]benzodiazepin-5-one]

8,8'-[5-(N-methyl-3-tert-butoxycarbonylaminopropyl)-1,3-benzenediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-{5-[3-(4-methyl-4-methyldisulfanyl-pentanoylamino)propyloxy]-1,3-benzenediylbis(methyleneoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methyleneoxy)]-bis[(S)-2-methylene-7-methoxy-1,2,3,11a-tetrahydro-5H-pyrrolo[2,1-c][1,4]benzodiazepin-5-one]bis-{2-[(S)-2-methylene-7-methoxy-5-oxo-1,2,3,11a-tetrahydro-5H-pyrrolo[2,1-c][1,4]benzodiazepin-8-yloxy]-ethyl}-carbamic acid tert-butyl ester 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

8,8'-[5-(N-4-mercapto-4,4-dimethylbutanoyl)amino-1,3-benzenediylbis(methyleneoxy)]-bis[7-methoxy-2-methylene-1,2,3,11a-tetrahydro-5H-pyrrolo[2,1-c][1,4]benzodiazepin-5-one]

8,8'-[5-(N-4-methyldithio-4,4-dimethylbutanoyl)-amino-1,3-benzenediylbis(methyleneoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-mercapto-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-methyldithio-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one]

8,8'-[(4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(4-(4-methyl-4-methyldisulfanyl)-pentanamido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo [2,1-c][1,4]benzodiazepin-5-one]

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one] or 8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]; or the corresponding mercapto compound thereof; or a pharmaceutically acceptable salt thereof.

\* \* \* \* \*